(12) United States Patent
Li et al.

(10) Patent No.: US 7,750,206 B2
(45) Date of Patent: Jul. 6, 2010

(54) REGULATION OF GENE EXPRESSION IN PLANTS

(75) Inventors: Zhongyi Li, Kaleen (AU); Matthew Morell, Aranda (AU); Sadegur Rahman, Melba (AU)

(73) Assignees: Commonwealth Scientific and Industrial Research Organisation, Campbell (AU); The Australian National University, Acton (AU); Biogemma SAS, Paris (FR)

( * ) Notice: Subject to any disclaimer, the term of this patent is extended or adjusted under 35 U.S.C. 154(b) by 300 days.

(21) Appl. No.: 11/144,630

(22) Filed: Jun. 6, 2005

(65) Prior Publication Data
US 2006/0010517 A1    Jan. 12, 2006

Related U.S. Application Data

(62) Division of application No. 09/508,377, filed as application No. PCT/AU98/00743 on Sep. 11, 1998, now Pat. No. 6,916,976.

(30) Foreign Application Priority Data

Sep. 12, 1997 (AU) .................................... PO 9108
Mar. 20, 1998 (AU) .................................... PP 2509

(51) Int. Cl.
C12N 15/29 (2006.01)
C12N 15/82 (2006.01)
A01H 5/00 (2006.01)
A01H 5/10 (2006.01)

(52) U.S. Cl. ..................... 800/285; 800/298; 800/320.1; 800/278; 800/284; 536/24.5; 435/320.1

(58) Field of Classification Search ....................... None
See application file for complete search history.

(56) References Cited

U.S. PATENT DOCUMENTS 6,570,066 B1*  5/2003  Willmitzer et al. .......... 800/284
2005/0071896 A1  3/2005  Regina et al.

FOREIGN PATENT DOCUMENTS

| AU | 65392/94 | 11/1994 |
| AU | 19028/95 | 10/1995 |
| AU | 77165/95 | 6/1997 |
| AU | 48747/97 | 5/1998 |
| AU | 703900 | 5/1998 |
| WO | WO 97/04113 | 2/1997 |
| WO | WO 97/20040 | 6/1997 |
| WO | WO 97/22703 A | 6/1997 |

OTHER PUBLICATIONS

Kossmann et al (1995, Carbohydrate Bioengineering, S.B. Petersen, B. Svensson and S Pedersen (Eds). pp. 271-278).*

Willmitzer et al (1993, Starch synthesis in transgenic plants, In Plant Polymeric Carbohydrates; International Symposium Meuser, F., D.J. Manners and W. Seibel (Eds) pp. 33-39).*
Colliver et al (1997, Plant Mol. Biol. 35:509-522).*
Emery et al (2003, Current Biology 13:1768-1774).*
Hartl, D. L. and Jones, E. W. eds ((1998) "Genetics, Principles and Analysis", 4th Edition, Jones and Bartlett Publishers, Sudbury, MA. p. 419).*
R.B. Nair et al., (1997), *Plant Science*, "Isolation characterization and expression analysis of a starch branching enzyme II cDNA from wheat", vol. 122 pp. 153-163.
Fisher et al., Plant Physiol, 102(3):1045-1046, 1993.
Mizuno et al., I. Biol. Chem. 268(25):19084-19091, Sep. 1993.
Chibbar et al., Proceedings of the International Wheat Quality Conference, Manhattan, Kansas, USA, May 18-22 1997, pp. 249-260.
Kossmann et al., (1995, Carbohydrate Bioengineering S.B. Peterson, B. Svensson & s. Pedersen (Eds). pp. 271-278).
Willmitzer et al. (1993 in Plant Polymeric Carbohydrates; International Symposium Meuser, F., D.J. Manners and W. Seibel (Eds) Starch synthes in transgenic plants, pp. 33-39).
Bowie et al. (1990, Science 247-1306-1310).
McConnell et al. (2001, Nature 411 (6838):709-713).
Doerks et al., (TIG 14:248-250 1998).
Smith et al. (Nature Biotechnology 15:1222-1223).
Brenner (TIG 15, 4:132-133, Apr. 1999).
Bork et al. (TIG 12, 10:425-427, Oct. 1996).
Morrell et al., "Differential Expression and Properties of Starch Branching Enzyme Isoforms in Developing Wheat Endosperm", Plant. Physiol. 113:201-208 (1997).
Rahman, "Comparison of Starch-Branching Enzyme Genes Reveals Evolutionary Relationships Among Isoforms", Characterization of a Gene fo Starch-Branching Enzyme 11a from the Wheat D Genome Donor Aegilops Tauschii, Plant Phys. 125: 1314-1324 (2001).
Sweetlove et al. (1996 Biochem., J. 320:493-498).
Fourgoux-Nicol et al., (1999, Plant Molecular Biology 40:857-872).
Morell, MK. et al (1995). The biochemistry and molecular biology of starch synthesis in cereals. Aust J Plant Physiol 22:647-660.
Rahman, S. et al (1995). The major proteins of wheat endosperm starch granules. Aust J Plant Physiol 22: 793-803.
Rahman, S. et al (1997). A complex arrangement of genes at a starch branching enzyme I locus in the D-genome donor of wheat. Genome 40:465-474.

(Continued)

*Primary Examiner*—Stuart F. Baum
(74) *Attorney, Agent, or Firm*—Stephen A. Bent; Foley & Lardner LLP

(57) ABSTRACT

The present invention relates to a nucleic acid sequence encoding an enzyme of the starch biosynthetic pathway in a cereal plant, wherein the enzyme is selected from the group consisting of starch branching enzyme I, starch branching enzyme II, starch soluble synthase I, and debranching enzyme, with the proviso that the enzyme is not soluble starch synthase I of rice, or starch branching enzyme I of rice or maize.

29 Claims, 44 Drawing Sheets

OTHER PUBLICATIONS

Rahman, S., et al (1993). Molecular analysis of starch synthesis in Triticum tauschii. Proceedings of the 43rd Australian Cereal Chemistry Conference. (Sydney. Ed. C.W. Wrigley) pp. 332-333.

Morell, M.K., et al (1995). Starch branching enzymes in developing wheat endosperm. Proceedings of the 45th Australian Cereal Chemistry Conference. (Eds. Williams, Y.A. and Wrigley C.W.) pp. 135-139.

Rahman, S., et al (1995). The major proteins of wheat starch granules. Proceedings of the 45th Australian Cereal Chemistry Conference. (Eds Williams Y,.A. and Wrigley, C.W.) pp. 133-134.

Rahman, S., et al (1996). A complex arrangement of genes at a starch branching enzyme-I locus in the D-genome donor of wheat. In: Cereal: '96, C.W. Wrigley(ed), Proceedings 46th Australian Cereal Chemistry Conference (Sydney: Sep. 1-6, 1996) pp. 231-233.

Li, Z., et al (1997). Advances in wheat genetic engineering-increased transformation efficiencies and the first field release. Proceedings of the 47th Australian Cereal Chemistry Conference. (Eds. A.W. Tarr, A.S. Ross and C.W.Wrigley). pp. 22-26.

Rahman, S., et al. (1997). Structure of starch branching enzyme genes from T. tauschii. Proceedings of the 47th Cereal Chemistry Conferenc (Eds. A.W. Tarr, A.S. Ross and C.W.Wrigley).pp. 360-364.

Rahman, S., et al (1998). Structure of branching enzyme genes in wheat. Proc. 4th Asia-Pacific Conference on Agricultural Biotechnology, Darwin. Jul. 13-16, 1998. pp. 388-390.

Rahman, S., et al (1999). Characterisation of gene encoding wheat endosperm starch branching enzyme-1. Theor. App. Genet. 98: 156-163.

Database GENEMBL Apr. 9, 1997 Chibbar, R.N:: "T. Aestivum mRNA for starch branching enzyme I", XP002301159 Database Accession No. Y12320 ABSTRACT.

Anne Repellin et al., "Isolation and characterization of a cDNA for a type I starch branching enzyme from developing wheat kernels", Cereal Foods World, vol. 41, No. 7, 1996, pp. 564, XP008037158 & 81ST Annual Meeting of the American Association of Cereal Chemistry; Baltimore, Maryland USA; Sep. 15-19, 1996, ISSN: 0146-6283.

Kawasaki T et al., "Molecular Analysis of the Gene Encoding a Rice Starch Branching Enzyme", Molecular and General Genetics, Springer, Verlag, Berlin, DE 1993, pp. 10-16, XP002923868 ISSN: 0026-8925.

Chibbar Ravi et al., "Molecular cloning and characterization of starch branching enzyme genes from wheat", Cereal Foods World, vol. 41, No. 7, 1996, p. 587, XP008037159 & 81ST, Annual Meeting of the American Association of Cereal Chemistry, Baltimore MD, USA; Sep. 15-19, 1996 ISSN: 0146-6283 ABSTRACT.

Ken-Ichiro Tanaka et al., "Structure, Organization and Chromosomal Location of the Gene Encoding a Form of Rice Soluble Starch Synthase", Plant Physiology, American Society of Plant Physiologists, Rockville, MD. US, vol. 108, No. 2, Jun. 1, 1995, pp. 677-683 XP000565743; ISSN: 0032-0889.

\* cited by examiner

```
              1                                                           50
RSBEI         ..........  .********  *....*pl  lp****  ag******
MSBEI         ..........  .****v*p  tplp*r  *h***aa*  pg********
D4cDNA        ..........  .*****ap*c  sl..*p  pa**g*  **s*......
PESBEII       ..........  ..........  ..........  ..........  ..........
POSBE         meinfkvlsk  pirgsfp*f*  pkv*sgas*n  kic*psqh*t  *lkf*sqers
D2cDNA        ..........  .****s**ll  prp*a*....  ....****l*  *******ggk
Consensus     ----------  -MLCLTSSSS  SP-S-APPR-  SRS-ADRPSP  GIIAGGGNVR 51                                                          100
RSBEI         l..**v*...  *p***g  *tn*pa  rk****v*vv  *..***
MSBEI         l..lqc  ka*gv*  ****ataa*v  q*d***ak  g..*****
D4cDNA        ..........  ..........  ******p*s*  prdy****a*  *g*..gd***
PESBEII       ..........  ..........  ........mt  d*ks**psv*  **f..*nig*
POSBE         w..d*s*t*k  *rv*kde*mk  h*saisa*lt  ds*pl*  ***kt*nigl
D2cDNA        rlsv*p*f  lll**a  *sf*s*  rgia..  tgygs***
Consensus     ---SV-SVP-  S-RRSWPRKV  KSKFSV-VTA  -DNKTMAT-E  EDV--DHLPI 101                                                         150
RSBEI         ********e*  **ni  *c  ******  *******v
MSBEI         ********i*  ********  *gse  nss*  ********n
D4cDNA        *******ag*  ****s****k  ******s*t*  **********  **********
PESBEII       lnv*ss**p*  **k*  hk*e  y*qa*  ******f*r*
POSBE         ln*tp*  l**h**  *v*m  yp**aq  ****f*r*
D2cDNA        **lae*  ****d*trn*  *i******  *s****  ********
Consensus     YDLDPKLE-F  KDHFRYRMKR  YLDQKHLIEK  HEGGLEEFSK  GYLKFGINTE 151                                                         200
RSBEI         *g******  ******  *****ak*  ***k  k*******
MSBEI         *dg*****  **e*  *d*a  *k  k*dk
D4cDNA        nd******  *m****  ******g*  r*tn  ********
PESBEII       *dgis***  ***i  *g*l  hq  q*pdad*n
POSBE         *gci****  *dev  *g**  mq  **pd*ds*
D2cDNA        hg*s****  *e****  ******g*  an**  ********
Consensus     --ATVYREWA  PAAQEAQLIG  DFNNWNGSNH  KMEKD-FGVW  SIRISHVNGK 201                                                         250
RSBEI         ********  *r**g*a*  ********  f*****  ********
MSBEI         **********  ***l*.g***  ******l***  **********  **********
D4cDNA        ********  *hr*d*l*  ********  f*****  ********
PESBEII       *******r**  ***k*sd***  ********k*  ****ptr*a*  *****y****
POSBE         *v***r  *kn*  ******k*  at**a*  ***y**
D2cDNA        ********  *r*.h*  q*****  *tes  **l***
Consensus     PAIPHNSKVK  FRF-HG-GVW  VDRIPAWIRY  ATVDASKFGA  PYDGVHWDPP 251                                                         300
RSBEI         ac******  ******  ******  ******  ********
MSBEI         a**t  sa  ********  k*a*****  ********
D4cDNA        sg******  r*****  ******  r*****  ******k*
PESBEII       l**q  k*  ****ss  r*ns**  d*****e
POSBE         p**hy*  ***r  ****ss  r*ns**  d****k*
D2cDNA        s******n**  ******v***  ******v**g  kl*ag*****  p*****cl**
Consensus     -SERYVFKHP  RPPKPDAPRI  YEAHVGMSGE  EPEVSTYREF  ADNVLPRIRA
```

Figure 4

```
                    301                                                                    350
RSBEI       **********  **********  ******.***  **********  **********
MSBEI       **********  **********  ******.***  **********  **********
D4cDNA      **********  *****ilcf*  w*****.***  **********  **********
PESBEII     **********  **********  w****kp***  ******s***  **********
POSBE       **********  *******g**  ******.***  ****y*n***  **********
D2cDNA      t********g  *****ds***  ******.***  **********  **********
Consensus   NNYNTVQLMA  IMEHSYYASF  GYHVTN-FFA  VSSRSGTPED  LKYL-DKAHS 351                                                                    400
RSBEI       ********  ******  *******n  *h***t  **********
MSBEI       **********  **********  **********  ******a**   **********
D4cDNA      **********  *****s*m**  *********n  *******t**  **********
PESBEII     *n**  ******  ********  s*q*a   **********
POSBE       *qv*  ******  *****g  s*a   **********
D2cDNA      ********  *****i*   ********  ah*yt   kn***ng*
Consensus   LGLRVLMDVV  HSHASNNVTD  GLNGYDVGQS  TQESYFH-GD  RGYHKLWDSR 401                                                                    450
RSBEI       ********  ******  ******  ******  *k**
MSBEI       **********  **********  **********  **********  *****v****
D4cDNA      **********  **********  **********  ********n   ******s*a*
PESBEII     ******ks.   s*********  ****k*****  **********  ******a***
POSBE       ********  ******  *n****  *****v  ********
D2cDNA      **********  **********  **********  *v*******n  *n****s*n*
Consensus   LFNYANWEVL  RFLLSNLRYW  -DEFMFDGFR  FDGVTSMLYH  HHGINMGFTG 451                                                                    500
RSBEI       ********  ******  **l   ********  ********
MSBEI       q***  a*****  **l   ********  ********
D4cDNA      ******g***  **********  ******i**   **********  *******s**
PESBEII     d*n**e  ********  s*v*di  *d****  *g*g***s
POSBE       n**ea*  ********  n*ii  ********  *g*g***s
D2cDNA      ***ig*  n*f*  ***l  i*v*  ********
Consensus   NYKEYFSLDT  DVDAVVYMML  ANHLMHK-LP  EATVVAEDVS  GMPVLCRPVD 501                                                                    550
RSBEI       ********  ******  *****rk*  ****.*vq  ********
MSBEI       **********  **********  **********  **g*.*ah**  **********
D4cDNA      **********  **********  *******l**  ***a.*ah**  **********
PESBEII     *v********  ******k***  *****k****  **k*.*sln*  **********
POSBE       **********  ******k***  *****n*e**  **k*.*tss*  **********
D2cDNA      *l*q  t*****  e**g*qq*  ***sv*sq  pf*
Consensus   EGGVGFDYRL  AMAIPDRWID  YLKNKDDSEW  SMSE-I--TL  TNRRYTEKCI 551                                                                    600
RSBEI       ********  ******  **t*  *******n  ********
MSBEI       **********  **********  ******t***  **********  **********
D4cDNA      **********  *****m****  ******t***  **********  **********
PESBEII     s*******  ******  e*ss  c*tml***  *s*h****
POSBE       **********  **********  ******s***  c*td***v**  ****h****
D2cDNA      **rqnh  sm**  w*t*s***  a*d*d*****  *a********
Consensus   AYAESHDQSI  VGDKTIAFLL  MDKEMY-GMS  DLQPASPTID  RGIALQKMIH
```

Figure 4 (cont..)

```
                    601                                                                   650
RSBEI       **********  **********  **********  **********  .*********
MSBEI       **********  **********  **********  **********  .*********
D4cDNA      **********  **********  **********  **********  .****s*i*
PESBEII     ********  ******  ******  g*****  ltn****n
POSBE       *f********  **********  **********  **********  .***n*a*s*
D2cDNA      *******s  k*****..  ..........  ..........  ..........
Consensus   FITMALGGDG  YLNFMGNEFG  HPEWIDFPRE  GNNWSYDKCR  -RQWSLVDTD 651                                                                   700
RSBEI       ********  ****e   ******  **k*  **********
MSBEI       **********  ********r   **********  **********  **********
D4cDNA      **********  **********  **********  ******k**   **********
PESBEII     **********  *r***l****  **i*a*t***  **st*n****  **********
POSBE       **********  *r*s  **a*g*  s*dn  **********
D2cDNA      .....***  vvdtps  c****n*t  a*h*****g   sa*tk*....
Consensus   HLRYKYMNAF  DQAMNALD-K  FSFLSSSKQI  VSDMNEE-KV  IVFERGDLVF 701                                                                   750
RSBEI       ****n*  k*******  ******  v*****  ********
MSBEI       ****k*  ********  ******  v*****  ********
D4cDNA      ****s*  ********  *k****  m*****  aqyn****
PESBEII     ******en**  **********  **********  *te*******  ***a*q****
POSBE       ******kn**  **********  **********  *we******t  **********
D2cDNA      .*thlrsgc*  *p.....s**  stssc**...  .*gpsnqspf  skpfig*pgc
Consensus   VFNFHP-KTY  EGYKVGCDLP  GKYRVALDSD  AL-FGGHGRV  GHDVDHFTSP 751                                                                   800
RSBEI       m***  *.....  ..........  .....*  ********
MSBEI       **********  *****.....  ..........  .....*****  **********
D4cDNA      **********  *****.....  ..........  .....*****  **********
PESBEII     **********  *****.....  ..........  .....*****  ****h***v*
POSBE       **********  **g*qipskc  cllrehvwli  telmnacq*l  kitrq*f*vs
D2cDNA      ifcc*lfkge  *.........  ..........  ..........  ..........
Consensus   EG-PGVPETN  FNNRP-----  ----------  -----NSFKV  LSPPRTCVAY 801                                                                   850
RSBEI       *...**dr  l*rgva  si.vte  es....  ..ti**gw
MSBEI       *...****ag  agr*lhak*e  t***s**es*  **k*s*....  ..a....ssk
D4cDNA      *...****ka  *kpkde**  waa*g.  e*vkda  adat**sk
PESBEII     *...*****q  **snnpnlg*  *ee**a*adt  **aripdvs*  e*..ed*nld
POSBE       *yqqp*sr*v  trnlkirylq  *sv**tna*q  klkf**qtf*  v*yyqqpilr
D2cDNA      ..........  ..........  ..........  ..........  ..........
Consensus   Y---RVDER-  EE-R--GAAS  -GKT-PA-YI  DV-ATR----  -SGE--SG--

851               876
RSBEI       kg***d*cg*  mk*r**  *e*c*d
MSBEI       edk*atagg*  **wk*arqp*  *q*t**
D4cDNA      ka*tgg*ss*  in*g*p  *k*n*.
PESBEII     r*e*ns**av  dagi*kvere  vvgdn*
POSBE       r*tr*lk*sl  stnist*...  ......
D2cDNA      ..........  ..........  ......
Consensus   --SEK-DD-K  KG--FVF-SS  D-D-K-
```

Figure 4 (cont..)

Genomic Clones from *T.tauschii* for SBE II.

*N-terminal sequences of cereal starch branching enzymes*

| Protein | 1 2 3 4 5 6 7 8 9 10 11 12 13 14 15 16 17 18 19 20 21 22 |
|---|---|
| RICEBEI[B] | A T A R K N K T M V T V V E E V |
| WBE-I[AD] | V S A P R D Y T M A T A E D G V |
| MAIZE BEI[C] | A T V Q E D K T M A T A K G D V |
| | |
| RICEBEII[D] | A A G A S G E - V M I P E G E S D G M P V S |
| WBE-II | A A S P G K - V L V P D G E S D D L A S Y |
| MAIZE BEII[E] | A A A A A R K A V M V P E G E N D G L A S |

[A] N-terminal amino acid of the mature polypeptide. [B] Kawasaki *et al.*(1993), [C] Baba *et al.* (1991),
[D] Mizuno *et al.* (1993), [E] Fisher *et al.* (1993)

Residues in the wheat sequences showing identity with the respective maize or rice branching enzyme isoforms are highlighted in bold text.

Figure 13a

```
                TTCCCTTTTTTTTTCTTTGGGNGGGGGATGGCCTGTTGGATGNTGTTCCCCAATGAATTT
      1        ----------+----------+----------+----------+----------+----------+ 60
                AAGGGAAAAAAAAAGAAACCCNCCCCCTACCGGACAACCTACNACAAGGGGTTACTTAAA a          F  P  F  F  F  F  G  ?  G  M  A  C  W  M  ?  F  P  N  E  F  -
    b           S  L  F  F  S  L  G  G  G  W  P  V  G  ?  C  S  P  M  N  F  -
    c            P  F  F  F  L  W  ?  G  D  G  L  L  D  ?  V  P  Q  *  I  S  -

CCATGGAGTGAGAGAGATAGTTGGATNAGGGATCGCGNTTCCNGGAACTGTATTTTTTTC
      61       ----------+----------+----------+----------+----------+----------+ 120
                GGTACCTCACTCTCTCTATCAACCTANTCCCTAGCGCNAAGGNCCTTGACATAAAAAAAG a          P  W  S  E  R  D  S  W  ?  R  D  R  ?  S  ?  N  C  I  F  F  -
    b           H  G  V  R  E  I  V  G  ?  G  I  A  ?  P  G  T  V  F  F  S  -
    c            M  E  *  E  R  *  L  D  ?  G  S  R  F  ?  E  L  Y  F  F  P  -

CCCNGCGGGGAAATGGCGTTAGTGTCNACCCAGGCCCTGGTGTTACCACGGCTTTGATC
      121      ----------+----------+----------+----------+----------+----------+ 180
                GGGNCGCCCCCTTTACCGCAATCACAGNTGGGTCCGGGACCACAATGGTGCCGAAACTAG a          ⇐P  ?  G  G  N  G  V  S  V  ?  P  G  P  G  V  T  T  A  L  I  -
    b           P  A  G  E  M  A  L  V  S  T  Q  A  L  V  L  P  R  L  *  S  -
    c            ?  R  G  K  W  R  *  C  ?  P  R  P  W  C  Y  H  G  F  D  H  -

ATTCTTCGTTTCATTCTGATATATATATTTTCTCATTCTTTTTCTTCCTGTTCTTGCTGTAA
      181      ----------+----------+----------+----------+----------+----------+ 240
                TAAGAAGCAAAGTAAGACTATATATAAAAGAGTAAGAAAAAGAAGGACAAGAACGACATT a          I  L  R  F  I  L  I  Y  I  F  S  F  F  F  F  L  F  L  L  *  -
    b           F  F  V  S  F  *  Y  I  F  S  H  S  F  S  S  C  S  C  C  N  -
    c            S  S  F  H  S  D  I  Y  F  L  I  L  F  L  P  V  L  A  V  T  -

CTGCAAGTTGTGGCGTTTTTTTCACTATTGTAGTCATCCTTGCATTTTGCAGGCGCCGTCC
      241      ----------+----------+----------+----------+----------+----------+ 300
                GACGTTCAACACCGCAAAAAAGTGATAACATCAGTAGGAACGTAAAACGTCCGCGGCAGG a          L  Q  V  V  A  F  F  H  Y  C  S  H  P  C  I  L  Q  A  P  S  -
    b           C  K  L  W  R  F  F  T  I  V  V  I  L  A  F  C  R  R  R  P  -
    c            A  S  C  G  V  F  S  L  L  *  S  S  L  H  F  A  G  A  V  L  -

TGAGCCGCGCGGCCTCTCCAGGGAAGGTCCTGGTGCCTGACGGCGAGAGNGACGACTTGG
      301      ----------+----------+----------+----------+----------+----------+ 360
                ACTCGGCGCGCCGGAGAGGTCCCTTCCAGGACCACGGACTGCCGCTCTCNCTGCTGAACC a          *  A  A  R  P  L  Q  G  R  S  W  C  L  T  A  R  ?  T  T  W  -
    b           E  P  R  G  L  S  R  E  G  P  G  A  *  R  R  E  ?  R  L  G  -
    c            S  R  A  A  S  P  G  K  V  L  V  P  D  G  E  ?  D  D  L  A  -

CAAGTCCGGCGCAACCTGAAGAATTACAGGTACACACACTCGTGCCGGTAAATCTTCATA
      361      ----------+----------+----------+----------+----------+----------+ 420
                GTTCAGGCCGCGTTGGACTTCTTAATGTCCATGTGTGTGAGCACGGCCATTTAGAAGTAT a          Q  V  R  R  N  L  K  N  Y  R  Y  T  H  S  C  R  *  I  F  I  -
    b           K  S  G  A  T  *  R  I  T  G  T  H  T  R  A  G  K  S  S  Y  -
    c            S  P  A  Q  P  E  E  L  Q  V  H  T  L  V  P  V  N  L  H  T  -

CAATCGTTATTCACTTACCAAATGCCGGATGAAACCAACCACGGATGCGTCAGGTTTCGA
      421      ----------+----------+----------+----------+----------+----------+ 480
                GTTAGCAATAAGTGAATGGTTTACGGCCTACTTTGGTTGGTGCCTACGCAGTCCAAAGCT a          Q  S  L  F  T  Y  Q  M  P  D  E  T  N  H  G  C  V  R  F  R  -
    b           N  R  Y  S  L  T  K  C  R  M  K  P  T  T  D  A  S  G  F  E  -
```

Figure 13b

Branching Enzyme-II Genes
Intron/Exon structure of wheat BE-II
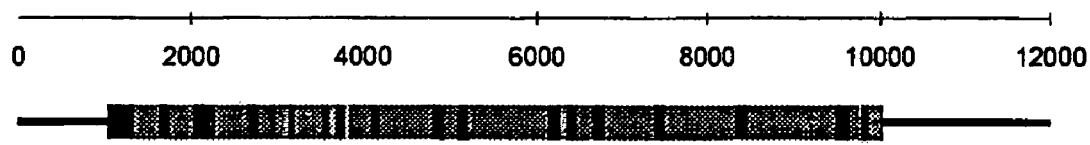
Schematic Diagram of a cDNA for BE-II
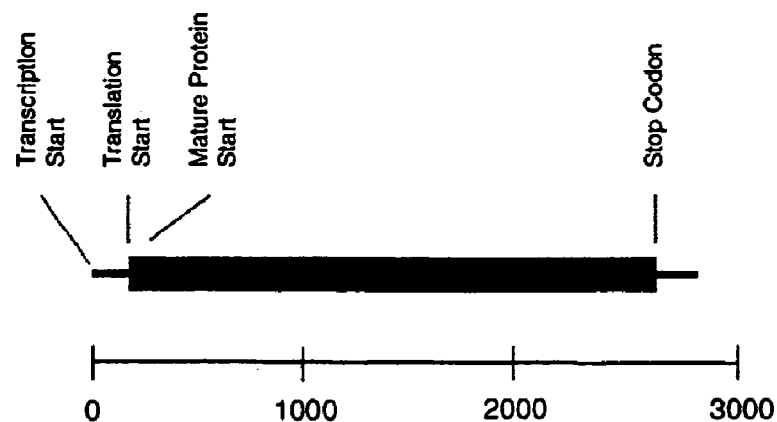
FIGURE 14

Wheat DNA probed with the 5' conserved sequence of SBE II.

COMPARISON OF N-TERMINAL SEQUENCES OF SOLUBLE STARCH SYNTHASE

GRYVAELSREGPAARP    Deduced from wheat cDNA

GPYVAELSPEGPAAPP    Wheat N-terminal

Figure 16

```
                ATACTACATACTATATGCTTGCACCCAAGGACACTTTATAACTATTCTGGCTGTGGGA
             80 +---------+---------+---------+---------+---------+---------+ 139
                TATGATGTATGATATACGAACGTGGGTTCCCTGTGAAATATTGATAAGACCGACACCCT a    T  T  Y  Y  M  L  A  P  K  G  H  F  Y  N  Y  S  G  C  G  N  -
             b     I  L  H  T  I  C  L  H  P  R  D  T  F  I  T  I  L  A  V  G   -
             c      Y  I  L  Y  A  C  T  Q  G  T  L  L  *  L  F  W  L  W  E     -

ATACCTTCAACTGTAATCATCCTGTCGTTCGTCAATTCATTGTAGATTGTTAAGATACT
            140 +---------+---------+---------+---------+---------+---------+ 199
                TATGGAAGTTGACATTAGTAGGACACCAAGCAGTTAAGTAACATCTAACAATTCTATGA a    T  F  N  C  N  H  P  V  V  R  Q  F  I  V  D  C  L  R  Y  W  -
             b     I  P  S  T  V  I  I  L  W  F  V  N  S  L  *  I  V  *  D  T   -
             c      Y  L  Q  L  *  S  S  C  G  S  S  I  H  C  R  L  F  K  I  L  -

GGGTGACGGAAATGCATGTTGATGGTTTTCGTTTTGACCTT
            200 +---------+---------+---------+---------+ 240
                CCCACTGCCTTTACGTACAACTACCAAAAGCAAAACTGGAA a    V  T  E  M  H  V  D  G  F  R  F  D  L    -
             b     G  *  R  K  C  M  L  M  V  F  V  L  T   -
             c      G  D  G  N  A  C  *  W  F  S  F  *  P  -

Enzymes that do cut:

NONE

Enzymes that do not cut:

EcoRI
```

Figure 20a

Comparison of Wheat Debranching Enzyme-1 (WDBE-1) PCR fragment with maize Sugary-1 DNA sequence

```
                      1098       1107       1117       1127       1137       1147       1157
SUGARY.DNA            TGAGGTGATCATGGATGTTGTCTTCAATCATACAGCTGAAGGTAATGAAGGCCCAAT
                                 ||||||||||||||||||||||||||||||||||||||||||| || |||||
WHEAT1.DNA            ....GTGATCATGGATGTTGTCTTCAACCATACAGCTGAGGGTAATGAGAATGGTCCAAT
                      -3          6         16         26         36         46         56

FILE NAME             1158       1167       1177       1187       1197       1207       1217
SUGARY.DNA            ATTATCCTTTAGGGGGATAGATAATAGTACATACTACATGCTTGCACCTAAGGAGAGTT
                      |||||| |||||||||||  |||||| |||||||||||||||||||||||||| || |
.WHEAT1.DNA           ATTATCATTTAGGGGGTCGATAATACTACATACTATATGCTTGCACCCAAGGACACTT
                      57         66         76         86         96        106        116

FILE NAME             1218       1227       1237       1247       1257       1267       1277
SUGARY.DNA            TTATAATTATTCTGGTGTGGAAATACCTTCAATTGTAATCATCCTGTAGTCCGTGAATT
                      ||||| ||||||||||||| ||||||| ||||||||||||||||||||| ||| ||||
WHEAT1.DNA            TTATAACTATTCTGGCTGTGGGNATACCTTCAACTGTAATCATCCTGTGGTTCGTCAATT
                      117        126        136        146        156        166        176

FILE NAME             1278       1287       1297       1307       1317       1327       1337
SUGARY.DNA            TATAGTGGATTGCTTGAGATACTGGGTAACAGAATGGTGATGTGATGCATGTTTCGTTTGA
                      ||| || |||||||| ||| || ||||| |||||||||||||||||||| |||||||||
WHEAT1.DNA            CATTGTAGATTGTTTAAGNTACTGGGTGACGGAAATGCATGTTGNTGGTTTTCGTTTTGA
                      177        186        196        206        216        226        236

FILE NAME             1338       1347       1357
SUGARY.DNA            CCTTGCATCTATACT-G...
                      |||||||||| || ||
WHEAT1.DNA            CCTTGCATCTN--CTTNAAA
                      237        246        256

MATCHING PERCENTAGE
  TOTAL WINDOW           84%     ( 219/ 260)
  ALIGNMENT WINDOW       86%     ( 219/ 253)
```

Figure 20b

Southern blot of T. *tauschii* Genomic DNA

T. *tauschii* Genomic DNA Probed With The Wheat Debranching Enzyme PCR Product

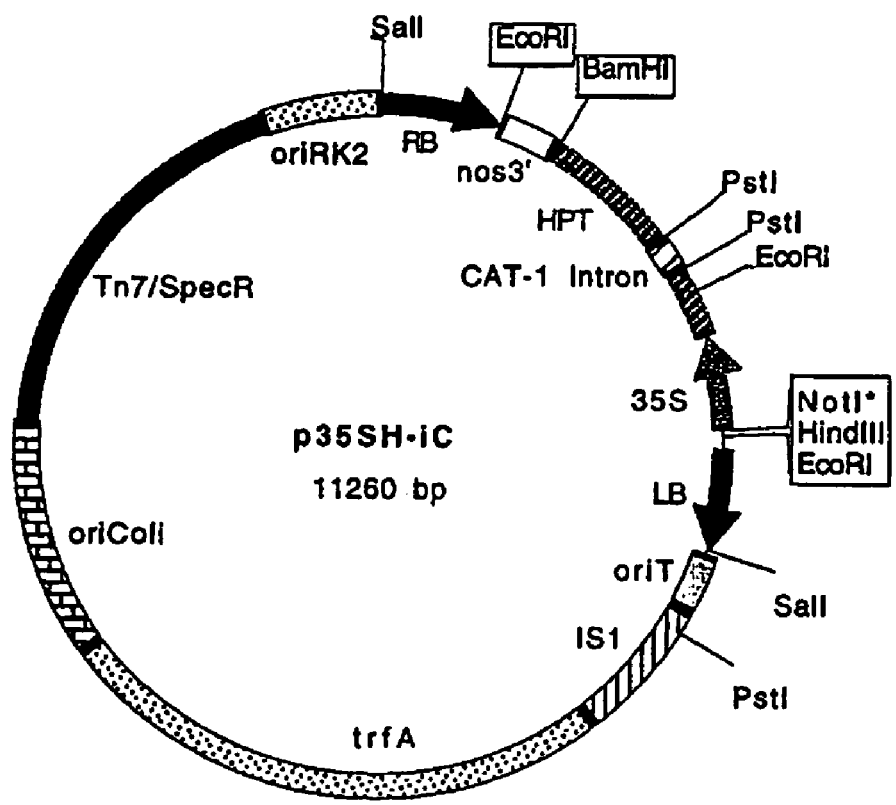
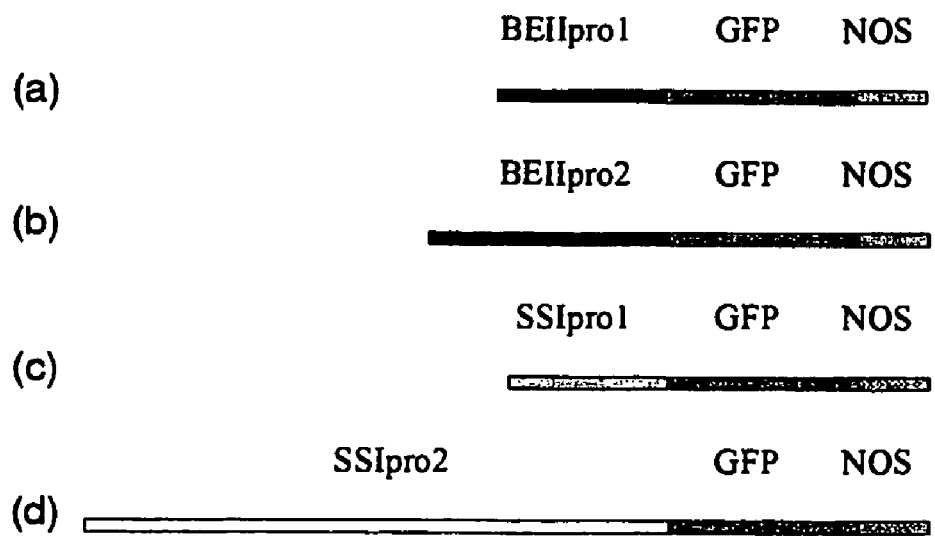
FIGURE 23

| Primer Set | Key | Forward Primer | Forward Primer Sequence |
|---|---|---|---|
| 1 | E01'/E02 | WBE2E1F | CGT CGC TGC TCC TCA GGA AG |
| 2 | E01/E02 | sr854.1180F | CTG GCT GAC TCA ATC ACT ACG |
| 3 | E02/E03 | WBE2E2F | CGC AAC CTG AAG AAT TAC AG |
| 4 | E03/E04 | WBE2E3F | ATT TTC GGA GCC ATC TTG AC |
| 5 | E04/E05 | WBE2E4F | TCG TGG TTA TGA AAA GCT TGG |
| 6 | E05/E06 | sr913F | ATC ACT TAC CGA GAA TGG G |
| 7 | E05/I05 | sr913F | ATC ACT TAC CGA GAA TGG G |
| 8 | E06/E07 | WBE2E6F | ACA ATT GGA ATC CAA ATG CA |
| 9 | E07/E08 | WBE2E7F | AGC TAT TCC TCA TGG CTC AC |
| 10 | E08/E09 | WBE2E8F | TGC AGG CTC CAG GTG AAA TA |
| 11 | E10/E11 | da5.seq | GGC TTG GAT ACA ATG CAG TGC |
| 12 | E12/E13 | da151.seq | TTG ACG GCT TGA ATG GTT TC |
| 13 | E17/E18 | WBE2E17F | TTT AGG TGG TGA AGG CTA TCT |
| 14 | E18/E19 | sr860R | AAT GGA TAG ATT TTC AAG AGG G |
| 15 | E19_3' | WBE2-2395F | AGC AGA ACT GCG GTC GTG TA |

| Reverse Primer | Reverse Primer Sequence | Temp | bp |
|---|---|---|---|
| WBE2E2R | CAG GAC CTT CCC TGG AGA GG | 57.4 | 401 |
| WSBE9E2R | GGC ACG AGT GTG TGT ACC TGT A | 57.7 | 601 |
| sr866F | TAT CTT CAG GTA TCT ACA GC | 49.8 | 309 |
| WBE2E4R2 | ATG CTT CCA ATC CAC CTT CA | - | >450 |
| WBE2E5R | GAG CCC ATT CTC GGT AAG TGA | 50.5 | 234 |
| WBE2E6R | CTG CAT TTG GAT TCC AAT TG | 49.9 | 232 |
| WBE2I5R | CAG TAA GCT AGT TGG TGA ATA | 46.6 | 106 |
| WBE2E7R | GGG AGG AAA ATC TCC CAA AC | 51.0 | 402 |
| sr915F | CCA TTG AAA GGT ATT TCA CC | 51.1 | 203 |
| sr912F | TAA CTT ATT GAC ATA CCG G | 48.4 | 439 |
| WBE2E11R | CTG GAG TTC CAA AAC GGC TAC | 51.2 | 289 |
| WBE2E13R | ATT CTT CAA GCC ACC ATC TC | 51.6 | 244 |
| WBE2E18R | TAT TGT TAT TTC CAG GGG AGA | 50.2 | 258 |
| da23.seq | TGC TGC ATT GCC TGA TCG AA | 50.4 | ~295 |
| WBE2-2634R | AAC ACC CAG GCC CGT CCA TT | 57.2 | 240 |

Figure 24

REGULATION OF GENE EXPRESSION IN PLANTS

This application is a Divisional of U.S. application Ser. No. 09/508,377, now U.S. Pat. No. 6,916,976, filed Jun. 9, 2000, which is the U.S. National Phase of PCT/AU98/00743 filed Sep. 11, 1998.

This invention relates to methods of modulating the expression of desired genes in plants, and to DNA sequences and genetic constructs for use in these methods. In particular, the invention relates to methods and constructs for targeting of expression specifically to the endosperm of the seeds of cereal plants such as wheat, and for modulating the time of expression in the target tissue. This is achieved by the use of promoter sequences from enzymes of the starch biosynthetic pathway. In a preferred embodiment of the invention, the sequences and/or promoters are those of starch branching enzyme I, starch branching enzyme II, soluble starch synthase I, and starch debranching enzyme, all derived from *Triticum tauschii*, the D genome donor of hexaploid bread wheat.

A further preferred embodiment relates to a method of identifying variations in the characteristics of plants.

BACKGROUND OF THE INVENTION

Starch is an important constituent of cereal grains and of flours, accounting for about 65-67% of the weight of the grain at maturity. It is produced in the amyloplast of the grain endosperm by the concerted action of a number of enzymes, including ADP-Glucose pyrophosphorylase (EC 2.7.7.27), starch synthases (EC 2.4.1.21), branching enzymes (EC 2.4.1.18) and debranching enzymes (EC 3.2.1.41 and EC 3.2.1.68) (Ball et al, 1996; Martin and Smith, 1995; Morell et al, 1995). Some of the proteins involved in the synthesis of starch can be recovered from the starch granule (Denyer et al, 1995; Rahman et al, 1995).

Most wheat cultivars normally produce starch containing 25% amylose and 75% amylopectin. Amylose is composed of large linear chains of α (1-4) linked α-D-glucopyranosyl residues, whereas amylopectin is a branching form of α-glycan linked by α (1-6) linkages. The ratio of amylose and amylopectin, the branch chain length and the number of branch chains of amylopectin are the major factors which determine the properties of wheat starch.

Starch with various properties has been widely used in industry, food science and medical science. High amylose wheat can be used for plastic substitutes and in paper manufacture to protect the environment; in health foods to reduce bowel cancer and heart disease; and in sports foods to improve the athletes, performance. High amylopectin wheat may be suitable for Japanese noodles, and is used as a thickener in the food industry.

Wheat contains three sets of chromosomes (A, B and D) in its very large genome of about $10^{10}$ base pairs (bp). The donor of the D genome to wheat is *Triticum tauschii*, and by using a suitable accession of this species the genes from the D genome can be studied separately (Lagudah et al, 1991).

There is comparatively little variation in starch structure found in wheat varieties, because the hexaploid nature of wheat prevents mutations from being readily identified. Dramatic alterations in starch structure are expected to require the combination of homozygous recessive alleles from each of the 3 wheat genomes, A, B and D. This requirement renders the probability of finding such mutants in natural or mutagenised populations of wheat very low. Variation in wheat starch is desirable in order to enable better tailoring of wheat starches for processing and end-user requirements.

Key commercial targets for the manipulation of starch biosynthesis are:
1. "Waxy" wheats in which amylose content is decreased to insignificant levels. This outcome is expected to be obtained by eliminating granule-bound starch synthase activity.
2. High amylose wheats, expected to be obtained by suppressing starch branching enzyme-II activity.
3. Wheats which continue to synthesise starch at elevated temperatures, expected to be obtained by identifying or introducing a gene encoding a heat-stable soluble starch synthase.
4. "Sugary types" of wheat which contain increased amylose content and free sugars, expected to be obtained by manipulating an isoamylase-type debranching enzyme.

There are two general strategies which may be used to obtain wheats with altered starch structure:
(a) using genetic engineering strategies to suppress the activity of a specific gene, or to introduce a novel gene into a wheat line; and
(b) selecting among existing variation in wheat for missing ("null") or altered alleles of a gene in each of the genomes of wheat, and combining these by plant breeding.

However, in view of the complexity of the gene families, particularly starch branching enzyme I (SBE I), without the ability to target regions which are unique to genes expressed in endosperm, modification of wheat by combination of null alleles of several enzymes in general represents an almost impossible task.

Branching enzymes are involved in the production of glucose α-1,6 branches. Of the two main constituents of starch, amylose is essentially linear, but amylopectin is highly branched; thus branching enzymes are thought to be directly involved in the synthesis of amylopectin but not amylose. There are two types of branching enzymes in plants starch branching enzyme I (SBE I) and starch branching enzyme II (SBE II), and both are about 85 kDa in size. At the nucleic acid level there is about 65% sequence identity between types I and II in the central portion of the molecules; the sequence identity between SBE I from different cereals is about 85% overall (Burton et al, 1995; Morell et al, 1995).

In cereals, SBE I genes have so far been reported only for rice (Kawasaki et al, 1991; Rahman et al, 1997). A cDNA sequence for wheat SBE I is available on the GenBank database (Accession No. Y12320; Repellin A., Nair R. B., Baga M., and Chibbar R. N.: Plant Gene Register PGR97-094, 1997). As far as we are aware, no promoter sequence for wheat SBE I has been reported.

We have characterised an SBE I gene, designated wSBE I-D2, from *Triticum tauschii*, the donor of the D genome to wheat (Rahman et al, 1997). This gene encoded a protein sequence which had a deletion of approximately 65 amino acids at the C-terminal end, and appeared not to contain some of the conserved amino acid motifs characteristic of this class of enzyme (Svensson, 1994). Although wSBE I-D2 was expressed as mRNA, no corresponding protein has yet been found in our analysis of SBE I isoforms from the endosperm, and thus it is possible that this gene is a transcribed pseudogene.

Genes for SBE II are less well characterised; no genomic sequences are available, although SBE II cDNAs from rice (Mizuno et al, 1993; Accession No. D16201) and maize (Fisher et al, 1993; Accession No. L08065) have been reported. In addition, a cDNA sequence for SBE II from wheat is available on the GenBank database (Nair et al, 1997; Accession No. Y11282); although the sequences are very similar to those reported herein, there are differences near the N-terminal of the protein, which specifies its intracellular location. No promoter sequences have been reported, as far as we are aware.

Wheat granule-bound starch synthase (GBSS) is responsible for amylose synthesis, while wheat branching enzymes together with soluble starch synthases are considered to be directly involved in amylopectin biosynthesis. A number of isoforms of soluble and granule-bound starch synthases have been identified in developing wheat endosperm (Denyer et al, 1995). There are three distinct isoforms of starch synthases, 60 kDa, 75-77 kDa and 100-105 kDa, which exist in the starch granules (Denyer et al, 1995; Rahman et al, 1995). The 60 kDa GBSS is the product of the wx gene. The 75-77 kDa protein is a wheat soluble starch synthase I (SSSI) which is present in both the soluble fraction and the starch granule-bound fraction of the endosperm. However, the 100-105 kDa proteins, which are another type of soluble starch synthase, are located only in starch granules (Denyer et al, 1995; Rahman et al, 1995). To our knowledge there has been no report of any complete wheat SSS I sequence, either at the protein or the nucleotide level.

Both cDNA and genomic DNA encoding a soluble starch synthase I of rice have been cloned and analysed (Baba et al, 1993; Tanaka et al, 1995). The cDNAs encoding potato soluble starch synthase SSSII and SSSIII and pea soluble starch synthase SSSII have also been reported (Edwards et al, 1995; Marshall et al, 1996; Dry et al, 1992). However, corresponding full length cDNA sequences for wheat have hitherto not been available, although a partial cDNA sequence (Accession No. U48227) has been released to the GenBank database.

Approach (b) referred to above has been demonstrated for the gene for granule-bound starch synthase. Null alleles on chromosomes 7A, 7D and 4A were identified by the analysis of GBSS protein bands by electrophoresis, and combined by plant breeding to produce a wheat line containing no GBSS, and no amylose (Nakamura et al, 1995). Subsequently, PCR-based DNA markers have been identified, which also identify null alleles for the GBSS loci on each of the three wheat genomes. Despite the availability of a considerable amount of information in the prior art, major problems remain. Firstly, the presence of three separate sets of chromosomes in wheat makes genetic analysis in this species extraordinarily complex. This is further complicated by the fact that a number of enzymes are involved in starch synthesis, and each of these enzymes is itself present in a number of forms, and in a number of locations within the plant cell. Little, if any, information has been available as to which specific form of each enzyme is expressed in endosperm. For wheat, a limited amount of nucleic acid sequence information is available, but this is only cDNA sequence; no genomic sequence, and consequently no information regarding promoters and other control sequences, is available. Without being able to demonstrate that the endosperm-specific gene within a family has been isolated, such sequence information is of limited practical usefulness.

SUMMARY OF THE INTENTION

In this application we report the isolation and identification of novel genes from *T. tauschii*, the D-genome donor of wheat, that encode SBE I, SBE II, a 75 kDa SSS I, and an isoamylase-type debranching enzyme (DBE). Because of the very close relationship between *T. tauschii* and wheat, as discussed above, results obtained with *T. tauschii* can be directly applied to wheat with little if any modification. Such modification as may be required represents routine trial and error experimentation. Sequences from these genes can be used as probes to identify null or altered alleles in wheat, which can then be used in plant breeding programmes to provide modifications of starch characteristics. The novel sequences of the invention can be used in genetic engineering strategies or to introduce a desired gene into a host plant, to provide antisense sequences for suppression of one or more specific genes in a host plant, in order to modify the characteristics of starch produced by the plant.

By using *T. tauschii*, we have been able to examine a single genome, rather than three as in wheat, and to identify and isolate the forms of the starch synthesis genes which are expressed in endosperm. By addressing genomic sequences we have been able to isolate tissue-specific promoters for the relevant genes, which provides a mechanism for simultaneous manipulation of a number of genes in the endosperm. Because *T. tauschii* is so closely related to wheat, results obtained with this model system are directly applicable to wheat, and we have confirmed this experimentally. The genomic sequences which we have determined can also be used as probes for the identification and isolation of corresponding sequences, including promoter sequences, from other cereal plant species.

In its most general aspect, the invention provides a nucleic acid sequence encoding an enzyme of the starch biosynthetic pathway in a cereal plant, said enzyme being selected from the group consisting of starch branching enzyme I, starch branching enzyme II, starch soluble synthase I, and debranching enzyme, with the proviso that the enzyme is not soluble starch synthase I of rice, or starch branching enzyme I of rice or maize.

Preferably the nucleic acid sequence is a DNA sequence, and may be genomic DNA or cDNA. Preferably the sequence is one which is functional in wheat. More preferably the sequence is derived from a *Triticum* species, most preferably *Triticum tauschii*.

Where the sequence encodes soluble starch synthase, preferably the sequence encodes the 75 kD soluble starch synthase of wheat.

Biologically-active untranslated control sequences of genomic DNA are also within the scope of the invention. Thus the invention also provides the promoter of an enzyme as defined above.

In a preferred embodiment of this aspect of the invention, there is provided a nucleic acid construct comprising a nucleic acid sequence of the invention, a biologically-active fragment thereof, or a fragment thereof encoding a biologically-active fragment of an enzyme as defined above, operably linked to one or more nucleic acid sequences facilitating expression of said enzyme in a plant, preferably a cereal plant. The construct may be a plasmid or a vector, preferably one suitable for use in the transformation of a plant. A particularly suitable vector is a bacterium of the genus *Agrobacterium*, preferably *Agrobacterium tumefaciens*. Methods of transforming cereal plants using *Agrobacterium tumefaciens* are known; see for example Australian Patent No. 667939 by Japan Tobacco Inc., International Patent Application Number PCT/US97/10621 by Monsanto Company and Tingay et al (1997).

In a second aspect, the invention provides a nucleic acid construct for targeting of a desired gene to endosperm of a cereal plant, and/or for modulating the time of expression of a desired gene in endosperm of a cereal plant, comprising one or more promoter sequences selected from SBE I promoter, SBE II promoter, SSS I promoter, and DBE promoter, operatively linked to a nucleic acid sequence encoding a desired protein, and optionally also operatively linked to one or more additional targeting sequences and/or one or more 3' untranslated sequences.

The nucleic acid encoding the desired protein may be in either the sense orientation or in the antisense orientation. Preferably the desired protein is an enzyme of the starch biosynthetic pathway. For example, the antisense sequences of GBSS, starch debranching enzyme, SBE II, low molecular weight glutenin, or grain softness protein I, may be used. Preferred sequences for use in sense orientation include those of bacterial isoamylase, bacterial glycogen synthase, or wheat high molecular weight glutenin Bx17. It is contemplated that any desired protein which is encoded by a gene which is capable of being expressed in the endosperm of a cereal plant is suitable for use in the invention.

In a third aspect, the invention provides a method of modifying the characteristics of starch produced by a plant, comprising the step of:
  (a) introducing a gene encoding a desired enzyme of the starch biosynthetic pathway into a host plant, and/or
  (b) introducing an anti-sense nucleic acid sequence directed to a gene encoding an enzyme of the starch biosynthetic pathway into a host plant,
  wherein said enzymes are as defined above.

Where both steps (a) and (b) are used, the enzymes in the two steps are different.

Preferably the plant is a cereal plant, more preferably wheat or barley.

As is well known in the art, anti-sense sequences can be used to suppress expression of the protein to which the antisense sequence is complementary. It will be evident to the person skilled in the art that different combinations of sense and anti-sense sequences may be chosen so as to effect a variety of different modifications of the characteristics of the starch produced by the plant.

In a fourth aspect, the invention provides a method of targeting expression of a desired gene to the endosperm of a cereal plant, comprising the step of transforming the plant with a construct according to the invention.

According to a fifth aspect, the invention provides a method of modulating the time of expression of a desired gene in endosperm of a cereal plant, comprising the step of transforming the plant with a construct according to the second aspect of the invention.

Where expression at an early stage following anthesis is desired, the construct preferably comprises the SBE II, SSS I or DBE promoters. Where expression at a later stage following anthesis is desired, the construct preferably comprises the SBE I promoter.

While the invention is described in detail in relation to wheat, it will be clearly understood that it is also applicable to other cereal plants of the family Gramineae, such as maize, barley and rice.

Methods for transformation of monocotyledonous plants such as wheat, maize, barley and rice and for regeneration of plants from protoplasts or immature plant embryos are well known in the art. See for example Lazzeri et al, 1991; Jahne et al, 1991 and Wan and Lemaux, 1994 for barley; Wirtzens et al, 1997; Tingay et al, 1997; Canadian Patent Application No. 2092588 by Nehra; Australian Patent Application No. 61781/94 by National Research Council of Canada, Australian Patent No. 667939 by Japan Tobacco Co, and International Patent Application Number PCT/US97/10621 by Monsanto Company.

The sequences of ADP glucose pyrophosphorylase from barley (Australian Patent Application No. 65392/94), starch debranching enzyme and its promoter from rice (Japanese Patent Publication No. Kokai 6261787 and Japanese Patent Publication No. Kokai 5317057), and starch debranching enzyme from spinach and potato (Australian Patent Application No. 44333/96) are all known.

DETAILED DESCRIPTION OF THE DRAWINGS

The invention will be described in detail by reference only to the following non-limiting examples and to the figures.

FIG. 1 shows the hybridisation of genomic clones isolated from *T. tauschii*.

DNA was extracted from the different clones, digested with BamHI and hybridised with the 5' end of the maize SBE I cDNA. Lanes 1, 2, 3 and 4 correspond to DNA from clones λE1, λE2, λE6 and λE7 respectively. Note that clones λE1 and λE2 give identical patterns, the SBE I gene in λE6 is a truncated form of that in λE1, and λE7 gives a clearly different pattern.

FIG. 2 shows the hybridisation of DNA from *T. tauschii*.

DNA from *T. tauschii* was digested with BamHI and the hybridisation pattern compared with DNA from λE1 and λE7 digested with the same enzyme. Fragment E1.1 (see FIG. 3) from λE1 was used as the probe; it contains some sequences that are over 80% identical to sequences in E7.8. Approximately 25 μg of *T. tauschii* DNA was electrophoresed in lane 1, and 200 pg each of λE1 and λE7 in lanes 2 and 3, respectively.

FIG. 3 shows the restriction maps of clone λE1 and λE7. The fragments obtained with EcoRI and BamHI are indicated. The fragments sequenced from λE1 are E1.1, E1.2, a part of E1.7 and a part of E1.5.

FIG. 4 shows the comparison of deduced amino acid sequence of wSBE I-D4 cDNA with the deduced amino acid sequence of rice SBE I (SEQ ID NO: 67) (RSBE I; Nakamura et al, 1992), maize SBE I (SEQ ID NO: 68) (MSBE I; Baba et al, 1991), wSBE I-D2 type cDNA (SEQ ID NO: 71) (D2 cDNA; Rabman et al, 1997), pea SBE II (SEQ ID NO: 69) (PESBE II, homologous to maize SBE I; Burton et al, 1995), and potato SBE I (SEQ ID NO: 70) (POSBE; Cangiano et al, 1993). The deduced amino acid sequence of the wSBE I-D4 cDNA is denoted by "D4cDNA" (SEQ ID NO: 6). Residues present in at least three of the sequences are identified in the consensus sequence in capitals.

FIG. 5 shows the intron-exon structure of wSBE I-D4 compared to the corresponding structures of rice SBE I (Kawasaki et al, 1993) and wSBE I-D2 (Rahman et al, 1997). The intron-exon structure of wSBE I-D4 is deduced by comparison with the SBE I cDNA reported by Repellin et al (1997).

The dark rectangles correspond to exons and the light rectangles correspond to introns. The bars above the structures indicate the percentage identity in sequence between the indicated exons and introns of the relevant genes. Note that intron 2 shares no significant sequence identity and is not indicated.

FIG. 6 shows the nucleotide sequence of part of wSBE I-D4 (SEQ ID NO: 74), the amino acid sequence deduced from this nucleotide sequence (SEQ ID NOS 35, 103, 75 and 36, respectively, in order of appearance), and the N-terminal amino acid sequence of the SBE I (SEQ ID NO: 76) purified from the wheat endosperm (Morell et al, 1997).

FIG. 7 shows the hybridisation of SBE I genomic clones with the following probes.
  A. wSBE I-D45 (derived from the 5' end of the gene and including sequence from fragments E1.1 and E1.7), and B. wSBE I-D43 (derived from the 3' end of the gene and containing sequences from fragment E1.5). For panel A, the tracks 1-13 correspond to clones λE1, λE2, λE6, λE7, λE9, λE14, λE22, λE27, Molecular weight markers, λE29, λE30, λE31 and λE52. For panel B, tracks 1-12 correspond to clones λE1, λE2, λE6, λE7, λE9, λE14, λE22, λE27, λE29, λE30, λE31 and λE52. Note that clones λE7 and λE22 do not hybridise to either of the probes and are wSBE I-D2 type genes. Also note that clone λE30 contains a sequence unrelated to SBE I. The size of the molecular weight markers in kb is indicated. Clones λE7 and λE22 do hybridise with a probe from E1.1. which is highly conserved between wSBE I-D2 and wSBE I-D4.

FIG. 8 shows the alignment of cDNA clones to obtain the sequence represented by wSBE I-D4 cDNA. BED4 and BED5 were obtained from screening the cDNA library with maize BEI (Baba et al, 1991). BED1, 2 and 3 were obtained by RT-PCR using defined primers.

FIG. 9a shows the expression of Soluble Starch Synthase I (SSS), Starch Branching Enzyme I (BE I) and Starch Branching Enzyme II (BE II) mRNAs during endosperm development.

RNA was purified from leaves, florets prior to anthesis, and endosperm of wheat cultivar Rosella grown in a glasshouse, collected 5 to 8 days after anthesis, 10 to 15 days after anthesis and 18 to 22 days after anthesis, and from the endosperm of wheat cultivar Rosella grown in the field and collected 12, 15 and 18 days after anthesis respectively. Equivalent amounts of RNA were electrophoresed in each lane. The probes were from the coding region of the SM2 SSS I cDNA (from nucleotide 1615 to 1919 of the SM2 cDNA sequence); wSBE I-D43C (see Table I), which corresponds to the untranslated 3' end of wSBE I-D4 cDNA (E1 (3'; and the 5' region of SBE9 (SBE9 (5'), corresponding to the region between nucleotides 743 to 1004 of Genbank sequence Y11282. No hybridisation to RNA extracted from leaves or preanthesis florets was detected.

Figure 9A:
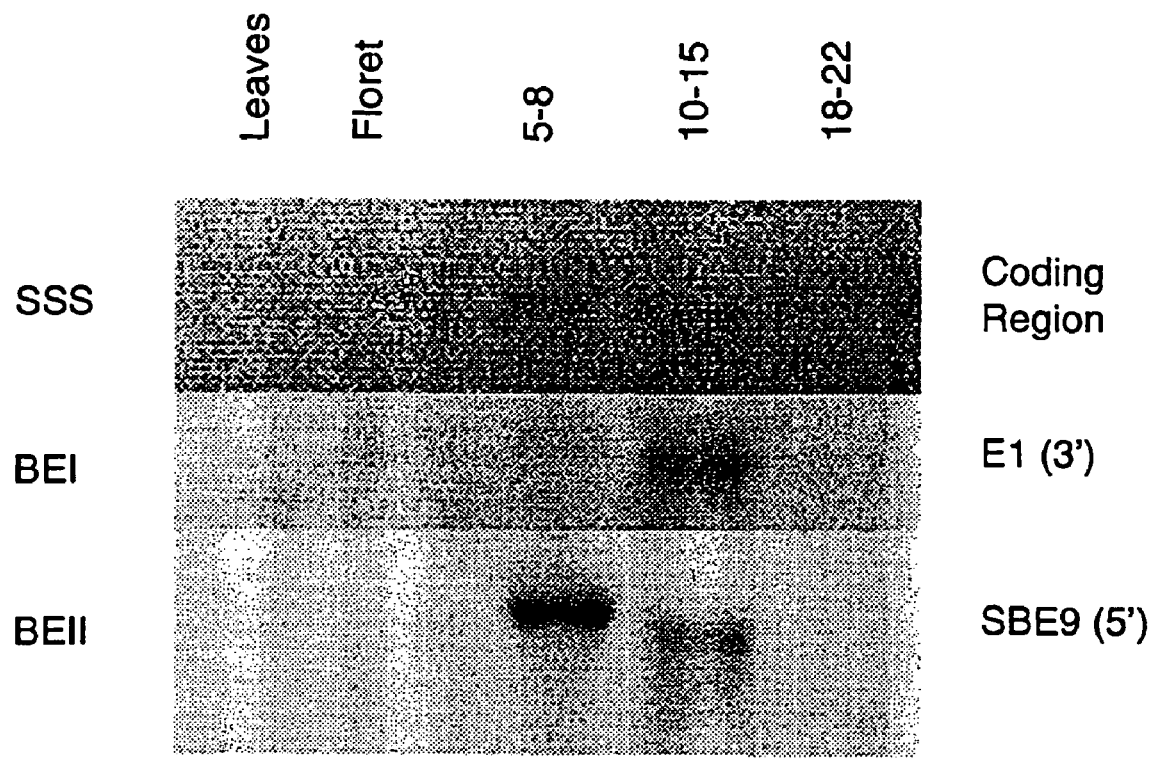
FIG. 9b shows the hybridisation of RNA from the endosperm of the hexaploid *T. aestivum* cultivar "Gabo" with the starch branching enzyme I gene. The probe, wSBEI-D43, is defined in Table 1.
FIG. 9c shows the hybridisation of RNA from the endosperm of the hexaploid *T. aestivum* cultivar "Wyuna" with the starch branching enzyme II gene. The probe, wSBE II-D13, is defined in Table 2.
FIG. 9d shows the hybridisation of RNA from the endosperm of the hexaploid *T. aestivum* cultivar "Gabo" with the SSS I gene. The probe spanned the region from nucleotides 2025 to 2497 of the SM2 cDNA sequence shown in SEQ ID No:11.
FIG. 9e shows the hybridisation of RNA from the endosperm of the hexaploid *T. aestivum* cultivar "Gabo" with the DBE I gene. The probe, a DBE3' 3'PCR fragment, extends from nucleotide position 281 to 1072 of the cDNA sequence in SEQ ID No:16.
FIG. 9f shows the hybridisation of RNA from the endosperm of the hexaploid *T. aestivum* cultivar "Gabo" with the wheat actin gene. The probe was a wheat actin DNA sequence generated by PCR from wheat endosperm cDNA using primers to conserved plant actin sequences.
FIG. 9g shows the hybridisation of RNA from the endosperm of the hexaploid *T. aestivum* cultivar "Gabo" with a probe containing wheat ribosomal RNA 26S and 18S fragments (plasmid pta250.2 from Dr Bryan Clarke, CSIRO Plant Industry).
Figure 9B:
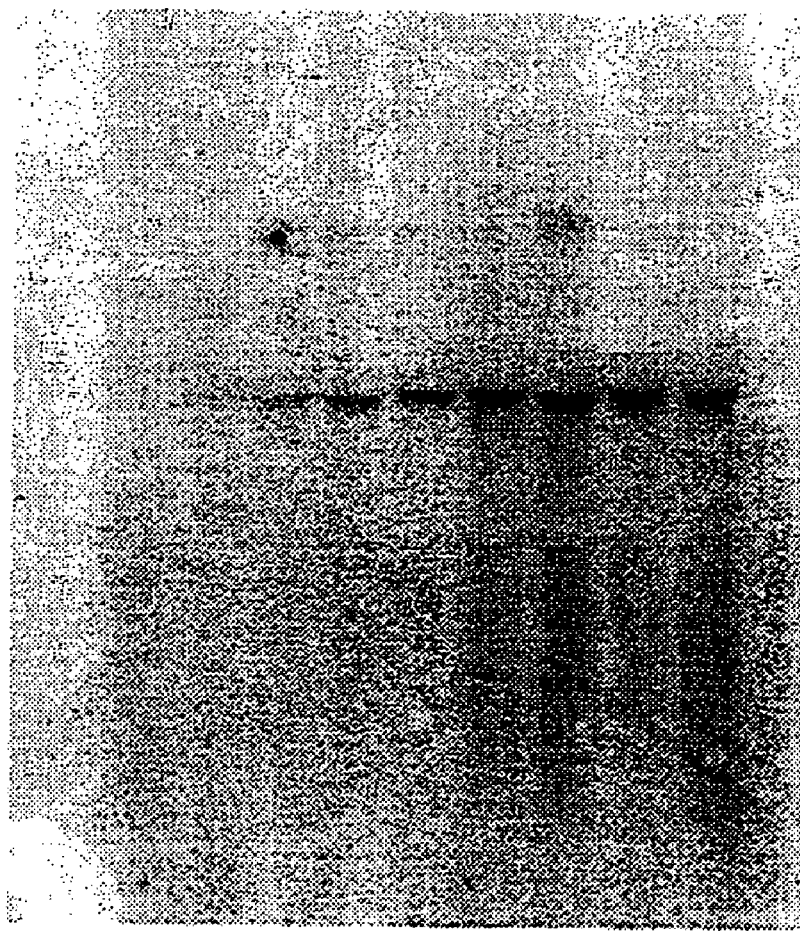
Figure 9C:
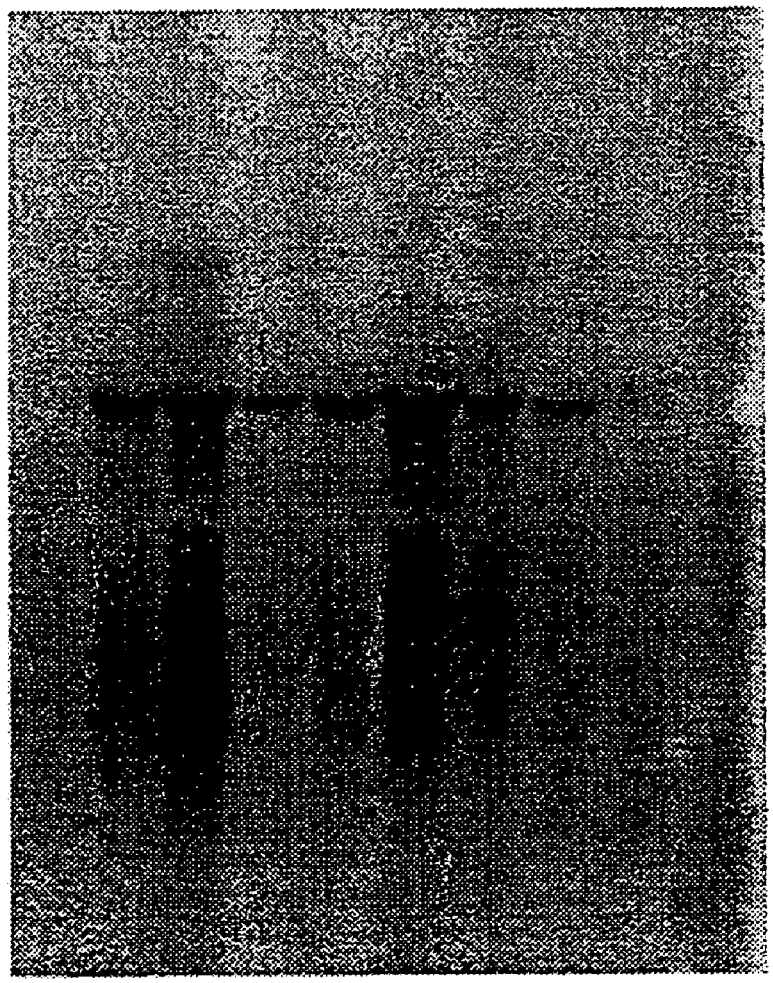
Figure 9D:
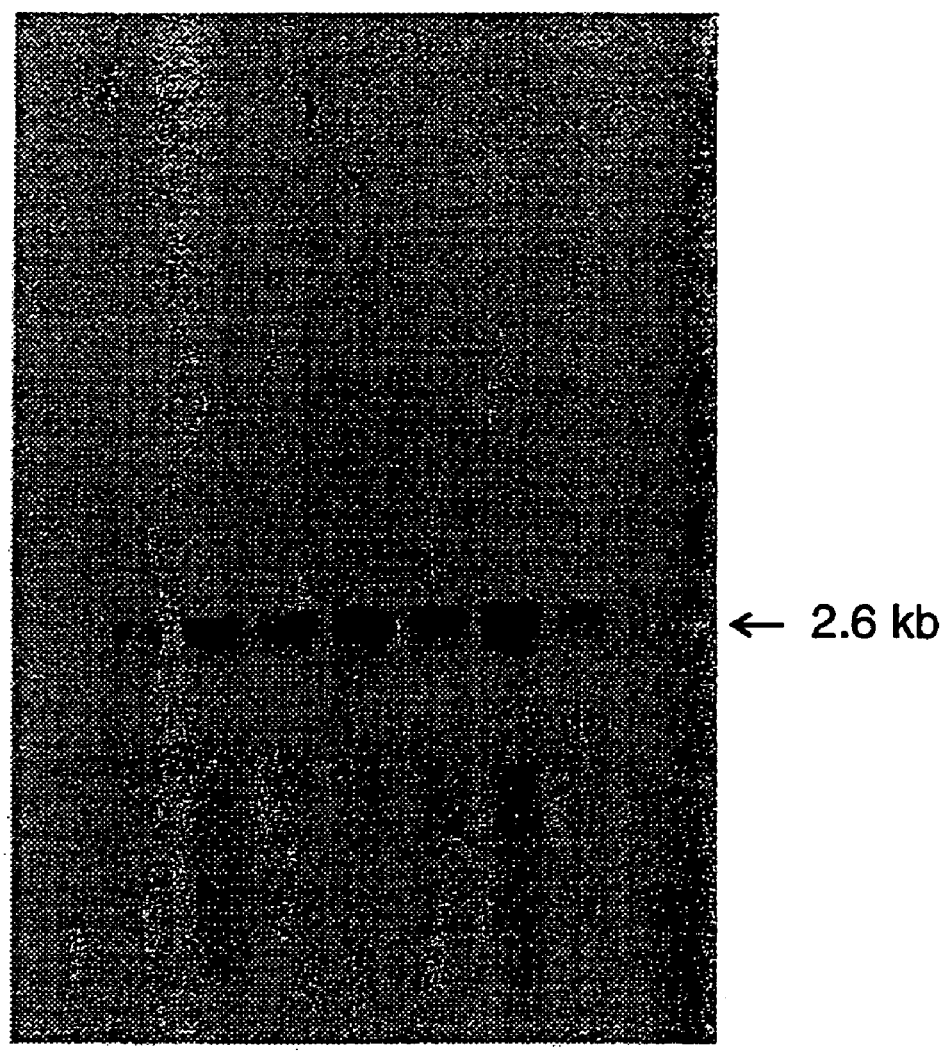
Figure 9E:
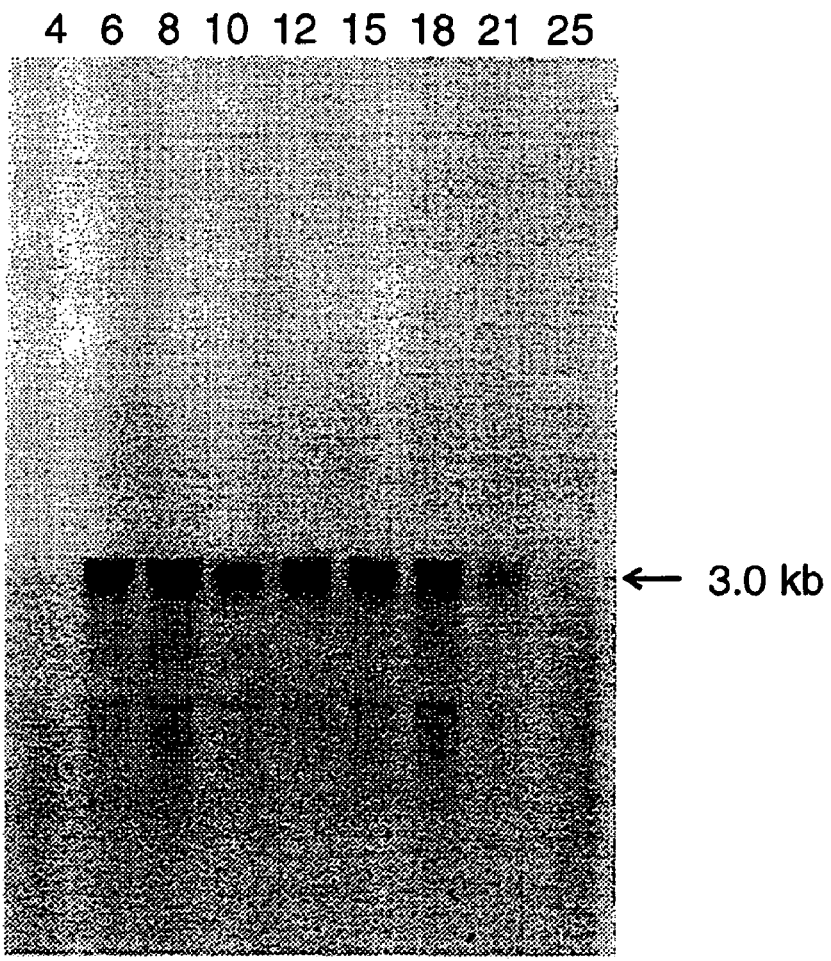
Figure 9F:
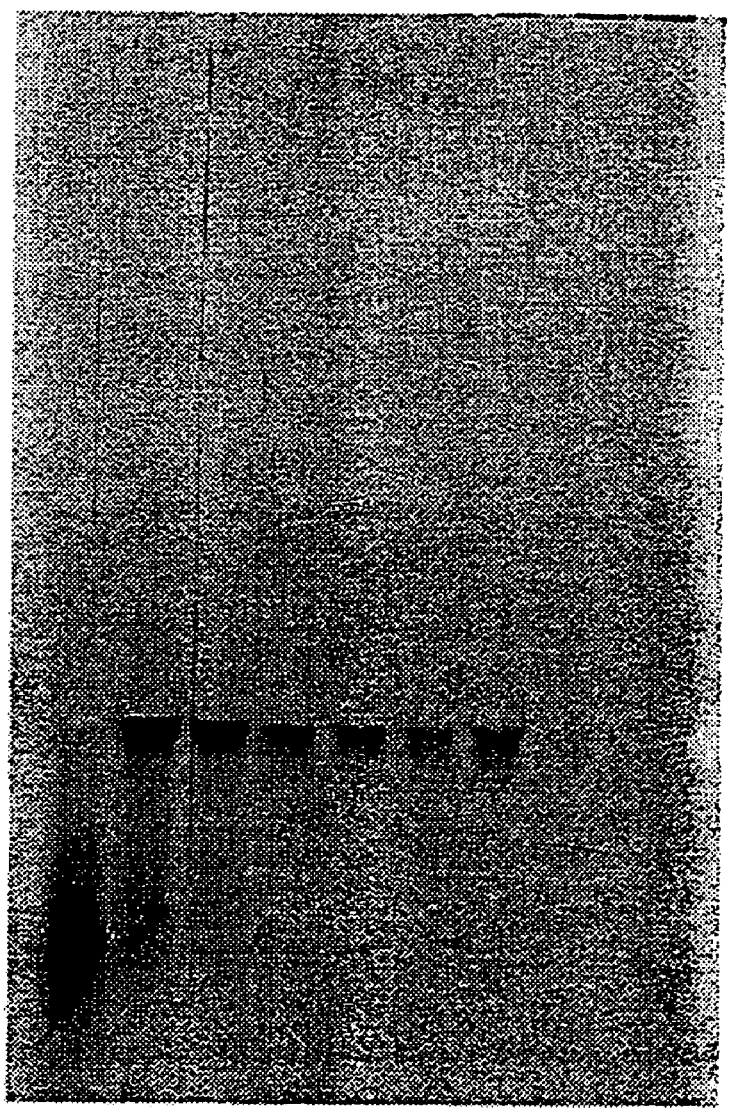
Figure 9G:
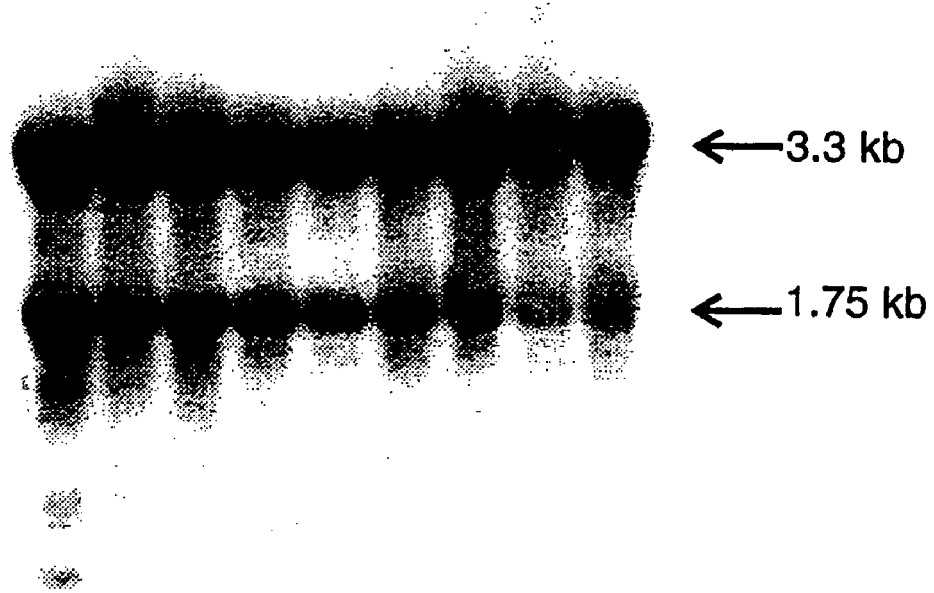
Figure 9H:
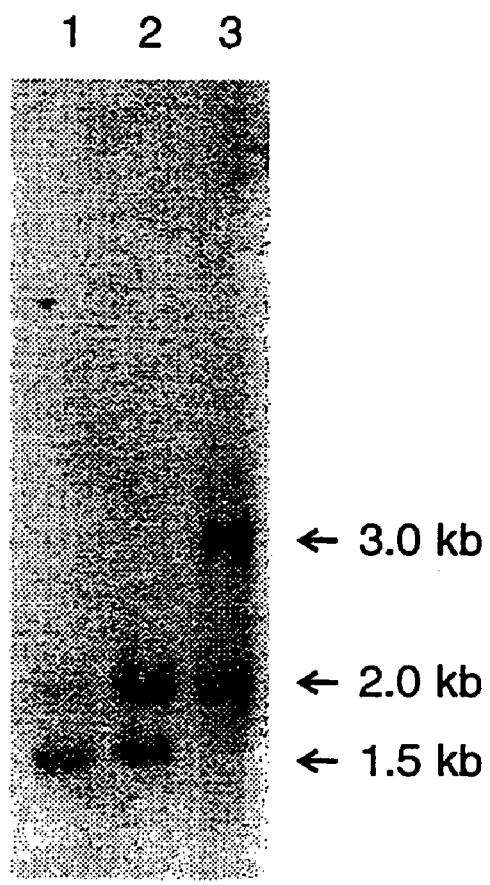

FIG. 9h shows the hybridisation of RNA from the hexaploid wheat cultivar "Gabo" with the DBE I probe described in FIG. 9e. Lane 1; leaf RNA; lane 2, pre-anthesis floret RNA; lane 3, RNA from endosperm harvested 12 days after anthesis.

Figure 10:
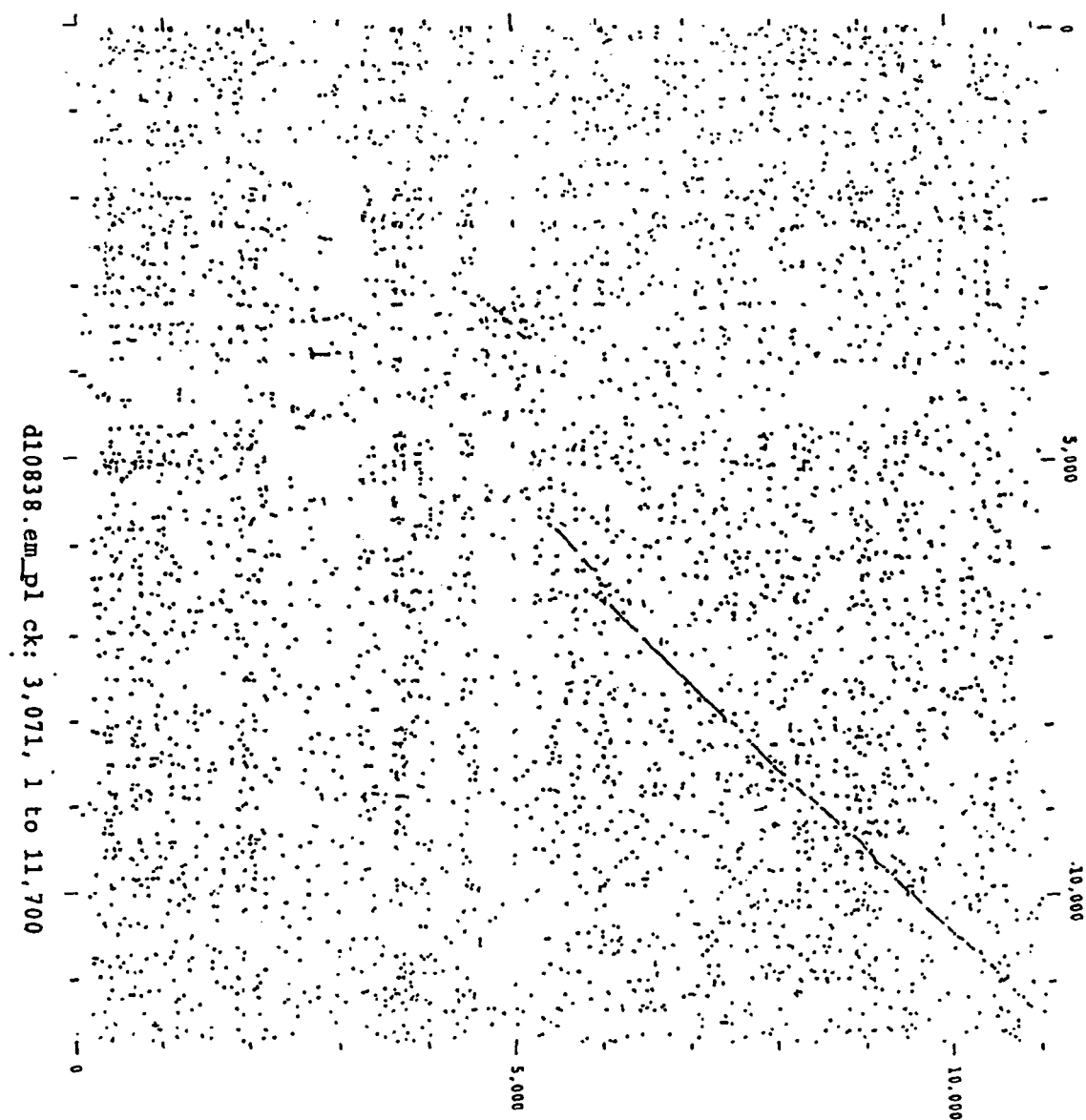

FIG. 10 shows the comparison of wSBE I-D4 (sr 427.res ck: 6,362,1 to 11,099) and rice SBE I genomic sequence (d10838.em_pl ck: 3,071,1 to 11,700)(Kawasaki et al, 1993; Accession Number D10838) using the programs Compares and DotPlot (Devereaux et al, 1984). The programs used a window of 21 bases with a stringency of 14 to register a dot.

Figure 11:
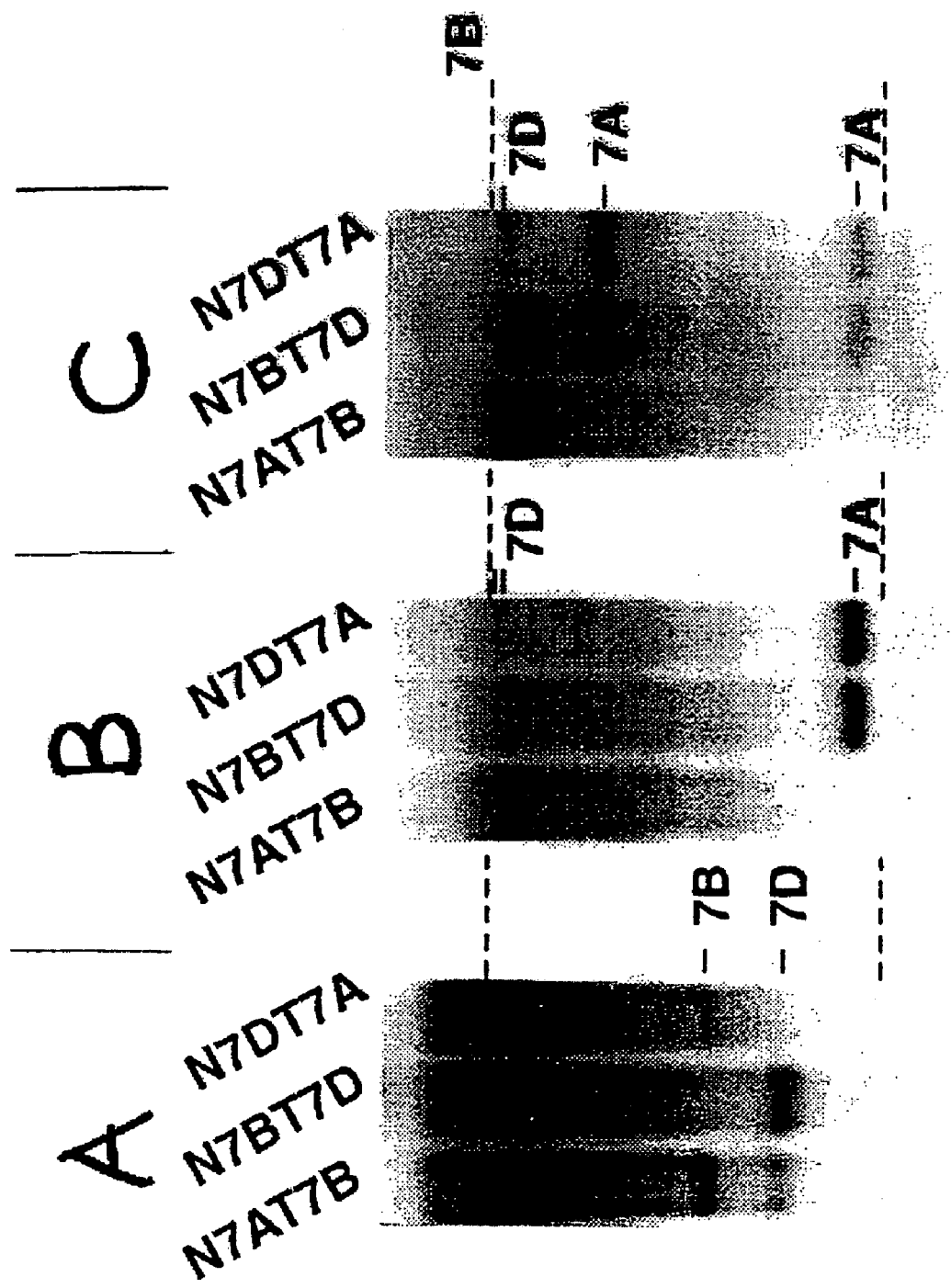

FIG. 11 shows the hybridisation of wheat DNA from chromosome-engineered lines using the following probes:
A. wSBE I-D45 (from the 5' end of the gene),
B. wSBE I-D43 (from the 3' end of the gene), and
C. wSBE I-D4R (repetitive sequence approximately 600 bp 3' to the end of wSBE I-D4 sequence.

N7AT7B, no 7A chromosome, four copies of 7B chromosome; N7BT7D, no 7B chromosome, four copies of 7D chromosome; NTDT7A, no 7D chromosome, four copies of 7A chromosome. The chromosomal origin of hybridising bands is indicated.

Figure 12:

FIG. 12 shows the hybridisation of genomic clones F1, F2, F3 and F4 with the entire SBE-9 sequence. The DNA from the clones was purified and digested with either BamHI or EcoRI, separated on agarose, blotted onto nitrocellulose and hybridised with labelled SBE-9 (a SBE II type cDNA). The pattern of hybridising bands is different in the four isolates.

FIG. 13a shows the N-terminal sequence of purified SBE II from wheat endosperm as in Morell et al, (1997). Figure discloses SEQ ID NOS 30, 76 and 31-34, respectively, in order of appearance.

FIG. 13b shows the deduced amino acid sequence from part of wSBE II-D 1 that encodes the N-terminal sequence as described in Morell et al, (1997). DNA sequence disclosed as SEQ ID NO: 63, amino acid "a" sequences disclosed as SEQ ID NOS 64 and 77-79, respectively, in order of appearance, amino acid "b" sequences disclosed as SEQ ID NOS 65 and 80-83, respectively, in order of appearance and amino acid "c" sequences disclosed as SEQ ID NOS 66 and 84-87 and 104, respectively, in order of appearance.

FIG. 14 shows the deduced exon-intron structure for a part of wSBE II-D1. The scale is marked in bases. The dark rectangles are exons.

Figure 15:
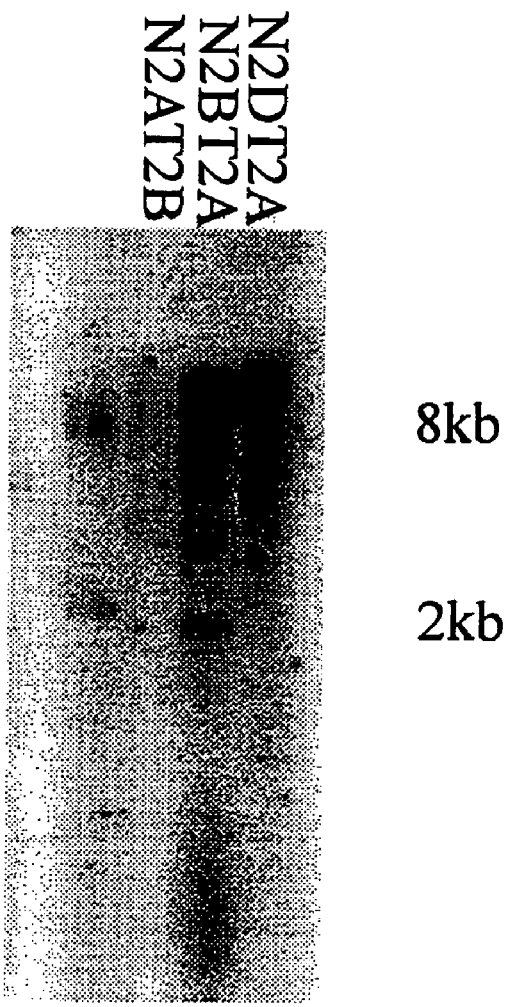

FIG. 15 shows the hybridisation of DNA from chromosome engineered lines of wheat (cultivar Chinese Spring) with a probe from nucleotides 550-850 from SBE-9.

The band of approximately 2.2 kb is missing in the line in which chromosome 2D is absent.
T2BN2A: four copies of chromosome 2B, no copies of chromosome 2A;
T2AN2B: four copies of chromosome 2A, no copies of chromosome 2B;
T2AN2D: four copies of chromosome 2A, no copies of chromosome 2D.

FIG. 16 shows the N-terminal sequence of SSS I protein isolated from starch granules (SEQ ID NO: 37) (Rabman et al, 1995) and deduced amino acid sequence of part of Sm2 (SEQ ID NO: 88).

Figure 17:
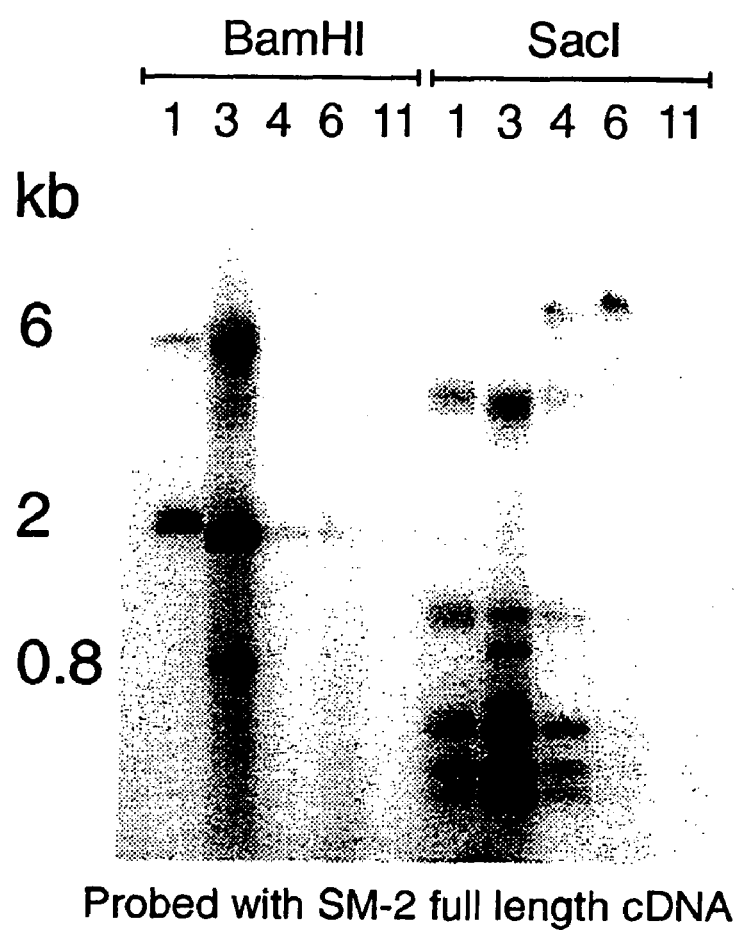

FIG. 17 shows the hybridisation of genomic clones sg1, 3, 4, 6 and 11 with the cDNA clone (sm2) for SSS I. DNA was purified from indicated genomic clones, digested with BamHI or SacI and hybridised to sm2. Note that the hybridisation patterns for sg1, 3 and 4 are clearly different from each other.

Figure 18:
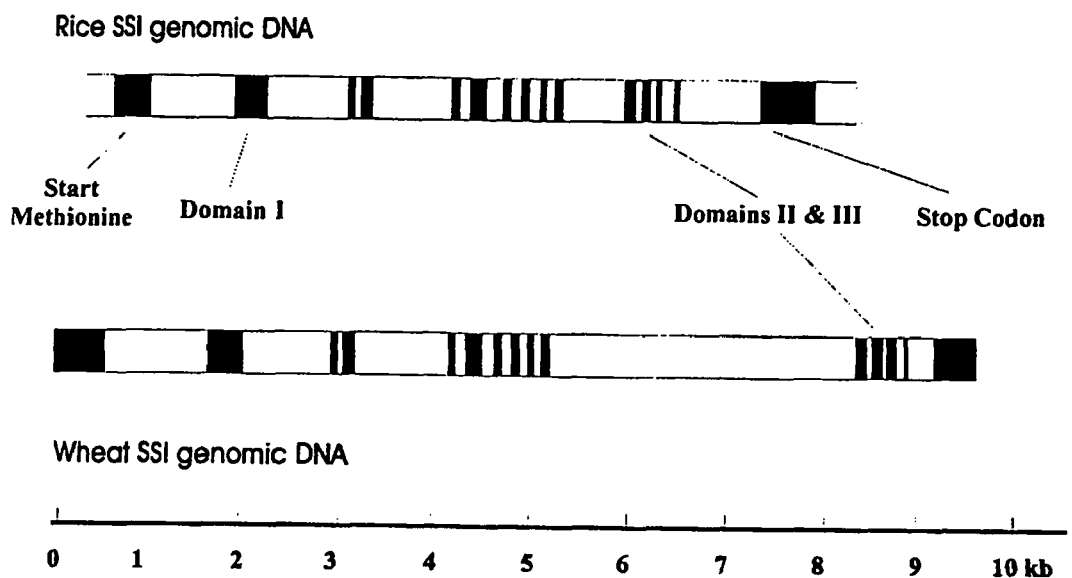

FIG. 18 shows a comparison of the intron/exon structures of the wheat and rice soluble starch synthase genomic sequences. The dark rectangles indicate exons and the light rectangles represent introns.

Figure 19:
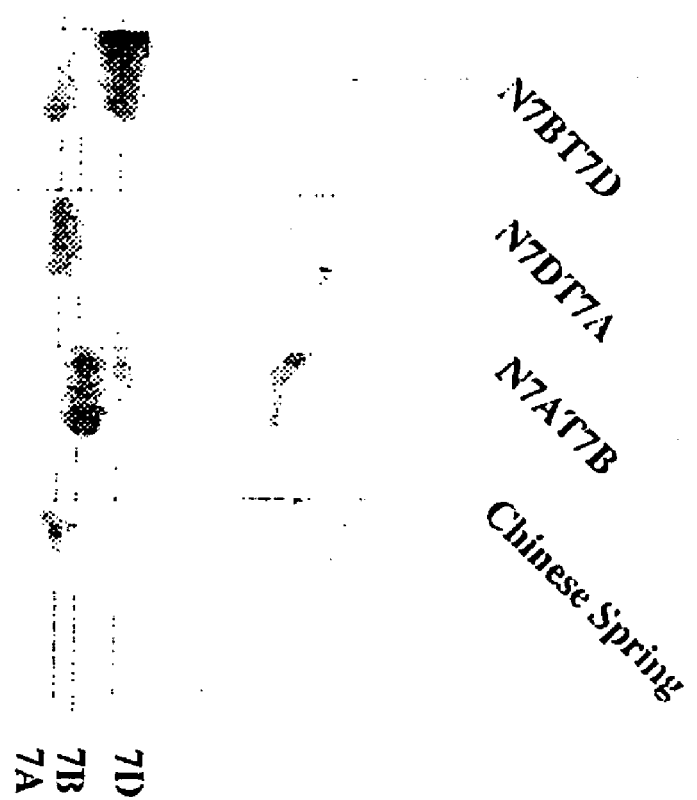

FIG. 19 shows the hybridisation of DNA from chromosome engineered lines of wheat (cultivar Chinese Spring) digested with PvuII, with the sm2 probe.

N7AT7B: no 7A chromosome, four copies of 7B chromosome;

N7BT7D: no 7B chromosome, four copies of 7D chromosome;

N7DT7A: no 7D chromosome, four copies of 7A chromosome.

A band is missing in the N7BT7A line.

FIG. 20a shows the DNA sequence (SEQ ID NO: 38) of a portion of the wheat debranching enzyme (WDBE-1) PCR product. The PCR product was generated from wheat genomic DNA (cultivar Rosella) using primers based on sequences conserved in debranching enzymes from maize and rice. Amino acid "a" sequence disclosed as SEQ ID NO: 39, amino acid "b" sequences disclosed as SEQ ID NOS 40 and 89, and amino acid "c" sequences disclosed as SEQ ID NOS 41 and 90-92.

FIG. 20b shows a comparison of the nucleotide sequence of wheat debranching enzyme I (WDBE-I) PCR fragment (SEQ ID NO: 43) (WHEAT.DNA) with the maize Sugary-1 sequence (SEQ ID NO: 42) (SUGARY.DNA).

Figure 20C:
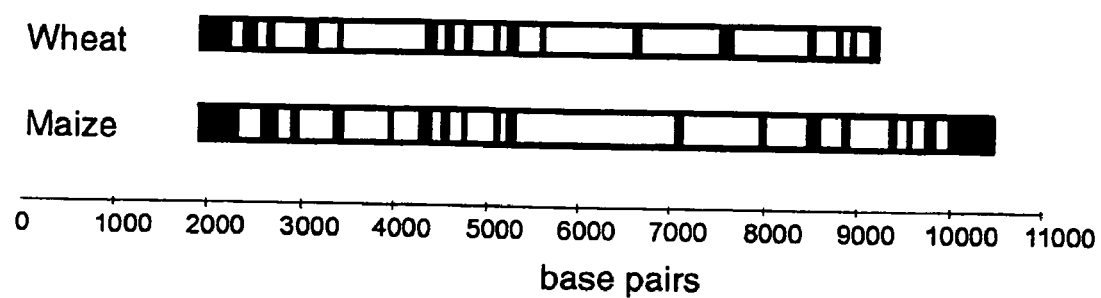

FIG. 20c shows a comparison between the intron/exon structures of wheat debranching enzyme gene and the maize sugary-1 debranching enzyme gene.

Figure 21A:
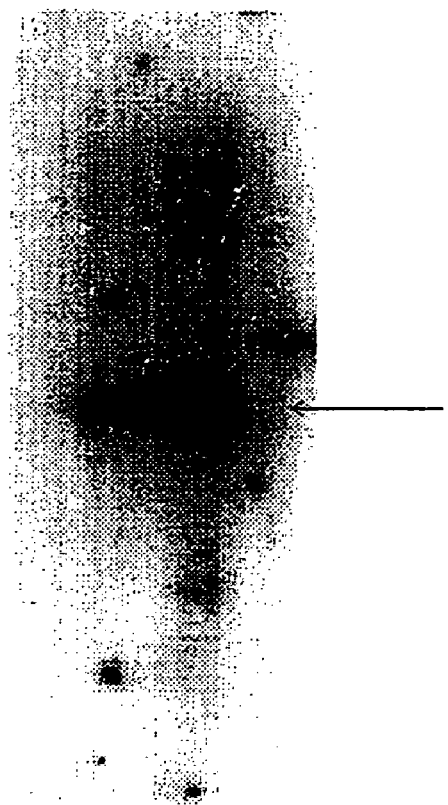

FIG. 21a shows the results of Southern blotting of *T. tauschii* DNA with wheat DBE-I PCR product. DNA from *T. tauschii* was digested with BamHI, electrophoresed, blotted and hybridised to the wheat DBE-I PCR product described in FIG. 20a. A band of approximately 2 kb hybridised.

Figure 21B:
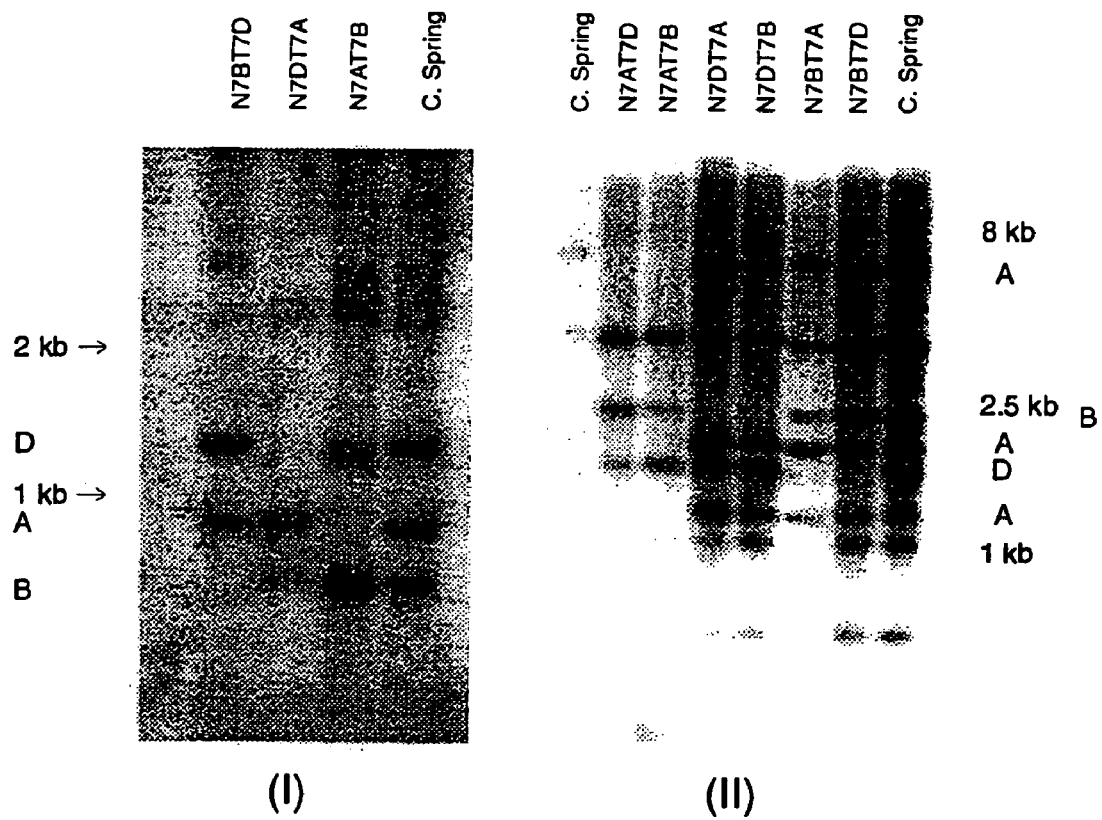

FIG. 21b shows Chinese Spring nullisomic/tetrasomic lines probed with probes from the DBE gene. Panel (I) shows hybridisation with a fragment spanning the region from nucleotide 270 to 465 of the cDNA sequence shown in SEQ ID No:16 from the central region of the DBE gene. Panel (II) shows hybridisation with a probe from the 3' region of the gene, from nucleotide 281 to 1072 of the cDNA sequence given in SEQ ID No-16.

FIGS. 22a to 22e show diagrammatic representations of the DNA vectors used for transient expression analysis. In each of the sequences the N-terminal methionine encoding ATG codon is shown in bold.

Figure 22A:
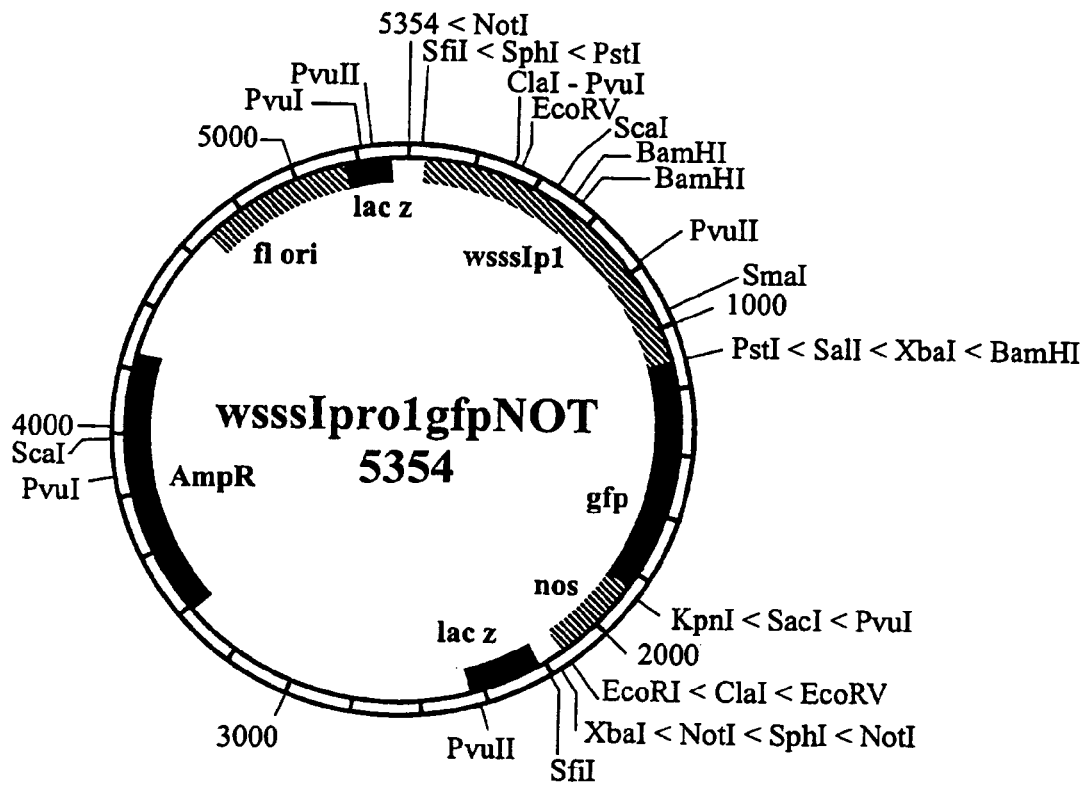

FIG. 22a shows a DNA construct pwsssIpro1gfpNOT containing a 1042 base pair region of the wheat soluble starch synthase I promoter (wSSSIpro1, from −1042 to −1, SEQ ID No:18) fused to the green fluorescent protein (GFP) reporter gene.

Figure 22B:
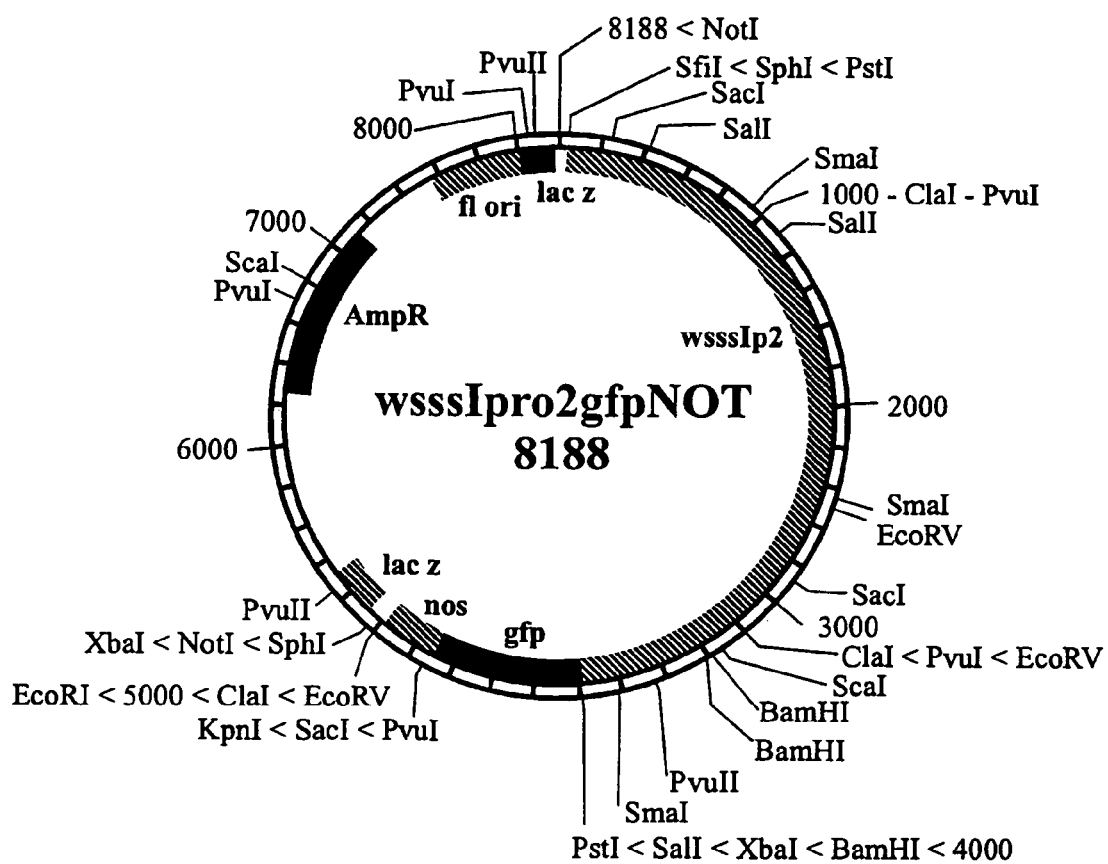

FIG. 22b shows a DNA construct pwsssIpro2gfpNOT containing a 3914 base pair region of the wheat soluble starch synthase I promoter (wSSSIpro2, from −3914 to −1, SEQ ID No:18) fused to the green fluorescent protein (GFP) reporter gene.

Figure 22C:
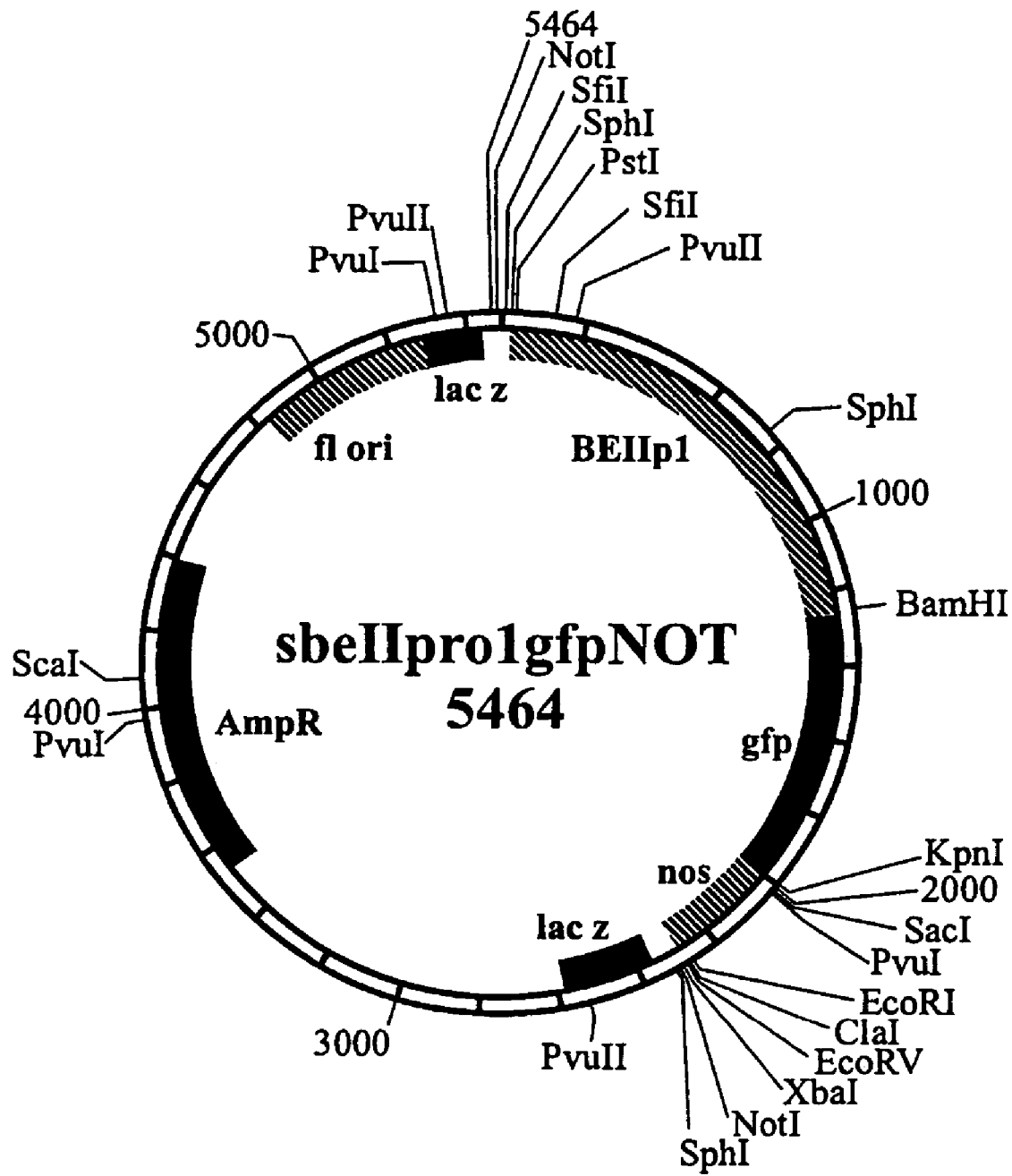

FIG. 22c shows a DNA construct psbeIIpro1gfpNOT containing an 1203 base pair region of the wheat starch branching enzyme II promoter (sbeIIpro1, from 1 to 1023 SEQ ID No:10 fused to the green fluorescent protein (GFP) reporter gene.

Figure 22D:
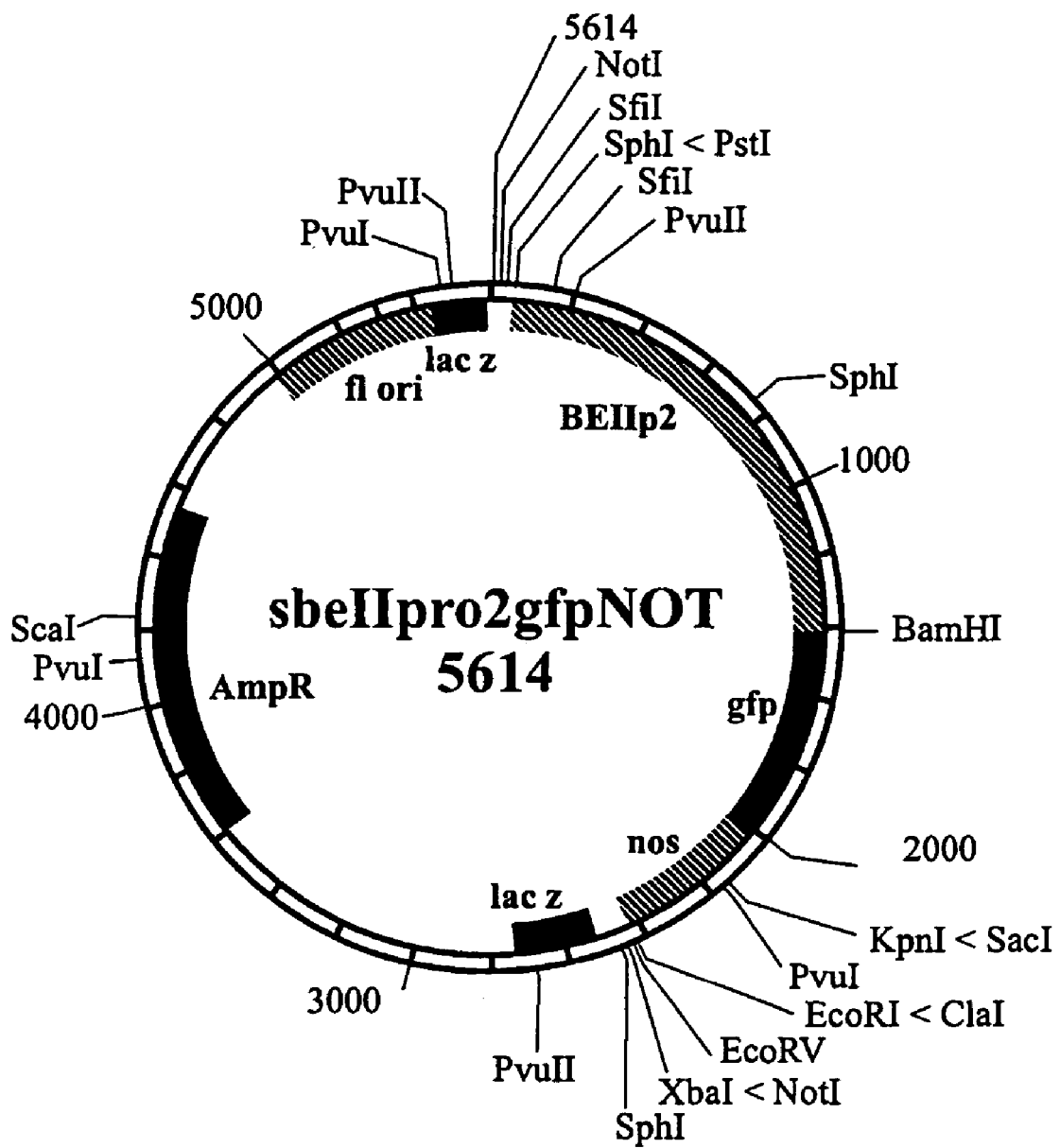

FIG. 22d shows a DNA construct psbeIIpro2gfpNOT containing a 1353 base pair region of the wheat starch branching enzyme II promoter and transit peptide coding region (sbeIIpro2, regions 1-1203, 1204 to 1336 and 1664 to 1680 of SEQ ID No:10 fused to the green fluorescent protein (GFP) reporter gene.

Figure 22E:
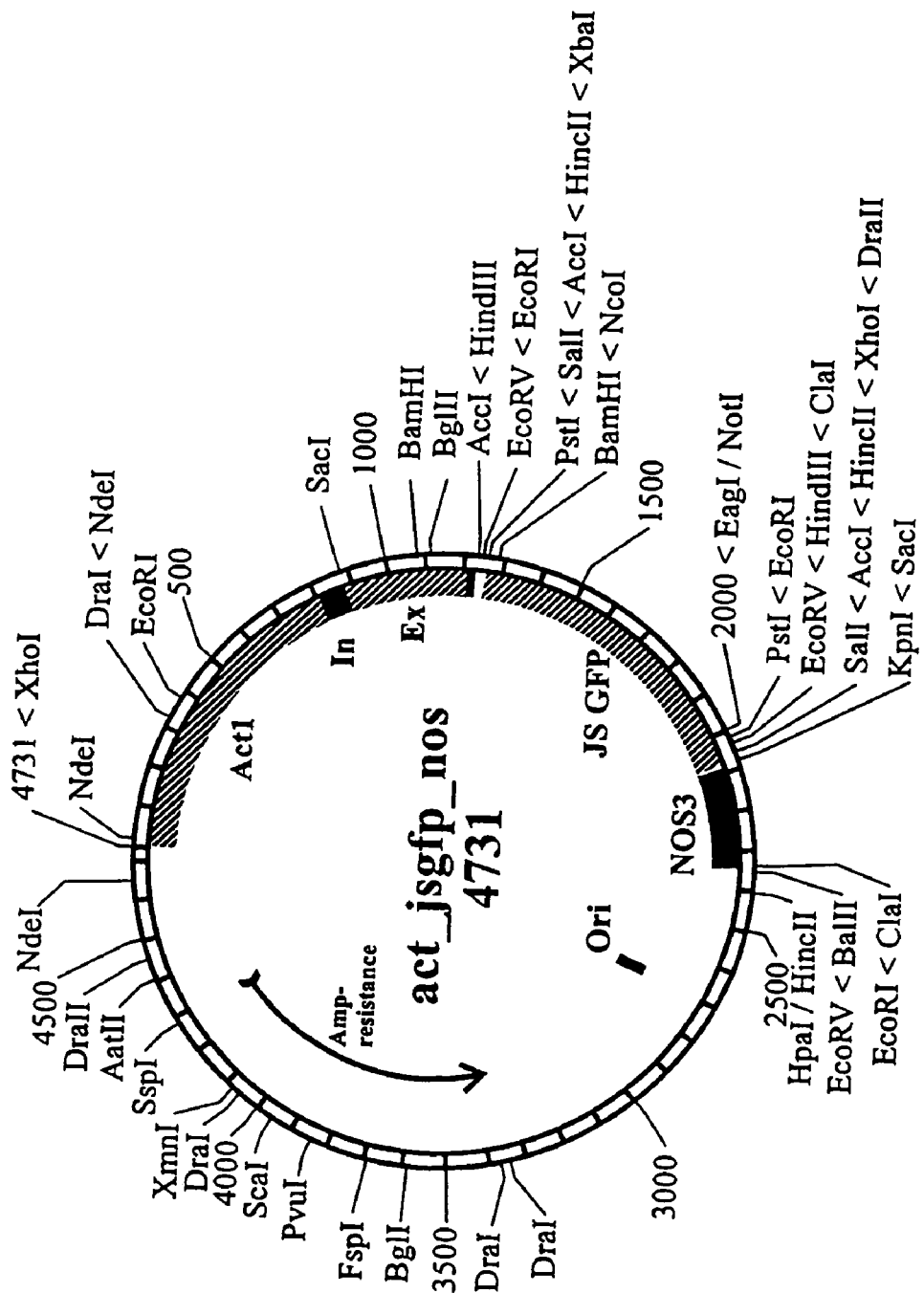

FIG. 22e shows a DNA construct pact_jsgfg_nos containing the plasmid backbone of pSP72 (Promega), the rice ActI actin promoter (McElroy et al. 1991), the GFP gene (Sheen et al. 1995) and the *Agrobacterium tumefaciens* nopaline synthase (nos) terminator (Bevan et al. 1983).

FIG. 23 shows T DNA constructs for stable transformation of rice by *Agrobacterium*. The backbone for each plasmid is p35SH-iC (Wang et al 1997). The various promoter-GFP-Nos regions inserted are shown in (a), (b), (c) and (d) respectively, and are described in detail in Example 24. Each of these constructs was inserted into the NotI site of p35SH-iC using the NotI flanking sites at each end of the promoter-GFP-Nos regions. The constructs were named (a) p35SH-iC-BEIIpro1_GFP_Nos, (b) p35SH-iC-BEIIpro2_GFP_Nos (c) p35SH-iC-SSIpro1_GFP_Nos and (d) p35SH-iC-SSIpro2GFP_Nos FIG. 24 illustrates the design of 15 intron-spanning BE II primer sets (SEQ ID NOS 93-96, 44, 97, 97, 45, 98-100, 46, 101, 47, 102 and 48-62, respectively, in order of appearance). Primers were based on wSBE II-D1 sequence (SEQ ID No: 10), and were designed such that intron sequences in the wSBE II-D1 sequence (deduced from FIG. 13b and Nair et al, 1997; Accession No. Y11282) were amplified by PCR.

Figure 25:
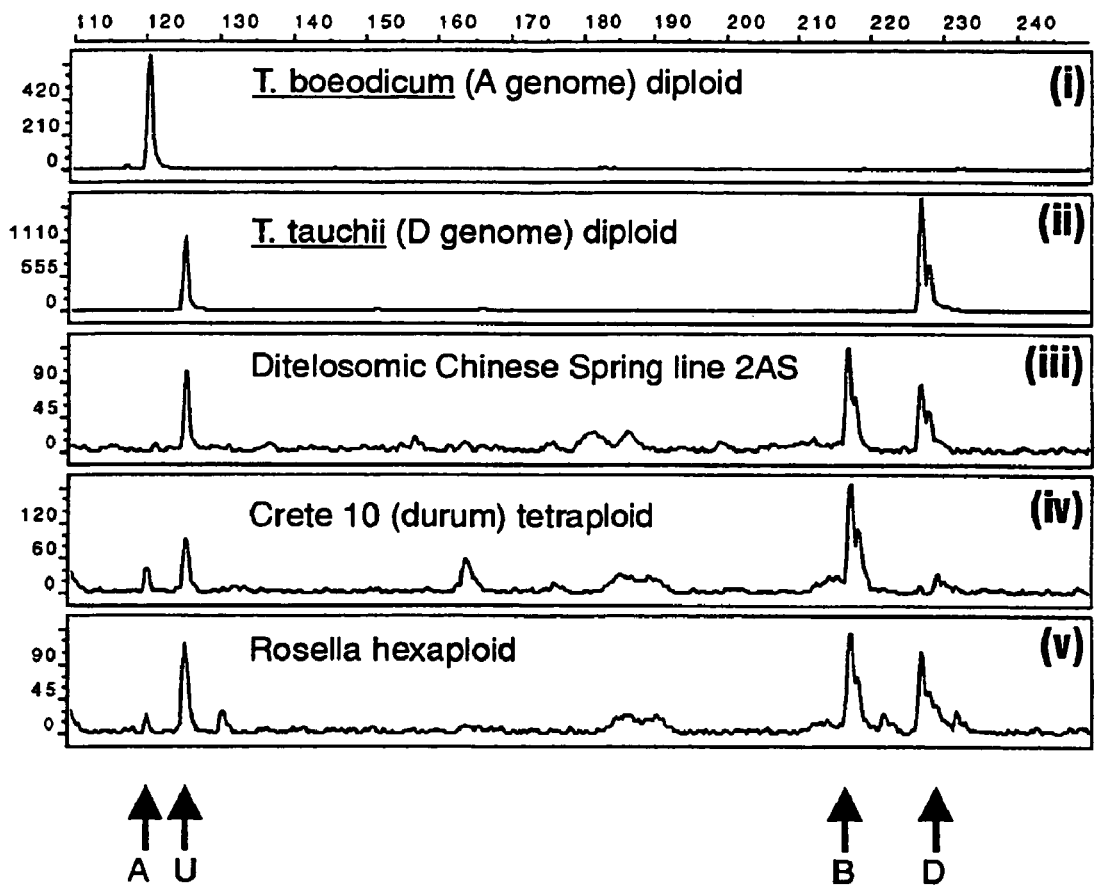

FIG. 25 shows the results of amplification using the SBE II-Intron 5 primer set (primer set 6: sr913F and WBE2E6 R) on various diploid, tetraploid and hexaploid wheats.

i) *T. boeodicum* (A genome diploid)
ii) *T. tauschii* (D genome diploid)
iii) *T. aestivum* cv. Chinese Spring ditelosomic line 2AS (lacking chromosome arm 2AL)
iv) Crete 10 (AABB tetraploid)
v) *T. aestivum* cv Rosella (hexaploid)

The horizontal axis indicates the size of the product in base pairs, the vertical axis shows arbitrary fluorescence units. The various arrows indicate the products of different genomes: A, A genome, B, B genome, D, D genome, U, unassigned additional product.

Figure 26:
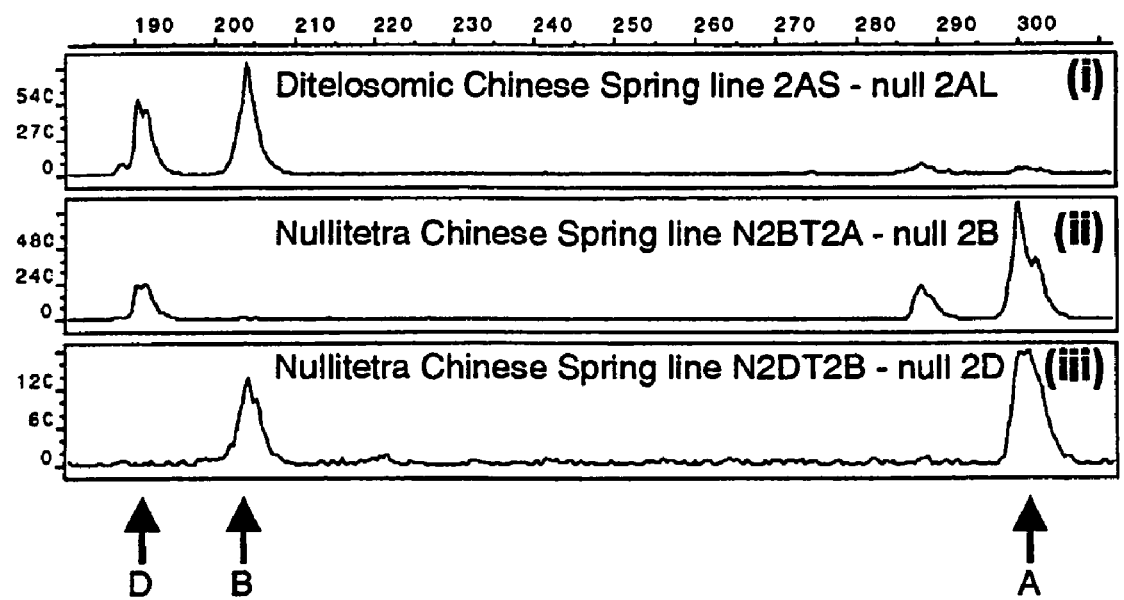

FIG. 26 shows the results obtained by amplification using the SBE II-Intron 10 primer set (primer set 11: da5.seq and WBE2E11R on the wheat lines:

(i) *T. aestivum* cv. Chinese Spring ditelosomic line 2AS.
(ii) *T. aestivum* Chinese Spring nullisomic/tetrasomic line N2BT2A.
(iii) *T. aestivum* Chinese Spring nullisomic/tetrasomic line N2DT2B.

The horizontal axis indicates the size of the product in base pairs, the vertical axis shows arbitrary fluorescence units. The various arrows indicate the products of different genomes: A, A genome, B, B genome, D, D genome.

Figure 27:
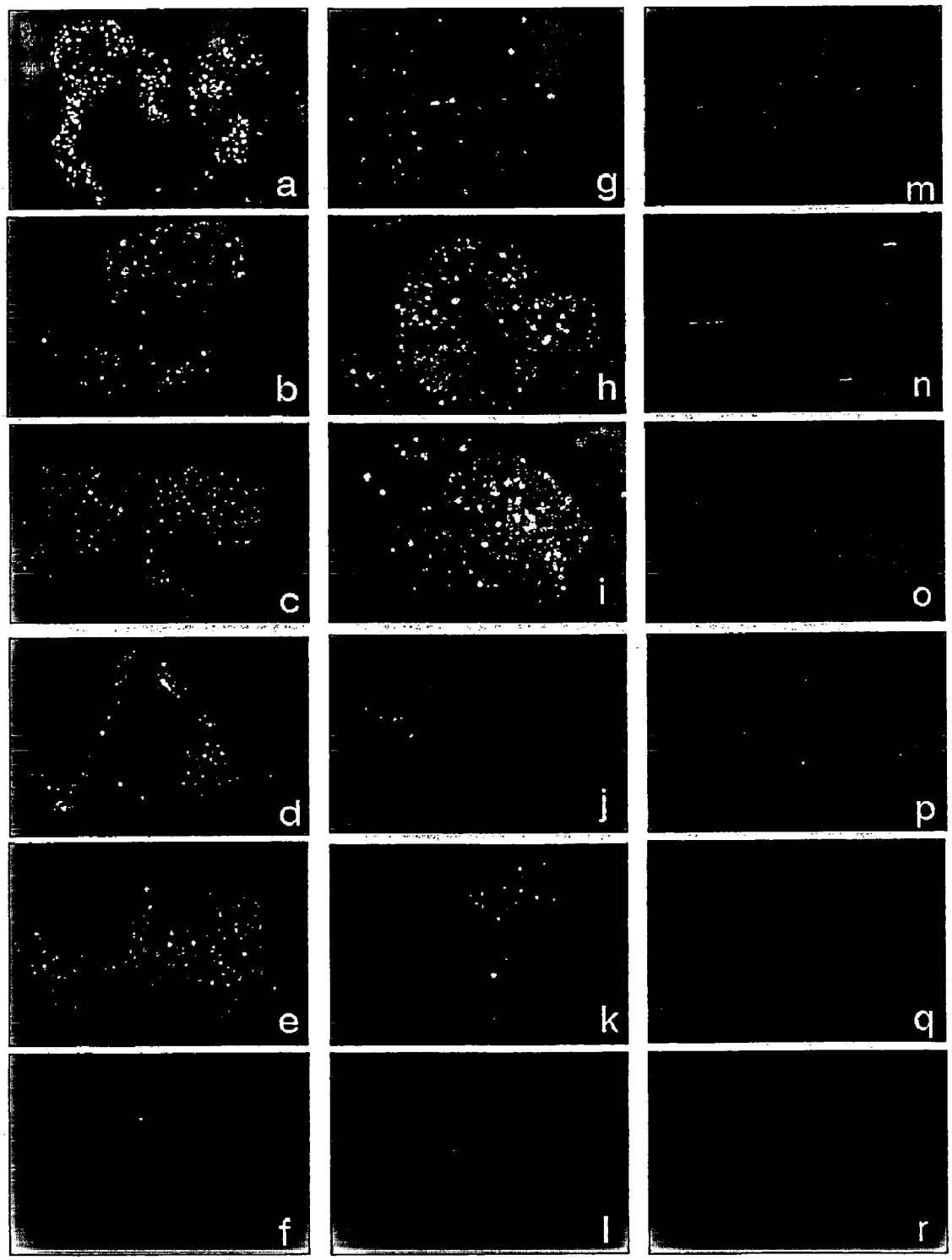

FIG. 27 shows the results of transient expression assays typical of each promoter and target tissue. The photographs (40× magnification) of representative tissue resulting from the transient expression assays typical of each promoter and target tissue revealed under a Leica microscope with blue light illumination. Photographs were taken 48 to 72 hours after tissue bombardment. The promoter constructs are listed as follows, (with the panels showing endosperm, embryo and leaf expression listed in respective order): pact_jsgfp_nos (panels a, g and m); pwsssIpro1gfpNOT (panels b, h and n); pwsssIpro2gfpNOT (panels c, i and o); psbeIIpro1gfpNOT (panels d, j and p); psbeIIpro2gfpNOT (panels e, k and q); pZLgfpNOT (Panels f, l and r).

EXAMPLE 1

Identification of Gene Encoding SBE I

Construction of Genomic Library and Isolation of Clones

The genomic library used in this study was constructed from *Triticum tauschii*, var. *strangulata*, accession number CPI 100799. Of all the accessions of *T. tauschii* surveyed, the genome of CPI 100799 is the most closely related to the D genome of hexaploid wheat.

*Triticum tauschii*, var *strangulata* (CPI accession number 110799) was kindly provided by Dr E Lagudah. Leaves were isolated from plants grown in the glasshouse.

DNA was extracted from leaves of *Triticum tauschii* using published methods (Lagudah et al, 1991), partially digested with Sau3A, size fractionated and ligated to the arms of lambda GEM 12 (Promega). The ligated products were used to transfect the methylation-tolerant strain PMC 103 (Doherty et al. 1992). A total of $2 \times 10^6$ primary plaques were obtained with an average insert size of about 15 kb. Thus the library contains approximately 6 genomes worth of *T. tauschii* DNA. The library was amplified and stored at 4° C. until required.

Positive plaques in the genomic library were selected as those hybridising with the 5' end of a maize starch branching enzyme I cDNA (Baba et al, 1991) using moderately stringent conditions as described in Rahman et al, (1997).

Preparation of Total RNA from Wheat

Total RNA was isolated from leaves, pre-anthesis pericarp and different developmental stages of wheat endosperm of the cultivar, Hartog and Rosella. This material was collected from both the glasshouse and the field. The method used for RNA isolation was essentially the same as that described by Higgins et al (1976). RNA was then quantified by UV absorption and by separation in 1.4% agarose-formaldehyde gels which were then visualized under UV light after staining with ethidium bromide (Sambrook et al, 1989).

DNA and RNA Analysis

DNA was isolated and analysed using established protocols (Sambrook et al, 1989). DNA was extracted from wheat (cv. Chinese Spring) using published methods (Lagudah et al, 1991). Southern analysis was performed essentially as described by Jolly et al (1996). Briefly, 20 μg wheat DNA was digested, electrophoresed and transferred to a nylon membrane. Hybridisation was conducted at 42° C. in 25% or 50% formamide, 2×SSC, 6% Dextran Sulphate for 16 h and the membrane was washed at 60° C. in 2×SSC for 3×1 h unless otherwise indicated. Hybridisation was detected by autoradiography using Fuji X-Omat film.

RNA analysis was performed as follows. 10 μg of total RNA was separated in a 1.4% agarose-formaldehyde gel and transferred to a nylon Hybond N+ membrane (Sambrook et al, 1989), and hybridized with cDNA probe at 42° C. in Khandjian hybridizing buffer (Khandjian, 1989). The 3' part of wheat SBE I cDNA (designated wSBE I-D43, see Table 1) was labelled with the Rapid Multiprime DNA Probe Labelling Kit (Amersham) and used as probe. After washing at 60° C. with 2×SSC, 0.1% SDS three times, each time for about 1 to 2 hours, the membrane was visualized by overnight exposure at −80° C. with X-ray film, Kodak MR.

EXAMPLE 2

Frequency of Recovery of SBE I Type Clones from the Genomic Library

An estimated $2 \times 10^6$ plaques from the amplified library were screened using an EcoRI fragment that contained 1200 bp at the 5' end of maize SBE I (Baba et al, 1991) and twelve independent isolates were recovered and purified. This corresponds to the screening of somewhat fewer than the $2 \times 10^6$ primary plaques that exist in the original library (each of which has an average insert size of 15 kb) (Maniatis et al, 1982), because the amplification may lead to the representation of some sequences more than others. Assuming that the amplified library contains approximately three genomes of *T. tauschii*, the frequency with which SBE I-positive clones were recovered suggests the existence of about 5 copies of SBE I type genes within the *T. tauschii* genome.

Figure 1:
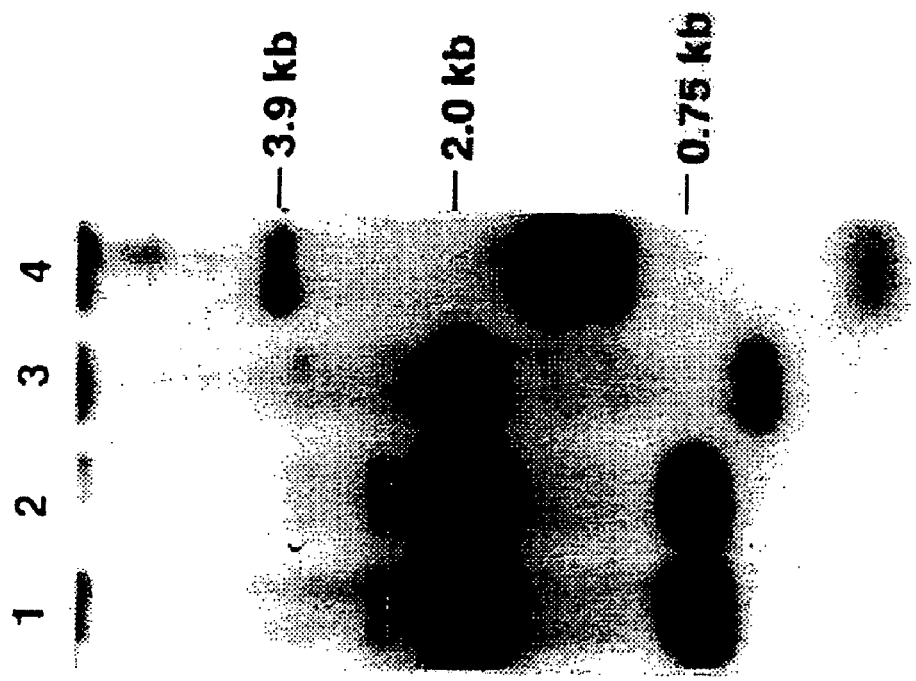

Digestion of DNA from the twelve independent isolates by the restriction endonuclease BamHI followed by hybridisation with a maize SBE I clone, suggested that the genomic clones could be separated into two broad classes (FIG. 1). One class had 10 members and a representative from this class is the clone λE1 (FIG. 1, lane 1); λE6 (FIG. 1, lane 3) is a member of this class, but is missing the 5' end of the E1-SBE I gene because the SBE I gene is at the extremity of the cloned DNA. Further hybridisation studies at high stringency with the extreme 5' and 3' regions of the SBE I gene contained in λE1 suggested that the other clones contained either identical or very closely related genes.

The second family had two members, and of these clone λE7 (FIG. 1, lane 4) was arbitrarily selected for further study. These two members did not hybridise to probes from the extreme 5' and 3' regions of the SBE I gene that were contained in λE1, indicating that they were a distinct sub-class.

Figure 2:
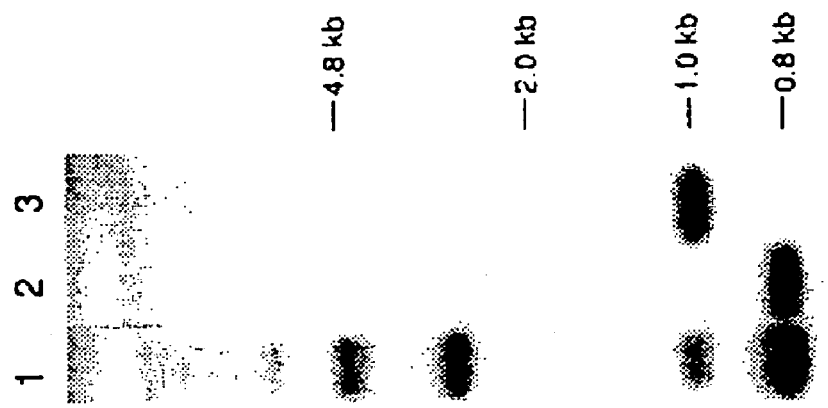

The DNA from *T. tauschii* and the lambda clones λE1 and λE7 was digested with BamHI and hybridised with fragment E1.1, as shown in FIG. 2. This fragment contains sequences that are highly conserved (85% sequence identity over 0.3 kB between λE1 and λE7), corresponding to exons 3, 4 and 5 of the rice gene. The bands in the genomic DNA at 0.8 kb and 1.0 kb correspond to identical sized fragments from λE1 and λE7, as shown in FIG. 2; these are fragments E1.1 and E7.8 of λE1 and λE7 genomic clones respectively. Thus the arrangement of genes in the genomic clones is unlikely to be an artefact of the cloning procedure. There are also bands in the genomic DNA of approximately 2.5 kb, 4.8 kb and 8 kb in size which are not found from the digestion of λE1 or λE7; these could represent genes such as the 5' sequences of wSBE I-D1 or wSBE I-D3; see below.

EXAMPLE 3

Tandem Arrangement of SBE I Type Genes in the *T. tauschii* Genome

Figure 3:
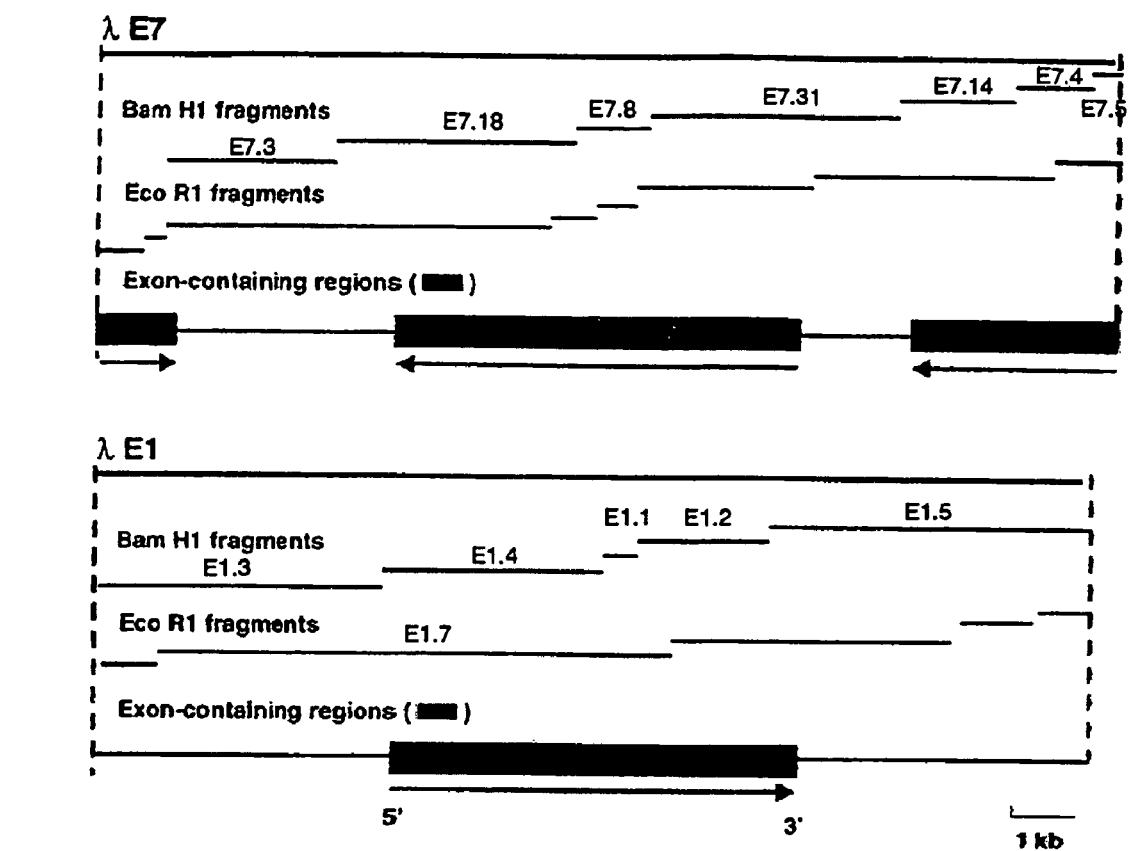

Basic restriction endonuclease maps for λE1 and λE7 are shown in FIG. 3. The map was constructed by performing a series of hybridisations of EcoRI or BamHI digested DNA from λE1 or λE7. The probes used were the fragments generated from BamHI digestion of the relevant clone. Confirmation of the maps was obtained by PCR analysis, using primers both within the insert and also from the arms of lambda itself. PCR was performed in 10 λl volume using reagents supplied by Perkin-Elmer. The primers were used at a concentration of 20 λM. The program used was 94° C., 2 min, 1 cycle, then 94° C., 30 sec; 55° C., 30 sec; 72° C., 1 min for 36 cycles and then 72° C., 5 min; 25° C., 1 min.

Sequencing was performed on an ABI sequencer using the manufacturer's recommended protocols for both dye primer and dye terminator technologies. Deletions were carried out using the Erase-a-base kit from Promega.

Sequence analysis was carried out using the GCG version 7 package of computer programs (Devereaux et al, 1984).

The PCR products were also used as hybridisation probes. The positioning of the genes was derived from sequencing the ends of the BamHI subclones and also from sequencing PCR products generated from primers based on the insert and the lambda arms. The results indicate that there is only a single copy of a SBE I type gene within λE1. However, it is clear that λE7 resulted from the cloning of a DNA fragment from within a tandem array of the SBE I type genes. Of the three genes in the clone, which are named as wSBE I-D1, wSBE I-D2 and wSBE I-D3); only the central one (wSBE I-D2) is complete.

EXAMPLE 4

Construction and Screening of cDNA Library

A wheat cDNA library was constructed from the cultivar Rosella using pooled RNA from endosperm at 8, 12, 18 and 20 days after anthesis.

The cDNA library was prepared from poly A+ RNA that was extracted from developing wheat grains (cv. Rosella, a hexaploid soft wheat cultivar) at 8, 12, 15, 18, 21 and 30 days after anthesis. The RNA was pooled and used to synthesise cDNA that was propagated in lambda ZapII (Stratagene).

The library was screened with a genomic fragment from λE7 encompassing exons 3, 4 and 5 (fragment E7.8 in FIG. 3). A number of clones were isolated. Of these an apparently full-length clone appeared to encode an unusual type of cDNA for SBE I. This cDNA has been termed SBE I-D2 type cDNA. The putative protein product is compared with the maize SBE I and rice SBE I type deduced amino acid sequences in FIG. 4. The main difference is that this putative protein product is shorter at the C-terminal end, with an estimated molecular size of approximately 74 kD compared with 85 kDa for rice SBE I (Kawasaki et al, 1993). Note that amino acids corresponding to exon 9 of rice are missing in SBE I-D2 type cDNA, but those corresponding to exon 10 are present. There are no amino acid residues corresponding to exons 11-14 of rice; furthermore, the sequence corresponding to the last 57 amino acids of SBE I-D2 type has no significant homology to the sequence of the rice gene.

We expressed SBE I-D2 type cDNA in E. coli in order to examine its function. The cDNA was expressed as a fusion protein with 22 N-terminal residues of β-galactosidase and two threonine residues followed by the SBE I-D2 cDNA sequence either in or out of frame. Although an expected product of about 75 kDa in size was produced from only the in-frame fusion, we could not detect any enzyme activity from crude extracts of E. coli protein. Furthermore the in-frame construct could not complement an E. coli strain with a defined deletion in glycogen branching, although other putative branching enzyme cDNAs have been shown to be functional by this assay (data not shown). It is therefore unclear whether the wSBE I-D2 gene in λE7 codes for an active enzyme in vivo.

EXAMPLE 5

Gene Structure in E7 i. Sequence of wSBE I-D2

Figure 5:
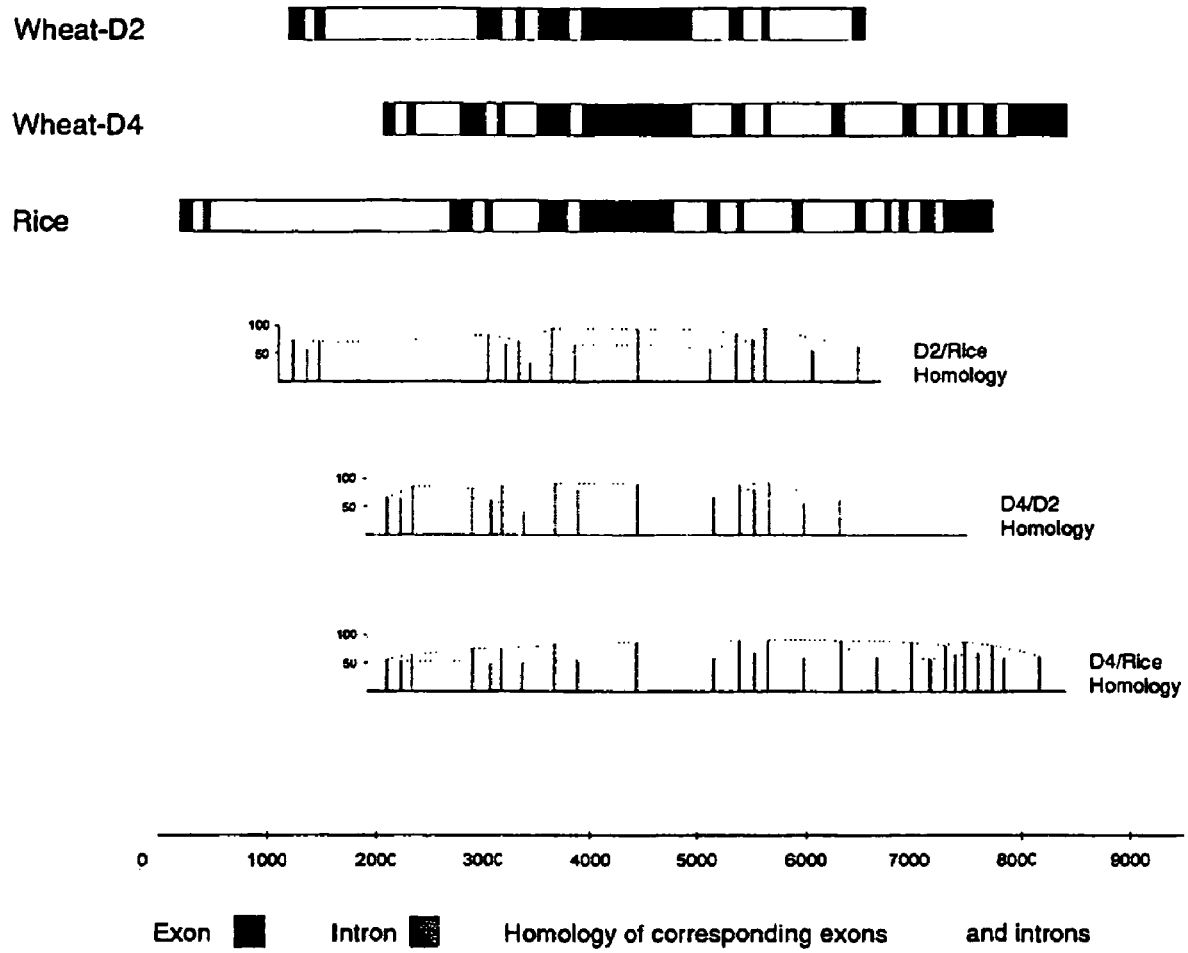

We sequenced 9.2 kb of DNA that contained wSBE I-D2. This corresponds to fragments 7.31, 7.8 and 7.18. Fragment 7.31 was sequenced in its entirety (4.1 kb), but the sequence of about 30 bases about 2 kb upstream of the start of the gene could not be obtained because it was composed entirely of Gs. Elevation of the temperature of sequencing did not overcome this problem. Fragments 7.8 (1 kb) and 7.18 (4 kb) were completely sequenced, and corresponded to 2 kb downstream of the last exon detected for this gene. It was clear that we had isolated a gene which was closely related (approximately 95% sequence identity) to the SBE I-D2 type cDNA referred to above, except that the last 200 bp at the 3' end of the cDNA are not present. The wSBE I-D2 gene includes sequences corresponding to rice exon 11 which are not in the cDNA clone. In addition it does not have exons 9, 12, 13 or 14; these are also absent from the SBE I-D2 type cDNA. The first two exons show lower identity to the corresponding exons from rice (approximately 60%) (Kawasaki et al, 1993) than to the other exons (about 80%). A diagrammatic exon-intron structure of the wSBE I-D2 gene is indicated in FIG. 5. The restriction map was confirmed by sequencing the PCR products that spanned fragments 7.18 and 7.8 and 7.8 and E7.31 (see FIG. 3) respectively.

ii. Sequence of wSBE I-D3

This gene was not sequenced in detail, as the genomic clone did not extend far enough to include the 5' end of the sequence. The sequence is of a SBE-I type. The orientation of the gene is evident from sequencing of the relevant BamHI fragments, and was confirmed by sequence analysis of a PCR product generated using primers from the right arm of lambda and a primer from the middle of the gene. The sequence homology with wSBEI-D2 is about 80% over the regions examined. The 2 kb sequenced corresponded to exons 5 and 6 of the rice gene; these sequences were obtained by sequencing the ends of fragments 7.5, 7.4 and 7.14 respectively, although the sequences from the left end of fragment 7.14 did not show any homology to the rice sequences. The gene does not appear to share the 3' end of SBE I-D2 type cDNA, as a probe from 500 bp at the 3' end of the cDNA (including sequences corresponding to exons 8 and 10 from rice) did not hybridise to fragment 7.14, although it hybridised to fragment 7.18.

iii. Sequence of wSBE I-D1

This gene was also not sequenced in detail, as it was clear that the genomic clone did not extend far enough to include the 5' sequences. Limited sequencing suggests that it is also a SBE I type gene. The orientation relative to the left arm of lambda was confirmed by sequencing a PCR product that used a primer from the left arm of lambda and one from the middle of the gene (as above). Its sequence homology with wSBE I-D2, D3 and D4 (see below) is about 75% in the region sequenced corresponding to a part of exon 4 of the rice gene.

Starch branching enzymes are members of the α-amylase protein family, and in a recent survey Svensson (1994) identified eight residues in this family that are invariant, seven in the catalytic site and a glycine in a short turn. Of the seven catalytic residues, four are changed in SBE I-D2 type. However, additional variation in the 'conserved' residues may come to light when more plant cDNAs for branching enzyme I are available for analysis. In addition, although exons 9, 11, 12, 13 and 14 from rice are not present in the SBE I-D2 type cDNA, comparison of the maize and rice SBE I sequences indicate that the 3' region (from amino acid residue 730 of maize) is much more variable than the 5' and central regions. The active sites of rice and maize SBE I sequences, as indicated by Svensson (1994), are encoded by sequences that are in the central portion of the gene. When SBE II sequences from *Arabidopsis* were compared by Fisher et al (1996) they also found variation at the 3' and 5' ends. SBE I-D2 type cDNA may encode a novel type of branching enzyme whose activity is not adequately detected in the current assays for detecting branching enzyme activity; alternatively the cDNA may correspond to an endosperm mRNA that does not produce a functional protein.

EXAMPLE 6

Cloning of the cDNA Corresponding to the wSBE I-D4 gene

The first strand cDNAs were synthesized from 1 μg of total RNA, derived from endosperm 12 days after pollination, as described by Sambrook et al (1989), and then used as templates to amplify two specific cDNA regions of wheat SBE I by PCR.

Two pairs of primers were used to obtain the cDNA clones BED1 and BED3 (Table 1). Primers used for cloning of BED3 were the degenerate primer NTS5'

5' GGC NAC NGC NGA G/AGA C/TGG 3', (SEQ ID NO. 1)

based on the N-terminal sequence of the purified wheat endosperm SBE I protein, in which the 5' end of the primer is at position 168 of wSBE I-D4 cDNA, as shown in Table 1, based on the N-terminal sequence of wheat SBE I, and the primer NTS3'.

5' TAC ATT TCC TTG TCC ATCA 3'    (SEQ ID NO. 2)

in which the 5' end is at position 1590 of wSBE I-D4 cDNA, (see Table 1), designed to anneal to the conserved regions of the nucleotide sequences of BED5 and the maize and rice SBE I cDNAs. For clone BED1, the primers used were BEC5'

5' ATC ACG AGA GCT TGC TCA    (SEQ ID NO. 3)

in which the 5' end is at position 1 of wSBE I-D4 cDNA (see Table 1); the sequence was based on the wSBE I-D4 gene, and BEC3'

5' CGG TAC ACA GTT GCG TCA TTT TC 3' (SEQ ID NO. 4)

in which the 5' end is at position 334 of wSBE I-D4 cDNA (see Table 1), and the sequence was based on BED 3.

EXAMPLE 7

Identification of the Gene from the *Triticum tauschii* SBE I Family which is Expressed in the Endosperm We have isolated two classes of SBE I genomic clones from *T. tauschii*. One class contained two genomic clone isolates, and this class has been characterised in some detail (Rahman et al, 1997). The complete gene contained within this class of clones was termed wSBE I-D2; there were additional genes at either ends of the clone, and these were designated wSBE I-D1 and wSBE I-D3. The other class contained nine genomic clone isolates. Of these λE1 was arbitrarily taken as a representative clone, and its restriction map is shown in FIG. 3; the SBE I gene contained in this clone was called wSBE I-D4.

Figure 6:
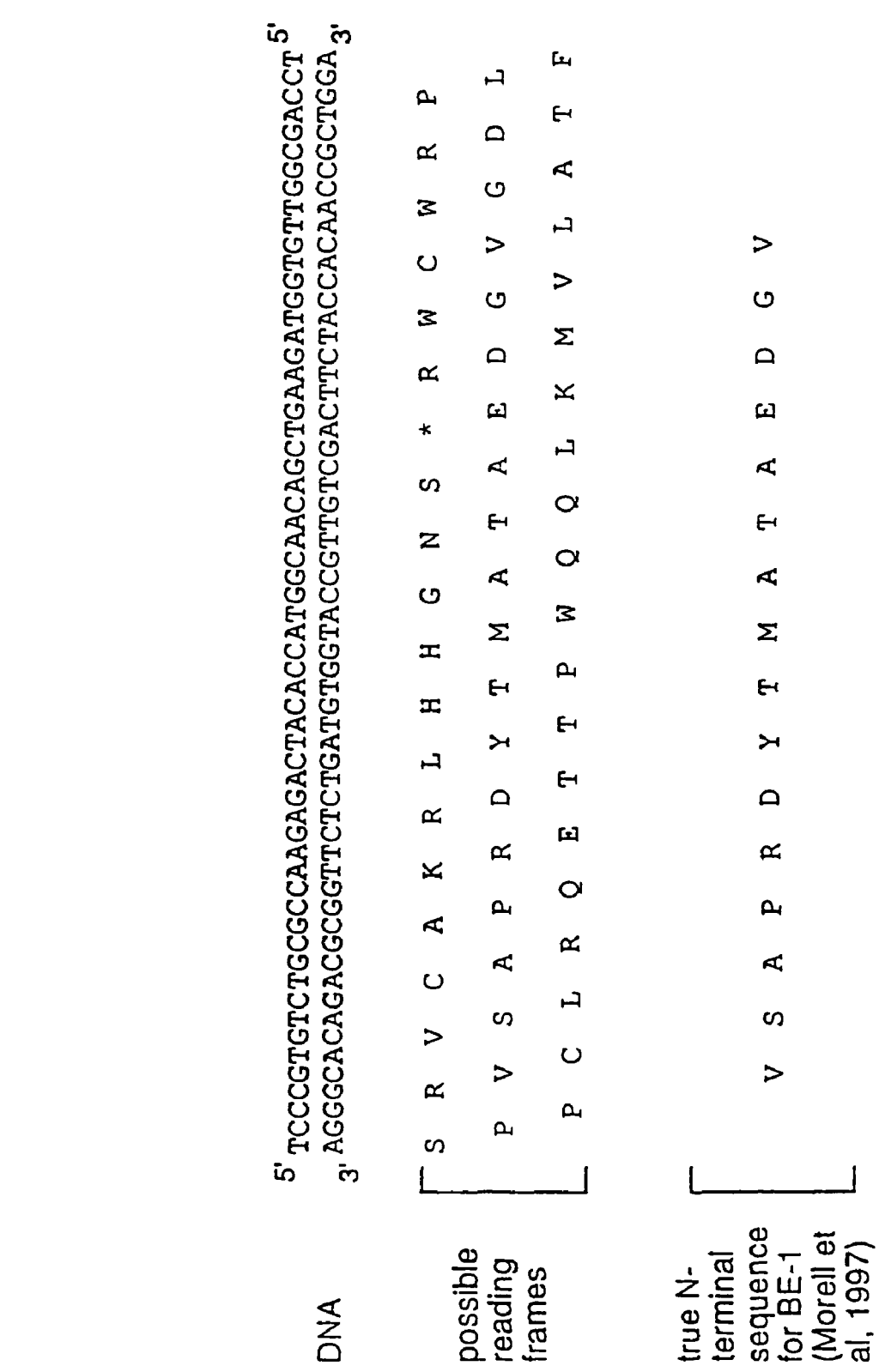

Fragments E1.1 (0.8 kb) and E1.2 (2.1 kb) and fragments E1.7 (4.8 kb) and E1.5 (3 kb) respectively were completely sequenced. Fragment E1.7 was found to encode the N-terminal of the SBE I, which is found in the endosperm as described in Morell et al (1997). This is shown in FIG. 6. Using antibodies raised against the N-terminal sequence, Morell et al (1997) found that the D genome isoform was the most highly expressed in the cultivars Rosella and Chinese Spring. We have thus isolated from *T. tauschii* a gene, wSBE I-D4, whose homologue in the hexaploid wheat genome encodes the major isoform for SBE I that is found in the wheat endosperm.

TABLE 1

Location of structural features and probes within wSBE I-D4 sequence.

A. Location of exons by comparison with the cDNA sequence of Repellin et al., (1997). Accession number Y12320.

| Exon number | Start posn | End posn |
|---|---|---|
| 1 | 4890 | 4987 |
| 2 | 5082 | 5149 |
| 3 | 5524 | 5731 |
| 4 | 5819 | 5888 |
| 5 | 6149 | 6318 |
| 6 | 6519 | 7424 |
| 7 | 7744 | 7860 |
| 8 | 8015 | 8077 |
| 9 | 8562 | 8670 |
| 10 | 9137 | 9237 |
| 11 | 9421 | 9488 |
| 12 | 9580 | 9661 |
| 13 | 9781 | 9897 |
| 14 | 9990 | 10480 |

B. Other features.

| Name of feature. | wSBE I-D4. sequence | D4 cDNA sequence. |
|---|---|---|
| Putative initiation of translation | 4900 | 11 |
| Mature N-terminal sequence of SBE I | 5550 | 124 |
| End of translated SBE I sequence | 10225 | 2431 |
| End of D4 cDNA sequence | 10461 | 2687 |
| wSBE I-D45 | 4870, 5860 | 1, 354 |
| wSBE I-D43 | 10116, 10435 | 2338, 2657 |
| E1.1 | 5680, 6400 | 380, 630 |
| BED 1 | | 1, 354 |
| BED 2 | | 169, 418 |
| BED 3 | | 151, 1601 |
| BED 4 | | 867, 2372 |
| BED 5 | | 867, 2687 |
| Endosperm box like motif TGAAAAGT | 4480, 590 | |
| CAAAT motif | 4863 | |
| TATAAA motif | 4833 | |

All nine genomic clones of the λE1 type isolated from *T. tauschii* appear to contain the wSBE I-D4 gene, or very similar genes, on the basis of PCR amplification and hybridisation experiments. However, the restriction patterns obtained for the clones differ with BamHI and EcoRI, among other enzymes, indicating that either the clones represent near-identical but distinct genes or they represent the same gene isolated in distinct products of the Sau3A digest used to generate the library.

EXAMPLE 8

Investigation of Other SBE I Genomic Clones Isolated

Figure 7:
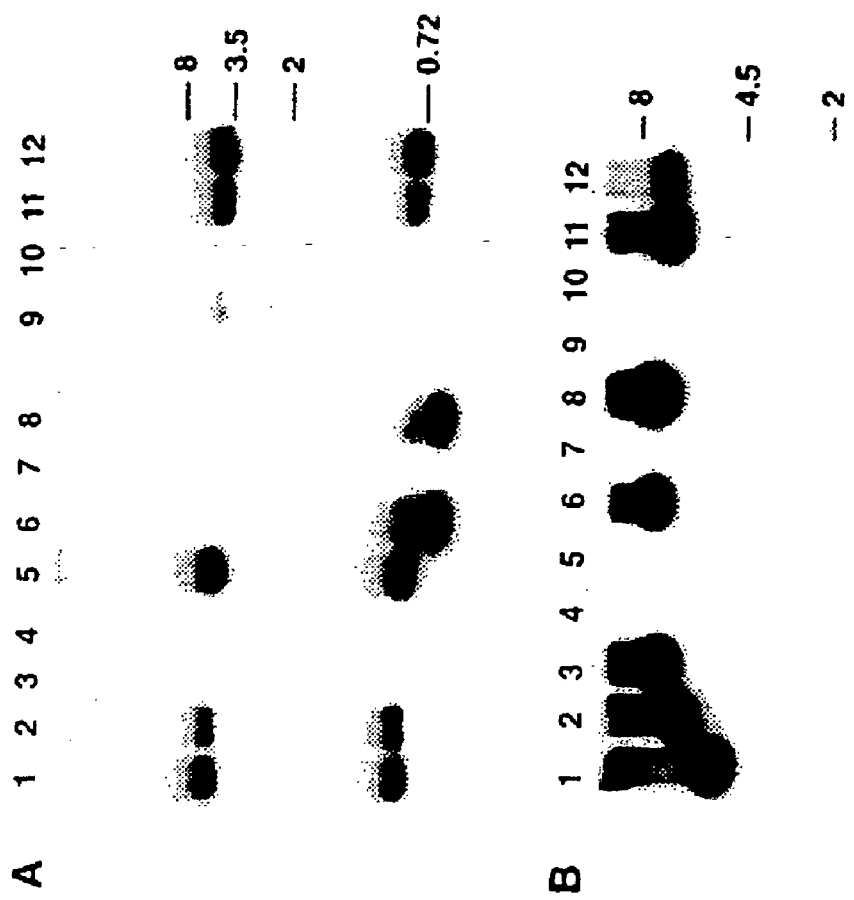

All ten members of the λE1-like class of SBE I genomic clones were investigated by hybridisation with probes derived from fragment E1.7 (sequence wSBE I-D45, encoding the translation start signal and the first 100 amino acids from the N-terminal end and intron sequences; see Table 1) and from fragment E1.5 (sequence wSBE I-D43, corresponding largely to the 3' untranslated sequence and containing intron sequences, see Table 1). The results obtained were consistent with one type of gene being isolated in different fragments in the different clones, as shown in FIG. 7. The PCR products were obtained from the clones λE1, 2, 9, 14, 27, 31 and 52. These hybridised to wSBE I-D45 using primers that amplify near the 5' end of the gene (positions 5590-6162 of wSBE I-D4). Sequencing showed no differences in sequence of a 200 bp product.

Analysis of the promoter for wSBE I-D4 allows us to investigate the presence of motifs previously described for promoters that regulate gene expression in the endosperm. Forde et al (1985) compared prolamin promoters, and suggested that the presence of a motif approximately −300 bp upstream of the transcription start point, called the endosperm box, was responsible for endosperm-specific expression. The endosperm box was subsequently considered to consist of two different motifs: the endosperm motif (EM) (canonical sequence TGTAAAG) and the GCN 4 motif (canonical sequence G/ATGAG/CTCAT (SEQ ID NO: 18)). The GCN4 box is considered to regulate expression according to nitrogen availability (Muller and Knudsen, 1993). The wSBE I-D4 promoter contains a number of imperfect EM-like motifs at approximately −100, −300 and −400 as well as further upstream. However, no GCN4 motifs could be found, which lends support to the idea that this motif regulates response to nitrogen, as starch biosynthesis is not as directly dependent on the nitrogen status of the plant as storage protein synthesis. Comparison of the promoters for wSBE I-D4 and D2 (Rabman et al, 1997) indicates that although there are no extensive sequence homologies there is a region of about 100 bp immediately before the first encoded methionine where the homology is 61% between the two promoters. In particular there is an almost perfect match in the sequence over twenty base pairs CTCGTTGCTTCC/TACTCCACT (SEQ ID NO: 19), (positions 4723-4742 of the wSBE I sequence), but the significance of this is hard to gauge, as it does not occur in the rice promoter for SBE I. The availability of more promoters for starch biosynthetic enzymes may allow firmer conclusions to be drawn. There are putative CAAT and TATA motifs at positions 4870 and 4830 respectively of wSBE I-D4 sequence. The putative start of translation of the mRNA is at position 4900 of wSBE I-D4.

FIG. 5 shows the structure of the wSBE I-D4 gene, compared with the genes from rice and wheat (Kawasaki et al, 1993; Rahman et al, 1997). The rice SBE I has 14 exons compared with 13 for wSBE I-D4 and 10 for wSBE I-D2. There is good conservation of exon-intron structure between the three genes, except at the extreme 5' end. In particular the sizes of intron 1 and intron 2 are very different between rice SBE I and wSBE I-D4.

EXAMPLE 9

Isolation of cDNA for SBE I

Figure 8:
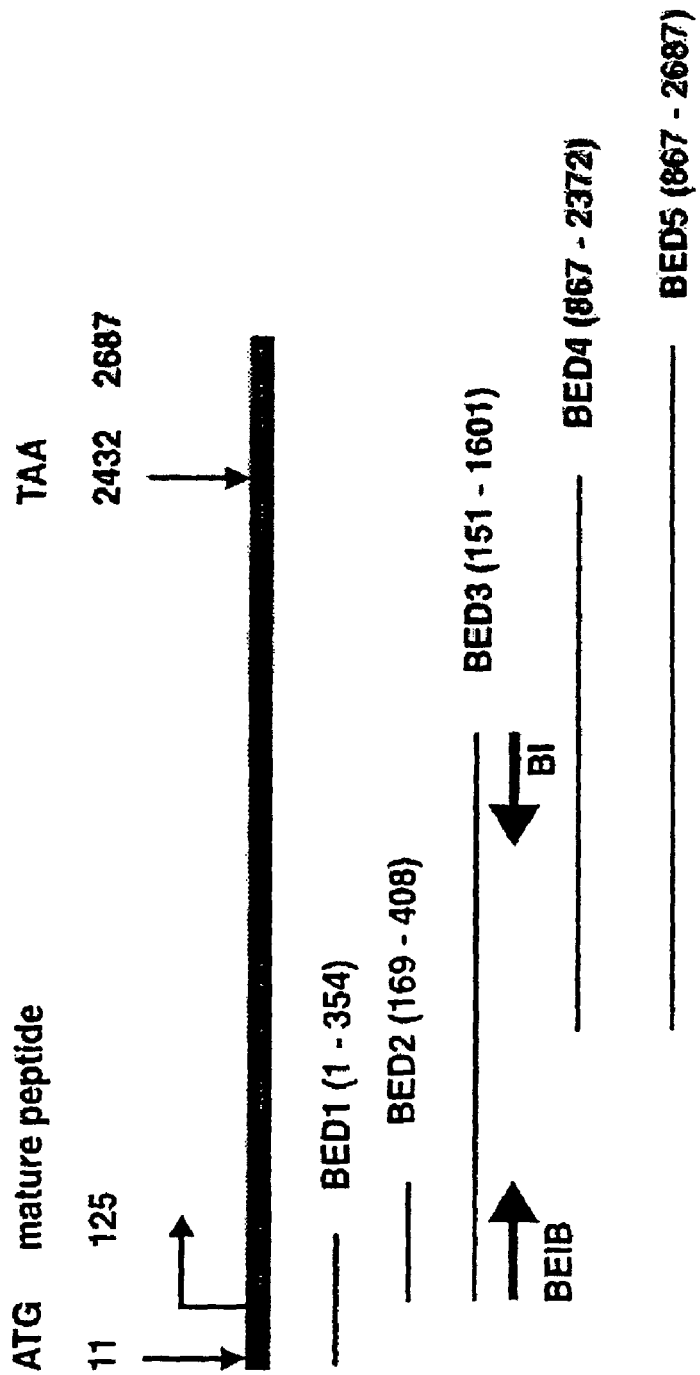

Using the maize starch branching enzyme I cDNA as a probe (Baba et al, 1991), 10 positive plaques were recovered by screening approximately $10^5$ plaques from a wheat endosperm cDNA library prepared from the cultivar Rosella, as described in Example 4. On purifying and sequencing these plaques it was clear that even the longest clone (BED5, 1822 bp) did not encode the N-terminal sequence obtained from protein analysis. Degenerate primers based on the wheat endosperm SBE I protein N-terminal sequence (Morell et al, 1997) and the sequence from BED5 were then used to amplify the 5' region: this produced a cDNA clone termed BED 3 (Table 1 and FIG. 8). This cDNA clone overlapped extensively and had 100% sequence identity with BED5 and BED4 (FIG. 8). As almost the entire protein N-terminal sequence had been included in the primer sequence design, this did not provide independent evidence of the selection of a cDNA sequence in the endosperm that encoded the protein sequence of the main form of SBE I. Using a BED3 to screen a second cDNA library produced BED2, which is shorter than BED3 but confirmed the BED3 sequence at 100% identity between positions 169 and 418 (FIG. 8 and Table 1). In addition the entire cDNA sequence for BED3 could be detected at a 100% match in the genomic clone λE1. Primers based on the putative transcription start point combined with a primer based on the incomplete cDNAs recovered were then used to obtain a PCR product from total endosperm RNA by reverse transcription. This led to the isolation of the cDNA clone, BED1, of 300 bp, whose location is shown in FIG. 8. By analysing this product, a sequence was again obtained that could be found exactly in the genomic clone λE1, and which overlapped precisely with BED3.

The N-terminal of the protein matches that of SBE I isolated from wheat endosperm by Morell et al (1997), and thus the wSBE I-D4 cDNA represents the gene for the predominant SBE I isoform expressed in the endosperm. The encoded protein is 87 kDa; this is similar to proteins encoded by maize (Baba et al, 1991) and rice (Nakamura et al, 1992) cDNAs for SBE I and is distinct from the wSBE I-D2 cDNA described previously, in which the encoded protein was 74 kDa (Rahman et al, 1997).

Five cDNA clones were sequenced and their sequences were assembled into one contiguous sequence using a GCG program (Devereaux et al, 1984). The arrangement of these sequences is illustrated in FIG. 8, the nucleotide sequence is shown in SEQ ID No:5, and the deduced amino acid sequence is shown in SEQ ID No:6. The intact cDNA sequence, wSBE I-D4 cDNA, is 2687 bp and contains one large open reading frame (ORF), which starts at nucleotides 11 to 13 and ends at nucleotides 2432 to 2434. It encodes a polypeptide of 807 amino acids with a molecular weight of 87 kDa. Comparison of the amino acid sequence encoded by wSBE I-D4 cDNA with that encoded by maize and rice SBE I cDNAs showed that there is 75-80% identity between any of two these sequences at the nucleotide level and almost 90% at the amino acid level. Alignment of these three polypeptide sequences, as shown in FIG. 4, along with the deduced sequences for pea, potato and wSBE I-D2 type cDNA, indicated that the sequences in the central region are highly conserved, and sequences at the 5' end (about 80 amino acids) and the 3' end (about 60 amino acids) are variable.

Svensson et al (1994) indicated that there were several invariant residues in sequences of the α-amylase super-family of proteins to which SBE I belongs. In the sequence of maize SBE I these are in motifs commencing at amino acid residue positions 341, 415, 472, 537 respectively; these are also encoded in the wSBE I-D4 sequence (SEQ ID No:9), further supporting the view that this gene encodes a functional enzyme. This is in contrast to the results with the wSBE I-D2 gene, where three of the conserved motifs appear not to be encoded (Rahman et al, 1997).

There is about 90% sequence identity in the deduced amino acid sequence between wSBE I-D4 cDNA and rice SBE I cDNA in the central portion of the molecule (between residues 160 and 740 for the deduced amino acid product from wSBE I-D4 cDNA). The sequence identity of the deduced amino acid sequence of the wSBE I-D4 cDNA to the deduced amino acid sequence of wSBE I-D2 is somewhat lower (85% for the most conserved region, between residues 285 to 390 for the deduced product of wSBE I-D4 cDNA). Surprisingly, however, wSBE I-D4 cDNA is missing the sequence that encodes amino acids at positions 30 to 58 in rice SBE I (see FIG. 4). This corresponds to residues within the transit peptide of rice SBE I. A corresponding sequence also occurs in the deduced amino acid sequence from maize SBE I (Baba et al, 1991) and wSBE I-D2 type cDNA (Rahman et al, 1997). Consequently the transit sequence encoded by wSBE I-D4 cDNA is unusually short, containing only 38 amino acids, compared with 55-60 amino acids deduced for most starch biosynthetic enzymes in cereals (see for example Ainsworth, 1993; Nair et al, 1997). The wSBE I-D4 gene does contain this sequence, but this does not appear to be transcribed into the major species of RNA from this gene, although it can be detected at low relative abundance. This raises the possibility of alternative splicing of the wSBE I-D4 transcript, and also the question of the relative efficiency of translation/transport of the two isoforms. The possibility of alternative splicing in both rice and wheat has been considered for soluble starch synthase (Baba et al, 1993 Rahman et al, 1995). Alternative splicing of soluble starch synthase would give a transit sequence of 40 amino acids, which is the same length proposed for the product of wSBE I-D4 cDNA.

We have previously used probes based on exons 4, 5 and 6 (E7.8 and E1.1, see Rahman et al., 1997) of wSBE-D2 to probe wheat and *T. tauschii* genomic DNA cleaved with PvuII and BamHI respectively. This region is highly conserved within rice SBE I, wSBE I-D2 and wSBE I-D4 and produced ten bands with wheat DNA and five with *T. tauschii* DNA. Neither PvuII nor BamHI cleaved within the probe sequences, suggesting that each band represented a single type of SBE I gene. We have described four SBE I genes from *T. tauschii*: wSBE I-D1, WSBE I-D2, WSBE I-D3 and WSBE I-D4 (Rahman et al, 1997 and this specification), and so we may have accounted for most of the genes in *T. tauschii* and, by extension, the genes from the D genome of wheat. In wheat, at least two hybridising bands could be assigned to each of chromosomes 7A, 7B and 7D.

EXAMPLE 10

Tissue Specificity and Expression During Endosperm Development

The 300 bp of 3' untranslated sequence of wSBE I-D4 cDNA does not show any homology with either the wSBE I-D2 type cDNA that we have described earlier (Rahman et al, 1997) or with BE-I from rice, as shown in FIG. 5. We have called this sequence wSBE I-D43C (see SEQ ID No:9). It seemed likely that wSBE I-D43C would be a specific probe for this class of SBE-I, and thus it was used to investigate the tissue specificity. Hybridization of RNA from endosperm of hexaploid *T. tauschii* cultures with SBE I, SBE II, SSS I, DBE I, wheat actin, and wheat ribosomal RNA was examined. RNA was purified at various numbers of days after anthesis from plants grown with a 16 h photoperiod at 13° C. (night) and 18° C. (day). The age of the endosperms from which RNA was extracted in days after anthesis is given above the lanes in the blot. Equivalent amounts of RNA were electrophoresed in each lane. The probes used are identified in Tables 1 and 2.

The results are shown in FIGS. 9a to 9g. An RNA species of about 2700 bases in size was found to hybridise. This is very close to the size of the wSBE I-D4 cDNA sequence. RNA hybridising to wSBE-1-D43C is most abundant at the mid-stage of endosperm development, as shown in FIG. 9a, and in field grown material is relatively constant during the period 12-18 days, the time at which there is rapid starch and storage protein accumulation (Morell et al, 1995).

The sequence contained within the wSBE I-D4 gene appears to be expressed only in the endosperm (FIG. 9a, FIG. 9b). We could not detect any expression in the leaf. This could be because another isoform is expressed in the leaf, and/or because the amount of SBE I present in the leaf is much less than what is required in the endosperm. Isolation of SBE I clones from a leaf cDNA library would enable this question to be resolved.

EXAMPLE 11

Intron-Exon Structure of SBE I

By comparison of the cDNA sequence of SBE I (Repellin et al, 1997) with that of wSBE I-D4 we can deduce the intron-exon structure of the gene for the major isoform of SBE I that is found in the endosperm. The structure contains 14 exons compared to 14 for rice (Kawasaki et al, 1993). These 14 exons are spread over 6 kb of sequence, a distance similar to that found in both rice SBE I and wSBE I-D2. A dotplot comparison of wSBE I-D4 sequence and that of rice SBE I sequence, depicted in FIG. 10, shows good sequence identity over almost the entire gene starting from about position 5100 of wSBE I-D4; the identity is poor over the first 5 kb of sequence corresponding largely to the promoter sequences. The sequence identity over introns (about 60%) is lower than over exons (about 85%).

EXAMPLE 12

Repeated Sequences in SBE I

Sequencing of wSBE I-D4 revealed there was a repeated sequence of at least 300 bp contained in a 2 kb fragment about 600 bp after the 3' end of the gene. We have called this sequence wSBE I-D4R (SEQ ID NO: 9). This repeated sequence is within fragment E1.5 (FIG. 3 and Table 1) and is flanked by non-repetitive sequences from the genomic clone. We have previously shown that the restriction pattern obtained by digesting λE1 with the restriction enzyme BamHI is also obtained when *T. tauschii* DNA is digested. Thus wSBE I-D4R is unlikely to be a cloning artefact. A search of the GenBank Database revealed that wSBE I-D4R shared no significant homology with any sequence in the database. Hybridisation experiments with wSBE I-D4R showed that all of the other SBE I-D4 type genomic clones (except number 29) contained this repeated sequence (data not shown). The wSBE I-D4R sequence was not highly repeated and occurred in the wheat genome with a similar frequency as the wSBE I-D4 sequence.

When SBE I-D4R was used as the probe on wheat DNA from the nulli-tetra lines, four bands were obtained; two of these bands could be assigned to chromosome 7A and the others to chromosomes 7B and 7D (FIG. 11). One of the two BamHI fragments from wheat DNA which could be assigned to chromosome 7A was distinct from the single band from chromosome 7A detected using wSBE I-D43 as the probe; the other three bands coincided in the autoradiograph with bands obtained with wSBE I-D43, and are likely to represent the same fragment. However, one of these fragments was distinct from the BamHI fragment that hybridised to the wSBE I-D43 sequence. In wSBE I-D4 (see SEQ ID No:9), the wSBE I-D43 sequence is only 300 bp upstream of wSBE I-D4R, and occurs in the same BamHI fragment. These results suggest that the wSBE I-D4R sequence can occur independently of wSBE I-D4 in the wheat genome.

EXAMPLE 13

Isolation of Genomic Clones Encoding SBE II

Screening of a cDNA library, prepared from the wheat endosperm as described in Example 4, with the maize BE I clone (Baba et al, 1991) at low stringency led to the isolation of two classes of positive plaques. One class was strongly hybridising, and led to the isolation of wheat SBE I-D2 type and SBE I-D4 type cDNA clones, as described in Example 5 and in Rahman et al (1997). The second class was weakly hybridising, and one member of this class was purified. This weakly hybridising clone was termed SBE-9, and on sequencing was found to contain a sequence that was distinct from that for SBE I. This sequence showed greatest homology to maize BE II sequences, and was considered to encode part of the wheat SBE II sequence.

The screening of approximately $5 \times 10^5$ plaques from a genomic library constructed from *T. tauschii* (see Example 1) with the SBE-9 sequence led to the isolation of four plaques that were positive. These were designated wSBE II-D1 to wSBE II-D4 respectively, and were purified and analysed by restriction mapping. Although they all had different hybridization patterns with SBE-9, as shown in FIG. 12, the results were consistent with the isolation of the same gene in different-sized fragments.

EXAMPLE 14

Identification of the N-Terminal Sequence of SBE II

Sequencing of the SBE II gene contained in clone 2, termed SBE II-D1 (see SEQ ID No:10), showed that it coded for the N-terminal sequence of the major isoform of SBE II expressed in the wheat endosperm, as identified by Morell et al (1997). This is shown in FIG. 13.

EXAMPLE 15

Intron-Exon Structure of the SBE II Gene

In addition to encoding the N-terminal sequence of sBE II, as shown in Example 10, the cDNA sequence reported by Nair et al (1997) was also found to have 100% sequence identity with part of the sequence of wSBE I-D1. Thus the intron-exon structure can be deduced, and this is shown in FIG. 14. The positions of exons and other major structural features of the SBE II gene are summarized in Table 2.

EXAMPLE 16

Number of SBE II Genes in *T. tauschii* and Wheat

Hybridisation of the SBE II conserved region with *T. tauschii* DNA revealed the presence of three gene classes. However, in our screening we only recovered one class. Hybridisation to wheat DNA indicated that the locus for SBE II was on chromosome 2, with approximately 5 loci in wheat; most of these appear to be on chromosome 2D, as shown in FIG. 15.

TABLE 2

Positions of structural features in wSBE II-D1.

A. Positions of exons.

| Exon number | Genomic start | Genomic finish |
|---|---|---|
| 1 | 1058 | 1336 |
| 2 | 1664 | 1761 |
| 3 | 2038 | 2279 |
| 4 | 2681 | 2779 |
| 5 | 2949 | 2997 |
| 6 | 3145 | 3204 |
| 7 | 3540 | 3620 |
| 8 | 3704 | 3825 |
| 9 | 4110 | 4188 |
| 10 | 4818 | 4939 |
| 11 | 5115 | 5234 |
| 12 | 6209 | 6338 |
| 13 | 6427 | 6549 |
| 14 | 6739 | 6867 |
| 15 | 7447 | 7550 |
| 16 | 8392 | 8536 |
| 17 | 9556 | 9703 |
| 18 | 9839 | 9943 |
| 19 | 10120 | 10193 |
| 20 | 10395 | 10550 |
| 21 | 10928 | 11002 |
| 22 | 11092 | 11475 |

B. Other structural features within the wSBE II-D1 DNA sequence

| | |
|---|---|
| Putative initiation of translation | 1214 |
| Mature N-terminal sequence of SBE II. | 1681 |
| wSBE II-D13 | 11116 to 11448 |
| Endosperm box like motif TGAAAAGT | 521 |
| Endosperm box like motif TGAAAGT | 565 |
| Endpsperm box like motif CGAAAAT | 669 |
| Endosperm box like motif TAAATGT | 768 |
| CAAAAT motif | 784 |
| TCAATT motif | 1108 |
| TATAAA motif | 799 |
| AATTAA motif | 1110 |

EXAMPLE 17

Expression of SBE II

Investigation of the pattern of expression of SBE II revealed that the gene was only expressed in the endosperm. However the timing of expression was quite distinct from that of SBE I, as illustrated in FIGS. 9a, 9b and 9c.

SBE I gene expression is only clearly detectable from the mid-stage of endosperm development (10 days after anthesis in FIG. 9b), whereas SBE II gene expression is clearly seen much earlier, in endosperm tissue at 5-8 days after development (FIGS. 9a and 9c), corresponding to an early stage of endosperm development. The hybridisation of wheat endosperm mRNA with the actin and ribosomal RNA genes is shown as controls (FIGS. 9fa and 9g, respectively).

EXAMPLE 18

Cloning of Wheat Soluble Starch Synthase cDNA

A conserved sequence region was used for the synthesis of primers for amplification of SSS I by comparison with the nucleotide sequences encoding soluble starch synthases of rice and pea. A 300 bp RT-PCR product was obtained by amplification of cDNA from wheat endosperm at 12 days post anthesis. The 300 bp RT-PCT product was then cloned, and its sequence analysed. The comparison of its sequence with rice SSS cDNA showed about 80% sequence homology. The 300 bp RT-PCR product was 100% homologous to the partial sequence of a wheat SSS I in the database produced by Block et al (1997).

The 300 bp cDNA fragment of wheat soluble starch synthase thus isolated was used as a probe for the screening of a wheat endosperm cDNA library (Rahman et al, 1997). Eight cDNA clones were selected. One of the largest cDNA clones (sm2) was used for DNA sequencing analysis, and gave a 2662 bp nucleotide sequence, which is shown in SEQ ID NO:14. A large open reading frame of this cDNA encoded a 647 amino acid polypeptide, starting at nucleotides 247 to 250 and terminating at nucleotides 2198 to 2200. The deduced polypeptide was shown by protein sequence analysis to contain the N-terminal sequence of a 75 kDa granule-bound protein (Rahman et al, 1995). This is illustrated in FIG. 16. The location of the 75 kDa protein was determined for both the soluble fraction and starch granule-bound fraction by the method of Denyer et al (1995). Thus this cDNA clone encoded a polypeptide comprising a 41 amino acid transit peptide and a 606 amino acid mature peptide (SEQ ID NO:12). The cleavage site LRRL was located at amino acids 36 to 39 of the transit peptide of this deduced polypeptide.

Comparison of wheat SSS I with rice SSS and potato SSS showed that there is 87.4% or 75.9% homology at the amino acid level and 74.7% or 58.1% homology at the nucleotide level. Some amino acids in the at N-terminal sequences of the SSS I of wheat and rice were conserved. Major features of the SSS I gene are summarized in Table 3.

EXAMPLE 19

Isolation of Genomic Clone of Wheat Soluble Starch Synthase

Seven genomic clones were obtained with a 300 bp cDNA probe by screening approximately $5\times10^5$ plaques from a genomic DNA library of *Triticum tauschii*, as described above. DNA was purified from 5 of these clones and digested with BamHI and SacI. Southern hybridization analysis using the 300 bp cDNA as probe showed that these clones could be classified into two classes, as shown in FIG. 17. One genomic clone, sg3, contained a long insert, and was digested with BamHI or SacI and subcloned into pBluescript KS+ vector.

TABLE 3

Comparison of exons and introns of soluble starch synthases I genes of wheat and rice

| | wSSI-D1 | rSSI | identity (%) | start site (wSSI-D1) | stop site (wSSI-D1) |
|---|---|---|---|---|---|
| (1) Identity of exons of soluble starch synthase I genes of wheat and rice | | | | | |
| Exons | | | | | |
| 1a | 255 | 113 | 57.52 | −253 | 0 |
| 1b | 316 | 298 | 58.92 | 1 | 316 |
| 2 | 356 | 356 | 82.87 | 1473 | 1828 |
| 3 | 78 | 78 | 92.31 | 2746 | 2823 |
| 4 | 125 | 125 | 90.40 | 2906 | 3028 |
| 5 | 82 | 82 | 89.02 | 4113 | 4194 |
| 6 | 174 | 174 | 93.10 | 4286 | 4459 |
| 7 | 82 | 82 | 93.90 | 4562 | 4643 |
| 8 | 92 | 92 | 92.39 | 4743 | 4835 |
| 9 | 63 | 63 | 90.48 | 4959 | 5021 |
| 10 | 90 | 90 | 82.22 | 5103 | 5192 |
| 11 | 125 | 125 | 88.80 | 8594 | 8718 |
| 12 | 109 | 109 | 91.74 | 8807 | 8915 |
| 13 | 53 | 53 | 81.13 | 8992 | 9044 |
| 14 | 40 | 41 | 80.00 | 9160 | 9199 |
| 15a | 159 | 113 | 79.65 | 9499 | 9657 |
| 15b | 392 | 539 | 46.46 | 9658 | 10098 |
| (2) Identity of introns of soluble starch synthase I genes of wheat and rice | | | | | |
| Introns | | | | | |
| 1 | 1156 | 907 | 41.05 | 317 | 1472 |
| 2 | 917 | 851 | 41.65 | 1829 | 2745 |
| 3 | 82 | 87 | 45.12 | 2824 | 2905 |
| 4 | 1084 | 835 | 48.50 | 3029 | 4112 |
| 5 | 91 | 96 | 57.78 | 4195 | 4285 |
| 6 | 102 | 189 | 52.48 | 4460 | 4561 |
| 7 | 99 | 96 | 52.08 | 4644 | 4742 |
| 8 | 123 | 110 | 45.46 | 4836 | 4958 |
| 9 | 81 | 78 | 58.97 | 5022 | 5102 |
| 10 | 3401 | 663 | 37.56 | 5193 | 8593 |
| 11 | 88 | 124 | 56.82 | 8719 | 8806 |
| 12 | 76 | 81 | 48.68 | 8916 | 8991 |
| 13 | 115 | 135 | 45.22 | 9045 | 9159 |
| 14 | 299 | 830 | 45.80 | 9200 | 9498 |

Note:
Exon 1a: non-coding region of exon 1.
Exon 1b: coding region of exon 1.
Exon 15a: coding region of exon 15.
Exon 15b: non-coding region of exon 15.
wSSI-D1: wheat soluble starch synthase I gene.
rSSI: rice soluble starch synthase I gene.

These subclones were analysed by sequencing. The intron/exon structure of the sg3 rice gene is shown in FIG. 18. The SSS I gene from *T. tauschii* is shown in SEQ ID No:13, while the deduced amino acid sequence is shown in SEQ ID NO:14.

EXAMPLE 20

Northern Hybridization Analysis of the Expression of Genes Encoding Soluble Starch Synthase Total RNAs were purified from leaves, pre-anthesis material, and various stages of developing endosperm at 5-8, 10-15 and 18-22 days post anthesis. Northern hybridization analysis showed that mRNAs encoding wheat SSS I were specifically expressed in developmental endosperm. Expression of this mRNAs in the leaves and pre-anthesis materials could not be detected by northern hybridization analysis under this experimental condition. Wheat SSS I mRNAs started to express at high levels at an early stage of endosperm, 5-8 days post anthesis, and the expression level in endosperm at 10-15 days post anthesis, was reduced. These results are summarized in FIG. 9a and FIG. 9d.

EXAMPLE 21

Genomic Localisation of Wheat Soluble Starch Synthase

DNA from chromosome engineered lines was digested with the restriction enzyme BamHI and blotted onto supported nitrocellulose membranes. A probe prepared from the 3' end of the cDNA sequence, from positions 2345 to 2548, was used to hybridise to this DNA. The presence of a specific band was shown to be associated with the presence of chromosomes 7A (FIG. 19). These data demonstrate location of the SSS I gene on chromosome 7.

EXAMPLE 22

Isolation of SSS I Promoter

We have isolated the promoter that drives this pattern of expression for SSS I. The pattern of expression for SSS I is very similar to that for SBE II: the SSS I gene transcript is detectable from an early stage of endosperm development until the endosperm matures. The sequence of this promoter is given in SEQ ID No:15.

EXAMPLE 23

Isolation of the Gene Encoding Debranching Enzyme from Wheat

The sugary-1 mutation in maize results in mature dried kernels that have a glassy and translucent appearance; immature mature kernels accumulate sucrose and other simple sugars, as well as the water-soluble polysaccharide phytoglycogen (Black et al, 1966). Most data indicates that in sugary-1 mutants the concentration of amylose is increased relative to that of amylopection. Analysis of a particular sugary-1 mutation (su-1Ref) by James et al, (1995) led to the isolation of a cDNA that shared significant sequence identity with bacterial enzymes that hydrolyse the α 1,6-glucosyl linkages of starch, such as an isoamylase from *Pseudomonas* (Amemura et al, 1988), ie. bacterial debranching enzymes.

We have now isolated a sequence amplified from wheat endosperm cDNA using the polymerase chain reaction (PCR). This sequence is highly homologous to the sequence for the sugary gene isolated by James et al, (1995). This sequence has been used to isolate homologous cDNA sequences from a wheat endosperm library and genomic sequences from *Triticum tauschii*.

Comparison of the deduced amino acid sequences of DBE from maize with spinach (Accession SOPULSPO, GenBank database), *Pseudomonas* (Amemura et al, 1988) and rice (Nakamura et al, 1997) enabled us to deduce sequences which could be useful in wheat. When these sequences were used as PCR amplification primers with wheat genomic DNA a product of 256 bp was produced. This was sequenced and was compared to the sequence of maize sugary isolated by James et al, (1995). The results are shown in FIG. 20a and FIG. 20b. This sequence has been termed wheat debranching enzyme sequence I (WDBE-I).

WDBE-1 was used to investigate a cDNA library constructed from wheat endosperm (Rahman et al, 1997) enables us to isolate two cDNA clones which hybridise strongly to the WDBE-I probe. The nucleotide sequence of the DNA insert in the longest of these clones is given in SEQ ID No:16.

Use of WDBE 1 to investigate a genomic library constructed from *T. tauschii*, as described above has led to the isolation of four genomic clones, designated I1, I2, I3 and I4, respectively, which hybridised strongly to the WDBE-I sequence. These clones were shown to contain copies of a single debranching enzyme gene. The sequence of one of these clones, I2, is given in SEQ ID No:17. The intron/exon structure of the gene is shown in FIG. 20c. Exons 1 to 4 were identified by comparison with the maize sugary-1 cDNA, while Exons 5 to 18 were identified by comparison with the cDNA sequence given in SEQ ID No:16. The major features of the DBE I gene are summarized in Table 4.

Hybridization of WDBE-I to DNA from *T. tauschii* indicates one hybridizing fragment (FIG. 21a). The chromosomal location of the gene was shown to be on chromosome 7 through hybridisation to nullisomic/tetrasomic lines of the hexaploid wheat cultivar Chinese Spring (FIG. 21b).

We have clearly isolated a sequence from the wheat genome that has high identity to the debranching enzyme cDNA of maize characterised by James et al (1997). The isolation of homologous cDNA sequences and genomic sequences enables further characterisation of the debranching enzyme cDNA and promoter sequences from wheat and *T. tauschii*. These sequences and the WDBE I sequences shown herein are useful in the manipulation of wheat starch structure through genetic manipulation and in the screening for mutants at the equivalent sugary locus in wheat.

FIG. 9e shows that the DBE I gene is expressed during endosperm development in wheat and that the timing of expression is similar to the SBEII and SSSI genes. FIG. 9h shows that the full length mRNA for the gene (3.0 kb) is found only in the wheat endosperm.

EXAMPLE 24

Transient Assays of Promoter-GFP Fusions

DNA Constructs

DNA constructs for transient expression assays were prepared by fusing sequences from the BEII and SSI promoters to the gene encoding the Green Fluorescent Protein. Green Fluorescent Protein (GFP) constructs contained the GFP gene described by Sheen et al. (1995). The nos 3' element (Bevan et al., 1983) was inserted 3' of the GFP gene. The plasmid vector (pWGEM_NZfp) was constructed by inserting the NotI to HindIII fragment from the following sequence:

```
5' GCGGCCGCTC CCTGGCCGAC TTGGCCGAAG CTTGCATGCC

TGCAGGTCGA CTCTAGAGGA TCCCCGGGTA CCGAGCTCGA

ATTCATCGAT GATATCAGAT CCGGGCCCTC TAGATGCGGC

CGCATGCATA AGCTT 3' (SEQ ID NO: 20)
``` into the NotI and HindIII sites of pGem-13Zf(-) vector (Promega). The sequences at the junction of the wSSSIpro1 and wSSSIpro2 and GFP were identical, and included the junction sequence:

```
5' ....CGCGCGCCCA CACCCTGCAG GTCGACTCTA GAGGATCCAT

GGTGAGCAAG 3' (SEQ ID NO: 21).
```

The sequence at the junction of wsbeIIpro1 and GFP was:

5' GCGACTGGCT GACTCAATCA CTACGCGGGG ATCCATGGTG

AGCAAGGGCG 3' (SEQ ID NO: 22).

The sequence at the junction of wsbeIIpro2 and GFP was:

5' GGACTCCTCT CGCGCCGTCC TGAGCCGCGG ATCCATGGTG

AGCAAGGGCG 3' (SEQ ID NO: 23).

The structures of the constructs are shown in FIGS. 22a to 22f.

TABLE 4

Structural features of wDBEI-D1

A. Position of exons

| Exon number | Start position | End position | Comments |
|---|---|---|---|
| 1 | 1890 | 2241 | (deduced by comparison with maize) |
| 2 | 2342 | 2524 | (deduced by comparison with maize) |
| 3 | 2615 | 2707 | (deduced by comparison with maize) |
| 4 | 3016 | 3168 | (deduced by comparison with maize) |
| 5 | 3360 | 3436 | |
| 6 | 4313 | 4454 | |
| 7 | 4526 | 4633 | |
| 8 | 4734 | 4819 | |
| 9 | 5058 | 5129 | |
| 10 | 5202 | 5328 | |
| 11 | 5558 | 5644 | |
| 12 | 6575 | 6671 | |
| 13 | 7507 | 7661 | |
| 14 | 8450 | 8527 | |
| 15 | 8739 | 8823 | |
| 16 | 8902 | 8981 | |
| 17 | 9114 | 9231 | |
| 18 | Still being sequenced | | |

Note that following nucleotides 3330, 6330 and 8419 there may be short regions of DNA not yet sequenced.

B.

| | |
|---|---|
| CAAAAT motif | 1833 |
| TCAAT motif | 1838 |
| ATAAATAA motif | 1804 |
| Endosperm box like motif TAAAACG | 1463 |

Preparation of Target Tissue

All explants used for transient assay were from the hexaploid wheat cultivar, Milliwang. Endosperm (10-12 days after anthesis), embryos (12-14 days after anthesis) and leaves (the second leaf from the top of plants containing 5 leaves) were used. Developing seed or leaves were collected, surface sterilized with 1.25% w/v sodium hypochlorite for 20 minutes and rinsed with sterile distilled water 8 times. Endosperms or embryos were carefully excised from seed in order to avoid contamination with surrounding tissues. Leaves were cut into 0.5 cm×1 cm pieces. All tissues were aseptically transferred onto SD1SM medium, which is an MS based medium containing 1 mg/L 2,4-D, 150 mg/L L-asparagine, 0.5 mg/L thiamine, 10 g/L sucrose, 36 g/L sorbitol and 36 g/L mannitol. Each agar plate contained either 12 endosperms, 12 embros or 2 leaf segments.

Preparation of Gold Particles and Bombardment

Five µg of each plasmid was used for the preparation of gold particles, as described by Witrzens et al. (1998). Gold particle-DNA suspension in ethanol (10 µl) was used for each bombardment using a Bio-Rad helium-driven particle delivery system, PDS-1000.

GFP Assay

The expression of GFP was observed after 36 to 72 hours incubation using a fluorescence microscope. Two plates were bombarded for each construct. The numbers of expressing regions were recorded for each target tissue, and are summarized in Table 5. The intensity of the expression of GFP from each of the promoters was estimated by visual comparison of the light intensity emitted, and is summarized in Table 6.

The DNA construct containing GFP without a promoter region (pZLGFPNot) gave no evidence of transient expression in embryo (panel 1) or leaf (panel r) and extremely weak and sporadic expression in endosperm (panel f), this construct gave only very weak expression in endosperm with respect to the number (FIG. 5) and intensity (FIG. 6) of transient expression regions. The constructs pwsssIpro1gfpNOT (panels b, h and n), psbeIIpro1gfpNOT (panels d, j and p), and psbeIIpro2gfpNOT (panels e, k and q) yielded low numbers (Table 5) of strongly (Table 6) expressing regions in leaves, and there was a very uneven distribution of expressing regions between target leaf pieces (Table 5). pwsssIpro2gfpNOT (panels c, i and o) gave no evidence of transient expression in leaves (Table 5). These results show that each of the promoter constructs is able to drive the transient expression of GFP in the grain tissues, endosperm and embryo. The ability of the short SSI promoter (pwsssIpro2gfpNOT containing 1042 bp 5' of the ATG translation start site) to drive expression in leaves (panel n) contrasts with the inability of the long SSI promoter (pwsssIpro2gfpNOT containing 3914 base pair region 5' of the ATG translation start site, panel O) suggesting that regions for controlling tissue specificity are located between −3914 and −1042 of the SSI promoter region (SEQ ID No:15).

EXAMPLE 25

Stable Transformation of Rice

Stable transformation of rice using *Agrobacterium* was carried out essentially as described by Wang et al. 1997. The plasmids containing the target DNA constructs containing the promoter-reporter gene fusions are shown in FIG. 23. These plasmids were transformed into *Agrobacterium tumefaciens* AGLL by electroporation. and cultured on selection plates of LB media containing rifampicillin (50 mg/L) and spectinomycin (50 mg/L) for 2 to 3 days, and then gently suspended in 10 ml NB liquid medium containing 100 µM acetosyringone and mixed well. Embryogenic rice calli (2 to 3 months old) derived from mature seeds were immersed in the *A. tumefaciens* AGL1

TABLE 5

Transient Assay of GFP based constructs

| Tissue | Construct | Plate No. | 1 | 2 | 3 | 4 | 5 | 6 | 7 | 8 | 9 | 10 | 11 | 12 | Ave. | S.D. |
|---|---|---|---|---|---|---|---|---|---|---|---|---|---|---|---|---|
| Endosperm | pact__jsgfg__nos | 1 | 0 | 0 | 1 | 158 | 152 | 148 | 0 | 2 | 12 | 159 | 95 | 64 | 65.9 | 71.6 |
| Endosperm | pact__jsgfg__nos | 2 | 3 | 13 | 2 | 83 | 18 | 9 | 6 | 188 | 0 | 102 | 5 | 3 | 36.0 | 58.6 |
| Embryo | pact__jsgfg__nos | 3 | 97 | 79 | 77 | 101 | 121 | 176 | 89 | 129 | 139 | 212 | 131 | 138 | 124.1 | 40.1 |
| Embryo | pact__jsgfg__nos | 4 | 18 | 39 | 89 | 82 | 7 | 52 | 94 | 147 | 19 | 66 | 106 | 85 | 67.0 | 41.6 |
| Leaf | pact__jsgfg__nos | 5 | 0 | 2 | 0 | 3 | 0 | 0 | | | | | | | 0.8 | 1.3 |
| Leaf | pact__jsgfg__nos | 6 | 0 | 0 | 0 | 1 | 0 | 0 | | | | | | | 0.2 | 0.4 |
| Leaf | pact__jsgfg__nos | 7 | 3 | 0 | 0 | 2 | 0 | 3 | | | | | | | 1.3 | 1.5 |
| Endosperm | pZLGFPNot | 8 | 13 | 0 | 4 | 0 | 14 | 0 | 0 | 0 | 0 | 0 | 0 | 1 | 2.7 | 5.2 |
| Endosperm | pZLGFPNot | 9 | 0 | 0 | 0 | 0 | 14 | 0 | 0 | 5 | 3 | 4 | 6 | 0 | 2.7 | 4.2 |
| Embryo | pZLGFPNot | 10 | 0 | 0 | 0 | 0 | 0 | 0 | 0 | 0 | 0 | 0 | 0 | 0 | 0.0 | 0.0 |
| Embryo | pZLGFPNot | 11 | 0 | 0 | 0 | 0 | 0 | 0 | 0 | 0 | 0 | 0 | 0 | 0 | 0.0 | 0.0 |
| Leaf | pZLGFPNot | 12 | 0 | 0 | 0 | 0 | 0 | 0 | | | | | | | 0.0 | 0.0 |
| Leaf | pZLGFPNot | 13 | 0 | 0 | 0 | 0 | 0 | 0 | | | | | | | 0.0 | 0.0 |
| Leaf | pZLGFPNot | 14 | 0 | 0 | 0 | 0 | 0 | 0 | | | | | | | 0.0 | 0.0 |
| Endosperm | psbeIIpro1gfpNOT | 15 | 111 | 0 | 77 | 142 | 0 | 127 | 7 | 35 | 39 | 191 | 95 | 34 | 71.5 | 62.3 |
| Endosperm | psbeIIpro1gfpNOT | 16 | 21 | 101 | 0 | 0 | 34 | 164 | 102 | 5 | 39 | 125 | 147 | 114 | 71.0 | 60.6 |
| Embryo | psbeIIpro1gfpNOT | 17 | 23 | 67 | 63 | 4 | 12 | 14 | 9 | 8 | 29 | 19 | 24 | 51 | 26.9 | 21.7 |
| Embryo | psbeIIpro1gfpNOT | 18 | 92 | 144 | 64 | 36 | 31 | 23 | 106 | 43 | 11 | 1 | 9 | 7 | 47.3 | 45.4 |
| Leaf | psbeIIpro1gfpNOT | 19 | 0 | 0 | 0 | 0 | 0 | 0 | | | | | | | 0.0 | 0.0 |
| Leaf | psbeIIpro1gfpNOT | 20 | 6 | 0 | 0 | 0 | 0 | 0 | | | | | | | 1.0 | 2.4 |
| Leaf | psbeIIpro1gfpNOT | 21 | 0 | 0 | 0 | 0 | 3 | 5 | | | | | | | 1.3 | 2.2 |
| Endosperm | psbeIIpro2fpNOT | 22 | 12 | 18 | 3 | 0 | 0 | 21 | 13 | 0 | 10 | 11 | 10 | 0 | 8.2 | 7.4 |
| Endosperm | psbeIIpro2fpNOT | 23 | 24 | 25 | 13 | 68 | 11 | 0 | 0 | 0 | 1 | 0 | 0 | 0 | 11.8 | 20.1 |
| Embryo | psbeIIpro2fpNOT | 24 | 9 | 13 | 4 | 7 | 6 | 21 | 0 | 9 | 3 | 5 | 2 | 4 | 6.9 | 5.7 |
| Embryo | psbeIIpro2fpNOT | 25 | 5 | 0 | 3 | 5 | 23 | 4 | 3 | 1 | 8 | 12 | 8 | 13 | 7.1 | 6.4 |
| Leaf | psbeIIpro2fpNOT | 26 | 0 | 2 | 0 | 0 | 0 | 0 | | | | | | | 0.3 | 0.8 |
| Leaf | psbeIIpro2fpNOT | 27 | 0 | 5 | 0 | 8 | 0 | 0 | | | | | | | 2.2 | 3.5 |
| Leaf | psbeIIpro2fpNOT | 28 | 0 | 0 | 0 | 0 | 0 | 0 | | | | | | | 0.0 | 0.0 |
| Endosperm | pwsssIpro1gfpNOT | 29 | 121 | 0 | 0 | 28 | 0 | 4 | 81 | 23 | 0 | 2 | 0 | 2 | 21.8 | 39.2 |
| Endosperm | pwsssIpro1gfpNOT | 30 | 3 | 0 | 0 | 92 | 12 | 0 | 0 | 102 | 4 | 159 | 41 | 24 | 36.4 | 52.8 |
| Embryo | pwsssIpro1gfpNOT | 31 | 112 | 106 | 74 | 54 | 33 | 73 | 77 | 49 | 42 | 38 | 59 | 46 | 63.6 | 25.6 |
| Embryo | pwsssIpro1gfpNOT | 32 | 97 | 48 | 110 | 22 | 191 | 112 | 53 | 6 | 9 | 145 | 6 | 10 | 67.4 | 62.4 |
| Leaf | pwsssIpro1gfpNOT | 33 | 0 | 0 | 0 | 0 | 0 | 0 | | | | | | | 0.0 | 0.0 |
| Leaf | pwsssIpro1gfpNOT | 34 | 0 | 0 | 0 | 0 | 0 | 0 | | | | | | | 0.0 | 0.0 |
| Leaf | pwsssIpro1gfpNOT | 35 | 12 | 0 | 0 | 0 | 0 | 0 | | | | | | | 2.0 | 4.9 |
| Endosperm | pwsssIpro2fpNOT | 36 | 0 | 0 | 0 | 18 | 81 | 0 | 0 | 6 | 0 | 0 | 1 | 0 | 8.8 | 23.3 |
| Endosperm | pwsssIpro2fpNOT | 37 | 0 | 18 | 14 | 6 | 63 | 8 | 8 | 23 | 79 | 7 | 46 | 51 | 26.9 | 26.1 |
| Embryo | pwsssIpro2fpNOT | 38 | 15 | 7 | 14 | 57 | 8 | 3 | 26 | 10 | 47 | 34 | 47 | 0 | 22.3 | 19.4 |
| Embryo | pwsssIpro2fpNOT | 39 | 9 | 15 | 48 | 103 | 31 | 22 | 107 | 22 | 27 | 82 | 51 | 63 | 48.3 | 33.8 |
| Leaf | pwsssIpro2fpNOT | 40 | 0 | 0 | 0 | 0 | 0 | 0 | | | | | | | 0.0 | 0.0 |
| Leaf | pwsssIpro2fpNOT | 41 | 0 | 0 | 0 | 0 | 0 | 0 | | | | | | | 0.0 | 0.0 |
| Leaf | pwsssIpro2fpNOT | 42 | 0 | 0 | 0 | 0 | 0 | 0 | | | | | | | 0.0 | 0.0 |

TABLE 6

Comparison of the Intensities of Transient Expression

| Tissue | pact__js-gfg__nos | pwsssIpro1gfpNOT | pwsssIpro2gfpNOT | psbeIIpro1gfpNOT | psbeIIpro2gfpNOT | pZLGFPNot |
|---|---|---|---|---|---|---|
| Endosperm | 10 | 4 | 2.5 | 3.5 | 1.5 | 0.5 |
| Embryo | 10 | 5.5 | 5.5 | 1.5 | 1 | 0 |
| Leaf | 10 | 20 | 0 | 10 | 10 | 0 |

All intensities are relative to pact__js-gfg__nos transient expression in the target tissue
Relative intensities were independently scored by three researchers and averaged.

suspension. After 3-10 minutes the *A. tumefaciens* AGL1 suspension medium was removed, and the rice calli were transferred to NB medium containing 100 µM acetosyringone for 48 h. The co-cultivated calli were washed with sterile Milli Q H$_2$O containing 150 mg/L timentin 7 times to remove all *Agrobacterium*, plated on to NB medium containing 150 mg/L timentin and 30 mg/L hygromycin, and cultured for 3 to 4 weeks. Newly-formed buds on the surface of rice calli were excised and plated onto NB Second Selection medium containing 150 mg/L timentin and 50 mg/L hygromycin. After 4 weeks of proliferation calli were plated onto NB Pre-Regeneration medium containing 150 mg/L timentin and 50 mg/L hygromycin, and cultured for 2 weeks. The calli were then transferred on to NB-Regeneration medium containing 150 mg/L timentin and 50 mg/L hygromycin for 3 to 4 weeks. Once shooting occurs, shoots are transferred onto rooting medium (½ MS) containing 50 mg/L hygromycin. Once adequate root formation occurs, the seedlings are transferred to soil, grown in a misting chamber for 1-2 weeks, and grown to maturity in a containment glasshouse.

EXAMPLE 26

Use of Probes from SSS I, SBE I, SBE II and DBE Sequences to Identify Null or Altered Alleles for Use in Breeding Programmes DNA primer sets were designed to enable amplification of the first 9 introns of the SBE II gene using PCR. The design of the primer sets is illustrated in FIG. 24. Primers were based on the wSBE II-D1 sequence (deduced from FIG. 13b and Nair et al, 1997; Accession No. Y11282) and were designed such that intron sequences in the wSBE II sequence were amplified by PCR. These primer sets individually amplify the first 9 introns of SBE II. One primer (sr913F) contained a fluorescent label at the 5' end. Following amplification, the products were digested with the restriction enzyme Dde1 and analysed using an ABI 377 DNA Sequencer with Genescan™ fragment analysis software. One primer set, for intron 5, was found to amplify products from each of chromosomes 2A, 2B and 2D of wheat. This is shown in FIG. 25, which illustrates results obtained with various wheat lines, and demonstrates that products from each of the wheat genomes from diverse wheats were amplified, and that therefore lines lacking the wSBEII gene on a specific chromosome could be readily identified. Lane (iii) illustrates the identification of the absence of the A genome wSBEII gene from the hexaploid wheat cultivar Chinese Spring ditelosomic line 2AS.

FIG. 26 compares results of amplification with an Intron 10 primer set for various nullisomic/tetrasomic lines of the hexaploid wheat Chinese Spring. Fluorescent dUTP deoxynucleotides were included in the amplification reaction. Following amplification, the products were digested with the restriction enzyme DdeI and analysed using an ABI 377 DNA Sequencer with Genescan™ fragment analysis software. In lane (i) Chinese Spring ditelosomic line 2AS, a 300 base product is absent; in lane (ii) N2BT2A, a 204 base product is absent, and in lane (iii) N2DT2B a 191 base product is absent. These results demonstrate that the absence of specific wSBEII genes on each of the wheat chromosomes can be detected by this assay. Lines lacking wSBEII forms can be used as a parental line for breeding programmes for generation of new lines in which expression of SBE II is diminished or abolished, with consequent increase in amylose content of the wheat grain. Thus a high amylose wheat can be produced.

Table 7 shows examples primers pairs for SBE I, SSS I and DBE I which can identify genes from individual wheat genomes and could therefore be used to identify lines containing null or altered alleles. Such tests could be used to enable the development of wheat lines carrying null mutations in each of the genomes for a specific gene (for example SBEI, SSI or DBE I) or combinations of null alleles for different genes.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

Reference cited herein are listed on the following pages, and are incorporated herein by this reference.

TABLE 7

PCR Primers for Starch Biosynthesis Genes

| Gene | Foward Primer | Foward Primer sequence | Reverse Primer | Reverse Primer sequence | Temp (° C.) | Product (bp) |
|---|---|---|---|---|---|---|
| SBE I | ZLE1 5d | GGC GGC GGC AAT GTG CGG CTG AG (SEQ ID NO: 72) | ZLBE1 63 | CCA GAT CGT ATA TCG GAA GGT CG (SEQ ID NO: 26) | 57.3 | A = 625, B = 600, D = 550 |
| SSS I | sssE01F | GAA CTC GCG CCC GAC CTC CT (SEQ ID NO: 73) | ZLSg7 | AGC CAC GAT TAT GCT GTC GAT GG (SEQ ID NO: 28) | 55.0 | A, 450; B = 450; D = 630 |
|  | sssE14F | TTC TCA CCG CTA ACC GTG GAC (SEQ ID NO: 24) | ZLSm19 | GTC TAC ATG ACG TAG GGT TGG TC (SEQ ID NO: 28) | 55.8 | B = 400, D = 500 no A product |
| DBE I | DBEE17F | TGG TCT GAG AAT AGC CGA TTC (SEQ ID NO: 25) | sr1536F | AAGGCCACATAGATCTCG (SEQ ID NO: 29) | 56.8 | B, 190; D, 190, A, 160. Non-specific product 220 bp |

Temp: = annealing temperature, bp = length of the product in base pairs

REFERENCES

Ainsworth, C., Clark, J. and Balsdon, J.
Plant Molecular Biology, 1993 22 67-82
Amemura, A., Chakrabort, R., Fujita, M., Noumi, T. and Futai, M.
Biol. Chem., 1988 263 9271-9275
Baba, T., Kimura, K., Mizuno, K., Etoh, H., Ishida, Y., Shida, O. and Arai, Y.
Biochem. Biophys. Res. Commun., 1991 181 87-94.
Baba, T.; Nishihara, M.; Mizuno, K.; Kawasaki, T.; Shimada, H.; Kobayashi, E.; Ohnishi, S.; Tanaka, K.; Arai, Y.
Plant Physiol, 1993, 103 565-573.
Ball, S.; Guan, H. P.; James, M.; Myers, A.; Keeling, P.; Mouille, G.; Buléon, A.; Colonna, P.; Preiss, J.
Cell, 1996, 86 349-352
Bevan, M., Barnes, W. M., and Chilton, M.
Nucleic Acids Research, 1983, 11 369-385
Black, R. C., Loerch, J. D., McARdle, F. J. and Creech, R. G.

Genetics, 1966 53 661-668
Block, M., Loerz, H., Lutticke, S.
Genbank database Accession number U48227
Burton, R. A., Bewley, J. D., Smith, A. M., Bhattacharya, M. K., Tatge, H., Ring, S., Bull, V., Hamilton, W. D. O. and Martin, C.
The Plant Journal, 1995 7 3-15.
Cangiano, G., La Volpe, A., Poulsen, P. and Kreiberg, J. D.
Plant Physiology, 1993 102 1053-1054.
Clarke, B. C., Mukai, Y. and Appels, R.
Chromosoma, 1996 105 269-275
Devereaux, J., Haeberli, P. and Smithies, O.
Nucleic Acids Res., 1984 12, 387-395.
Denyer, K., Hylton, C. M., Jenner, C. F. and Smith, A. M.
Planta, 1995 196 256-265
Doherty, J. P., Lindeman, R., Trent, R. J., Graham, M. W. and Woodcock, D. M.
Gene, 1992 124 113-120
Dry, I., Smith, A., Edwards, A., Bhattacharyya, M., Dunn, P., Martin, C.
Plant J 1992, 2 193-202
Edwards, A., Marshall, J., Sidebottom, C., Visser, R. G. F., Smith, A. M., Martin, C.
Plant J, 1995 8 283-294
Fisher, D. K., Boyer, C. D. and Hannah, L. C.
Plant Physiology, 1993 102 1045-1046
Forde, B. G., Heyworth, A., Pywell, J. and Forde, M.
Nucleic Acids Research, 1985 13 7327-7339
Gill, B. S. and Appels, R.
Plant Syst. Evol., 1988 160 77-90.
Higgins, T. J. V., Zwar, J. A., Jacobsen, J. V. (1976)
Nature, 1976, 260 166-168
Khandjian, E. W.
Bio/Technology, 1987, 5 165-167
Jahne, A., Lazzeri, P. A., Jager-Gussen, M. and Lorz, H.
Theor. Appl. Genet., 1991 82 47-80
James, M. G., Robertson, D. S. and Myers, A. M.
Plant Cell, 1995 7 417-429
Jolly, C. J., Glenn, G. M. and Rahman, S.
Proc. Natl. Acad. Sci., 1996 93 2408-2413.
Kawasaki, T., Mizuno, K., Baba, T. and Shimada, H.
Molec. Gen. Genet., 1993 237 10-16.
Lagudah, E. S., Appels, R. and McNeill, D.
Genome, 1991 34 387-395
Lazzeri, P. A., Brettschneider, R., Luhrs, R. and Lorz, H.
Theor. Appl. Genet., 1991 81 437-444
Maniatis, T., Fritsch, E. F. and Sambrook, J.
Molecular cloning. A Laboratory Manual., New York. Cold Spring Harbor Laboratory, 1982
Marshall, J.; Sidebottom, C.; Debet, M.; Martin, C.; Smith, A. M.; Edwards, A.
The Plant Cell, 1996 8 1121-1135
Martin, C. and Smith, A.
The Plant Cell, 1995 7 971-985.
McElroy, D., Blowers, A. D., Jenes, B., Wu R.
Mol. Gen. Genet., 1991 231 150-160.
Mizuno, K., Kawasaki, T., Shimada, H., Satoh, H., Koyabashi, E., Okumura, S., Arai, Y. and Baba, T.
J. Biol. Chem., 1993 268 19084-19091.
Muller, M.; Knudsen, S.
Plant J, 1993, 4 343-355
Morell, M. K., Blennow, A., Kosar-Hashemi, B. and Samuel, M. S.
Plant Physiol., 1997 113 201-208.
Morell, M. K., Rahman, S., Abrahams, S. L. and Appels, R.
Aust. J. of Plant Physiol., 1995 22 647-660.
Nair, R., Baga, M., Scoles, G. J., Kartha, K. and Chibbar, R.
Plant Science, 1997 1222 153-163
Nakamura, Y.; Kubo, A.; Shimamune, T.; Matsuda, T.; Harada, K.; Satoh, H.
Plant J, 1997, 12 143-153
Nakamura, T., Yanamori, M., Hirano, H., Hidaka, S. and Nagamine, T.
Molecular and General Genetics, 1995 248 253-259
Nakamura, Y., Takeichi, T., Kawaguchi, K. and Yamanouchi, H.
Physiologia Plantarum, 1992 84 329-335.
Nakamura, Y., Umemoto, T. and Sasaki, T.
Planta, 1996 199 209-214
Rahman, S., Kosar-Hashemi, B., Samuel, M., Hill, A., Abbott, D. C., Skerritt, J. H., Preiss, J., Appels, R. and Morell, M.
Aust. J. Plant Physiol., 1995 22 793-803.
Rahman, S., Abrahams, S., Mukai, Y., Abbott, D., Samuel, M., Morell, M. and Appels, R.
Genome, 1997 40 465-474
Repellin, A., Nair, R. B., Baga, M. and Chibbar, R. N.
Plant Gene Register PGR97-094 (1997)
Sambrook, J., Fritsch, E. F. and Maniatis, T.
Molecular Cloning: A Laboratory Manual (Cold Spring Harbor Laboratory Press, 2$^{nd}$ ed 1989)
Sheen, J., Hwang, S., Niwa, Y., Kobayashi, H., and Galbraith, D. W.
The Plant Journal, 1995 8 777-784
Svensson, B.
Plant Mol. Biol., 1994 25 141-157.
Tanaka, K., Ohnishi, S., Kishimoto, N., Kawasaki, T., Baba, T.
Plant Physiol 1995, 108 677-683
Tingay, S., McElroy, D., Kalla, R., Fieg, S., Wang, M., Thornton, S. and Bretell, R.
The Plant Journal, 1997 11 1369-1376
Wan, Y. and Lemaux, P. G.
Plant Physiology, 1994 104 37-48
Wang, M. B., Upadhyaya, N. M., Brettell, R. I. S., and Waterhouse, P. M.
Journal of Genetics and Breeding, 1997 51 325-334.

The invention claimed is:

1. An isolated nucleic acid molecule, comprising an antisense nucleotide sequence which is at least 90% identical to the complement of a transcript of exon 1 of the SBE II-D1 gene having the sequence set forth in SEQ ID NO: 10, wherein expression of the antisense nucleotide sequence suppresses expression of the SBE II-D1 gene in a plant.

2. The isolated nucleic acid molecule of claim 1, wherein the antisense nucleotide sequence is complementary to a cDNA sequence.

3. The isolated nucleic acid molecule of claim 1, wherein the antisense nucleotide sequence is derived from a *Triticum* species.

4. A recombinant nucleic acid construct, comprising a nucleic acid molecule comprising a nucleotide sequence which is at least 90% identical to exon 1 of the SBE-II D1 gene having the sequence set forth in SEQ ID NO: 10, wherein the nucleic acid molecule is operably linked in an antisense orientation to one or more nucleic acid sequences facilitating expression of said nucleic acid molecule in a plant and suppresses expression of the SBE-II D1 gene when expressed in the plant.

5. The nucleic acid construct of claim 4, wherein the one or more nucleic acid sequences facilitating expression of said nucleotide sequence in a plant functions in the endosperm of a cereal plant.

6. The nucleic acid construct of claim 4, wherein the plant is a cereal plant.

7. The nucleic acid construct of claim 6, wherein the cereal plant is wheat, maize, barley or rice.

8. The nucleic acid construct of claim 7, wherein the cereal plant is wheat.

9. The nucleic acid construct of claim 7, wherein the cereal plant is barley.

10. The nucleic acid construct of claim 4, which is a plasmid or vector which is suitable for use in transformation of a plant.

11. A plant transformed with the nucleic acid construct of claim 4, wherein the nucleic acid construct suppresses expression of the SBE II-D1 gene in the endosperm of a wheat plant relative to a corresponding plant lacking the nucleic acid construct when the nucleic acid construct is expressed in the endosperm of the wheat plant.

12. The transformed plant of claim 11, which is a cereal plant of the family Gramineae.

13. The transformed plant of claim 12, wherein the cereal plant is wheat, maize, barley or rice.

14. The transformed plant of claim 13, wherein the cereal plant is wheat.

15. The transformed plant of claim 13, wherein the cereal plant is barley.

16. The transformed plant of claim 11, wherein said nucleic acid construct further comprises a nucleotide sequence comprising at least a fragment of SEQ ID NO: 10.

17. Seed from the transformed plant of claim 11, comprising said nucleic acid construct.

18. A product comprising plant material from the transformed plant of claim 11, said plant material comprising said nucleic acid construct.

19. The product of claim 18 which is a food product.

20. The food product of claim 19, comprising starch with modified characteristics.

21. A method of reducing the expression of a gene encoding starch branching enzyme II in a plant, comprising the step of introducing the nucleic acid construct of claim 4 into a host plant, wherein said nucleic acid construct suppresses expression of the SBE II-D1 gene in a wheat plant when expressed in the wheat plant.

22. The method of claim 21, wherein the expression of starch branching enzyme II is decreased in the endosperm of the plant.

23. The method of claim 21, wherein the plant is a cereal plant of the family Gramineae.

24. The method of claim 21, wherein the plant is wheat, maize, barley or rice.

25. The method of claim 24, wherein the plant is wheat.

26. The method of claim 25, wherein the plant is barley.

27. The method of claim 21, wherein said nucleic acid construct further comprises a sense nucleotide sequence comprising at least a fragment of SEQ ID NO: 10.

28. The transformed plant of claim 11, wherein expression of the gene encoding starch branching enzyme II is reduced in the endosperm 5 to 8 days after anthesis.

29. The method of claim 22, wherein the expression of starch branching enzyme II in the endosperm is reduced 5 to 8 days after anthesis.

* * * * *

SEQUENCE LISTING

<160> NUMBER OF SEQ ID NOS: 104

<210> SEQ ID NO 1
<211> LENGTH: 18
<212> TYPE: DNA
<213> ORGANISM: Artificial Sequence
<220> FEATURE:

```
<223> OTHER INFORMATION: Description of Artificial Sequence: Synthetic
      primer
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other

<400> SEQUENCE: 1
ggcnacngcn gargaygg                                                18

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tacatttcct tgtccatca                                               19

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
atcacgagag cttgctca                                                18

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cggtacacag ttgcgtcatt ttc                                          23

<210> SEQ ID NO 5
<211> LENGTH: 2687
<212> TYPE: DNA
<213> ORGANISM: Triticum tauschii

<400> SEQUENCE: 5
atcgacgaag atgctctgcc tcaccgcccc ctcctgctcg ccatctctcc cgccgcgccc    60
ctcccgtccc gctgctgacc ggcccggacc ggggatttcg gccaagagca agttctctgt   120
tcccgtgtct gcgccaagag actacaccat ggcaacagct gaagatggtg ttggcgacct   180
tccgatatac gatctggatc cgaagtttgc cggcttcaag gaacacttca gttataggat   240
gaaaaagtac cttgaccaga aacattcgat tgagaagcac gagggaggcc ttgaagagtt   300
ctctaaaggc tatttgaagt ttgggatcaa cacagaaaat gacgcaactg tgtaccggga   360
atgggcccct gcagcaatgg atgcacaact tattggtgac ttcaacaact ggaatggctc   420
```

```
tgggcacagg atgacaaagg ataattatgg tgtttggtca atcaggattt cccatgtcaa    480
tgggaaacct gccatccccc ataattccaa ggttaaattt cgatttcacc gtggagatgg    540
actatgggtc gatcgggttc ctgcatggat tcgttatgca acttttgacg cctctaaatt    600
tggagctcca tatgacggtg ttcactggga tccaccttct ggtgaaaggt atgtgtttaa    660
gcatcctcgg cctcgaaagc ctgacgctcc acgtatttac gaggctcatg tggggatgag    720
tggtgagagg cctgaagtaa gcacatacag agaatttgca gacaatgtgt taccgcgcat    780
aaaggcaaac aactacaaca cagttcagct gatggcaatc atggaacatt ccatattatg    840
cttcttttgg taccatgtga cgaatttctt cgcagttagc agcagatcag gaacaccaga    900
ggacctcaaa tatcttgttg acaaggcaca tagcttaggg ttgcgtgttc tgatggatgt    960
tgtccatagc catgcgagca gtaatatgac agatggtcta aatggctatg atgttggaca   1020
aaacacacag gagtcctatt tccatacagg agaaagggt tatcataaac tgtgggatag    1080
tcgcctgttc aactatgcca attgggaggt cttacggtat cttcttttcta atctgagata   1140
ttggatggac gaattcatgt ttgacggctt ccgatttgat ggagtaacat ccatgctata   1200
taatcaccat ggtatcaata tgtcattcgc tggaaattac aaggaatatt ttggtttgga   1260
taccgatgta gatgcagttg tttacatgat gcttgcgaac catttaatgc acaaaatctt   1320
gccagaagca actgttgttg cagaagatgt ttcaggcatg ccagtgcttt gtcggtcagt   1380
tgatgaaggt ggagtagggt ttgactatcg ccttgctatg gctattcctg atagatggat   1440
tgactacttg aagaacaaag atgaccttga atggtcaatg agtgcaatag cacatactct   1500
gaccaacagg agatatacgg aaaagtgcat tgcatatgct gagagccacg atcagtctat   1560
tgttggcgac aagactatgg catttctctt gatggacaag gaaatgtata ctggcatgtc   1620
agacttgcag cctgcttcac ctacaattga tcgtggaatt gcacttcaaa agatgattca   1680
cttcatcacc atggcccttg gaggtgatgg ctacttgaat tttatgggta atgagtttgg   1740
ccacccagaa tggattgact tccaagaga aggcaacaac tggagttatg ataaatgcag   1800
acgccagtgg agcctctcag acattgatca cctacgatac aagtacatga acgcatttga   1860
tcaagcaatg aatgcgctcg acgacaagtt ttccttccta tcgtcatcaa agcagattgt   1920
cagcgacatg aatgaggaaa agaagattat tgtatttgaa cgtggagatc tggtcttcgt   1980
cttcaatttt catcccagta aaacttatga tggttacaaa gtcggatgtg atttgcctgg   2040
gaagtacaag gtagctctgg actccgatgc tctgatgttt ggtggacatg aagagtggc    2100
ccagtacaac gatcacttca cgtcacctga aggagtacca ggagtacctg aaacaaactt   2160
caacaaccgc cctaattcat tcaaagtcct gtctccaccc cgcacttgtg tggcttacta   2220
tcgcgtcgag gaaaaagcgg aaaagcctaa ggatgaagga gctgcttctt ggggcaaagc   2280
tgctcctggg tacatcgatg ttgaagccac tcgtgtcaaa gacgcagcag atggtgaggc   2340
gacttctggt tccaaaaagg cgtctacagg aggtgactcc agcaagaagg gaattaactt   2400
tgtcttcggg tcacctgaca agataacaa ataagcacca tatcaacgct tgatcagaac    2460
cgtgtaccga cgtccttgta atattcctgc tattgctagt agtagcaata ctgtcaaact   2520
gtgcagactt gagattctgg cttggacttt gctgaggtta cctactatat agaaagataa   2580
ataagaggtg atggtgcggg tcgagtccgg ctatatgtgc caaatatgcg ccatcccgag   2640
tcctctgtca taaggaagt ttcgggctt cagcccagaa taaaaaa                   2687
```

<210> SEQ ID NO 6

<211> LENGTH: 807
<212> TYPE: PRT
<213> ORGANISM: Triticum tauschii

<400> SEQUENCE: 6

Met Leu Cys Leu Thr Ala Pro Ser Cys Ser Pro Ser Leu Pro Pro Arg
1               5                   10                  15

Pro Ser Arg Pro Ala Ala Asp Arg Pro Gly Pro Gly Ile Ser Ala Lys
            20                  25                  30

Ser Lys Phe Ser Val Pro Val Ser Ala Pro Arg Asp Tyr Thr Met Ala
        35                  40                  45

Thr Ala Glu Asp Gly Val Gly Asp Leu Pro Ile Tyr Asp Leu Asp Pro
50                  55                  60

Lys Phe Ala Gly Phe Lys Glu His Phe Ser Tyr Arg Met Lys Lys Tyr
65                  70                  75                  80

Leu Asp Gln Lys His Ser Ile Glu Lys His Glu Gly Gly Leu Glu Glu
                85                  90                  95

Phe Ser Lys Gly Tyr Leu Lys Phe Gly Ile Asn Thr Glu Asn Asp Ala
            100                 105                 110

Thr Val Tyr Arg Glu Trp Ala Pro Ala Ala Met Asp Ala Gln Leu Ile
        115                 120                 125

Gly Asp Phe Asn Asn Trp Asn Gly Ser Gly His Arg Met Thr Lys Asp
130                 135                 140

Asn Tyr Gly Val Trp Ser Ile Arg Ile Ser His Val Asn Gly Lys Pro
145                 150                 155                 160

Ala Ile Pro His Asn Ser Lys Val Lys Phe Arg Phe His Arg Gly Asp
                165                 170                 175

Gly Leu Trp Val Asp Arg Val Pro Ala Trp Ile Arg Tyr Ala Thr Phe
            180                 185                 190

Asp Ala Ser Lys Phe Gly Ala Pro Tyr Asp Gly Val His Trp Asp Pro
        195                 200                 205

Pro Ser Gly Glu Arg Tyr Val Phe Lys His Pro Arg Pro Arg Lys Pro
210                 215                 220

Asp Ala Pro Arg Ile Tyr Glu Ala His Val Gly Met Ser Gly Glu Arg
225                 230                 235                 240

Pro Glu Val Ser Thr Tyr Arg Glu Phe Ala Asp Asn Val Leu Pro Arg
                245                 250                 255

Ile Lys Ala Asn Asn Tyr Asn Thr Val Gln Leu Met Ala Ile Met Glu
            260                 265                 270

His Ser Ile Leu Cys Phe Phe Trp Tyr His Val Thr Asn Phe Phe Ala
        275                 280                 285

Val Ser Arg Ser Gly Thr Pro Glu Asp Leu Lys Tyr Leu Val Asp
290                 295                 300

Lys Ala His Ser Leu Gly Leu Arg Val Leu Met Asp Val Val His Ser
305                 310                 315                 320

His Ala Ser Ser Asn Met Thr Asp Gly Leu Asn Gly Tyr Asp Val Gly
                325                 330                 335

Gln Asn Thr Gln Glu Ser Tyr Phe His Thr Gly Glu Arg Gly Tyr His
            340                 345                 350

Lys Leu Trp Asp Ser Arg Leu Phe Asn Tyr Ala Asn Trp Glu Val Leu
        355                 360                 365

Arg Tyr Leu Leu Ser Asn Leu Arg Tyr Trp Met Asp Glu Phe Met Phe
370                 375                 380

Asp Gly Phe Arg Phe Asp Gly Val Thr Ser Met Leu Tyr Asn His His

-continued

```
            385                 390                 395                 400
        Gly Ile Asn Met Ser Phe Ala Gly Asn Tyr Lys Glu Tyr Phe Gly Leu
                            405                 410                 415
        Asp Thr Asp Val Asp Ala Val Val Tyr Met Met Leu Ala Asn His Leu
                            420                 425                 430
        Met His Lys Ile Leu Pro Glu Ala Thr Val Val Ala Glu Asp Val Ser
                            435                 440                 445
        Gly Met Pro Val Leu Cys Arg Ser Val Asp Glu Gly Val Gly Phe
                    450                 455                 460
        Asp Tyr Arg Leu Ala Met Ala Ile Pro Asp Arg Trp Ile Asp Tyr Leu
        465                 470                 475                 480
        Lys Asn Lys Asp Asp Leu Glu Trp Ser Met Ser Ala Ile Ala His Thr
                            485                 490                 495
        Leu Thr Asn Arg Arg Tyr Thr Glu Lys Cys Ile Ala Tyr Ala Glu Ser
                        500                 505                 510
        His Asp Gln Ser Ile Val Gly Asp Lys Thr Met Ala Phe Leu Leu Met
                        515                 520                 525
        Asp Lys Glu Met Tyr Thr Gly Met Ser Asp Leu Gln Pro Ala Ser Pro
                    530                 535                 540
        Thr Ile Asp Arg Gly Ile Ala Leu Gln Lys Met Ile His Phe Ile Thr
        545                 550                 555                 560
        Met Ala Leu Gly Gly Asp Gly Tyr Leu Asn Phe Met Gly Asn Glu Phe
                            565                 570                 575
        Gly His Pro Glu Trp Ile Asp Phe Pro Arg Glu Gly Asn Asn Trp Ser
                        580                 585                 590
        Tyr Asp Lys Cys Arg Arg Gln Trp Ser Leu Ser Asp Ile Asp His Leu
                        595                 600                 605
        Arg Tyr Lys Tyr Met Asn Ala Phe Asp Gln Ala Met Asn Ala Leu Asp
                    610                 615                 620
        Asp Lys Phe Ser Phe Leu Ser Ser Ser Lys Gln Ile Val Ser Asp Met
        625                 630                 635                 640
        Asn Glu Glu Lys Lys Ile Ile Val Phe Glu Arg Gly Asp Leu Val Phe
                            645                 650                 655
        Val Phe Asn Phe His Pro Ser Lys Thr Tyr Asp Gly Tyr Lys Val Gly
                            660                 665                 670
        Cys Asp Leu Pro Gly Lys Tyr Lys Val Ala Leu Asp Ser Asp Ala Leu
                        675                 680                 685
        Met Phe Gly Gly His Gly Arg Val Ala Gln Tyr Asn Asp His Phe Thr
                    690                 695                 700
        Ser Pro Glu Gly Val Pro Gly Val Pro Glu Thr Asn Phe Asn Asn Arg
        705                 710                 715                 720
        Pro Asn Ser Phe Lys Val Leu Ser Pro Pro Arg Thr Cys Val Ala Tyr
                            725                 730                 735
        Tyr Arg Val Glu Glu Lys Ala Glu Lys Pro Lys Asp Glu Gly Ala Ala
                            740                 745                 750
        Ser Trp Gly Lys Ala Ala Pro Gly Tyr Ile Asp Val Glu Ala Thr Arg
                        755                 760                 765
        Val Lys Asp Ala Ala Asp Gly Glu Ala Thr Ser Gly Ser Lys Lys Ala
                    770                 775                 780
        Ser Thr Gly Gly Asp Ser Ser Lys Lys Gly Ile Asn Phe Val Phe Gly
        785                 790                 795                 800
        Ser Pro Asp Lys Asp Asn Lys
                    805
```

<210> SEQ ID NO 7
<211> LENGTH: 319
<212> TYPE: DNA
<213> ORGANISM: Triticum tauschii

<400> SEQUENCE: 7

```
gcgacttctg gttccaaaaa ggcgtctaca ggaggtgact ccagcaagaa gggaattaac      60
tttgtcttcg ggtcacctga caaagataac aaataagcac catatcaacg cttgatcaga     120
accgtgtacc gacgtccttg taatattcct gctattgcta gtagtagcaa tactgtcaaa     180
ctgtgcagac ttgagattct ggcttggact ttgctgaggt tacctactat atagaaagat     240
aaataagagg tgatggtgcg ggtcgagtcc ggctatatgt gccaaatatg cgccatcccg     300
agtcctctgt cataaagga                                                   319
```

<210> SEQ ID NO 8
<211> LENGTH: 4890
<212> TYPE: DNA
<213> ORGANISM: Triticum tauschii

<400> SEQUENCE: 8

```
gggtggcggg tcgggcggca aggcgcgggg cggcggggcg gccggggcgg cgcggcggcg      60
cgggcggcag cggcggctag ggtttcgcgg cggcggcgac ttgggctgag gcggggcacg     120
ggctgcggct ttaaaggccg gccaggctga ggtgtccggg tcggacacgg cccgtaaggc     180
ggttgacttt aaaaaataat aattcggaca tgcaaaaaag taagaaaaga aataataaac     240
ggactccaaa atcccgaag taaattttc cccattctta aaaataagcc ggacaagatg     300
aacatttatt tgggcctaaa atgcaatttt gaaaaatgcg tattttcct aattcggaat     360
aaaatcaaat aaaatccaaa taaaatcaaa tatttgtttt taatattttt cctccaatat     420
ttcattattt gtgaagaagt cattttatcc catctcatat atttgatat gaaatatttt     480
cggagagaaa ataattaaa acaaatgatc ctatttcaa aatttgagaa acccaaata      540
tgaaaataac gaaatcccca actctctccg tgggtccttg agttgcgtga aatttctagg     600
atcacaaatc aaaatgcaat aaaatatgat atgcatgatg atctaatgta taacattcca     660
attgaaaatt tgggatgtta catataactc aaattctata attatgaaca cagaaatatt     720
aatgtagaac tctattttgt tttgaaattg tattattttt tagaattagt ctagagcatt     780
tcgtgaactt gaatcaaacc tttaaataaa acaaagcata aaaatgacaa attcacatat     840
gaaataactt gtgttacata gatttattac aatagcgttg tatgtgtgta tgtgtgcgtg     900
agtgcctatg gtaatatcaa taaatatctt gatagatgtt tctacaattc acgggtctaa     960
ctagtaatgc aatgcaatgc atgctaaaag aatagaacct tagtttcatt taactaacaa    1020
ttttcaaatg tatgagttgc caacaagtgg catacttggc actgtttgtt tgttcatttt    1080
atggaaagtt cttctctttt tacatggttt agattccagc atgtagccac aaaatatgat    1140
tgtcaaaaga taatacctca taatacaatt ccactaaagt cacctagccc aagtgaccga    1200
cctgatcctg aaataaaatc agaagatttg gtgtcatcat catgacaaca aattattagg    1260
cggtagatct tgtggtagta ctcatgatgt aaaattatca agaggagag aatgtatgga     1320
gatttatgtg aagtacatcg tacaccagac atagttgaca catcgatttt ttaagataca    1380
tttgacgcg ccttgtggga gtgtaaagta ctaccatgta ttagaagagg tgaaatgaga     1440
aatgccatag ctagcaagta ggcctagtta aggaaattct tccttagatc cccttctccc    1500
```

```
gaagagtgaa gtgcttcaac taaaggttag acccacttaa aaaatgtcac tttgaatctt    1560
tgcttccctt gtcgtaatcc tgtgcatttg taggtccctc ggatctgagc cctttctcca    1620
agcccttcat tggattcccc tggatgtctt tttgttacat tttattgaag tgagagtgaa    1680
ttattatatg cccataggag gtgggatata aaggctgttg gtattctgca ccatacatgc    1740
tagagtaggg aggagaggct ggtgcatgat acatggtgga ctagcccata tatttacccc    1800
tcccccaccc actaacaagt tttttttatt aggtcttcat cctctgattt gttttctgt     1860 tagcccattc ttcatcatgg acttattaat catgattagt ttcttggatt tttgtttact    1920
tgacttgaat ttgacaatgt gcctcatata tggcatgtgg gactgatagg aagatatatt    1980
ctcacaacat taacttaaaa aggattattt ttttggtgca gtcgtaaaga aaactacttt    2040
cttttatgct aaaagttatt caaacataga tttataaaca aaggatatca ccatgcatga    2100
ccatgcgctc tctcatgttt actctagaaa ccatatatct ctttgttgca aaatatttaa    2160
tctatcctcc ttgtttctgg gaatgagtcg gggaaggtaa tcttagggaa ggttaaagtg    2220
aggcaagtaa gagcaactct agcagagtcg cgatatgccc aatcgccata atgccaatat    2280
ggcatttttg gcccaaaatg gcacttcaga agagtcacca tatcccttcg gatagccata    2340
atttagggag ctcgctccac aaacaagctt cgagcctcca aatatggagg ccatggattc    2400
gttgtttggc actcactcca tatccaaccg caagcgcatg catgagggaa gttttagctt    2460
cttcctcctt gcgccaacgc cgggatttta cacagcgcat tacaggtaca tgaaccagca    2520
tgcacagata atcaccgacg agtggggtga caagaaggat aagcaccctc ccattagtgg    2580
tgcgcccact cccctcaaat tcatgaggca gccatttgga tggtcatcgc gtggcataag    2640
ctccgactat aaaatctcaa cggcatcacc aaaaccatag ctgccgcctc cccccttcctc   2700 ggcatcacct ccccaagaca tctcctcccc tctatgccac aatgtcatca ttatggagag    2760
acacaactac tggtaaaccg catacccaat catggtttac cggcagtgcg aaccccacct    2820
tcctcccacg atggtaggat attctcctcc tagaatggcg cgtgtggcgc ttcctcctcc    2880
cgaggctgat atgtcggctc ccatgatggc gtgcatcatt gatttggcgc ttcgggtcca    2940
tcatacatgt taacgaggtc atccccattg atgtcgttgg tccccttgcc ccccagtcgg    3000
atcctgagga cccgttcgat gtcgcaatgc gactctccaa actcaaagct cacaatgagg    3060
agtacgtcct ctaggagttc cgccccgcaa ccatctataa ggaggagcaa cgatagctct    3120
cccctacgcc ttcctcgacg atctctctta ggaggacaac ggctagacga cggcggcggc    3180
ggcgaaggta ctgcaggtag tagaacatag caatgtcgaa tggcgacatt gcatattttg    3240
aaaatgtcgc tcaacgactt ttgaagtcgc aaataaaatg tagtgtgact acttttggcc    3300
agcaatataa gtttatcaca tttgataatg atttgaaccg gtgtggttca actaaatgta    3360
ccataaattg aacatacaaa tttttagcaa atgaaaaaag aaacaagtaa gaccacaaat    3420
atgaaagccg catatcgcga ctatgtgttt gagccgcagc tgccaagtac atatgaagcg    3480
tactccatat gacatacgac aaccatacat atgaagactc tactagagtt ctctaaggcc    3540
gcttttagcg cctttcgtgc agtggtgccc ataggggagtg agggtagttg gactgttcgt   3600 ttccccttt ttcatttctt tgaaatctat tttattttt ttctctttg taggtttccc       3660 aaatttatat accattttc tgtttctcgc tatttttgt tgttatattc tagtttcata      3720 ttttctatt attaatttgt gtctcttatg agaagtccag acttgcatat ggaggtgcac     3780
acacaaacat ataagtata aatactaact tgagaagtat gtttgcgtgg tcaaaaaaac      3840
atcatcaaaa cctgccaata tgagatatag ttttgaatat atcaatatga gcaacgcaac    3900
```

-continued

```
catttaaaat gtgaacaatt gttttttag aaaaaatata agaaataact ccaacccagc    3960
caaaccacat gctatacact tgctccatat gaaaccatgt ttgctattgg gcagttgcct    4020
gaaaccgaaa gtaatgttag ccgttttct attcaaagaa gaaggagagt cgaggtgacg    4080
cgatgcttag acgtgagatg gggatgacca caacgtccct acagagacct caccggagat    4140
ggggacattg cagttgacac gagagcggtg aggggctgcg atgcgtgtgc ggcaacatgt    4200
ggcgaggcgg acgtcgggct ggcaggtagg ggggagggg aaggaccggg ggaggaagaa     4260
gaggagtagc ctgcaaaaca tggtacacca gttttctgcc ctacgaaaac ctcatttcat    4320
tcccccaccc tgacaagcaa caaccaacca tcgcagtccc acatgtccct ctggtctttg    4380
caaaaagtaa ttgttcttgc tggacagcgc aaagagtaaa cttttgttag ttttcatttc    4440
tagaaaaagc aatccttta tagttctttt gtgaaagtaa tgcttttata gtgattggga     4500
tgttcttta gagcaaatat cttctttttt ttttagggaa aagagcaaat atcttccact     4560
tttcacaaaa ctgacgaagg ctgaaagtgg cgagacagtg agggcccata gctttcgtcc    4620
ggcccagcgg cgcacgaccg tccacgtgca ccccggccct ccccggcccg cagatccgtt    4680
ctccctcgcc cccgtttccc cctccctccc tctcgttgct tccactccac tgttctcctc    4740
ttcctgtcca aagcggccac ggaccggaaa aaaatcacgc ctttccgttg ggtctccggc    4800
gccacactcc tcctccggcc gatataaagc gcgcggggcc acgggcccgg cgcaaaatgg    4860
gattcccgtc cgccgccatg gaggaagatg                                     4890
```

<210> SEQ ID NO 9
<211> LENGTH: 6228
<212> TYPE: DNA
<213> ORGANISM: Triticum tauschii

<400> SEQUENCE: 9

```
acgggcccgg cgcaaaatgg gattcccgtc cgccgccatc gacgaagatg ctctgcctca      60
ccgcccctc ctgctcgcca tctctcccgc cgcgcccctc ccgtcccgct gctgaccggc      120
ccggaccggg gatctcggtg agtcagtcgg gatcttcatt tcttttcttt tctttcgttt     180
ccggctccgt tctgccgggg tttccctgat gcgatgccgc gcgcgcgcag ggcggcggca     240
atgtgcggct gagcgcggtg cccgcgcccc cttcgctccg ctggtcgtgg ccgcggaagg     300
tgagccctct cccctgtcta cccagatttg cgaccgtgat cccctgttgt cgccgggcaa     360
acggaatctg atccacggtg gttattggaa atagtatata ctactaataa acttgaggct     420
gggattcgtc cactgaggaa caagtggatg cgatttcgat tggatttctc tgctttatgc     480
gatccgtacg cagaatatcc ctcctgcagt gtctcaaccg tattactgga tgtacaaccc     540
aaatgtgtat aatctgtgct gaatgtatca accataatt gctgcattgt gaaaacataa      600
tcctgtgttg tgtctctact acttgttcag tcctgatctg ccgcttatcc taactttttgt    660
tcatttatgg aaggccaaga gcaagttctc tgttcccgtg tctgcgccaa gagactacac     720
catggcaaca gctgaagatg gtgttggcga ccttccgata tacgatctgg atccgaagtt     780
tgccggcttc aaggaacact tcagttatag gatgaaaaag taccttgacc agaaacattc     840
gattgagaag cacgagggag gccttgaaga gttctctaaa ggttagcttt tgtttcatgt     900
gtttgaaaca atagttacat cttgtggcgt ccgcagcaca aaagacataa tgcgactctg     960
ttttgtaggc tatttgaagt ttgggatcaa cacagaaaat gacgcaactg tgtaccggga    1020
atgggcccct gcagcaatgt aagttctagt gttgtcacgc aactaattgc aatggtcgtt    1080
```

```
ggttaactta tgaagtgctg atgaaactgt cttaagagtt tatggcttgt cttttctgat    1140
tctagctagt aaagagtaga taaatatgaa atatgttttc ccttttctag ttatggtcat    1200
ggttggctgg tattcatttc ttttatggca atacttgctt ctaactatct ttagtagatt    1260
catgtattta cttgtgagtc attactttat gggtgtaggg atgcacaact tattggtgac    1320
ttcaacaact ggaatggctc tgggcacagg atgacaaagg ataattatgg tgtttggtca    1380
atcaggattt cccatgtcaa tgggaaacct gccatccccc ataattccaa ggttaaattt    1440
cgatttcacc gtggagatgg actatgggtc gatcgggttc ctgcatggat tcgttatgca    1500
acttttgatg cctctaaatt tggagctcca tatgacggtg ttcactggga tccaccttct    1560
ggtgaaaggt ctacttttag tggctcgaga gcaagaaatc taagtaaaac ccacacaatt    1620
aacttacatt aatgtggaga catgatactt ttattgctcg ttttgcaggt atgtgtttaa    1680
gcatcctcgg cctcgaaagc ctgacgctcc acgtatttac gaggctcatg tggggatgag    1740
tggtgaaaag cctgaagtaa gcacatacag agaatttgca gacaatgtgt taccgcgcat    1800
aaaggcaaac aactacaaca cagttcagct gatggcaatc atggaacatt catattatgc    1860
ttcttttggg taccatgtga cgaatttctt cgcagttagc agcagatcag aacgccagag    1920
acctcaatat cttgttgaca aggcacatag tttacggttg cgtgttctga tggatgttgt    1980
ccatagccat gcgagcagta ataagacaga tggtcttaat ggctatgatg ttgggcaaaa    2040
cacacaggag tcctatttcc acacaggaga aaggggctat cataaactgt gggatagccg    2100
cctgttcaac tatgccaatt gggagtctta cgatttcttc tttctaatct gagatattgg    2160
atggacgaat tcatgtttga tggcttccga tttgatgggg taacatccat gctatataat    2220
caccatggta tcaatatgtc attcgctgga agttacaagg aatattttgg tttggatact    2280
gatgtagatg cagttgttta cctgatgctt gcgaaccatt taatgcacaa actcttgcca    2340
gaagcaactg ttgttgcaga agatgtttca ggcatgccag tgcttttgtcg gtcagttgat    2400 gaaggtggag tagggtttga ctatcgcctg gctatggcta ttcctgatag atggatcgac    2460
tacttgaaga acaaagatga ccttgaatgg tcaatgagtg aaatagcaca tactctgacc    2520
aacaggagat atacggaaaa gtgcattgca tatgctgaga gccatgatca ggtatgtttt    2580
ccctcctttg tcgctgtgcg tgagtatgtg ttcttttttt atggggcact ggtctaagaa    2640
catacagttc aaaggtgaga cactttcttt gcctggtaga caaatttgag aaataaacat    2700
ttcgcttgat gacttttagt tgcttcacaa gttcgaatta agttagttat attctgataa    2760
ctagtgatag tacccactaa ccagctatta cggaccatgt aagaatgtcc gaagactgca    2820
gttatatatc gttgactttg tgttcatcta ttgaaacaac ttagtagtta actttcacgc    2880
aaattttcag tctattgttg gcgacaagac tatggcattt ctcttgatgg acaaggaaat    2940
gtatactggc atgtcagact tgcagcctgc ttcgcctaca attgatcgtg gaattgcact    3000
tcaaaaggtt cgattcgttt taagtattcc tgaatttgat gttctagttc cagacgagta    3060
ttgtaatgtt cgttgttact cagagttctg cttagtcctt gaagataatg tattccagtc    3120 cctttggta catttggctt attttgttac aaatatttca gatgattcac ttcatccacca    3180 tggcccttgg aggtgatggc tacttgaatt ttatgggtaa tgaggtaata tctggttatc    3240
tgtcaaaact tatttctgat caatatgttt cgggattccc tcgaaaaaaa tcctttgggc    3300
agggcgaaaa gtttaaacat ctgttttcta tgatagccaa gtactcccca gctatttcca    3360
tgttatcacg tatcatttag ctgtgccggt agtaatcctt tattctaatt cattgttgtt    3420
ttttagcgtg gcagtctatt gttggatcct cttattccaa ttacatatat gccgacatca    3480
```

-continued

```
cacacttatg aatattccct gtttaaaaga ttttattttt ataccaatgt ttctccgtaa    3540
atgatgcaaa catgatagag atgttagcat gtctttctta acctactcat gttttacata    3600
tcacgacaag cttcttgcag aaaatcagca gtatatggca aattgctgca acctgacaac    3660
gtttatatct gttttctaac tcatactgac ggtgcaattt ccttttagtt tggccaccca    3720
gaatggattg actttccaga agaaggcaac aactggagtt atgataaatg cagacgccag    3780
tggagcctcg cagacattga tcacctacga tacaaggtta tgcctatgta tattttaca    3840 gtttctggtc tggtagctct cttgggatct tgacctcact tagttccttc atctctgact    3900
gtagcttatt tacactgtgt tccaacttct gtcttgtgga taaattctcc cttctaacgt    3960
ttcatattaa gcctttcaaa ctaaactaaa ttgctgatct actactagtt gctcagtacg    4020
atgaccaaat cttgcctgtg gtaacctagt aattttcttg attcttacac attagtgata    4080
tgcagtgcat acattatcca tataaattga cattgcaatt tcccaaatat tatttgaagg    4140
ctgtgttctt ttgttaacag gaagttattt tctctgcatc tgataaataa taatagcctt    4200
tcacgatttt tctcatattt tatccaactt ttctgcattc aagcattttt tgtttctcgc    4260
ctaacatata taatttgaac agtacatgaa cgcatttgat caagcaatga atgcgctcga    4320
cgacaaattt tccttcctat catcatcaaa gcagattgtc agcgacatga atgaggaaaa    4380
gaagtagtta actatacaat gtttagtcag ggcagctgtt gcatcatttg attcactcct    4440
actcttaaga atagcaactc tgacttgtgc gttttatgtt accaaataag ttgaaaccgt    4500
atctgtttga tatgaaccat tgttgtctca aaatgggcta tggactcaat ccaacttcct    4560
ttccagatta ttgtatttga acgtggaatc tggtcttcgt cttcaatttt catcccagta    4620
aaacttatga tgggtaactg atctcttgca agctttgcct ttcaatattt cttctgctta    4680
atgactaatg tgcttaatct cgtttccact tttaaaacac gcagttacaa agtcggatgt    4740
gacttgcctg ggaagtacaa ggtagctctg gactctgatg ctctgatgtt tggtggacat    4800
ggaagagtaa gcaatgttaa tgatgttcaa gatctgtttt gcaacactat gttcttctat    4860 agaagggggcc atcaaggctg catcagataa tcttatttgc agtgttgatc tgtgctgcat    4920
cgcaggtggc ccatgacaac gatcacttta cgtcacctga aggagtacca ggagtacctg    4980
aaacaaactt caacaaccgc cctaactcat tcaaaatcct gtctccatcc cgcacttgtg    5040
tggtaatgct aattactagg aggatttagt aacaataaat aaataacagc aaaagatatc    5100
tgcagtacga tctcacaaaa tgctctcttg ccaggcttac tatcgcgtcg aggagaaagc    5160
ggaaaagccc aaggatgaag gagctgcttt cttggggggaa actgctctcg ggtacatcga    5220
tgttgaagcc actggcgtca aagacgcagc agatggtgag cgacttctg gttccgaaaa    5280 ggcgtctaca ggaggtgact ccagcaagaa gggaattaac tttgtctttc tgtcacccga    5340
caaagacaac aaataagcac catatcaacg cttgatcagg accgtgtgcc gacgtccttg    5400
taatactcct gctattgcta gtagtagcaa tactgtcaaa ctgtgcagac ttgaaattct    5460
ggcttggact ttgctgaggt tacctactat atagaaagat aaataagcgg tgatggtgcg    5520
ggtcgagtcc agctatatgt gccaaatatg cgccatcccg agtcctctgt cataaagaaa    5580
gtttcgggct tccatcccag aataaaaaca gttgtctgtt tgcaatttct ttttgtcttg    5640
catagttaca tgataattga tgcatattgc tataagcctg gattgcatct tcttttgcta    5700
ataactgcag ggccaagaaa gcctagattg tatcttttt tgctaataac tgcagtgctg    5760
gggaagcttc agtccttgtt tccgttctcg agacaaggcg tcatgtttgg cgcacaaagg    5820
```

-continued

```
taagccatca tcttatcaag tcccaaaatt ctctggttga aagaaaccat cactaacttg      5880
ttccaggtgt tggttcctcc acaaccaaaa ggcgaccatc gtcgtcatca tcgctcacag      5940
cactgaccat cgaagccacg gtgggcatga aatgcgcatc gcccaagact tgggaccgtt      6000
tcaaaatatc acaaactgcc atggcatctt ctgccaaagg ctgcactgca cctttggcat      6060
gaacagaagc aacaggggct tggaactgaa cgccgaaaat aaagtcaaac cggctgggcc      6120
ggattgaaag gggaaacgcc aaaatccact taatttgaat ggaaggagga atggttcttg      6180
ctggtttcaa ctctgcaggc ttccctctga atttcacacg gagccatt                   6228
```

<210> SEQ ID NO 10
<211> LENGTH: 11463
<212> TYPE: DNA
<213> ORGANISM: Triticum tauschii

<400> SEQUENCE: 10

```
agaaacacct ccattttaga tttttttttt gttcttttcg gacggtgggt cgtggagaga        60
ttagcgtcta gttttcttaa aagaacaggc catttaggcc ctgctttaca aaaggctcaa       120
ccagtccaaa acgtctgcta ggatcaccag ctgcaaagtt aagcgcgaga ccaccaaaac       180
aggcgcattc gaactggaca gacgctcacg caggagccca gcaccacagg cttgagcctg       240
acagcggacg tgagtgcgtg acacatgggg tcatctatgg gcgtcggagc aaggaagaga       300
gacgcacatg aacaccatga tgatgctatc aggcctgatg gagggagcaa ccatgcacct       360
tttcccctct ggaaattcat agctcacact ttttttttaat ggaagcaaga gttggcaaac      420
acatgcattt tcaaacaagg aaaattaatt ctcaaaccac catgacatgc aattctcaaa       480
ccatgcaccg acgagtccat gcgaggtgga aacgaagaac tgaaaatcaa catcccagtt       540
gtcgagtcga aagaggatg acactgaaag tatgcgtatt acgatttcat ttacatacat        600
gtacaaatac ataatgtacc ctacaatttg ttttttggag cagagtggtg tggtcttttt       660 ttttttacacg aaaatgccat agctggcccg catgcgtgca gatcggatga tcggtcggag      720
acgacggaca atcagacact caccaactgc ttttgtctgg gacacaataa atgttttttgt      780 aaacaaaata aatacttata aacgagggta ctagaggccg ctaacggcat ggccaggtaa       840
acgcgctccc agccgttggt ttgcgatctc gtcctcccgc acgcagcgtc gcctccaccg       900
tccgtccgtc gctgccacct ctgctgtgcg cgcgcacgaa gggaggaaga acgaacgccg       960
cacacacact cacacacggc acactccccg tgggtcccct ttccggcttg gcgtctatct      1020
cctctccccc gcccatcccc atgcactgca ccgtacccgc cagcttccac cccgccgca      1080 cacgttgctc ccccttctca tcgcttctca attaatatct ccatcactcg ggttccgcgc     1140
tgcatttcgg ccggcgggtt gagtgagatc tgggcgactg gctgactcaa tcactacgcg     1200
gggatggcga cgttcgcggt gtccggcgcg actctcggtg tggcgcgggc cggcgtcgga     1260
gtggcgcggg ccggctcgga gcggagggg ggggcggact gccgtcgct gctcctcagg      1320 aagaaggact cctctcgtac gcctcgctct ctcgaatctc ccccgtctgg ctttggctcc     1380
ccttctctct cctctgcgcg cgcatggcct gttcgatgct gttccccaat tgatctccat     1440
gagtgagaga gatagctgga ttaggcgatc gcgcttcctg aacctgtatt ttttcccccg     1500
cggggaaatg cgttagtgtc acccaggccc tggtgttacc acggctttga tcattcctcg     1560
tttcattctg atatatattt tctcattctt tttcttcctg ttcttgctgt aactgcaagt     1620
tgtggcgttt tttcactatt gtagtcatcc ttgcattttg caggcgccgt cctgagccgc     1680
gcggcctctc cagggaaggt cctggtgcct gacggcgaga ggacgacttg gcaagtccgg     1740
```

```
cgcaacctga agaattacag gtacacacac tcgtgccggt aaatcttcat acaatcgtta    1800
ttcacttacc aaatgccgga tgaaaccaac cacggatgcg tcaggtttcg agcttcttct    1860
atcagcattg tgcagtactg cactgccttg ttcattttgt tagccttggc cccgtgctgg    1920
ctcttgggcc actgaaaaaa tcagatggat gtgcattcta gcaagaactt cacaacataa    1980
tgcaccgttt ggggtttcgt cagtctgctc tacaattgct attttcgtg ctgtagatac      2040
ctgaagatat cgaggagcaa acggcggaag tgaacatgac agggggact gcagagaaac      2100
ttcaatcttc agaaccgact cagggcattg tggaaacaat cactgatggt gtaaccaaag    2160
gagttaagga actagtcgtg ggggagaaac cgcgagttgt cccaaaacca ggagatgggc    2220
agaaaatata cgagattgac ccaacactga aagattttcg gagccatctt gactaccggt    2280
aatgcctacc cgctgctttc gctcattttg aattaaggtc ctttcatcat gcaaatttgg    2340
ggaacatcaa agagacaaag actagggacc accatttcat acagatccct tcgtggtctg    2400
agaatatgct gggaagtaaa tgtataattg atggctacaa tttgctcaaa attgcaatac    2460
gaataactgt ctccgatcat tacaattaaa gagtggcaaa ctgatgaaaa tgtggtggat    2520
gggttataga ttttactttg ctaattcctc taccaaattc ctagggggga aatctaccag    2580
ttgggaaact tagtttctta tctttgtggc cttttgttt tggggaaaac acattgctaa      2640
attcgaatga ttttgggtat acctcggtgg attcaacaga tacagcgaat acaagagaat    2700
tcgtgctgct attgaccaac atgaaggtgg attggaagca ttttctcgtg gttatgaaaa    2760
gcttggattt acccgcaggt aaatttaaag ctttattatt atgaaacgcc tccactagtc    2820
taattgcata tcttataaga aaatttataa ttcctgtttt cccctctctt ttttccagtg    2880
ctgaaggtat cgtctaattg catatcttat aagaaaattt atattcctgt tttcccctat    2940
tttccagtgc tgaaggtatc acttaccgag aatgggctcc ctggagcgca tgttatgttc    3000
ttttaagttc cttaacgaga caccttccaa tttattgtta atggtcacta ttcaccaact    3060
agcttactgg acttacaaat tagcttactg aatactgacc agttactata aatttatgat    3120
ctggcttttg caccctgtta cagtctgcag cattagtagg tgacttcaac aattggaatc    3180
caaatgcaga tactatgacc agagtatgtc tacagcttgg caattttcca cctttgcttc    3240
ataactactg atacatctat ttgtatttat ttagctgttt gcacattcct taaagttgag    3300
cctcaactac atcatatcaa aatggtataa tttgtcagtg tcttaagctt cagcccaaag    3360
attctactga atttagtcca tcttttttgag attgaaaatg agtatattaa ggatgaatga    3420
atacgtgcaa cactcccatc tgcattatgt gtgcttttcc atctacaatg agcatatttc    3480
catgctatca gtgaaggttt gctcctattg atgcagatat ttgatatggt cttttcagga    3540
tgattatggt gtttgggaga ttttcctccc taacaacgct gatggatcct cagctattcc    3600
tcatggctca cgtgtaaagg taagctggcc aattatttag tcgaggatgt agcattttcg    3660
aactctgcct actaagggtc ccttttcctc tctgtttttt agatacggat ggatactcca    3720
tccggtgtga aggattcaat ttctgcttgg atcaagttct ctgtgcaggc tccaggtgaa    3780
atacctttca atggcatata ttatgatcca cctgaagagg taagtatcga tctacattac    3840
attattaaat gaaatttcca gtgttacagt tttttaatac ccacttctta ctgacatgtg    3900
agtcaagaca atacttttga atttggaagt gacatatgca ttaattcacc ttctaagggc    3960
taaggggcaa ccaaccttgg tgatgtgtgt atgcttgtgt gtgacataag atcttatagc    4020
tcttttatgt gttctctgtt ggttaggata ttccatttg gcctttgtg accatttact       4080
```

```
aaggatattt acatgcaaat gcaggagaag tatgtcttcc aacatctcaa ctaaacgacc    4140
agagtcacta aggatttatg aatcacacat tggaatgagc agcccggtat gtcaataagt    4200
tatttcacct gtttctggtc tgatggttta ttctatggat tttctagttc tgttatgtac    4260
tgttaacata ttacatggtg cattcacttg acaacctcga ttttattttc taatgtcttc    4320
atattggcaa gtgcaaaact ttgcttcctc tttgtctgct tgttcttttg tcttctgtaa    4380
gatttccatt gcatttggag gcagtgggca tgtgaaagtc atatctattt tttttttgtc    4440
agagcatagt tatatgaatt ccattgttgt tgcaatagct cggtataatg taaccatgtt    4500
actagcttaa gatttcccac ttaggatgta agaaatattg cattggagcg tctccagcaa    4560
gccatttcct accttattaa tgagagagag acaagggggg gggggggggg ggggttccct    4620
tcattattct gcgagcgatt caaaaacttc cattgttctg aggtgtacgt actgcaggga    4680
tctcccatta tgaagaggat atagttaatt ctttgtaacc tacttggaaa cttgagtctt    4740
gaggcatcgc taatatatac tatcatcaca atacttagag gatgcatctg aaattttagt    4800
gtgatcttgc acaggaaccg aagataaatt catatgctaa ttttagggat gaggtgttgc    4860
caagaattaa aaggcttgga tacaatgcag tgcagataat ggcaatccag gagcattcat    4920
actatgcaag ctttgggtat tcacacaatc cattttttc tgtatacact cttcacccat    4980
ttggagctat tacatcctaa tgcttcatgc acataaaata tttggatata atcctttatt    5040
agatatatag tacaactaca cttagtattc tgaaaaagat cattttattg ttgttggctt    5100
gttccaggta ccatgttact aatttttttg caccaagtag ccgttttgga actccagagg    5160
acttaaaatc cttgatcgat agagcacatg agcttggttt gcttgttctt atggatattg    5220
ttcataggta attagtccaa tttaattta gctgttttac tgtttatctg gtattctaaa    5280
gggaaattca ggcaattatg atacattgtc aaaagctaag agtggcgaaa gtgaaatgtc    5340
aaaatctaga gtggcataag gaaaattggc aaaaactaga gtggcaaaaa taaaattttc    5400
ccatcctaaa tggcagggcc ctatcgccga atattttcc attctatata attgtgctac    5460
gtgacttctt ttttctcaga tgtattaaac cagttggaca tgaaatgtat ttggtacatg    5520
tagtaaactg acagttccat agaatatcgt tttgtaatgg caacacaatt tgatgccata    5580
gatgtggatt gagaagttca gatgctatca atagaattaa tcaactggcc atgtactcgt    5640
ggcactacat atagtttgca agttggaaaa ctgacagcaa tacctcactg ataagtggcc    5700 aggcccccact tgccagcttc atactagatg ttacttccct gttgaattca tttgaacata    5760
ttacttaaag ttcttcattt gtcctaagtc aaacttcttt aagtttgacc aagtctattg    5820
gaaaatatat caacatctac aacaccaaat tactttgatc agattaacaa ttttattt    5880 attatattag cacatctttg atgttgtaga tatcagcaca ttttctata gacttggtca    5940 aatatagaga agtttgactt aggacaaatc tagaacttca atcaatttgg atcagaggga    6000
acatcaaata atatagatag atgtcaacac ttcaacaaaa aaatcagacc ttgtcaccat    6060
atatgcatca gaccatctgt ttgctttagc cacttgcttt catatttatg tgtttgtacc    6120
taatctactt ttccttctac ttggtttggt tgattctatt tcagttgcat tgcttcatca    6180
atgattttgt gtaccctgca gtcattcgtc aaataatacc cttgacggtt tgaatggttt    6240
cgatggcact gatacacatt acttccacg tggtccacgc ggccatcatt ggatgtggga    6300
ttctcgtcta ttcaactatg ggagttggga agtatgtagc tctgacttct gtcaccatat    6360
ttggctaact gttcctgtta atctgttctt acacatgttg atattctatt cttatgcagg    6420
tattgagatt cttactgtca aacgcgagat ggtggcttga agaatataag tttgatggat    6480
```

```
ttcgatttga tggggtgacc tccatgatgt atactcacca tggattacaa gtaagtcatc    6540
aagtggtttc agtaactttt ttagggcact gaaacaattg ctatgcatca taacatgtat    6600
catgatcagg acttgtgcta cggagtctta gatagttccc tagtatgctt gtacaatttt    6660
acctgatgag atcatggaag attggaagtg attattattt attttctttc taagtttgtt    6720
tcttgttcta gatgacattt actgggaact atggcgaata ttttggattt gctactgatg    6780
ttgatgcggt agtttacttg atgctggtca acgatctaat tcatggactt tatcctgatg    6840
ctgtatccat tggtgaagat gtaagtgctt acagtattta tgatttttaa ctagttaagt    6900
agttttattt tggggatcag tctgttacac tttttgttag gggtaaaatc tctcttttca    6960
taacaatgct aatttatacc ttgtatgata atgcatcact tagtaatttg aaaagtgcaa    7020
gggcattcaa gcttacgagc atattttttg atggctgtaa tttatttgat agtatgcttg    7080
tttgggtttt tcaataagtg gggtgtgtg actaatgttg tattatttat ttaattgcgg    7140
aagaaatggg caaccttgtc aattgcttca gaaggctaac tttgattcca taaacgcttt    7200
ggaaatgaga ggctattccc aaggacatga attatacttc agtgtgttct gtacatgtat    7260
ttgtaatagt ggtttaactt aaattcctgc actgctatgg aatctcactg tatgttgtag    7320
tgtacacatc cacaaacaag taatcctgag ctttcaactc atgagaaaat agagtccgct    7380
tctgccagca ttaactgttc acagttctaa tttgtgtaac tgtgaaattg ttcaggtcag    7440
tggaatgcct acattttgca tccctgttcc agatggtggt gttggttttg actaccgcct    7500
gcatatggct gtagcagata aatggattga actcctcaag taagtgcagg aatattggtg    7560
attacatgcg cacaatgatc tagattacat tttctaaatg gtaaaaagga aaatatgtat    7620
gtgaatatct agacatttgc ctgttatcag cttgaatacg agaagtcaaa tacatgattt    7680
aaatagcaaa tctcggaaat gtaatggcta gtgtctttat gctgggcagt gtacattgcg    7740
ctgtagcagg ccagtcaaca cagttagcaa tattttcaga aacaatatta tttatatccg    7800
tatatgagaa agttagtata taaactgtgg tcattaattg tgttcacctt ttgtcctgtt    7860
taaggatggg cagtaggtaa taaatttagc cagataaaat aaatcgttat taggtttaca    7920
aaaggaatat acagggtcat gtagcatatc tagttgtaat taatgaaaag gctgacaaaa    7980
ggctcggtaa aaaaaacttt atgatgatcc agatagatat gcaggaacgc gactaaagct    8040
caaatactta ttgctactac acagctgcca atctgtcatg atctgtgttc tgctttgtgc    8100
tatttagatt taaatactaa ctcgatacat tggcaataat aaacttaact attcaaccaa    8160
tttggtggat accagaattt ctgccctctt gttagtaatg atgtgctccc tgctgctgtt    8220
ctctgccgtt acaaaagctg ttttcagttt tttgcatcat tattttttgtg tgtgagtagt    8280 ttaagcatgt ttttttgaagc tgtgagctgt tggtacttaa tacattcttg gaagtgtcca    8340
aatatgctgc agtgtaattt agcatttctt taacacaggc aaagtgacga atcttggaaa    8400
atgggcgata ttgtgcacac cctaacaaat agaaggtggc ttgagaagtg tgtaacttat    8460
gcagaaagtc atgatcaagc actagttggt gacaagacta ttgcattctg gttgatggat    8520
aaggtactag ctgttacttt tggacaaaag aattactccc tcccgttcct aaatataagt    8580
ctttgtagag attccactat ggaccacata gtatatagat gcattttaga gtgtagattc    8640
actcattttg cttcgtatgt agtccatagt gaaatctcta cagagactta tatttaggaa    8700
cggagggagt acataattga tttgtctcat cagattgcta gtgttttctt gtgataaaga    8760
ttggctgcct cacccatcac cagctatttc ccaactgtta cttgagcaga atttgctgaa    8820
```

```
aacgtaccat gtggtactgt ggcggcttgt gaactttgac agttatgttg caattttctg   8880
ttcttattta tttgattgct tatgttaccg ttcatttgct cattcctttc cgagaccagc   8940
caaagtcacg tgttagctgt gtgatctgtt atctgaatct tgagcaaatt ttattaatag   9000
gctaaaatcc aacgaattat ttgcttgaat ttaaatatac agacgtatag tcacctggct   9060
ctttcttaga tgattaccat agtgcctgaa ggctgaaata gttttggtgt ttcttggatg   9120
ccgcctaaag gagtgatttt tattggatag attcctggcc gagtcttcgt tacaacataa   9180
cattttggag atatgcttag taacagctct gggaagtttg gtcacaagtc tgcatctaca   9240
cgctccttga ggttttatta tggcgccatc tttgtaacta gtggcacctg taaggaaaca   9300
cattcaaaag gaaacggtca catcattcta atcaggacca ccatactaag agcaagattc   9360
tgttccaatt ttatgagttt ttgggactcc aaagggaaca aaagtgtctc atattgtgct   9420
tataactaca gttgttttta taccagtgta gttttattcc aggacagttg atacttggta   9480
ctgtgctgta aattatttat ccgacataga acagcatgaa catatcaagc tctctttgtg   9540
caggatatgt atgatttcat ggctctggat aggcttcaac tcttcgcatt gatcgtggca   9600
tagcattaca taaaatgatc aggcttgtca ccatgggttt aggtggtgaa ggctatctta   9660
acttcatggg aaatgagttt gggcatcctg gtcagtcttt acaacattat tgcattctgc   9720
atgattgtga tttactgtaa tttgaaccat gcttttcttt cacattgtat gtattatgta   9780
atctgttgct tccaaggagg aagttaactt ctatttactt ggcagaatgg atagattttc   9840
caagaggccc acaaactctt ccaaccggca aagttctccc ctggaaataa caatagttat   9900
gataaatgcc gccgtagatt tgatcttgta agttttagct gtgctattac attccctcac   9960
tagatcttta ttggccattt atttcttgat gaaatcataa tgtttgttag gaaagatcaa  10020
cattgctttt gtagttttgt agacgttaac ataagtatgt gttgagagtt gttgatcatt  10080
aaaaatatca tgattttttg cagggagatg cagattttct tagatatcgt ggtatgcaag  10140
agttcgatca ggcaatgcag catcttgagg aaaaatatgg ggtatgtcac tggtttgtct  10200
ttgttgcata acaagtcaca gtttaacgtc agtctcttca agtggtaaaa aaagtgtaga  10260
attaattcct gtaatgagat gaaaactgtg caaaggcgga gctggaattg cttttcacca  10320
aaactatttt cttaagtgct tgtgtattga tacatatacc agcactgaca atgtaactgc  10380
agtttatgac atctgagcac cagtatgttt cacggaaaca tgaggaagat aaggtgatca  10440
tcctcaaaag aggagatttg gtatttgttt tcaacttcca ctggagcaat agcttttttg  10500
actaccgtgt tgggtgttcc aagcctggga agtacaaggt atgcttgcct tttcattgtc  10560
cacccttcac cagtagggtt agtggggggct tctacaactt ttaattccac atggatagag  10620
tttgttggtc gtgcagctat caatataaag aatagggtaa tttgtaaaga aaagaatttg  10680
ctcgagctgt tgtagccata ggaaggttgt tcttaacagc cccgaagcac ataccattca  10740
ttcatattat ctacttaagt gttttgtttca atctttatgc tcagttggac tcggtctaat  10800
actagaacta ttttccgaat ctaccctaac catcctagca gttttagagc agccccattt  10860
ggacaattgg ctgggttttt gttagttgtg acagtttctg ctatttctta atcaggtggc  10920
cttggactct gacgatgcac tctttggtgg attcagcagg cttgatcatg atgtcgacta  10980
cttcacaacc gtaagtctgg gctcaagcgt cacttgactc gtcttgactc aactgcttac  11040
aaatctgaat caacttccca attgctgatg cccttgcagg aacatccgca tgacaacagg  11100
ccgcgctctt tctcggtgta cactccgagc agaactgcgg tcgtgtatgc ccttacagag  11160
taagaaccag cagcggcttg ttacaaggca aagagagaac tccagagagc tcgtggatcg  11220
```

```
tgagcgaagc gacgggcaac ggcgcgaggc tgctccaagc gccatgactg ggagggatc     11280 gtgcctcttc cccagatgcc aggaggagca gatggatagg tagcttgttg gtgagcgctc    11340
gaaagaaaat ggacgggcct gggtgtttgt tgtgctgcac tgaaccctcc tcctatcttg    11400
cacattcccg gttgttttg tacatataac taataattgc ccgtgcgctc aacgtgaaaa     11460
tcc                                                                  11463
```

<210> SEQ ID NO 11
<211> LENGTH: 2662
<212> TYPE: DNA
<213> ORGANISM: Triticum tauschii

<400> SEQUENCE: 11

```
tctcccactc ttctctcccc gcgcacaccg agtcggcacc ggctcatcac ccatcacctc      60
ggcctcggcc accggcaaac cccccgatcc gcttttgcag gcagcgcact aaaaccccgg     120
ggagcgcgcc ccgcggcagc agcagcaccg cagtgggaga gagaggcttc gccccggccc     180
gcaccgagcg gggcgatcca ccgtccgtgc gtccgcacct cctccgcctc ctccctgtc     240 ccgcgcgccc acacccatgg cggcgacggg cgtcggcgcc gggtgcctcg cccccagcgt     300
ccgcctgcgc gccgatccgg cgacggcggc ccggggcgtcc gcctgcgtcg tccgcgcgcg    360
gctccggcgc ttggcgcggg gccgctacgt tgccgagctc agcagggagg gccccgcggc    420
gcgccccgcg cagcagcagc aactggcccc gccgctcgtg ccaggcttcc tcgcgccgcc    480
gccgcccgcg ccgcccagt cgccggcccc gacgcagccg cccctgccgg acgccggcgt     540
gggggaactc gcgcccgacc tcctgctcga agggattgct gaggattcca tcgacagcat    600
aattgtggct gcaagtgagc aggattctga gatcatggat gcgaatgagc aacctcaagc    660
taaagttaca cgtagcatcg tgtttgtgac tggtgaagct gctccttatg caaagtcagg    720
ggggctggga gatgtttgtg gttcgttacc aattgctctt gctgctcgtg gtcaccgtgt    780
gatggttgta atgccaagat acttgaatgg gtcctctgat aaaaactatg caaaggcatt    840
atacactggg aagcacatta agattccatg ctttgggga tcacatgaag tgacctttt     900 tcatgagtat agagacaacg tcgattgggt gtttgtcgat catccgtcat atcatagacc    960
aggaagttta tatggagata ttttggtgc tttggtgat aatcagttca gatacacact    1020
cctttgctat gctgcatgcg aggccccact aatccttgaa ttgggaggat atatttatgg    1080
acagaattgc atgtttgttg tgaacgattg gcatgccagc cttgtgccag tccttcttgc    1140
tgcaaaatat agaccatacg gtgtttacag agattcccgc agcacccttg ttatacataa    1200
tttagcacat caggtctgg agcctgcaag tacatatcct gatctgggat tgccacctga    1260
atggtatgga gctttagaat gggtatttcc agaatgggca aggaggcatg cccttgacaa    1320
gggtgaggca gttaactttt tgaaaggagc agtcgtgaca gcagatcgaa ttgtgaccgt    1380
cagtcagggt tattcatggg aggtcacaac tgctgaaggt ggacagggcc tcaatgagct    1440
cttaagctcc cgaaaaagtg tattgaatgg aattgtaaat ggaattgaca ttaatgattg    1500
gaaccccacc acagacaagt gtctccctca tcattattct gtcgatgacc tctctggaaa    1560
ggccaaatgt aaagctgaat tgcagaagga gctgggttta cctgtaaggg aggatgttcc    1620
tctgattggc tttattggaa gactggatta ccagaaaggc attgatctca ttaaaatggc    1680
cattccagag ctcatgaggg aggacgtgca gtttgtcatg cttggatctg gggatccaat    1740
ttttgaaggc tggatgagat ctaccgagtc gagttacaag gataaattcc gtggatgggt    1800
```

```
tggatttagt gttccagttt cccacagaat aactgcaggt tgcgatatat tgttaatgcc      1860
atccaggttt gaaccttgtg gtcttaatca gctatatgct atgcaatatg gtacagttcc      1920
tgtagttcat ggaactgggg gcctccgaga cacagtcgag accttcaacc cttttggtgc      1980
aaaaggagag gagggtacag ggtgggcgtt ctcaccgcta accgtggaca agatgttgtg      2040
ggcattgcga accgcgatgt cgacattcag ggagcacaag ccgtcctggg aggggctcat      2100
gaagcgaggc atgacgaaag accatacgtg ggaccatgcc gccgagcagt acgagcagat      2160
cttcgaatgg gccttcgtgg accaacccta cgtcatgtag acgggactg gggaggtcga       2220 agcgcgggtc tccttgagct ctgaagacat gttcctcatc cttccgcggc ccggaaggat      2280 accctgtac attgcgttgt cctgctacag tagagtcgca atgcgcctgc ttgcttggtc       2340
cgccggttcg agagtagatg acggctgtgc tgctgcggcg gtgacagctt cgggtggatg      2400
acagttacag ttttggggaa taaggaaggg atgtgctgca ggatggttaa cagcaaagca      2460
ccactcagat ggcagcctct ctgtccgtgt tacagctgaa atcagaaacc aactggtgac      2520
tctttagcct tagcgattgt gaagtttgtt gcattctgtg tatgttgtct tgtccttagc      2580
tgacaaatat tagacctgtt ggagaatttt atttatcttt gctgctgttg tttttgtttt      2640
gttaaaaaaa aaaaaaaaaa aa                                               2662
```

<210> SEQ ID NO 12
<211> LENGTH: 768
<212> TYPE: PRT
<213> ORGANISM: Triticum tauschii

<400> SEQUENCE: 12

```
Met Ala Thr Phe Ala Val Ser Gly Ala Thr Leu Gly Val Ala Arg Pro
1               5                   10                  15

Pro Ala Ala Ala Gln Pro Glu Glu Leu Gln Ile Pro Glu Asp Ile Glu
                20                  25                  30

Glu Gln Thr Ala Glu Val Asn Met Thr Gly Gly Thr Ala Glu Lys Leu
            35                  40                  45

Glu Ser Ser Glu Pro Thr Gln Gly Ile Val Glu Thr Ile Thr Asp Gly
        50                  55                  60

Val Thr Lys Gly Val Lys Glu Leu Val Val Gly Glu Lys Pro Arg Val
65                  70                  75                  80

Val Pro Lys Pro Gly Asp Gly Gln Lys Ile Tyr Glu Ile Asp Pro Thr
                85                  90                  95

Leu Lys Asp Phe Arg Ser His Leu Asp Tyr Arg Tyr Ser Glu Tyr Arg
            100                 105                 110

Arg Ile Arg Ala Ala Ile Asp Gln His Glu Gly Gly Leu Glu Ala Phe
        115                 120                 125

Ser Arg Gly Tyr Glu Lys Leu Gly Phe Thr Arg Ser Ala Glu Gly Ile
    130                 135                 140

Thr Tyr Arg Glu Trp Ala Pro Gly Ala His Ser Ala Ala Leu Val Gly
145                 150                 155                 160

Asp Phe Asn Asn Trp Asn Pro Asn Ala Asp Thr Met Thr Arg Asp Asp
                165                 170                 175

Tyr Gly Val Trp Glu Ile Phe Leu Pro Asn Asn Ala Asp Gly Ser Pro
            180                 185                 190

Ala Ile Pro His Gly Ser Arg Val Lys Ile Arg Met Asp Thr Pro Ser
        195                 200                 205

Gly Val Lys Asp Ser Ile Ser Ala Trp Ile Lys Phe Ser Val Gln Ala
    210                 215                 220
```

```
Pro Gly Glu Ile Pro Phe Asn Gly Ile Tyr Tyr Asp Pro Pro Glu Glu
225                 230                 235                 240

Glu Lys Tyr Val Phe Gln His Pro Gln Pro Lys Arg Pro Glu Ser Leu
                245                 250                 255

Arg Ile Tyr Glu Ser His Ile Gly Met Ser Ser Pro Glu Pro Lys Ile
            260                 265                 270

Asn Ser Tyr Ala Asn Phe Arg Asp Glu Val Leu Pro Arg Ile Lys Arg
        275                 280                 285

Leu Gly Tyr Asn Ala Val Gln Ile Met Ala Ile Gln Glu His Ser Tyr
    290                 295                 300

Tyr Ala Ser Phe Gly Tyr His Val Thr Asn Phe Phe Ala Pro Ser Ser
305                 310                 315                 320

Arg Phe Gly Thr Pro Glu Asp Leu Lys Ser Leu Ile Asp Arg Ala His
                325                 330                 335

Glu Leu Gly Leu Leu Val Leu Met Asp Ile Val His Ser His Ser Ser
            340                 345                 350

Asn Asn Thr Leu Asp Gly Leu Asn Gly Phe Asp Gly Thr Asp Thr His
        355                 360                 365

Tyr Phe His Gly Gly Pro Arg Gly His His Trp Met Trp Asp Ser Arg
    370                 375                 380

Leu Phe Asn Tyr Gly Ser Trp Glu Val Leu Arg Phe Leu Leu Ser Asn
385                 390                 395                 400

Ala Arg Trp Trp Leu Glu Glu Tyr Lys Phe Asp Gly Phe Arg Phe Asp
                405                 410                 415

Gly Val Thr Ser Met Met Tyr Thr His His Gly Leu Gln Met Thr Phe
            420                 425                 430

Thr Gly Asn Tyr Gly Glu Tyr Phe Gly Phe Ala Thr Asp Val Asp Ala
        435                 440                 445

Val Val Tyr Leu Met Leu Val Asn Asp Leu Ile His Gly Leu His Pro
    450                 455                 460

Asp Ala Val Ser Ile Gly Glu Asp Val Ser Gly Met Pro Thr Phe Cys
465                 470                 475                 480

Ile Pro Val Pro Asp Gly Gly Val Gly Phe Asp Tyr Arg Leu His Met
                485                 490                 495

Ala Val Ala Asp Lys Trp Ile Glu Leu Leu Lys Gln Ser Asp Glu Ser
            500                 505                 510

Trp Lys Met Gly Asp Ile Val His Thr Leu Thr Asn Arg Arg Trp Leu
        515                 520                 525

Glu Lys Cys Val Thr Tyr Ala Glu Ser His Asp Gln Ala Leu Val Gly
    530                 535                 540

Asp Lys Thr Ile Ala Phe Trp Leu Met Asp Lys Asp Met Tyr Asp Phe
545                 550                 555                 560

Met Ala Leu Asp Arg Pro Ser Thr Pro Arg Ile Asp Arg Gly Ile Ala
                565                 570                 575

Leu His Lys Met Ile Arg Leu Val Thr Met Gly Leu Gly Gly Glu Gly
            580                 585                 590

Tyr Leu Asn Phe Met Gly Asn Glu Phe Gly His Pro Glu Trp Ile Asp
        595                 600                 605

Phe Pro Arg Gly Pro Gln Thr Leu Pro Thr Gly Lys Val Leu Pro Gly
    610                 615                 620

Asn Asn Asn Ser Tyr Asp Lys Cys Arg Arg Arg Phe Asp Leu Gly Asp
625                 630                 635                 640
```

```
Ala Asp Phe Leu Arg Tyr His Gly Met Gln Glu Phe Asp Gln Ala Met
            645                 650                 655
Gln His Leu Glu Glu Lys Tyr Gly Phe Met Thr Ser Glu His Gln Tyr
        660                 665                 670
Val Ser Arg Lys His Glu Glu Asp Lys Val Ile Ile Phe Glu Arg Gly
    675                 680                 685
Asp Leu Val Phe Val Phe Asn Phe His Trp Ser Asn Ser Phe Phe Asp
690                 695                 700
Tyr Arg Val Gly Cys Ser Arg Pro Gly Lys Tyr Lys Val Ala Leu Asp
705                 710                 715                 720
Ser Asp Asp Ala Leu Phe Gly Gly Phe Ser Arg Leu Asp His Asp Val
                725                 730                 735
Asp Tyr Phe Thr Thr Glu His Pro His Asp Asn Arg Pro Arg Ser Phe
            740                 745                 750
Ser Val Tyr Thr Pro Ser Arg Thr Ala Val Val Tyr Ala Leu Thr Glu
        755                 760                 765
```

<210> SEQ ID NO 13
<211> LENGTH: 10337
<212> TYPE: DNA
<213> ORGANISM: Triticum tauschii
<220> FEATURE:
<221> NAME/KEY: modified_base
<222> LOCATION: (10232)..(10232)
<223> OTHER INFORMATION: a, c, t, g, unknown or other

<400> SEQUENCE: 13

| | | | | |
|---|---|---|---|---|
| atggcggcga | cgggcgtcgg | cgccgggtgc | ctcgccccca | gcgtccgcct | gcgcgccgat | 60 |
| ccggcgacgg | cggcccgggc | gtccgcttgc | gtcgtccgcg | cgcggctccg | gcgcttggcg | 120 |
| cggggccgct | acgtcgccga | gctcagcagg | gagggccccg | cggcgcgccc | cgcgcagcag | 180 |
| cagcaactgg | ccccgccgct | cgtgccaggc | ttcctcgcgc | cgccgccgcc | cgcgcccgcc | 240 |
| cagtcgccgg | ccccgacgca | gccgcccctg | ccggacgccg | gcgtggggga | actcgcgccc | 300 |
| gacctcctgc | tcgaaggtaa | aaaacaaggc | tgaatcctca | gatcactccg | cgtcttcgtt | 360 |
| ttaccaaata | cggtactgcg | aagtggtgct | gtatatgtga | agtttctgtc | gatttcttcc | 420 |
| tgacggatgt | tcagtcgatt | cagttgtata | tatgtgatac | gttcgttgtt | catcgatcgt | 480 |
| acagatttac | cagcacacta | gatagaaatc | gagaccgacg | cgggcagatc | aatagatttt | 540 |
| tctagacgtt | ttattggatc | gtgagatgat | tgattggggt | ggcgtgtcga | tacgatagcg | 600 |
| gtgcaccgcc | gatgtatcgg | ggcatgtgca | cgtggttggg | tctcagcaga | catatcacta | 660 |
| gactggtatc | gtaatttact | agtactactg | gaaagaggac | taaaaaggct | aggccaagtg | 720 |
| cacgcatgtt | gggaacgttg | ttaaattgat | gagtttgtcc | tttgcttggg | ctggtattat | 780 |
| taccaaaaaa | tggtgttagt | ccctgtactt | attaatggga | aaatcttaac | atgacactgg | 840 |
| ggtttatgag | tctccaattg | tatattctca | gcactcaact | gattttactg | atactgtagt | 900 |
| ggaaatgaca | cgtgagcacc | ccccttcaag | gaatgcaatg | cttctttctg | ttttatatta | 960 |
| caggaactag | aaggagcttc | cacctttgag | tacagaagta | ctccctccgt | tccaaaatag | 1020 |
| atgactcaac | tttgtactaa | ttttgtacta | tagttagtac | aaagttgagt | catctatttt | 1080 |
| agaacggagg | gagtagtatc | gaaattgaag | acccttgtat | tactgtcttg | ttttcaatg | 1140 |
| aaaatgggag | gcccatgcag | taagtcacat | gggcacctgg | gaggctggga | tcatgtgtgc | 1200 |
| tttgcagagt | actagaccca | gctcacccte | tgttagatta | cttgttgggc | tgctactttg | 1260 |
| tgtttgctgt | gcagtatatc | agacatcctg | aatttggcat | ctagctgaga | acagaatgca | 1320 |

```
ggttgcacca ttcttattat tgctaaactg ttgtcacgca atttataaag aatgtgatct   1380
tctgagtatt aattaatcat gttctgctaa tatctgtcct cgctctggtg ttgacaaata   1440
taccatatga atattttcca ttttgcaacc agggattgct gaggattcca tcgacagcat   1500
aatcgtggct gcaagtgagc aggattctga gatcatggat gcgaatgagc aacctcaagc   1560
taaagttaca cgtagcatcg tgtttgtgac tggtgaagct gctccttatg caaagtcagg   1620
ggggctggga gatgtttgtg gttcgttacc aattgctctt gctgctcgtg gtcaccgtgt   1680
gatggttgta atgccaagat acttgaatgg gtccctctgat aaaaactatg caaaggcatt   1740
atacactgcg aagcacatta agattccatg ctttggggga tcacatgaag tgaccttttt   1800
tcatgagtat agagacaacg tcgattgggt gggtacacaa tcaccttctt attctctgtt   1860
gaattgtagc aactgtttat ccttgtttac acttctttta gccctgcaaa gacatatgtg   1920
atttccatac tttttgtta tttcccttgt actcttgctc atgaaggtca aaatatcata   1980
tatccatgga agtcatgcat gtgcctagta tttttggtgt cggtgccttt aactttcagg   2040
gattaatacg tggaatttga taactaaagt ttatttttatt gaaaaaaatt gtaggttggc   2100
tgagcccaca gccacgcagt ggcaccactg cttgcacatg attttgcatt tctgtttgca   2160
ccgagcactt catgtgaata aggtgtaaaa tcataaagta ccaattttat tctgccaatt   2220
gcacttaaga gtatatacat ttatcttggc ctcaatcatg ggagtactgt gcattcagtg   2280
caccatcatt gttctaagga gaaaatgtgg gtgcaaggaa gacacttttg tcccttaata   2340
aaaggcaggc actctgttgt catatagata gaaagcaaca aacttatttc aaagagctaa   2400
caatggcaaa agaaccaaaa aaagcatgct aaggcggtga caccaaaagg tgaggggggc   2460
cttgtgactg acagcacccc aaactattgc cattgtttta ctaaatgaag atcattttag   2520
aagctctcag gaacttcgaa acagtggctt ttccgtccac agatcgtctg ttaatatttt   2580
tgtccagtga tactttttttt gctccttaca agagtgccta tgttgacata tacattgtta   2640
agttgttcat aagtttactt cttattctaa acagcaagtg cctaatgctt gcatttattt   2700
tggctattta ttttttattct catttcaatc aacacttttg ttcaggtgtt tgtcgatcat   2760
ccgtcatatc atagaccagg aagtttatat ggagataatt ttggtgcttt tggtgataat   2820
caggtacact acactatact aagctcctag ttgactaagt cgtaagttgt acctcctcgc   2880
tgaccggctg ctctatgtcg tgcagttcag atacacactc ctttgctatg ctgcatgcga   2940
ggccccacta atccttgaat tgggaggata tatttatgga cagaattgca tgtttgttgt   3000
gaacgattgg catgccagcc ttgtgccagt gtacgttgtt tgtggatctg aaagtccaat   3060
cctttattca ttctctgctt tgcagtgtgc ccatgtctac atttcttttta tgctttttttc   3120 atgtctgttc ttatattgca tatatgctta tggagtctaa aagttaccgg agggaataac   3180
tcttaaggat ttcctcaatc aattatcttt agctttagtt aacatttact gtggcaaaca   3240
taatgtgttt tgagatttac aagttcagag attgcacttc actagttcgt agctaatctg   3300
atgttttccc cgagaaaatg cctaaagctt tgtgtcttga tgcattgata gaaaagagt   3360 ttatgtacac tcccaaagag gggacccaaa attacaacac cacacccctg agaactaggc   3420
gctgccggaa gaagcgatgc aagcccccact gcccctgcct tagctcaaag ccgggcgtca   3480
gcttgattgt gtcaagtaag ctagcagtgc tagattgcgc aaggtcgatt cgtcgaagat   3540
gacagtgttg cgctgcttcc aaatccacca aactatgagc atgatcactg gagaagtacc   3600 tttctcgcg gctgaggggg tggactggtg gtctgctgct gccagttttc agataatctg   3660
```

```
aaaaatgcat gttttgatga ttttagtatc ttgcggaccc tgggtaccac ctaagctttc   3720
acacagtaat ttgcagttac acctataaaa gtaacggtca tgatatgcat gtgttttggg   3780
tagatcatgg tgcatgcatt ttaggaatta ggacatgcca gaaccacgtg aggcttatgg   3840
ggcaattcat ttgttccatt atacgagtca tgaatatggt tcagcatgtt tggacgctac   3900
ttgtttgggg caatttcaga tggtgaattg tagctgcttg atgttggcta gctggcttat   3960
tttgtacaag tatcgatgtt agatgcatat ttccttttgt tcttgtgctg tttgccatgt   4020
tgtattcccc ttttctgtcg ccagtgttgc atgttaaatt ggttttcatt acataatcaa   4080
ctttgttgct gacatcagtc attttattc agccttcttg ctgcaaaata tagaccatac   4140
ggtgtttaca gagattcccg cagcaccctt gttatacata atttagcaca tcaggtttgg   4200
gtctatcacc tttcattatc cgtacatggc tttgtaagtc ggttcacacg tatcgtcata   4260
ctgtatgtta tttcaatgtc attagggtgt ggagcctgca agtacatatc ctgatctggg   4320
attgccacct gaatggtatg gagctttaga atgggtattt ccagaatggg caaggaggca   4380
tgcccttgac aagggtgagg cagttaactt tttgaaagga gcagttgtga cagcagatcg   4440
aattgtgacc gtcagtcagg tgaaatactc aatacttctc ttttttcttt gcgggatgtt   4500
cttcagttca attgccctgt ctttcaccca attaagaaat gatttaatct tttgtttcta   4560
gggttattca tgggaggtca caactgctga aggtggacag ggcctcaatg agctcttaag   4620
ctcccgaaaa agtgtattga atggtaacta tatttgaatc cacttatctt cttctgaaac   4680
atatttacag aaatagatgg atgggttgca agaataaatt cagtttgctc tttcggtatg   4740
aaggaattgt aaatggaatt gacattaatg attggaaccc caccacagac aagtgtctcc   4800
ctcatcatta ttctgtcgat gacctctctg gaaaggtgtg tggatagtac cctatataat   4860
aacatgtata tctgatctag tactttcttt ttctttgcta gtttgcttcc catgatgttc   4920
tcactaacta atcctatgtg gtttggcata cttgtcaggc caaatgtaaa gctgaattgc   4980
agaaggagct gggtttacct gtaagggagg atgttcctct ggttagatac aaacccctaa   5040
gatatatatt ttttaaatcc ctaaaaaaaa cttgccgatc atctcattag cttgattcac   5100
agattggctt tattggaaga ctggattacc agaaaggcat tgatctcatt aaaatggcca   5160
ttccagagct catgagggag gacgtgcagt ttgtaagttc atattctttt tcttgagact   5220
agagtataaa tcaaacatgt aggtgtgggg tggtataata cagacataag ttccagctat   5280
tgcttccatg agaattttaa tgctattcag taatatgcta ctgcaagttt tgaaacaaag   5340
ttggaagcaa taaatatatg tgtagcactg accatgcagt gccactatag ctggaatgtc   5400
ctgtagtcta tgtgatctaa cacactcaac aacatgtttt cgcatacaaa cacatgcgtg   5460
cgcgcaacaa acatactcta caataaaatt ggcttggtga actgcagaca tgctcttatc   5520
tccattccaa catttcttgt ttcaacattg gctgaagact aagagaaggg ggacccaggg   5580
tgatgtagcc aactagatcc agtaaggaag ctagccgagc ctaggaggat tcgcttaggt   5640
agctggaacg tagggtctct gacagggaag cttcgggagc tagtcgatgc agtggtgagg   5700
agaggtgttg atatcctttg cgtccaagaa accaaatgta ggggacagaa ggcgaaggag   5760
gtggaggata ccggcttcaa gctgtggtac atgggacggc tgcaaacaga aatggcgtag   5820
gcatcttgat caacaagagc cttaagtatg gagtggtaga cgtcaagaga cgtgggaccc   5880
ggattatcct cgtcaagctg gtagttgggg acttagttct caatgttatc agcgtgtatg   5940
ccccgcaagt aggccacaat gagaacgcca agagggagtt ctgggaaggc ctggaagaca   6000
tggttaggag tgtaccgatt ggcgagaagc tcttcatagg aggagacctc aatggccacg   6060
```

```
tgggtacatc taacataggt tttgaagggg cacatgggggg ctttggctat ggcatcaaga    6120
atcaagaaga agatgtctta cgctttgctc tagcctacga catgattgta gctaacaccc    6180
tctttagaaa gagagaatca catctggtga cttttagtag tggccaacac tagccagatc    6240
gatttcatcc tctcgagaag agaagatagg tgtgcgcgcc tagactgcaa ggtgatacct    6300
tcggattcgt gtccagcggg ataagcgtgc caaagtcgct agaatgaagt ggtggaagct    6360
caaggggggag gtagctcagg cgttcaagga gagggtcatt agggagggcc cttgggagga    6420
aggagggggat gcggacaatg tgtggatgaa gatggcgact tgcattcgta aggtggcctc    6480
ggaggagtgt ggagtgtcca ggggatggag aagcgaagat aaggatacct ggtggtggaa    6540
tgatgatgtc cagaaggcaa ttaaagaaa gaaagattgc tttagacgcc tatacttgga    6600
taggagtgca gtcaacatag aaaagtacaa gatggcgaag aaggccgcaa agcgagctgt    6660
cagtgaagca aggggtcggg catatgagga tctctaccaa cggttaggca cgaaggaagg    6720
cgaaagggac atctataaga tggccaagat ccgagagaga ggaagacgag ggatattggc    6780
caagtcaaat gcatcaagga tggagcagac caactcttgg tgaaggacga ggagattaag    6840
catagatggc gggagtactt cgacaagctg ttcaatgggg aggatgagag tcctaccatt    6900
gaacttgacg actcctttga tgagaccatc atgcgtttta tgcggcgaat ccaggagtcc    6960
gaggtcaagg aggctttaaa aaggaggcaa ggcgatgggc cctgattgta tccccattga    7020
ggtgtggaaa ggcctcgggg acatagcgat agtatggcta accaagctat tcaacctcat    7080
ttttcgggca aacaagatgc cagaagaatg gagacgaagt atattagtac caatcatcaa    7140
acagggggga tgttcagagt tgtactaatt accatggaat taagctgatg agccatacaa    7200
tgaagctatg ggagagaatc attgagcacc gcttaagaag aatgacaagc gtgaccaaaa    7260
atcagtttgg tttcatgcct gggaggtcga ccatggaaac catttctg gtacgacaac    7320
ttatggagag atacagggag caaaagaagg acttgcatat ggtgttcatt gacttgaaga    7380
aggcctataa taagataccg cggaatgtca tgtggtgggc cttggagaaa cacaaagtcc    7440
cagcaaagta cattaccctc atcaaggaca tgtacgataa tgttgtgaca agtgttcgaa    7500
caagtgatgt cgacactaat gacttcccga ttaagatagg actgcatcag gggtcagctt    7560
tgagccctta tcttttttgcc ttggtgatgg atgaggtcac aagggatata caaggagata    7620
tcccatggtg tatgctcttt gtggatgatt tggtgctagt tgacgatagt cgggcggggg    7680
taaataacaa gttagagtta tggagacaaa ccttggaatc gaaagggttt aggcttagta    7740
gaactaaaac cgagtacatg atgtgcggtt tcagtactac taggtgtgag gaggaggagg    7800
ttagccttga tgggcaggtg gtaccccaga aggacaccttc tcgatatttg gggtcaatgc    7860
tgcaggagga tgggggtatt gatgaagatg tgaaccatcg aatcaaagct ggatggatga    7920
agtggcgcca agcttctggc attctttgtg acaagagagt gccacaaaag ctaaggcaag    7980
ttctacagga cggcggttcg acccgcaatg ttgtatggcg ctgagtgttg gccgactaaa    8040
aggcgacatg ttcaacagtt aggtgtggcg gagatgcgta tgttgagatg gatgtgtggc    8100
cacacgagga agratcgagt ccggaatgat gatatacgag atagagttgg ggtagcacca    8160
attgaagaga agcttgtcca acatcgtctg agatggtttg gcatattca gcgcacgcct    8220
ccgaaaactc cagtgcataa cggacggcta aagcgtgcgg agaatgtcaa gagagggcgg    8280
ggtagaccga attgacatg ggaggagtcc gttaagagag acctgaaggt ttggagtatt    8340
acgaaagaac tagctatgga carggtgcg tggaagcttg ttatccatgt gccagagcca    8400
```

```
tgagttgatc acgagatctt atgggtttca cctctagcct accccaactt gtttgggact    8460
aaaggctttg ttgttgttgt tgttgttgtt gttgtagcca actaaatcca gttgatcagt    8520
ggtttttact cttattttta caggtcatgc ttggatctgg ggatccaatt tttgaaggct    8580
ggatgagatc taccgagtcg agttacaagg ataaattccg tggatgggtt ggatttagtg    8640
ttccagtttc ccacagaata actgcagggt atgccgagaa cttcttaaca agaccttcgt    8700
tatcagcttg gatatattat aatgttcaaa acatttatgt ctctcttttt gtgcagttgc    8760
gatatattgt taatgccatc caggtttgaa ccttgtggtc ttaatcagct atatgctatg    8820
caatatggta cagttcctgt agttcatgga actgggggcc tccgagtaag caactgcct     8880 tgaaaattat cgttatcttg gctccaacgc aaatgttcta attggctcgt gtattcaaca    8940
ggacacagtc gagaccttca acccttttgg tgcaaaagga gaggaggggta cagggtacgc   9000 actgctcaat tttagctaac tttcagttta tcttttgca atgtcttggg ggttcattgc     9060
gccataaatc aacttgtgat aattaactgt tactgttctg tacttgcagg tgggcgttct    9120
caccgctaac cgtggacaag atgttgtggg taagtttttg ctgagctctt gtccggttat    9180
aggatcgacc ttggctgtag catggtacct tagtgccct tgtatataga cctaacctga     9240
tggactcact ttgtctacac taatcatagt agtcgattgc ccggaggcgt tttgcttgga    9300
ttctgctaat ttaattttca tgacgataac tcataccatg gtttggttct ccgatggggg    9360
ccagaatggc gtctagtgtc tgcgatctgt gtaactagcc aatgccgggt tgttccaagt    9420 gaaaattttac cttttgacca ttgtgcaggc attgcgaacc gcgatgtcga cattcaggga   9480
gcacaagccg tcctgggagg ggctcatgaa gcgaggcatg acgaaagacc atacgtggga    9540
ccatgccgcc gagcagtacg agcagatctt cgaatgggcc ttcgtggacc aaccctacgt    9600
catgtagacg gggactgggg aggtcgaagc gcgggtctcc ttgagctctg aagacatgtt    9660
cctcatcctt ccgcggcccg gaaggatacc cctgtacatt gcgttgtcct gctacagtag    9720
agtcgcaatg cgcctgcttg cttggtccgc cggttcgaga gtagatgacg gctgtgctgc    9780
tgcggcggtg acagcttcgg gtggatgaca gttacagttt tggggaataa ggaagggatg    9840
tgctgcagga tggttaacag caaagcacca ctcagatggc agcctctctg tccgtgttac    9900
agctgaaatc agaaaccaac tggtgactct ttagccttag cgattgtgaa gtttgttgca    9960
ttctgtgtat gttgtcttgt ccttagctga caaatatttg acctgttgga taattctatc   10020
tttgctgctg ttttttcttt ggtcaaaaga ggggttccct ccgatttcat taacgaaacc   10080
accaaaataa cagcacccag tgcaggtctc aggttcagat atacttaaga ctactaaatc   10140
taacagcagc taaaaagctt aaagattcag gcgacataac cgaacaaaat ccacaaccga   10200
agggaccaaa gcaggacaag taaaaaggca gncgacacaa agcgcaggtc gctgaaaagg   10260
caagcagaca gaggtctgca ttctgtcaac accacttgtg aaaaatgaag agaagatcga   10320
gaattcccgg gaatccg                                                  10337
```

<210> SEQ ID NO 14
<211> LENGTH: 647
<212> TYPE: PRT
<213> ORGANISM: Triticum tauschii

<400> SEQUENCE: 14

Met Ala Ala Thr Gly Val Gly Ala Gly Cys Leu Ala Pro Ser Val Arg
1               5                   10                  15

Leu Arg Ala Asp Pro Ala Thr Ala Ala Arg Ala Ser Ala Cys Val Val
            20                  25                  30

```
Arg Ala Arg Leu Arg Arg Leu Ala Arg Gly Arg Tyr Val Ala Glu Leu
         35                  40                  45

Ser Arg Glu Gly Pro Ala Ala Arg Pro Ala Gln Gln Gln Gln Leu Ala
 50                  55                  60

Pro Pro Leu Val Pro Gly Phe Leu Ala Pro Pro Pro Ala Pro Ala
 65                  70                  75                  80

Gln Ser Pro Ala Pro Thr Gln Pro Pro Leu Pro Asp Ala Gly Val Gly
                 85                  90                  95

Glu Leu Ala Pro Asp Leu Leu Leu Glu Gly Ile Ala Glu Asp Ser Ile
                100                 105                 110

Asp Ser Ile Ile Val Ala Ala Ser Glu Gln Asp Ser Glu Ile Met Asp
                115                 120                 125

Ala Asn Glu Gln Pro Gln Ala Lys Val Thr Arg Ser Ile Val Phe Val
                130                 135                 140

Thr Gly Glu Ala Ala Pro Tyr Ala Lys Ser Gly Gly Leu Gly Asp Val
145                 150                 155                 160

Cys Gly Ser Leu Pro Ile Ala Leu Ala Ala Arg Gly His Arg Val Met
                165                 170                 175

Val Val Met Pro Arg Tyr Leu Asn Gly Ser Ser Asp Lys Asn Tyr Ala
                180                 185                 190

Lys Ala Leu Tyr Thr Gly Lys His Ile Lys Ile Pro Cys Phe Gly Gly
                195                 200                 205

Ser His Glu Val Thr Phe Phe His Glu Tyr Arg Asp Asn Val Asp Trp
                210                 215                 220

Val Phe Val Asp His Pro Ser Tyr His Arg Pro Gly Ser Leu Tyr Gly
225                 230                 235                 240

Asp Asn Phe Gly Ala Phe Gly Asp Asn Gln Phe Arg Tyr Thr Leu Leu
                245                 250                 255

Cys Tyr Ala Ala Cys Glu Ala Pro Leu Ile Leu Glu Leu Gly Gly Tyr
                260                 265                 270

Ile Tyr Gly Gln Asn Cys Met Phe Val Val Asn Asp Trp His Ala Ser
                275                 280                 285

Leu Val Pro Val Leu Leu Ala Ala Lys Tyr Arg Pro Tyr Gly Val Tyr
                290                 295                 300

Arg Asp Ser Arg Ser Thr Leu Val Ile His Asn Leu Ala His Gln Gly
305                 310                 315                 320

Leu Glu Pro Ala Ser Thr Tyr Pro Asp Leu Gly Leu Pro Pro Glu Trp
                325                 330                 335

Tyr Gly Ala Leu Glu Trp Val Phe Pro Glu Trp Ala Arg Arg His Ala
                340                 345                 350

Leu Asp Lys Gly Glu Ala Val Asn Phe Leu Lys Gly Ala Val Val Thr
                355                 360                 365

Ala Asp Arg Ile Val Thr Val Ser Gln Gly Tyr Ser Trp Glu Val Thr
                370                 375                 380

Thr Ala Glu Gly Gly Gln Gly Leu Asn Glu Leu Leu Ser Ser Arg Lys
385                 390                 395                 400

Ser Val Leu Asn Gly Ile Val Asn Gly Ile Asp Ile Asn Asp Trp Asn
                405                 410                 415

Pro Thr Thr Asp Lys Cys Leu Pro His His Tyr Ser Val Asp Asp Leu
                420                 425                 430

Ser Gly Lys Ala Lys Cys Lys Ala Glu Leu Gln Lys Glu Leu Gly Leu
                435                 440                 445
```

```
Pro Val Arg Glu Asp Val Pro Leu Ile Gly Phe Ile Gly Arg Leu Asp
    450                 455                 460

Tyr Gln Lys Gly Ile Asp Leu Ile Lys Met Ala Ile Pro Glu Leu Met
465                 470                 475                 480

Arg Glu Asp Val Gln Phe Val Met Leu Gly Ser Gly Asp Pro Ile Phe
                485                 490                 495

Glu Gly Trp Met Arg Ser Thr Glu Ser Ser Tyr Lys Asp Lys Phe Arg
            500                 505                 510

Gly Trp Val Gly Phe Ser Val Pro Val Ser His Arg Ile Thr Ala Gly
        515                 520                 525

Cys Asp Ile Leu Leu Met Pro Ser Arg Phe Glu Pro Cys Gly Leu Asn
    530                 535                 540

Gln Leu Tyr Ala Met Gln Tyr Gly Thr Val Pro Val Val His Gly Thr
545                 550                 555                 560

Gly Gly Leu Arg Asp Thr Val Glu Thr Phe Asn Pro Phe Gly Ala Lys
                565                 570                 575

Gly Glu Glu Gly Thr Gly Trp Ala Phe Ser Pro Leu Thr Val Asp Lys
            580                 585                 590

Met Leu Trp Ala Leu Arg Thr Ala Met Ser Thr Phe Arg Glu His Lys
        595                 600                 605

Pro Ser Trp Glu Gly Leu Met Lys Arg Gly Met Thr Lys Asp His Thr
    610                 615                 620

Trp Asp His Ala Ala Glu Gln Tyr Glu Gln Ile Phe Glu Trp Ala Phe
625                 630                 635                 640

Val Asp Gln Pro Tyr Val Met
                645

<210> SEQ ID NO 15
<211> LENGTH: 5072
<212> TYPE: DNA
<213> ORGANISM: Triticum tauschii

<400> SEQUENCE: 15
tctagatgca tgctggatag cggtcgatgt gtggagtaat agtagtagat gcagaatcgt    60
ttcggtctac ttgtcgcgga cgtgatgcct atatacatga tcatacctag atattctcat   120
aactatgctc aattctatca attgctcgac agtaattcgt ttaccaccg taatacttat    180 gatcttgaga gaagtcacta gtgaaaccta tgcccccag gtctattttg catcatatta   240
atcttccaat acttagttat ttccattgcc gtttatttta ctttgtatct ttatttcttt   300
ttattataaa aaataccaaa aatattatct tatcatatct atcagatctc attctcgtaa   360
gtgaccgtga agggattgac aacccctta tcgtgttggt tgcgaggttc ttgtttgttt    420
gtgtaggtgc gtgtgactcg cacgtctcct actggattga taccttgggt tttcaaaaac   480
tgagaaaaat acttacgcta ctttactgca taacccttc ctctttaaaa aaaaaaacca    540
acgtagtatt caagaggtag cacgctacca tcctctccaa caggagcgcg gagatctttg   600
tccggcaggt tgatgcgggc cggggaagaa ctccagctgc cttggccagc ttggtcgtga   660 gccgcccag cggcgtcttg aacctgtcca cgtagcgctc cctgacacgc ggcgtgaact    720
gagaaggctt gtcgatgaac tccagctgtt gtgccagcct agcttgcgcc ttcttctgct   780
gggtcatgcc cttcgagaaa cccaccttgg ccacccttgt gcttgagcgg cgcgccacct   840
cagcaggcgg cggcgtgggg atgaagaggg tgtctgcttc cggagcaggc gggtcggcgt   900
tgaacttgaa aggcggtggc cccatgatgg atggggggag catgccaaag acttggttga   960
```

```
ggaaagtggt gttggcgtcc acctccagtg cctgcagttt ggaagccaga cgattggcgt    1020
cgatctctgg ctccggctgg aaggaggctc gacgctccgg tgtgccagaa cgcaaaggga    1080
ggagcggcag ctctggctga gcagaccccg cgcccatgta ctctgcattg gccaaggct     1140 gcagggcaa gccaccggga tgggggcgcg aggtggactg cgcaccggag gaaggccaag     1200
ctcaacctcg gtgaggttcg ccccagacca gggcggcagg ctcgggtcca caaagggcca    1260
aaccgcctcg tccgccccga aactgtccag gacagacggc ggacgacgga aggccgtgtc    1320
gtcgagctcg agcagcagag ggtccgtgcg ggtgatgtct tgccaaatgg actccacctc    1380
cagcaggaag ggggactggt ccatcgcccc tggccaagcc actggtacgc caaagatggc    1440
atcagcagcg tttgcaccag ggggagcagc cacaccttgg aggacaggga gggtgcggac    1500
gtcgacggca gcaaaacgtg gctggagcaa gttgccgtcg cgtgccggcc tcggcgagcg    1560
cgagcggctg taggagcgct cggtgccctc agactcggac agtgcgccag tgggagagcc    1620
atggcgacgc cggccaccac tggacgtgcc atggcgctgg tcctgacggc gcctggatgg    1680
cccgtcctcg cgggcagctc cacctgagcg gcacccgagg agcacacccc gccaagctgg    1740
gccagggcgc ctgcggcgac ggcgacggcc gcggtcgcgg tctgcaccat catcttcatc    1800
ttcgtcatcg tggcgcctcg gacaaggatg ctcgctgtca ccgacgcgag ggacgtgagc    1860
cggctcagcc cgcccttcct cgacgtggcg agccctgcgg atatgctcct cgagcggca    1920 ttgggggtcg ttggcgcgcg gcatctcggg gtcgcggtca gctatcgggg tgtagtcctt    1980
tgtggtgtcc aggtggatga gcagagagaa atccggcccc tctagcccct cgtcccgggg    2040
gcagccctcc ggcagcgtct ggcggcccct ggggtccagg ggtcgatcga tgatggagaa    2100
cccccttttg gtggggatgt cgtccggact ccatgcccac acccaggcaa agaggcaggc    2160
cgtgttggag agggaggtcg tctgccgctc caaccagtcg acgtggcatg tcttcccgag    2220
cgcatcctgc cccgcctcct tgttccagga ctgcaccggc atgttctcga cggcgatgcg    2280
gcagtagtac cgccagacac ggcggtggcc gtgtgccgat ggtgaccagg ccgacaggga    2340
gagcgcgacg ccccagcagg agacgacccc agcgtcgaaa gcgatgtccc ggtgcctgaa    2400
gtggacgagc ccagagatgg ccaggcgcat tgacgcgggg aagggaagg agttaggatg     2460 ggcgacgcgg ccggagtgaa ccgcggcgtg gtggccgacg gggctggaga ggcagaggcg    2520
gagtcatccg agagaggtgt atcagtggct ctgcacaata cccagtgtcg ccacatcata    2580
tcctgctgaa taaccacaca tgtgtactgt cgttaaataa atcattggtc acgcgaaccc    2640
ggaaaaagac ggcgaaaaat tcacggacac acgactagta gtacccaata tactcggcaa    2700
aaacagtgac acgtcgtttt gcgttgtcgg ccggtgttgt cgagtcattg tactatgttt    2760
tgtcgtttct ttctttctc caaatcgaca aaccgtttgt ctttggttaa aaacagaaa      2820 catacaaaat caaatgaatg cattcaaggg ccggtaatcc aattctgagc ccaggctcag    2880
ctacacccgc ccttacaaaa aaatcaaaat aaatactaga aaaattcaaa aaattccaat    2940
ttgtttgtgc gtggtagata atttgatgcg tgaggtacgc ttcaattttc aaattatttg    3000
gacatctgag cagctctcag caaaaaagac aaattcgggg tctgtaaaaa tgtttactgt    3060
tcatgcactg ttctgacccg atttgtcttt tttgctgaga gcttctcaga agtccaaatg    3120
agctaaaatt ttgagcggag cttacgtgat aaaatgtcta tcatgcaaaa aaggattgga    3180 atttttttgaa ttttttttat ttttttgtgat ttgtttcctg gacgggtgca gataagcctg    3240
ggcaccgaaa cgccgcactc aggctcatcc tttttctataa aagaaaagaa atacatacaa    3300
tttccctctg ttttttgagc aaggggcacc acccaccaaa gagttttcaa ctcacatggt    3360
```

-continued

| | |
|---|---|
| attagagcat ctacagccgg gcgtctcaaa ccagcctcat acgcttgagc gggtcgcctt | 3420 |
| ggtcacgatt ttttgaccca gacgggcccc tcaaacggtc cttaaacgcc caggctgacc | 3480 |
| gacaacccac atatccagcc caaatatggg gtggatatgg gggcgcccgg gcacgccagc | 3540 |
| ccgcggacac cacacatctt cagtttctaa tttgagatat ccggatgtgg aatgcgtttt | 3600 |
| tgaggggtga ccggtccctg tccgtggatg cgcccggacg tttgaggggt tggatttgcc | 3660 |
| aagtctgatt agagatgctc ttaggtgttc cacccccatc ccttgatggc tagggcaaac | 3720 |
| tctcccctcc aaactttgtc ggcgagcctg tggattcttc tctcctctgc ccgctgctcc | 3780 |
| ggcggctgat ggcggggagg agaatcccgg tgtcttcgct tggttagttg tttaagttac | 3840 |
| gtacttttt agtcctcgca ggtgcggcgt tcggacgtat ggtcgtgctt cttttttgag | 3900 |
| tttgtcttcc gggctctgat cctcctcgag ttcgtccatc tggacgtact cgacggagct | 3960 |
| ccggcataga ttcctatcat cgtcttggtg aggtgaggtt atggtttctt gtcatgtggg | 4020 |
| cagatttggt gccagatgct tcatatctat tcaagggttc agcggcaaca actgcggctc | 4080 |
| cagagcgatg gtccttaagg gcacgtgcac gaagacttca cggctgttat cgacaaggtc | 4140 |
| aagccggctc cgataggga gcagcgacag cggcgcgtca accgctcgtt ctggcggcag | 4200 |
| tagtggtcgt tcggtgctct cggaacctcg atgtaatttt tatgatttta gagatgcttt | 4260 |
| gtacttccga tcgatgaact ctgataatag atatctcttc tctcgcaaaa aaagagagtt | 4320 |
| ttcaactgaa acaaaagag tttcactagt tcttcttta gaaacagagt ttcactagca | 4380 |
| ctttttttg cgagaagtcg agtttcacta agtactaaac ccacgcaatt attctcaaaa | 4440 |
| aaaaaaccca cgcaactgtc tggatccatc ttcgttttt ccccgagaat cgtctggatc | 4500 |
| catttcgtg tgcgaggcat cctctcattt tgcacggccc agctctcttc tcgccggcgt | 4560 |
| acgctgctac atgtcggcac tccacgcaaa caaaagaag cccaaccgaa acgcacgcg | 4620 |
| cctttccagg ctcaccacgg aaaaaaatac cacgcgccgc tcacgagcaa accgtgacaa | 4680 |
| cagccagcca gatatggcaa cggaggcacg ggccgcacac agccactgaa accgcagct | 4740 |
| gctcttccgt ccgtccgtcc ctccgcccgt ccgcgccact ccactcgcct tgccccactc | 4800 |
| ccactcttct ctccccgcgc acaccgagtc ggcaccggct catcacccat cacctcggcc | 4860 |
| tcggccaccg gcaaaccccc cgatccgctt ttgcaggcag cgcactaaaa ccccggggag | 4920 |
| cgcgccccgc ggcagcagca gcaccgcagt gggagagaga ggcttcgccc cggcccgcac | 4980 |
| cgagcggggc gatccaccgt ccgtgcgtcc gcacctcctc cgcctcctcc cctgtcccgc | 5040 |
| gcgcccacac ccatggcggc gacgggcgtc gg | 5072 |

<210> SEQ ID NO 16
<211> LENGTH: 1706
<212> TYPE: DNA
<213> ORGANISM: Triticum tauschii

<400> SEQUENCE: 16

| | |
|---|---|
| gctgtgtcga agcttgacta tttgaaggag cttggagtta attgtattga attaatgccc | 60 |
| tgccatgagt tcaacgagct ggagtactca acctcttctt ccaagatgaa cttttgggga | 120 |
| tattctacca taaacttctt ttcaccaatg acgagataca catcaggcgg gataaaaaac | 180 |
| tgtgggcgtg atgccataaa tgagttcaaa acttttgtaa gagaggctca caaacgggga | 240 |
| attgaggtga tcctggatgt tgtcttcaac catacagctg agggtaatga gaatggtcca | 300 |
| atattatcat ttagggggggt cgataatact acatactata tgcttgcacc caaggggagag | 360 |

```
ttttataact attctggctg tgggaatacc ttcaactgta atcatcctgt ggttcgtcaa      420
ttcattgtag attgtttaag atactgggtg atggaaatgc atgttgatgg ttttcgtttt      480
gatcttgcat ccataatgac cagaggttcc agtctgtggg atccagttaa cgtgtatgga      540
gctccaatag aaggtgacat gatcacaaca gggacacctc ttgttactcc accacttatt      600
gacatgatca gcaatgaccc aattcttgga ggcgtcaagc tcattgctga agcatgggat      660
gcaggaggcc tctatcaagt aggtcaattc cctcactgga atgtttggtc tgagtggaat      720
gggaagtacc gggacattgt gcgccaattc attaaaggca ctgatggatt tgctggtggt      780
tttgccgaat gtctttgtgg aagtccacac ctataccagg caggaggaag gaaaccttgg      840
cacagtatca actttgtatg tgcacatgat ggatttacac tgggtgattt ggtaacatat      900
aataacaagt acaatttacc aaatggggag aacaatagag atggagaaaa tcacaatctt      960
agctggaatt gtgggaggag gagaattgca agattgt ctgtcaaaag attgaggaag           1020
aggcagatgc gcaatttctt tgtttgtctc atggtttctc aaggagttcc aatgttttac      1080
atgggcgatg aatatggcca cacaaagggg gcaacaaca atacatactg ccatgattct       1140
tatgtcaatt attttcgctg gataaaaaa gaacaatact ctgacttgca cagattctgc        1200
tgcctcatga ccaaattccg caaggagtgc gagggtcttg gccttgagga cttccaacg       1260 gccgaacggc tgcagtggca tggtcatcag cctgggaagc ctgattggtc tgagaatagc      1320
cgattcgttg cctttccat gaaagatgaa agacagggcg agatctatgt ggccttcaac       1380
accagccact accggccgt tgttgagctc ccagagcgcg cagggcgccg gtgggaaccg        1440
gtggtggaca caggcaagcc agcaccatat gacttcctca ccgacgactt acctgatcgc      1500
gctctcacca taccagtt ctctcatttc ctcaactcca acctctaccc catgctcagc         1560
tactcatcgg tcatcctagt attgcgccct gatgtttgag agacaaatat atacagtaaa      1620
taatatgtct atatgtagtc ctttggcgta ttatcagtgt gcacaattgc tctattgcca      1680
gtgatctatt cgatagcggc cgcgaa                                           1706
```

<210> SEQ ID NO 17
<211> LENGTH: 9289
<212> TYPE: DNA
<213> ORGANISM: Triticum tauschii

<400> SEQUENCE: 17

```
cgggaccgtc ccttggcaac ttgggttacg ttgggacctg acgcttcgct tatccggtgt       60
gccctgagac gagatatgtg cagctcctat cggatttgtc ggcacattcg gcggctttgc      120
tggtcttgtt ttaccattgt cgaaatgtct tataaaccgg gattccgaga ctgatcgggt      180
cttcccggga gaaggtttat ccttcgttga ccgtgagagc ttataatggg ctaagttggg      240
acacccctgc agggtattat ctttcgaaag ccgtgcccgc ggttatgagg cagatgggaa      300
tttgttaatg tccgattgta gagaacctgt cacttgactt aatttaaaat tcatcaaccg      360
tgtgtgtagc cgtgatggtc tcttttcggc ggagtccggg aagtgaacac ggtttgagtt      420
atgcatgaac gtaagtagtt tcaggatcac tccttgatca cttctagctc cgcgaccgtt      480
gcgttgtttc tcttctcgct ctcatttgcg tatgttagcc accatatatg cttagtgtct      540
gctgcagctc cacctcatta ccccttcctt tcctataagc ttaaatagtc ttgatctcgc      600
gggtgtgaga ttgctgagtc ctcgtgactt acagattcta ccaaaacagt tgcaggtgtc      660
gacgatgcca gtgcaggtga cgcaaccgag ctcaagtggg agttcgacga ggaacgtggt      720
cgttactatg tttcttttcc tgatgatcag tagtggagcc cagttgggac gatcggggat      780
```

```
ctagcatttg gggttatctt aatttctttt agatttgacc gtaatcggtc tatgtgtgga    840
ttttggatga tgtatgaatt atttatgtat tgtgtgaagt ggcgattgta agccaactct    900
cgttatccca ttcttgttca ttacatggga ttgtgtgaag atgacccttc ttgcgacaaa    960
accacaatgc ggttatgcct ctaagtcgtg cctcgacacg tgggagatat agccgcatcg   1020
tgggcgttac acgcaagtct tcatagcaac caaaactcct ctccgcatta caagccacca   1080
atcgcagcca ccatgacttt cttcaccact gtcaatgcca tgaaaatcta tatgtagaca   1140
tgtcccattg catcggcaag aaagcgaagc ttcacggcac accttcatga agcctctctg   1200
gccgaagaca aggatgcgcc cgaccggatc aattcctatc tagataccta gtggagccat   1260
cgcgcaatag cggagatctc cgagaggaag accggaactc gtcggacgtc ggcgtccaaa   1320
tcgaggaggc cggcatgaag cacatcgagg atggtgatcc ccatacgggt agatcgggtc   1380
ggccgccatc tcacaccgag attaggatgc ttaaaacggt ttttttggca ctagcattat   1440
tttgcatcat ccgttggaga aacatgaga gagccccatt tcttccacgg ttctacctat   1500
gggatcttgt tctgcttgca accgggcctc acggaaaacc cgcgccagcg acccaccccc   1560
atgctagcag ggcacggcac ccgcagcggc cggtccaaat ggacggtgag aaccgcaacg   1620
cgacacgccc ggcactgtca gcaaagcgag agcgcgcgca cggcacacgc acgctcggac   1680
gaacggacgg tgcgatcgat ccctccccc tcgctcaacc acagtagtac cctgccacac   1740
tatcacgcac gcactcgagt cacacctccc acgaagaacc aacaggaggc gcggatccca   1800
ccgataaata accccgcctc gccgctcctc cccaaaatca atcaccgatc gctcggggtt   1860
cccggcatga cgatgatggc catggccaag gcgccctgcc tctgcgcgcg cccgtccctc   1920
gccgcgcgcg cgaggcggcc ggggccgggg ccggcgccgc gcctgcgacg gtggcgaccc   1980
aatgcgacgg cggggaaggg ggtcggcgag gtgtgcgccg cggttgtcga ggcggcgacg   2040
aaggccgagg atgaggacga cgacgaggag gaggcggtgg cggaggacag gtacgcgctc   2100
ggcggcgcgt gcagggtgct cgccggaatg cccgcgccgc tgggcgccac cgcgctcgcc   2160
ggcggggtca atttcgccgt ctactccggt ggagccaccg ccgcggcgct ctgcctcttc   2220
acgccagaag atctcaaggc ggtgggggttg cctcccgagt agagttcatc agctttgcgt   2280
gcgccgcgcg cccccttttc tggcctgcga tttaagtttt gtactggggg aaatgctgca   2340
ggatagggtg acggaggagg tttcccttga cccctgatg aatcggactg ggaacgtgtg   2400
gcatgtcttc attgaaggcg agctgcacga catgctttac gggtacaggt tcgacggcac   2460
ctttgctcct cactgcgggc actaccttga tatttccaat gtcgtggtgg atccttatgc   2520
taaggtgatc atactttagc tttacctgca tcttggtatt tacagtagaa attgttacgt   2580
ggacccttat ttgttgcctt ttgtgttgct ctaggcagtg ataagccgag gggagtatgg   2640
cgttccggcg cgtggtaaca attgctggcc tcagatggct ggcatgatcc ctcttccata   2700
tagcacggta tgcctgattg ctgaaaatat tggctgcatt tgtttctctc tttttctcat   2760
attttctcc tgtctttcac ttgtactaca ttgcctcaga cagtcatgat caaagagagc   2820
agtgtcatta gacatttgta gttgtctgct gactttgacc aaaacttgta atttactgtt   2880
gttaaaggtc cttgaatcat attttttat aatattatgt ttgcaagtgg aagtaaagtg   2940
aaattgcatc tagtatttgt tgttgctgtc ttagtcgttt aattggacat gcagtaaaaa   3000
ggtttgcatc tgcagtttga ttgggaaggc gacctacctc taagatatcc tcaaaaggac   3060
ctggtaatat atgagatgca cttgcgtgga ttcacgaagc atgattcaag caatgtagaa   3120
```

```
catccgggta ctttcattgg agctgtgtcg aagcttgact atttgaaggt acagctgtac      3180
ttgctgacta cataggataa tttttaaaga aagctacata ttagccagaa tttgggttat      3240
tacaaaaact actgcatact atagcagtta catgctcatt atcgaggaga tgctcacacg      3300
catcttattt ggatttaata cccaattctg ttttgatatt ggactgttcc ctctacagga      3360
gcttggagtt aattgtattg aattaatgcc ctgccatgag ttcaacgagc tggagtactc      3420
aacctcttct tccaagtaag gacatgaatt tagtattagc ctgccagcac tgtttgagtg      3480
agagttcata cacattttgt gcctgcataa ctgatatttg ttcaaactat ttttttttagc     3540
agtcactcaa cagtttttaca tatatatata atatagacta ttcgtcaccc tgggtgagga    3600
atagttattc ttcacccacc tctattttaa catctatgca ccgtaatttt acgtttcgta     3660
aatttgtctt attttagaga taaaagaga acgtaagaaa acctataatc gtcgtaaaaa      3720
aaaatatgtt acgtaaaatt acaaatgtaa aaacatagtg taaaatgtac ataaaataca     3780
ttttttgacc tatatttttt ttgttaatgc caaattttat acagtaaatc aatatgaatg     3840
taactatttg tatttcaaat gtaatttatt tatgaaatgg tcgtaagatt acctcgggtg     3900
aagaataact tattctgcac cctgggtgat gaatagtaac actatatata tatatatata    3960
tatatatata tatatatacc ggctgctgct aatgatgtta atatttcgca agtacctaag    4020
ctggatttt ctccatgaga catcaatcca taattgaaat tggtcacgac agttgaatag     4080
ttgatagctg aaaatgaaat ccagcatgct actgtcttgc catctccaga cttgctaaca    4140
tgaatttttgt ctgcctacct gtcatttgta ccaacgttcc caattgccct ctcattattc   4200
gtgtgtacca tgcatatgtg ttttaacatg attattgttg gctatatttc tctttggaaa    4260
catgactaat ttatcacccg ttttgtataa actgcttgtt ttcatatcag gatgaacttt    4320
tggggatatt ctaccataaa cttctttttca ccaatgacga gatacacatc aggcgggata   4380
aaaaactgtg ggcgtgatgc cataaatgag ttcaaaactt tgtaagaga ggctcacaaa     4440
cggggaattg aggtaagcaa gtcgtacgag ttagttgctc cttttgaact tatcaatttg    4500
atgcgaagac atgttactgc taggtgatcc tggatgttgt cttcaaccat acagctgagg    4560
gtaatgagaa tggtccaata ttatcattta gggggtcga taatactaca tactatatgc     4620
ttgcacccaa ggtgacagat cttcttgct gcgtaattgt tctttcatag atgtatagag     4680
catagatgtg ttatgtagta gttctttttc aaggggatta tgttcatgca gggagagttt    4740
tataactatt ctggctgtgg gaataccttc aactgtaatc atcctgtggt tcgtcaattc    4800
attgtagatt gtttaaggta cagatataca ttttacttct agaactactt tttcatttct    4860
tttgctgctt gtcatttga tatgattaat ttgcaagctt gtggggtaa atcttttggt     4920
cagcatattg tatcttttaaa tgtcacaaat actaatgtcc tggtgcttat tgatttggca    4980
tcttcaaatt cttctccaat gaaaagggaa aaatctactg tatgtctcgt caactaattt    5040
actttttgttt tgcagatact gggtgatgga aatgcatgtt gatggttttc gttttgatct   5100
tgcatccata atgaccagag gttccaggta atttgtattt attgtttgtt tgcgtgttgc    5160
cttttcagaa gattcttaaa agaatgtttc ttttacaagt ctgtgggatc cagttaacgt    5220
gtatggagct ccaatagaag gtgacatgat cacaacaggg acacctcttg ttactccacc   5280
acttattgac atgatcagca atgacccaat tcttggaggc gtcaaggtac ttgtttcatc    5340
caacacctgt tgtctgtgtg cattcaattg ttttaatatg gtaatgatca atttcccaat    5400
gttgataagg aaaaaaaatg caagtagctc tctttatctg cttcttgtga gttatgctaa    5460
acatgtagat actactatat ttcaactgta tatacttgac atattattgc ttccttggga    5520
```

```
ggctctctta ttcctttccc ccgttgcaat tatagctcat tgctgaagca tgggatgcag    5580
gaggcctcta tcaagtaggt caattccctc actggaatgt ttggtctgag tggaatggga    5640
aggtaaggta cctgttaaaa gtttgaatgg caaatactga tagaaatata acttatattt    5700
gcgacatata tagataaagc aaaataatac gcattccacc tgaactttaa aggggcacgc    5760
agaattatcc cgcatctgtc tacaagaatg ataacacatg tgctgaatag tgaagtacta    5820
cttctcaaat gtctgaatga acgcactaac tcttgtgagt gtcaaccgag caagaaatat    5880
ttgagttttc tgcaagaaat tgttcatgtt gtgctgtatt atactccctc cgtccgaaat    5940
tatttgtcgg agaaatggat gtatctagac gtattttagt tctagataca tccattttta    6000
tccatttctg caacaagtag ttccggacgg agggagtatc atttaacaaa tatatgcatg    6060
ttcgaagtaa atccccacga ataagcatat aagacgatat tgcttttgga cttgcaacac    6120
ctaaacctca ttgttttctc ctaggatttt gggtgttcga agcaagcagc tggtgatatt    6180
taatttacct ttgcctttat ttgtagcttg atttgagggt gcggcaaagg ttttagctta    6240
gtagtgtttt gtaaattatt atagtttatg tatatactcc tcatttgggc acttccgtac    6300
tggtcccata gaagataaaa atggaatgat gtctggccaa taattgttga caacactgtt    6360
gcgcatttga tttttatcag ggaatggaaa attgaaatcg gtaagaaaca ttgcgatatt    6420
aagcttgtat atgctaatgc tggtggatct ttaagaggga acatatgatc tcgtgtgcat    6480
ccatcttcaa ctaaaaaaat atgttgcaca tctcccacgt cacttactag ctatttcatc    6540
caagtactaa cttgtgtggt tgtctcctca gtaccgggac attgtgcgcc aattcattaa    6600
aggcactgat ggatttgctg gtggttttgc cgaatgtctt tgtggaagtc cacacctata    6660
ccaggtaagt tgtggcaata cttggaaatg ggttgagtga atgtcacatg gattttttat    6720
atataccaca tgatgataca catgtaaata tataacgatt atagtgtatg catatgcatt    6780
tggctaagaa gtactccctc ccttagtaaa agttagtaca aagttgagtc atctattttg    6840
gaacggaggg agtataagtg tatacactag tgcaatatat aggttttaac acccaacttg    6900
ccaatgaagg aacatagggc tttctagtta tcttatttat ttgtctggtg aataatccac    6960
tgaaaaattc cagccatgtc attttttagg gggggagaag aaactacatt gattttttccc    7020 cctaaaaaaa gccatctcag atttcatagg taacttgctt ttctgtaaag aaatgaaaac    7080
gacttcatac tttctgtcga ttataagtgt atacactagt gcaatatata ggttttaaca    7140
cccaacttgc caatgaagga acatagggct ttctagttat cttatttatt tgctggtgaa    7200
taatccactg aaaaattcca gccatgtcat tttttagggg ggagaagaaa ctatattgat    7260 tttttccccct aaaaaagcc atctcagatt cataggaact tgcttttctg taaagaaatg    7320
aaaacgactt catactttct gcggcgctta cttagctcga tggatatttg taagatgaat    7380
gccaaattat ttggcgggat ttgatcgtta ttccaaattt catttggttt ctctagcaat    7440
caacccagta ccttgttatt ggcactgcaa tttcttattg attaatcagg caggaggaag    7500
gaaaccttgg cacagtatca acttggtatg tgcacatgat ggatttacac tgggtgattt    7560
ggtacatata ataccaagtc aatttaccaa atggggagac caatagagat ggagaaaatc    7620
acaatcttag ctggaattgt ggggaggtaa ttctgaactc tccttttttt ttgaaatttt    7680
catgctttac ataatagtca aatggctgac aaatgtcgtt gtatggttct ctctacctaa    7740
accgttaagg cagtaagagt ttccctacaa gatctctttg ttcgtataat tgtattttct    7800
agagaaaagt tgccttcaat tttgtgcacg cggcagtaca ggaattgtgg ttataaatat    7860
```

-continued

```
tgatacaggc tgaccatcgt tactaatagg gggaacaata agcacatttt tttaatagca    7920
aaggcatcac ccttgttccg tttccaatga aatcacagta tccgaaccat aagttttaca    7980
agtatgcgta gagagaaata aagtatcaac ccggcagaaa cagttgtttc aggcgcaaag    8040
agaaaaggaa acgatatgct ctattacatc aaccttttag catttaggga cgaccagcat    8100
catcccatct tcaatcaact ggagcgaggt cacctccaat cttctcagca gcctcagagt    8160
ggtgacctcc caagcaagtg catcagcatc catcatctgg gggttgggca cataccatga    8220
gcacaatcac ctgaatttga tgaattttcc tctgtttacc ttgcagcaga cccctgccgt    8280
ataaatggtt ttaaatgaca gcatgttctt tcagtttgag caaaatttgt gcaattgcaa    8340
agaagcttta gaatcatgtg aacatgcac ttacatttca tctgacaata taggaaggag    8400
agcccgacgt cgcatgctcc tctagactcg aggaattcgc aagattgtct gtcaaaagat    8460
tgaggaagag gcagatgcgc aatttctttg tttgtctcat ggtttctcaa gtaagactta    8520
tatctgatct cttcaatttt tgagattgcc tgttttcac aatggcatat gttgtcaggt    8580
gaaacatcca atcccagtat taatagagcc aacatgaagg gattgcttat ctgagatatc    8640
tgccaaagtt gaattcttag attccacttc ttcagtattt cagaccttct aagcattttc    8700 atttttttt tcaattgtta gggagttcca atgttttaca tgggcgatga atatggccac    8760
acaaaagggg gcaacaacaa tacatactgc catgattctt atgtcagtac aatttggtca    8820
catattgttg ttctaagtaa ctatcttcaa atctttgcat tcatccgtca tggctcttct    8880
gtaggtcaat tattttcgct gggataaaaa agaacaatac tctgacttgc aaagattctg    8940
ctgcctcatg accaaattcc gcaagtaagt attccgttga ataatttctg tgtagaacca    9000
ctgaaggtgc ctccaaacgc taagcgagca aggtcaattt cacaccctaa tcaagttggt    9060
gttgtctatt tgtgtatttg atctgctgca ctgtagggag tgcgagggtc ttggccttga    9120
ggactttcca acggccgaac ggctgcagtg gcatggtcat cagcctggga agcctgattg    9180
gtctgagaat agccgattcg ttgccttttc catggtacac atatagttct gacacttcac    9240
tatagttgtt ttaaaaaaga aaatttaact caaaagtaaa ttatggaga                9289
```

<210> SEQ ID NO 18
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18 rtgastcat                                                              9

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ctcgttgctt cyactccact                                                 20

<210> SEQ ID NO 20
<211> LENGTH: 135
<212> TYPE: DNA
<213> ORGANISM: Artificial Sequence

```
<220> FEATURE:
<223> OTHER INFORMATION: Description of Artificial Sequence: Synthetic
      construct

<400> SEQUENCE: 20
gcggccgctc cctggccgac ttggccgaag cttgcatgcc tgcaggtcga ctctagagga      60
tccccgggta ccgagctcga attcatcgat gatatcagat ccgggccctc tagatgcggc    120
cgcatgcata agctt                                                     135

<210> SEQ ID NO 21
<211> LENGTH: 50
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 21
cgcgcgccca caccctgcag gtcgactcta gaggatccat ggtgagcaag                50

<210> SEQ ID NO 22
<211> LENGTH: 50
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 22
gcgactggct gactcaatca ctacgcgggg atccatggtg agcaagggcg                50

<210> SEQ ID NO 23
<211> LENGTH: 50
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 23
ggactcctct cgcgccgtcc tgagccgcgg atccatggtg agcaagggcg                50

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ttctcaccgc taaccgtgga c                                               21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tggtctgaga atagccgatt c                                               21

<210> SEQ ID NO 26
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ccagatcgta tatcggaagg tcg                                               23

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
agccacgatt atgctgtcga tgg                                               23

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gtctacatga cgtagggttg gtc                                               23

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
aaggccacat agatctcg                                                     18

<210> SEQ ID NO 30
<211> LENGTH: 16
<212> TYPE: PRT
<213> ORGANISM: Oryza sativa

<400> SEQUENCE: 30

Ala Thr Ala Arg Lys Asn Lys Thr Met Val Thr Val Val Glu Glu Val
1               5                   10                  15

<210> SEQ ID NO 31
<211> LENGTH: 16
<212> TYPE: PRT
<213> ORGANISM: Zea mays

<400> SEQUENCE: 31

Ala Thr Val Gln Glu Asp Lys Thr Met Ala Thr Ala Lys Gly Asp Val
1               5                   10                  15

<210> SEQ ID NO 32
<211> LENGTH: 21
<212> TYPE: PRT
<213> ORGANISM: Oryza sativa

<400> SEQUENCE: 32
```

Ala Ala Gly Ala Ser Gly Glu Val Met Ile Pro Glu Gly Glu Ser Asp
1               5                   10                  15

Gly Met Pro Val Ser
            20

<210> SEQ ID NO 33
<211> LENGTH: 20
<212> TYPE: PRT
<213> ORGANISM: Triticum tauschii

<400> SEQUENCE: 33

Ala Ala Ser Pro Gly Lys Val Leu Val Pro Asp Gly Glu Ser Asp Asp
1               5                   10                  15

Leu Ala Ser Tyr
            20

<210> SEQ ID NO 34
<211> LENGTH: 21
<212> TYPE: PRT
<213> ORGANISM: Zea mays

<400> SEQUENCE: 34

Ala Ala Ala Ala Ala Arg Lys Ala Val Met Val Pro Glu Gly Glu Asn
1               5                   10                  15

Asp Gly Leu Ala Ser
            20

<210> SEQ ID NO 35
<211> LENGTH: 13
<212> TYPE: PRT
<213> ORGANISM: Triticum tauschii

<400> SEQUENCE: 35

Ser Arg Val Cys Ala Lys Arg Leu His His Gly Asn Ser
1               5                   10

<210> SEQ ID NO 36
<211> LENGTH: 20
<212> TYPE: PRT
<213> ORGANISM: Triticum tauschii

<400> SEQUENCE: 36

Pro Cys Leu Arg Gln Glu Thr Thr Pro Trp Gln Gln Leu Lys Met Val
1               5                   10                  15

Leu Ala Thr Phe
            20

<210> SEQ ID NO 37
<211> LENGTH: 16
<212> TYPE: PRT
<213> ORGANISM: Triticum tauschii

<400> SEQUENCE: 37

Gly Pro Tyr Val Ala Glu Leu Ser Pro Glu Gly Pro Ala Ala Pro Pro
1               5                   10                  15

<210> SEQ ID NO 38
<211> LENGTH: 161
<212> TYPE: DNA
<213> ORGANISM: Triticum tauschii
<220> FEATURE:
<221> NAME/KEY: CDS
<222> LOCATION: (3)..(161)

```
<400> SEQUENCE: 38 at act aca tac tat atg ctt gca ccc aag gga cac ttt tat aac tat        47
   Thr Thr Tyr Tyr Met Leu Ala Pro Lys Gly His Phe Tyr Asn Tyr
    1               5                  10                  15 tct ggc tgt ggg aat acc ttc aac tgt aat cat cct gtg gtt cgt caa       95
Ser Gly Cys Gly Asn Thr Phe Asn Cys Asn His Pro Val Val Arg Gln
                 20                  25                  30 ttc att gta gat tgt tta aga tac tgg gtg acg gaa atg cat gtt gat      143
Phe Ile Val Asp Cys Leu Arg Tyr Trp Val Thr Glu Met His Val Asp
             35                  40                  45 ggt ttt cgt ttt gac ctt                                              161
Gly Phe Arg Phe Asp Leu
         50

<210> SEQ ID NO 39
<211> LENGTH: 53
<212> TYPE: PRT
<213> ORGANISM: Triticum tauschii

<400> SEQUENCE: 39

Thr Thr Tyr Tyr Met Leu Ala Pro Lys Gly His Phe Tyr Asn Tyr Ser
 1               5                  10                  15

Gly Cys Gly Asn Thr Phe Asn Cys Asn His Pro Val Val Arg Gln Phe
             20                  25                  30

Ile Val Asp Cys Leu Arg Tyr Trp Val Thr Glu Met His Val Asp Gly
         35                  40                  45

Phe Arg Phe Asp Leu
     50

<210> SEQ ID NO 40
<211> LENGTH: 34
<212> TYPE: PRT
<213> ORGANISM: Triticum tauschii

<400> SEQUENCE: 40

Ile Leu His Thr Ile Cys Leu His Pro Arg Asp Thr Phe Ile Thr Ile
 1               5                  10                  15

Leu Ala Val Gly Ile Pro Ser Thr Val Ile Ile Leu Trp Phe Val Asn
             20                  25                  30

Ser Leu

<210> SEQ ID NO 41
<211> LENGTH: 13
<212> TYPE: PRT
<213> ORGANISM: Triticum tauschii

<400> SEQUENCE: 41

Tyr Tyr Ile Leu Tyr Ala Cys Thr Gln Gly Thr Leu Leu
 1               5                  10

<210> SEQ ID NO 42
<211> LENGTH: 256
<212> TYPE: DNA
<213> ORGANISM: Zea mays

<400> SEQUENCE: 42
tgaggtgatc atggatgttg tcttcaatca tacagctgaa ggtaatgaga aaggcccaat      60
attatccttt aggggataga taatagtac atactacatg cttgcaccta agggagagtt     120
ttataattat tctggttgtg gaaataccctt caattgtaat catcctgtag tccgtgaatt    180
```

```
tatagtggat tgcttgagat actgggtaac agaaatgcat gttgatggtt ttcgttttga      240
ccttgcatct atactg                                                     256

<210> SEQ ID NO 43
<211> LENGTH: 254
<212> TYPE: DNA
<213> ORGANISM: Triticum tauschii
<220> FEATURE:
<221> NAME/KEY: modified_base
<222> LOCATION: (139)..(139)
<223> OTHER INFORMATION: a, c, t, g, unknown or other
<220> FEATURE:
<221> NAME/KEY: modified_base
<222> LOCATION: (195)..(195)
<223> OTHER INFORMATION: a, c, t, g, unknown or other
<220> FEATURE:
<221> NAME/KEY: modified_base
<222> LOCATION: (221)..(221)
<223> OTHER INFORMATION: a, c, t, g, unknown or other
<220> FEATURE:
<221> NAME/KEY: modified_base
<222> LOCATION: (247)..(247)
<223> OTHER INFORMATION: a, c, t, g, unknown or other
<220> FEATURE:
<221> NAME/KEY: modified_base
<222> LOCATION: (251)..(251)
<223> OTHER INFORMATION: a, c, t, g, unknown or other

<400> SEQUENCE: 43
gtgatcatgg atgttgtctt caaccataca gctgagggta atgagaatgg tccaatatta      60
tcatttaggg gggtcgataa tactacatac tatatgcttg cacccaaggg acacttttat     120
aactattctg gctgtgggna taccttcaac tgtaatcatc ctgtggttcg tcaattcatt     180
gtagattgtt taagntactg ggtgacggaa atgcatgttg ntggttttcg ttttgacctt     240 gcatctncttt naaa                                                      254

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tcgtggttat gaaaagcttg g                                               21

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
acaattggaa tccaaatgca                                                 20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
```

-continued ttgacggctt gaatggtttc                                              20

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
aatggataga ttttccaaga gg                                           22

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
caggaccttc cctggagagg                                              20

<210> SEQ ID NO 49
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ggcacgagtg tgtgtacctg ta                                           22

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
tatcttcagg tatctacagc                                              20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
atgcttccaa tccaccttca                                              20

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gagcccattc tcggtaagtg a          21

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ctgcatttgg attccaattg          20

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
cagtaagcta gttggtgaat a          21

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
gggaggaaaa tctcccaaac          20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
ccattgaaag gtatttcacc          20

<210> SEQ ID NO 57
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
taacttattg acataccgg          19

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ctggagttcc aaaacggcta c          21

```
<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
attcttcaag ccaccatctc                                               20

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
tattgttatt tccaggggag a                                             21

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
tgctgcattg cctgatcgaa                                               20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
aacacccagg cccgtccatt                                               20

<210> SEQ ID NO 63
<211> LENGTH: 480
<212> TYPE: DNA
<213> ORGANISM: Triticum tauschii
<220> FEATURE:
<221> NAME/KEY: CDS
<222> LOCATION: (1)..(480)
<220> FEATURE:
<221> NAME/KEY: modified_base
<222> LOCATION: (22)..(22)
<223> OTHER INFORMATION: a, c, t, g, unknown or other
<220> FEATURE:
<221> NAME/KEY: modified_base
<222> LOCATION: (43)..(43)
<223> OTHER INFORMATION: a, c, t, g, unknown or other
<220> FEATURE:
<221> NAME/KEY: modified_base
<222> LOCATION: (87)..(87)
<223> OTHER INFORMATION: a, c, t, g, unknown or other
<220> FEATURE:
<221> NAME/KEY: modified_base
<222> LOCATION: (98)..(98)
<223> OTHER INFORMATION: a, c, t, g, unknown or other
<220> FEATURE:
<221> NAME/KEY: modified_base
```

```
<222> LOCATION: (103)..(103)
<223> OTHER INFORMATION: a, c, t, g, unknown or other
<220> FEATURE:
<221> NAME/KEY: modified_base
<222> LOCATION: (124)..(124)
<223> OTHER INFORMATION: a, c, t, g, unknown or other
<220> FEATURE:
<221> NAME/KEY: modified_base
<222> LOCATION: (148)..(148)
<223> OTHER INFORMATION: a, c, t, g, unknown or other
<220> FEATURE:
<221> NAME/KEY: modified_base
<222> LOCATION: (350)..(350)
<223> OTHER INFORMATION: a, c, t, g, unknown or other

<400> SEQUENCE: 63
```

| | | | | | | | | | | | | | | | | |
|---|---|---|---|---|---|---|---|---|---|---|---|---|---|---|---|---|
| ttc | cct | ttt | ttt | ttc | ttt | ggg | ngg | ggg | atg | gcc | tgt | tgg | atg | ntg | ttc | 48 |
| Phe | Pro | Phe | Phe | Phe | Phe | Gly | Xaa | Gly | Met | Ala | Cys | Trp | Met | Xaa | Phe | |
| 1 | | | | 5 | | | | | 10 | | | | | 15 | | |
| ccc | aat | gaa | ttt | cca | tgg | agt | gag | aga | gat | agt | tgg | atn | agg | gat | cgc | 96 |
| Pro | Asn | Glu | Phe | Pro | Trp | Ser | Glu | Arg | Asp | Ser | Trp | Xaa | Arg | Asp | Arg | |
| | | | 20 | | | | | 25 | | | | | 30 | | | |
| gnt | tcc | ngg | aac | tgt | att | ttt | ttc | ccc | ngc | ggg | gga | aat | ggc | gtt | agt | 144 |
| Xaa | Ser | Xaa | Asn | Cys | Ile | Phe | Phe | Pro | Xaa | Gly | Gly | Asn | Gly | Val | Ser | |
| | | 35 | | | | | 40 | | | | | 45 | | | | |
| gtc | nac | cca | ggc | cct | ggt | gtt | acc | acg | gct | ttg | atc | att | ctt | cgt | ttc | 192 |
| Val | Xaa | Pro | Gly | Pro | Gly | Val | Thr | Thr | Ala | Leu | Ile | Ile | Leu | Arg | Phe | |
| | 50 | | | | | 55 | | | | | 60 | | | | | |
| att | ctg | ata | tat | att | ttc | tca | ttc | ttt | ttc | ttc | ctg | ttc | ttg | ctg | taa | 240 |
| Ile | Leu | Ile | Tyr | Ile | Phe | Ser | Phe | Phe | Phe | Phe | Leu | Phe | Leu | Leu | | |
| 65 | | | | | 70 | | | | | 75 | | | | | | |
| ctg | caa | gtt | gtg | gcg | ttt | ttt | cac | tat | tgt | agt | cat | cct | tgc | att | ttg | 288 |
| Leu | Gln | Val | Val | Ala | Phe | Phe | His | Tyr | Cys | Ser | His | Pro | Cys | Ile | Leu | |
| 80 | | | | | 85 | | | | | 90 | | | | | 95 | |
| cag | gcg | ccg | tcc | tga | gcc | gcg | cgg | cct | ctc | cag | gga | agg | tcc | tgg | tgc | 336 |
| Gln | Ala | Pro | Ser | | Ala | Ala | Arg | Pro | Leu | Gln | Gly | Arg | Ser | Trp | Cys | |
| | | | | 100 | | | | | 105 | | | | | 110 | | |
| ctg | acg | gcg | aga | gng | acg | act | tgg | caa | gtc | cgg | cgc | aac | ctg | aag | aat | 384 |
| Leu | Thr | Ala | Arg | Xaa | Thr | Thr | Trp | Gln | Val | Arg | Arg | Asn | Leu | Lys | Asn | |
| | | | | 115 | | | | | 120 | | | | | 125 | | |
| tac | agg | tac | aca | cac | tcg | tgc | cgg | taa | atc | ttc | ata | caa | tcg | tta | ttc | 432 |
| Tyr | Arg | Tyr | Thr | His | Ser | Cys | Arg | | Ile | Phe | Ile | Gln | Ser | Leu | Phe | |
| | | | 130 | | | | | | 135 | | | | | 140 | | |
| act | tac | caa | atg | ccg | gat | gaa | acc | aac | cac | gga | tgc | gtc | agg | ttt | cga | 480 |
| Thr | Tyr | Gln | Met | Pro | Asp | Glu | Thr | Asn | His | Gly | Cys | Val | Arg | Phe | Arg | |
| | | | 145 | | | | | | 150 | | | | | 155 | | |

```
<210> SEQ ID NO 64
<211> LENGTH: 79
<212> TYPE: PRT
<213> ORGANISM: Triticum tauschii
<220> FEATURE:
<221> NAME/KEY: MOD_RES
<222> LOCATION: (8)..(8)
<223> OTHER INFORMATION: Variable amino acid
<220> FEATURE:
<221> NAME/KEY: MOD_RES
<222> LOCATION: (15)..(15)
<223> OTHER INFORMATION: Variable amino acid
<220> FEATURE:
<221> NAME/KEY: MOD_RES
<222> LOCATION: (29)..(29)
<223> OTHER INFORMATION: Variable amino acid
<220> FEATURE:
<221> NAME/KEY: MOD_RES
<222> LOCATION: (33)..(33)
<223> OTHER INFORMATION: Variable amino acid
<220> FEATURE:
```

```
<221> NAME/KEY: MOD_RES
<222> LOCATION: (35)..(35)
<223> OTHER INFORMATION: Variable amino acid
<220> FEATURE:
<221> NAME/KEY: MOD_RES
<222> LOCATION: (42)..(42)
<223> OTHER INFORMATION: Variable amino acid
<220> FEATURE:
<221> NAME/KEY: MOD_RES
<222> LOCATION: (50)..(50)
<223> OTHER INFORMATION: Variable amino acid

<400> SEQUENCE: 64

Phe Pro Phe Phe Phe Phe Gly Xaa Gly Met Ala Cys Trp Met Xaa Phe
1               5                   10                  15

Pro Asn Glu Phe Pro Trp Ser Glu Arg Asp Ser Trp Xaa Arg Asp Arg
            20                  25                  30

Xaa Ser Xaa Asn Cys Ile Phe Phe Pro Xaa Gly Gly Asn Gly Val Ser
        35                  40                  45

Val Xaa Pro Gly Pro Gly Val Thr Thr Ala Leu Ile Ile Leu Arg Phe
    50                  55                  60

Ile Leu Ile Tyr Ile Phe Ser Phe Phe Phe Leu Phe Leu Leu
65                  70                  75

<210> SEQ ID NO 65
<211> LENGTH: 58
<212> TYPE: PRT
<213> ORGANISM: Triticum tauschii
<220> FEATURE:
<221> NAME/KEY: MOD_RES
<222> LOCATION: (14)..(14)
<223> OTHER INFORMATION: Variable amino acid
<220> FEATURE:
<221> NAME/KEY: MOD_RES
<222> LOCATION: (29)..(29)
<223> OTHER INFORMATION: Variable amino acid
<220> FEATURE:
<221> NAME/KEY: MOD_RES
<222> LOCATION: (33)..(33)
<223> OTHER INFORMATION: Variable amino acid

<400> SEQUENCE: 65

Ser Leu Phe Phe Ser Leu Gly Gly Gly Trp Pro Val Gly Xaa Cys Ser
1               5                   10                  15

Pro Met Asn Phe His Gly Val Arg Glu Ile Val Gly Xaa Gly Ile Ala
            20                  25                  30

Xaa Pro Gly Thr Val Phe Phe Ser Pro Ala Gly Glu Met Ala Leu Val
        35                  40                  45

Ser Thr Gln Ala Leu Val Leu Pro Arg Leu
    50                  55

<210> SEQ ID NO 66
<211> LENGTH: 17
<212> TYPE: PRT
<213> ORGANISM: Triticum tauschii
<220> FEATURE:
<221> NAME/KEY: MOD_RES
<222> LOCATION: (7)..(7)
<223> OTHER INFORMATION: Variable amino acid
<220> FEATURE:
<221> NAME/KEY: MOD_RES
<222> LOCATION: (14)..(14)
<223> OTHER INFORMATION: Variable amino acid

<400> SEQUENCE: 66

Pro Phe Phe Phe Leu Trp Xaa Gly Asp Gly Leu Leu Asp Xaa Val Pro
1               5                   10                  15
```

Gln

<210> SEQ ID NO 67
<211> LENGTH: 816
<212> TYPE: PRT
<213> ORGANISM: Oryza sativa

<400> SEQUENCE: 67

```
Met Leu Cys Leu Thr Ser Ser Ser Ser Ala Pro Pro Leu Leu
1               5                   10                  15

Pro Ser Ala Asp Arg Pro Ser Pro Gly Ile Ala Gly Gly Gly Asn
                20                  25                  30

Val Arg Leu Ser Val Val Ser Ser Pro Arg Arg Ser Trp Pro Gly
            35                  40                  45

Lys Val Lys Thr Asn Phe Ser Val Pro Ala Thr Ala Arg Lys Asn Lys
        50                  55                  60

Thr Met Val Thr Val Val Glu Asp Val Asp His Leu Pro Ile Tyr Asp
65                  70                  75                  80

Leu Asp Pro Lys Leu Glu Glu Phe Lys Asp His Phe Asn Tyr Arg Ile
                85                  90                  95

Lys Arg Tyr Leu Asp Gln Lys Cys Leu Ile Glu Lys His Glu Gly Gly
                100                 105                 110

Leu Glu Glu Phe Ser Lys Gly Tyr Leu Lys Phe Gly Ile Asn Thr Val
            115                 120                 125

Gly Ala Thr Val Tyr Arg Glu Trp Ala Pro Ala Ala Gln Glu Ala Gln
130                 135                 140

Leu Ile Gly Asp Phe Asn Asn Trp Asn Gly Ala Lys His Lys Met Glu
145                 150                 155                 160

Lys Asp Lys Phe Gly Val Trp Ser Ile Lys Ile Ser His Val Asn Gly
                165                 170                 175

Lys Pro Ala Ile Pro His Asn Ser Lys Val Lys Phe Arg Phe Arg His
                180                 185                 190

Gly Gly Gly Ala Trp Val Asp Arg Ile Pro Ala Trp Ile Arg Tyr Ala
            195                 200                 205

Thr Phe Asp Ala Ser Lys Phe Gly Ala Pro Tyr Asp Gly Val His Trp
210                 215                 220

Asp Pro Pro Ala Cys Glu Arg Tyr Val Phe Lys His Pro Arg Pro Pro
225                 230                 235                 240

Lys Pro Asp Ala Pro Arg Ile Tyr Glu Ala His Val Gly Met Ser Gly
                245                 250                 255

Glu Glu Pro Glu Val Ser Thr Tyr Arg Glu Phe Ala Asp Asn Val Leu
            260                 265                 270

Pro Arg Ile Arg Ala Asn Asn Tyr Asn Thr Val Gln Leu Met Ala Ile
        275                 280                 285

Met Glu His Ser Tyr Tyr Ala Ser Phe Gly Tyr His Val Thr Asn Phe
290                 295                 300

Phe Ala Val Ser Ser Arg Ser Gly Thr Pro Glu Asp Leu Lys Tyr Leu
305                 310                 315                 320

Asp Lys Ala His Ser Leu Gly Leu Arg Val Leu Met Asp Val Val His
                325                 330                 335

Ser His Ala Ser Asn Asn Val Thr Asp Gly Leu Asn Gly Tyr Asp Val
            340                 345                 350

Gly Gln Asn Thr His Glu Ser Tyr Phe His Thr Gly Asp Arg Gly Tyr
        355                 360                 365
```

```
His Lys Leu Trp Asp Ser Arg Leu Phe Asn Tyr Ala Asn Trp Glu Val
    370                 375                 380

Leu Arg Phe Leu Leu Ser Asn Leu Arg Tyr Trp Asp Glu Phe Met Phe
385                 390                 395                 400

Asp Gly Phe Arg Phe Asp Gly Val Thr Ser Met Leu Tyr His His His
                405                 410                 415

Gly Ile Asn Lys Gly Phe Thr Gly Asn Tyr Lys Glu Tyr Phe Ser Leu
            420                 425                 430

Asp Thr Asp Val Asp Ala Val Val Tyr Met Met Leu Ala Asn His Leu
        435                 440                 445

Met His Lys Leu Leu Pro Glu Ala Thr Val Val Ala Glu Asp Val Ser
    450                 455                 460

Gly Met Pro Val Leu Cys Arg Pro Val Asp Glu Gly Val Gly Phe
465                 470                 475                 480

Asp Tyr Arg Leu Ala Met Ala Ile Pro Asp Arg Trp Ile Asp Tyr Leu
                485                 490                 495

Lys Asn Lys Asp Asp Arg Lys Trp Ser Met Ser Glu Ile Val Gln Thr
            500                 505                 510

Leu Thr Asn Arg Arg Tyr Thr Glu Lys Cys Ile Ala Tyr Ala Glu Ser
        515                 520                 525

His Asp Gln Ser Ile Val Gly Asp Lys Thr Ile Ala Phe Leu Leu Met
    530                 535                 540

Asp Lys Glu Met Tyr Thr Gly Met Ser Asp Leu Gln Pro Ala Ser Pro
545                 550                 555                 560

Thr Ile Asn Arg Gly Ile Ala Leu Gln Lys Met Ile His Phe Ile Thr
                565                 570                 575

Met Ala Leu Gly Gly Asp Gly Tyr Leu Asn Phe Met Gly Asn Glu Phe
            580                 585                 590

Gly His Pro Glu Trp Ile Asp Phe Pro Arg Glu Gly Asn Asn Trp Ser
        595                 600                 605

Tyr Asp Lys Cys Arg Arg Gln Trp Ser Leu Val Asp Thr Asp His Leu
    610                 615                 620

Arg Tyr Lys Tyr Met Asn Ala Phe Asp Gln Ala Met Asn Ala Leu Asp
625                 630                 635                 640

Glu Phe Ser Phe Leu Ser Ser Lys Gln Ile Val Ser Asp Met Asn
                645                 650                 655

Glu Lys Lys Val Ile Val Phe Glu Arg Gly Asp Leu Val Phe Val Phe
            660                 665                 670

Asn Phe His Pro Asn Lys Thr Tyr Lys Gly Tyr Lys Val Gly Cys Asp
        675                 680                 685

Leu Pro Gly Lys Tyr Arg Val Ala Leu Asp Ser Asp Ala Leu Val Phe
    690                 695                 700

Gly Gly His Gly Arg Val Gly His Asp Val Asp His Phe Thr Ser Pro
705                 710                 715                 720

Glu Gly Met Pro Gly Val Pro Glu Thr Asn Phe Asn Asn Arg Pro Asn
                725                 730                 735

Ser Phe Lys Val Leu Ser Pro Pro Arg Thr Cys Val Ala Tyr Tyr Arg
            740                 745                 750

Val Asp Glu Asp Arg Glu Leu Arg Arg Gly Gly Ala Val Ala Ser
        755                 760                 765

Gly Lys Ile Val Thr Glu Tyr Ile Asp Val Glu Ala Thr Ser Gly Glu
    770                 775                 780
```

```
Thr Ile Ser Gly Gly Trp Lys Gly Ser Glu Lys Asp Asp Cys Gly Lys
785                 790                 795                 800

Lys Gly Met Lys Phe Val Phe Arg Ser Ser Asp Glu Asp Cys Lys Asp
            805                 810                 815
```

<210> SEQ ID NO 68
<211> LENGTH: 817
<212> TYPE: PRT
<213> ORGANISM: Zea mays

<400> SEQUENCE: 68

```
Met Leu Cys Leu Val Ser Pro Ser Ser Pro Thr Pro Leu Pro Pro
1               5                   10                  15

Pro Arg Arg Ser Arg Ser His Ala Asp Arg Ala Ala Pro Pro Gly Ile
                20                  25                  30

Ala Gly Gly Gly Asn Val Arg Leu Ser Val Leu Ser Val Gln Cys Lys
            35                  40                  45

Ala Arg Arg Ser Gly Val Arg Lys Val Lys Ser Lys Phe Ala Thr Ala
50                  55                  60

Ala Thr Val Gln Asp Asp Lys Thr Met Ala Thr Ala Lys Gly Asp Val
65                  70                  75                  80

Asp His Leu Pro Ile Tyr Asp Leu Asp Pro Lys Leu Glu Ile Phe Lys
                85                  90                  95

Asp His Phe Arg Tyr Arg Met Lys Arg Tyr Leu Asp Gln Lys Gly Ser
                100                 105                 110

Ile Glu Glu Asn Glu Gly Ser Leu Glu Ser Phe Ser Lys Gly Tyr Leu
            115                 120                 125

Lys Phe Gly Ile Asn Thr Asn Asp Gly Thr Val Tyr Arg Glu Trp Ala
130                 135                 140

Pro Ala Ala Gln Glu Ala Glu Leu Ile Gly Asp Phe Asn Asp Trp Asn
145                 150                 155                 160

Gly Ala Asn His Lys Met Glu Lys Asp Lys Phe Gly Val Trp Ser Ile
                165                 170                 175

Lys Ile Asp His Val Lys Gly Lys Pro Ala Ile Pro His Asn Ser Lys
            180                 185                 190

Val Lys Phe Arg Phe Leu His Gly Gly Val Trp Val Asp Arg Ile Pro
        195                 200                 205

Ala Leu Ile Arg Tyr Ala Thr Val Asp Ala Ser Lys Phe Gly Ala Pro
210                 215                 220

Tyr Asp Gly Val His Trp Asp Pro Pro Ala Ser Glu Arg Tyr Thr Phe
225                 230                 235                 240

Lys His Pro Arg Pro Ser Lys Pro Ala Ala Pro Arg Ile Tyr Glu Ala
                245                 250                 255

His Val Gly Met Ser Gly Glu Lys Pro Ala Val Ser Thr Tyr Arg Glu
            260                 265                 270

Phe Ala Asp Asn Val Leu Pro Arg Ile Arg Ala Asn Asn Tyr Asn Thr
        275                 280                 285

Val Gln Leu Met Ala Ile Met Glu His Ser Tyr Tyr Ala Ser Phe Gly
290                 295                 300

Tyr His Val Thr Asn Phe Phe Ala Val Ser Ser Arg Ser Gly Thr Pro
305                 310                 315                 320

Glu Asp Leu Lys Tyr Leu Asp Lys Ala His Ser Leu Gly Leu Arg Val
                325                 330                 335

Leu Met Asp Val Val His Ser His Ala Ser Asn Asn Val Thr Asp Gly
            340                 345                 350
```

```
Leu Asn Gly Tyr Asp Val Gly Gln Ser Thr Gln Glu Ser Tyr Phe His
        355                 360                 365

Ala Gly Asp Arg Gly Tyr His Lys Leu Trp Asp Ser Arg Leu Phe Asn
    370                 375                 380

Tyr Ala Asn Trp Glu Val Leu Arg Phe Leu Leu Ser Asn Leu Arg Tyr
385                 390                 395                 400

Trp Asp Glu Phe Met Phe Asp Gly Phe Arg Phe Asp Gly Val Thr Ser
                405                 410                 415

Met Leu Tyr His His His Gly Ile Asn Val Gly Phe Thr Gly Asn Tyr
            420                 425                 430

Gln Glu Tyr Phe Ser Leu Asp Thr Ala Val Asp Ala Val Val Tyr Met
        435                 440                 445

Met Leu Ala Asn His Leu Met His Lys Leu Leu Pro Glu Ala Thr Val
        450                 455                 460

Val Ala Glu Asp Val Ser Gly Met Pro Val Leu Cys Arg Pro Val Asp
465                 470                 475                 480

Glu Gly Gly Val Gly Phe Asp Tyr Arg Leu Ala Met Ala Ile Pro Asp
                485                 490                 495

Arg Trp Ile Asp Tyr Leu Lys Asn Lys Asp Asp Ser Glu Trp Ser Met
                500                 505                 510

Gly Glu Ile Ala His Thr Leu Thr Asn Arg Arg Tyr Thr Glu Lys Cys
            515                 520                 525

Ile Ala Tyr Ala Glu Ser His Asp Gln Ser Ile Val Gly Asp Lys Thr
        530                 535                 540

Ile Ala Phe Leu Leu Met Asp Lys Glu Met Tyr Thr Gly Met Ser Asp
545                 550                 555                 560

Leu Gln Pro Ala Ser Pro Thr Ile Asp Arg Gly Ile Ala Leu Gln Lys
                565                 570                 575

Met Ile His Phe Ile Thr Met Ala Leu Gly Gly Asp Gly Tyr Leu Asn
            580                 585                 590

Phe Met Gly Asn Glu Phe Gly His Pro Glu Trp Ile Asp Phe Pro Arg
        595                 600                 605

Glu Gly Asn Asn Trp Ser Tyr Asp Lys Cys Arg Arg Gln Trp Ser Leu
    610                 615                 620

Val Asp Thr Asp His Leu Arg Tyr Lys Tyr Met Asn Ala Phe Asp Gln
625                 630                 635                 640

Ala Met Asn Ala Leu Asp Arg Phe Ser Phe Leu Ser Ser Ser Lys Gln
                645                 650                 655

Ile Val Ser Asp Met Asn Glu Glu Lys Val Ile Val Phe Glu Arg Gly
            660                 665                 670

Asp Leu Val Phe Val Phe Asn Phe His Pro Lys Lys Thr Tyr Glu Gly
        675                 680                 685

Tyr Lys Val Gly Cys Asp Leu Pro Gly Lys Tyr Arg Val Ala Leu Asp
    690                 695                 700

Ser Asp Ala Leu Val Phe Gly Gly His Gly Arg Val Gly His Asp Val
705                 710                 715                 720

Asp His Phe Thr Ser Pro Glu Gly Pro Gly Val Pro Glu Thr Asn Phe
                725                 730                 735

Asn Asn Arg Pro Asn Ser Phe Lys Val Leu Ser Pro Pro Arg Thr Cys
            740                 745                 750

Val Ala Tyr Tyr Arg Val Asp Glu Ala Gly Ala Gly Arg Arg Leu His
        755                 760                 765
```

```
Ala Lys Ala Glu Thr Gly Lys Thr Ser Pro Ala Glu Ser Ile Asp Val
770                 775                 780

Lys Ala Ser Arg Ala Ser Ser Lys Glu Asp Lys Glu Ala Thr Ala Gly
785                 790                 795                 800

Gly Lys Lys Gly Trp Lys Phe Ala Arg Gln Pro Ser Asp Gln Asp Thr
            805                 810                 815

Lys

<210> SEQ ID NO 69
<211> LENGTH: 758
<212> TYPE: PRT
<213> ORGANISM: Pisum sp.

<400> SEQUENCE: 69

Met Thr Asp Asp Lys Ser Thr Met Pro Ser Val Glu Glu Asp Phe Asp
1               5                   10                  15

Asn Ile Gly Ile Leu Asn Val Asp Ser Ser Leu Glu Pro Phe Lys Asp
            20                  25                  30

His Phe Lys Tyr Arg Met Lys Arg Tyr Leu His Gln Lys Lys Leu Ile
        35                  40                  45

Glu Glu Tyr Glu Gly Gly Leu Gln Glu Phe Ala Lys Gly Tyr Leu Lys
    50                  55                  60

Phe Gly Phe Asn Arg Glu Asp Gly Ile Ser Tyr Arg Glu Trp Ala Pro
65                  70                  75                  80

Ala Ala Gln Glu Ala Gln Ile Ile Gly Asp Phe Asn Gly Trp Asn Gly
                85                  90                  95

Ser Asn Leu His Met Glu Lys Asp Gln Phe Gly Val Trp Ser Ile Gln
            100                 105                 110

Ile Pro Asp Ala Asp Gly Asn Pro Ala Ile Pro His Asn Ser Arg Val
        115                 120                 125

Lys Phe Arg Phe Lys His Ser Asp Gly Val Trp Val Asp Arg Ile Pro
130                 135                 140

Ala Trp Ile Lys Tyr Ala Thr Val Asp Pro Thr Arg Phe Ala Ala Pro
145                 150                 155                 160

Tyr Asp Gly Val Tyr Trp Asp Pro Pro Leu Ser Glu Arg Tyr Gln Phe
                165                 170                 175

Lys His Pro Arg Pro Pro Lys Pro Lys Ala Pro Arg Ile Tyr Glu Ala
            180                 185                 190

His Val Gly Met Ser Ser Ser Glu Pro Arg Val Asn Ser Tyr Arg Glu
        195                 200                 205

Phe Ala Asp Asp Val Leu Pro Arg Ile Arg Glu Asn Asn Tyr Asn Thr
    210                 215                 220

Val Gln Leu Met Ala Ile Met Glu His Ser Tyr Tyr Ala Ser Phe Trp
225                 230                 235                 240

Tyr His Val Thr Lys Pro Phe Phe Ala Val Ser Ser Arg Ser Gly Ser
                245                 250                 255

Pro Glu Asp Leu Lys Tyr Leu Asp Lys Ala His Ser Leu Gly Leu Asn
            260                 265                 270

Val Leu Met Asp Val Val His Ser His Ala Ser Asn Asn Val Thr Asp
        275                 280                 285

Gly Leu Asn Gly Tyr Asp Val Gly Gln Ser Ser Gln Ser Tyr Phe
    290                 295                 300

His Ala Gly Asp Arg Gly Tyr His Lys Leu Trp Asp Ser Arg Leu Phe
305                 310                 315                 320
```

-continued

```
Asn Tyr Ala Asn Trp Lys Ser Ser Phe Leu Leu Ser Asn Leu Arg Tyr
            325                 330                 335

Trp Asp Glu Phe Lys Phe Asp Gly Phe Arg Phe Asp Gly Val Thr Ser
        340                 345                 350

Met Leu Tyr His His His Gly Ile Asn Met Ala Phe Thr Gly Asp Tyr
            355                 360                 365

Asn Glu Tyr Phe Ser Glu Asp Thr Asp Val Asp Ala Val Val Tyr Met
        370                 375                 380

Met Leu Ala Asn Ser Leu Val His Asp Ile Leu Pro Glu Ala Thr Asp
385                 390                 395                 400

Val Ala Glu Asp Val Ser Gly Met Pro Gly Leu Gly Arg Pro Val Ser
                405                 410                 415

Glu Val Gly Val Gly Phe Asp Tyr Arg Leu Ala Met Ala Ile Pro Asp
            420                 425                 430

Lys Trp Ile Asp Tyr Leu Lys Asn Lys Lys Asp Ser Glu Trp Ser Met
        435                 440                 445

Lys Glu Ile Ser Leu Asn Leu Thr Asn Arg Arg Tyr Thr Glu Lys Cys
        450                 455                 460

Ile Ser Tyr Ala Glu Ser His Asp Gln Ser Ile Val Gly Asp Lys Thr
465                 470                 475                 480

Ile Ala Phe Leu Leu Met Asp Glu Glu Met Tyr Ser Ser Met Ser Cys
                485                 490                 495

Leu Thr Met Leu Ser Pro Thr Ile Asp Arg Gly Ile Ser Leu His Lys
            500                 505                 510

Met Ile His Phe Ile Thr Met Ala Leu Gly Gly Asp Gly Tyr Leu Asn
        515                 520                 525

Phe Met Gly Asn Glu Phe Gly His Pro Glu Trp Ile Asp Phe Pro Arg
530                 535                 540

Glu Gly Asn Gly Trp Ser Tyr Asp Lys Cys Arg Leu Thr Gln Trp Asn
545                 550                 555                 560

Leu Val Asp Thr Asn His Leu Arg Tyr Lys Tyr Met Asn Ala Phe Asp
                565                 570                 575

Arg Ala Met Asn Leu Leu Asp Lys Phe Ser Ile Leu Ala Ser Thr Lys
            580                 585                 590

Gln Ile Val Ser Ser Thr Asn Asn Glu Lys Val Ile Val Phe Glu Arg
        595                 600                 605

Gly Asp Leu Val Phe Val Phe Asn Phe His Pro Glu Asn Thr Tyr Glu
610                 615                 620

Gly Tyr Lys Val Gly Cys Asp Leu Pro Gly Lys Tyr Arg Val Ala Leu
625                 630                 635                 640

Asp Ser Asp Ala Thr Glu Phe Gly Gly His Gly Arg Val Gly His Asp
                645                 650                 655

Ala Asp Gln Phe Thr Ser Pro Glu Gly Pro Gly Val Pro Glu Thr Asn
            660                 665                 670

Phe Asn Asn Arg Pro Asn Ser Phe Lys Val Leu Ser Pro Pro His Thr
        675                 680                 685

Cys Val Val Tyr Tyr Arg Val Asp Glu Arg Gln Glu Ser Asn Asn
        690                 695                 700

Pro Asn Leu Gly Ser Glu Glu Thr Ala Ala Asp Thr Asp Val Ala
705                 710                 715                 720

Arg Ile Pro Asp Val Ser Glu Ser Glu Asp Ser Asn Leu Asp Arg Glu
                725                 730                 735

Glu Asn Ser Asp Asp Ala Val Asp Ala Gly Ile Phe Lys Val Glu Arg
```

```
                    740                 745                 750
Glu Val Val Gly Asp Asn
            755

<210> SEQ ID NO 70
<211> LENGTH: 852
<212> TYPE: PRT
<213> ORGANISM: Solanum sp.

<400> SEQUENCE: 70

Met Glu Ile Asn Phe Lys Val Leu Ser Lys Pro Ile Arg Gly Ser Phe
1               5                   10                  15

Pro Ser Phe Ser Pro Lys Val Ser Ser Gly Ala Ser Arg Asn Lys Ile
            20                  25                  30

Cys Pro Ser Gln His Ser Thr Gly Leu Lys Phe Gly Ser Gln Glu Arg
        35                  40                  45

Ser Trp Asp Val Ser Ser Thr Pro Lys Ser Arg Val Arg Lys Asp Glu
    50                  55                  60

Arg Met Lys His Ser Ser Ala Ile Ser Ala Val Leu Thr Asp Asp Asn
65                  70                  75                  80

Ser Thr Met Ala Pro Leu Glu Glu Asp Val Lys Thr Asp Asn Ile Gly
                85                  90                  95

Leu Leu Asn Leu Asp Pro Thr Leu Glu Pro Phe Leu Asp His Phe Arg
            100                 105                 110

His Arg Met Lys Arg Tyr Val Asp Gln Lys Met Leu Ile Glu Lys Tyr
        115                 120                 125

Glu Gly Pro Leu Glu Glu Phe Ala Gly Gly Tyr Leu Lys Phe Gly Phe
    130                 135                 140

Asn Arg Glu Gly Cys Ile Val Tyr Arg Glu Trp Ala Pro Ala Ala Gln
145                 150                 155                 160

Glu Asp Glu Val Ile Gly Asp Phe Asn Gly Trp Asn Gly Ser Asn His
                165                 170                 175

Met Met Glu Lys Asp Gln Phe Gly Val Trp Ser Ile Arg Ile Pro Asp
            180                 185                 190

Val Asp Ser Lys Pro Val Ile Pro His Asn Ser Arg Val Lys Phe Arg
        195                 200                 205

Phe Lys His Gly Asn Gly Val Trp Val Asp Arg Ile Pro Ala Trp Ile
    210                 215                 220

Lys Tyr Ala Thr Ala Asp Ala Thr Lys Phe Ala Ala Pro Tyr Asp Gly
225                 230                 235                 240

Val Tyr Trp Asp Pro Pro Ser Glu Arg Tyr His Phe Lys Tyr Pro Arg
                245                 250                 255

Arg Pro Pro Lys Pro Arg Ala Pro Arg Ile Tyr Glu Ala His Val Gly
            260                 265                 270

Met Ser Ser Ser Glu Pro Arg Val Asn Ser Tyr Arg Glu Phe Ala Asp
        275                 280                 285

Asp Val Leu Pro Arg Ile Lys Ala Asn Asn Tyr Asn Thr Val Gln Leu
    290                 295                 300

Met Ala Ile Met Glu His Ser Tyr Tyr Gly Ser Phe Gly Tyr His Val
305                 310                 315                 320

Thr Asn Phe Phe Ala Val Ser Ser Arg Tyr Gly Asn Pro Glu Asp Leu
                325                 330                 335

Lys Tyr Leu Asp Lys Ala His Ser Leu Gly Leu Gln Val Leu Val Asp
            340                 345                 350
```

-continued

```
Val Val His Ser His Ala Ser Asn Asn Val Thr Asp Gly Leu Asn Gly
        355                 360                 365

Tyr Asp Val Gly Gln Gly Ser Gln Glu Ser Tyr Phe His Ala Gly Asp
        370                 375                 380

Arg Gly Tyr His Lys Leu Trp Asp Ser Arg Leu Phe Asn Tyr Ala Asn
385                 390                 395                 400

Trp Glu Val Leu Arg Phe Leu Leu Ser Asn Leu Arg Tyr Trp Asp Glu
                405                 410                 415

Phe Asn Phe Asp Gly Phe Arg Phe Asp Gly Val Thr Ser Met Leu Tyr
                420                 425                 430

Val His His Gly Ile Asn Met Gly Phe Thr Gly Asn Tyr Asn Glu Tyr
            435                 440                 445

Phe Ser Glu Ala Thr Asp Val Asp Ala Val Val Tyr Met Met Leu Ala
        450                 455                 460

Asn Asn Leu Ile His Lys Ile Leu Pro Glu Ala Thr Val Val Ala Glu
465                 470                 475                 480

Asp Val Ser Gly Met Pro Gly Leu Gly Arg Pro Val Ser Glu Gly Gly
                485                 490                 495

Val Gly Phe Asp Tyr Arg Leu Ala Met Ala Ile Pro Asp Lys Trp Ile
                500                 505                 510

Asp Tyr Leu Lys Asn Lys Asn Asp Glu Glu Trp Ser Met Lys Glu Ile
            515                 520                 525

Thr Ser Ser Leu Thr Asn Arg Arg Tyr Thr Glu Lys Cys Ile Ala Tyr
        530                 535                 540

Ala Glu Ser His Asp Gln Ser Ile Val Gly Asp Lys Thr Ile Ala Phe
545                 550                 555                 560

Leu Leu Met Asp Lys Glu Met Tyr Ser Gly Met Ser Cys Leu Thr Asp
                565                 570                 575

Ala Ser Pro Val Ile Asp Arg Gly Ile Ala Leu His Lys Met Ile His
            580                 585                 590

Phe Phe Thr Met Ala Leu Gly Gly Asp Gly Tyr Leu Asn Phe Met Gly
        595                 600                 605

Asn Glu Phe Gly His Pro Glu Trp Ile Asp Phe Pro Arg Glu Gly Asn
        610                 615                 620

Asn Trp Ser Tyr Asp Lys Cys Arg Arg Gln Trp Asn Leu Ala Asp Ser
625                 630                 635                 640

Asp His Leu Arg Tyr Lys Tyr Met Asn Ala Phe Asp Arg Ala Met Asn
                645                 650                 655

Ser Leu Asp Lys Phe Ser Phe Leu Ala Ser Gly Lys Gln Ile Val Ser
            660                 665                 670

Ser Met Asp Glu Glu Asn Lys Val Ile Val Phe Glu Arg Gly Asp Leu
        675                 680                 685

Val Phe Val Phe Asn Phe His Pro Lys Asn Thr Tyr Glu Gly Tyr Lys
        690                 695                 700

Val Gly Cys Asp Leu Pro Gly Lys Tyr Arg Val Ala Leu Asp Ser Asp
705                 710                 715                 720

Ala Trp Glu Phe Gly His Gly Arg Thr Gly His Asp Val Asp His
                725                 730                 735

Phe Thr Ser Pro Glu Gly Pro Val Pro Glu Thr Asn Phe Asn Gly
            740                 745                 750

Arg Gln Ile Pro Ser Lys Cys Cys Leu Leu Arg Glu His Val Trp Leu
        755                 760                 765

Ile Thr Glu Leu Met Asn Ala Cys Gln Lys Leu Lys Ile Thr Arg Gln
```

```
               770                 775                 780
Thr Phe Val Val Ser Tyr Tyr Gln Gln Pro Val Ser Arg Arg Val Thr
785                 790                 795                 800

Arg Asn Leu Lys Ile Arg Tyr Leu Gln Ser Val Thr Thr Asn Ala Tyr
                805                 810                 815

Gln Lys Leu Lys Phe Thr Arg Gln Thr Phe Val Ser Tyr Tyr Gln Gln
                820                 825                 830

Pro Ile Leu Arg Arg Thr Arg Lys Leu Lys Asp Ser Leu Ser Thr Asn
                835                 840                 845

Ile Ser Thr Phe
        850

<210> SEQ ID NO 71
<211> LENGTH: 686
<212> TYPE: PRT
<213> ORGANISM: Triticum tauschii

<400> SEQUENCE: 71

Met Leu Cys Leu Ser Ser Leu Leu Pro Arg Pro Ser Ala Ala Pro
1               5                   10                  15

Pro Arg Ala Asp Arg Pro Leu Pro Gly Ile Ile Ala Gly Gly Gly Gly
                20                  25                  30

Gly Lys Arg Leu Ser Val Val Pro Ser Val Pro Phe Leu Leu Arg Arg
                35                  40                  45

Leu Trp Pro Arg Lys Ala Lys Ser Lys Ser Phe Val Ser Val Thr Ala
50                  55                  60

Arg Gly Asn Lys Ile Ala Ala Thr Thr Gly Tyr Gly Ser Asp His Leu
65                  70                  75                  80

Pro Ile Tyr Asp Leu Asp Leu Lys Leu Ala Glu Phe Lys Asp His Phe
                85                  90                  95

Asp Tyr Thr Arg Asn Arg Tyr Ile Asp Gln Lys His Leu Ile Glu Lys
                100                 105                 110

His Glu Gly Ser Leu Glu Glu Phe Ser Lys Gly Tyr Leu Lys Phe Gly
                115                 120                 125

Ile Asn Thr Glu His Gly Ala Ser Val Tyr Arg Glu Trp Ala Pro Ala
                130                 135                 140

Ala Glu Glu Ala Gln Leu Ile Gly Asp Phe Asn Asn Trp Asn Gly Ser
145                 150                 155                 160

Gly His Lys Met Ala Lys Asp Asn Phe Gly Val Trp Ser Ile Arg Ile
                165                 170                 175

Ser His Val Asn Gly Lys Pro Ala Ile Pro His Asn Ser Lys Val Lys
                180                 185                 190

Phe Arg Phe Arg His His Gly Val Trp Val Asp Gln Ile Pro Ala Trp
                195                 200                 205

Ile Arg Tyr Ala Thr Val Thr Ala Ser Glu Ser Gly Ala Pro Tyr Asp
                210                 215                 220

Gly Leu His Trp Asp Pro Pro Ser Ser Glu Arg Tyr Val Phe Asn His
225                 230                 235                 240

Pro Arg Pro Pro Lys Pro Asp Val Pro Arg Ile Tyr Glu Ala His Val
                245                 250                 255

Gly Val Ser Gly Gly Lys Leu Glu Ala Gly Thr Tyr Arg Glu Phe Pro
                260                 265                 270

Asp Asn Val Leu Pro Cys Leu Arg Ala Thr Asn Tyr Asn Thr Val Gln
                275                 280                 285
```

```
Leu Met Gly Ile Met Glu His Ser Asp Ser Ala Ser Phe Gly Tyr His
    290                 295                 300

Val Thr Asn Phe Phe Ala Val Ser Ser Arg Ser Gly Thr Pro Glu Asp
305                 310                 315                 320

Leu Lys Tyr Leu Asp Lys Ala His Ser Leu Gly Leu Arg Val Leu Met
                325                 330                 335

Asp Val Val His Ser His Ala Ser Asn Asn Val Ile Asp Gly Leu Asn
            340                 345                 350

Gly Tyr Asp Val Gly Gln Ser Ala His Glu Ser Tyr Phe Tyr Thr Gly
        355                 360                 365

Asp Lys Gly Tyr Asn Lys Leu Trp Asn Gly Arg Leu Phe Asn Tyr Ala
    370                 375                 380

Asn Trp Glu Val Leu Arg Phe Leu Leu Ser Asn Leu Arg Tyr Trp Asp
385                 390                 395                 400

Glu Phe Met Phe Asp Gly Phe Arg Phe Val Gly Val Thr Ser Met Leu
                405                 410                 415

Tyr Asn His Asn Gly Ile Asn Met Ser Phe Asn Gly Asn Tyr Lys Glu
            420                 425                 430

Tyr Ile Gly Leu Asp Thr Asn Val Asp Ala Phe Val Tyr Met Met Leu
        435                 440                 445

Ala Asn His Leu Met His Lys Leu Leu Pro Glu Ala Ile Val Val Ala
    450                 455                 460

Val Asp Val Ser Gly Met Pro Val Leu Cys Arg Pro Val Asp Glu Gly
465                 470                 475                 480

Gly Leu Gly Phe Asp Tyr Arg Gln Ala Met Thr Ile Pro Asp Arg Trp
                485                 490                 495

Ile Asp Tyr Leu Glu Asn Lys Gly Asp Gln Gln Trp Ser Met Ser Ser
            500                 505                 510

Val Ile Ser Gln Thr Leu Thr Asn Arg Arg Tyr Pro Glu Lys Phe Ile
    515                 520                 525

Ala Tyr Ala Glu Arg Gln Asn His Ser Ile Val Gly Ser Lys Thr Met
530                 535                 540

Ala Phe Leu Leu Met Asp Trp Glu Thr Tyr Ser Gly Met Ser Ala Leu
545                 550                 555                 560

Asp Pro Asp Ser Pro Thr Ile Asp Arg Ala Ile Ala Leu Gln Lys Met
                565                 570                 575

Ile His Phe Ile Thr Met Ala Leu Gly Gly Asp Ser Tyr Leu Lys Phe
            580                 585                 590

Met Gly Asn Glu Tyr Met Asn Ala Phe Val Gln Ala Val Asp Thr Pro
        595                 600                 605

Ser Lys Cys Ser Phe Leu Ser Ser Asn Gln Thr Ala Ser His Met
    610                 615                 620

Asn Glu Glu Lys Gly Ser Ala Phe Thr Lys Gly Phe Thr His Leu Arg
625                 630                 635                 640

Ser Gly Cys Tyr Glu Pro Ser Leu Pro Ser Thr Ser Ser Cys Ala Leu
                645                 650                 655

Leu Gly Pro Ser Asn Gln Ser Pro Phe Ser Lys Pro Phe Ile Gly Phe
            660                 665                 670

Pro Gly Cys Ile Phe Cys Cys Gly Leu Phe Lys Gly Glu Phe
        675                 680                 685

<210> SEQ ID NO 72
<211> LENGTH: 23
<212> TYPE: DNA
```

<210> SEQ ID NO 72
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 72
ggcggcggca atgtgcggct gag                                    23

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 73
gaactcgcgc ccgacctcct                                        20

<210> SEQ ID NO 74
<211> LENGTH: 60
<212> TYPE: DNA
<213> ORGANISM: Triticum tauschii

<400> SEQUENCE: 74
tcccgtgtct gcgccaagag actacaccat ggcaacagct gaagatggtg ttggcgacct    60

<210> SEQ ID NO 75
<211> LENGTH: 20
<212> TYPE: PRT
<213> ORGANISM: Triticum tauschii

<400> SEQUENCE: 75

Pro Val Ser Ala Pro Arg Asp Tyr Thr Met Ala Thr Ala Glu Asp Gly
1               5                   10                  15

Val Gly Asp Leu
            20

<210> SEQ ID NO 76
<211> LENGTH: 16
<212> TYPE: PRT
<213> ORGANISM: Triticum tauschii

<400> SEQUENCE: 76

Val Ser Ala Pro Arg Asp Tyr Thr Met Ala Thr Ala Glu Asp Gly Val
1               5                   10                  15

<210> SEQ ID NO 77
<211> LENGTH: 20
<212> TYPE: PRT
<213> ORGANISM: Triticum tauschii

<400> SEQUENCE: 77

Leu Gln Val Val Ala Phe Phe His Tyr Cys Ser His Pro Cys Ile Leu
1               5                   10                  15

Gln Ala Pro Ser
            20

<210> SEQ ID NO 78
<211> LENGTH: 35
<212> TYPE: PRT
<213> ORGANISM: Triticum tauschii
<220> FEATURE:
<221> NAME/KEY: MOD_RES
<222> LOCATION: (16)..(16)

<223> OTHER INFORMATION: Variable amino acid

<400> SEQUENCE: 78

Ala Ala Arg Pro Leu Gln Gly Arg Ser Trp Cys Leu Thr Ala Arg Xaa
1               5                   10                  15

Thr Thr Trp Gln Val Arg Arg Asn Leu Lys Asn Tyr Arg Tyr Thr His
            20                  25                  30

Ser Cys Arg
        35

<210> SEQ ID NO 79
<211> LENGTH: 23
<212> TYPE: PRT
<213> ORGANISM: Triticum tauschii

<400> SEQUENCE: 79

Ile Phe Ile Gln Ser Leu Phe Thr Tyr Gln Met Pro Asp Glu Thr Asn
1               5                   10                  15

His Gly Cys Val Arg Phe Arg
            20

<210> SEQ ID NO 80
<211> LENGTH: 6
<212> TYPE: PRT
<213> ORGANISM: Triticum tauschii

<400> SEQUENCE: 80

Ser Phe Phe Val Ser Phe
1               5

<210> SEQ ID NO 81
<211> LENGTH: 46
<212> TYPE: PRT
<213> ORGANISM: Triticum tauschii

<400> SEQUENCE: 81

Tyr Ile Phe Ser His Ser Phe Ser Ser Cys Ser Cys Asn Cys Lys
1               5                   10                  15

Leu Trp Arg Phe Phe Thr Ile Val Val Ile Leu Ala Phe Cys Arg Arg
            20                  25                  30

Arg Pro Glu Pro Arg Gly Leu Ser Arg Glu Gly Pro Gly Ala
        35                  40                  45

<210> SEQ ID NO 82
<211> LENGTH: 12
<212> TYPE: PRT
<213> ORGANISM: Triticum tauschii
<220> FEATURE:
<221> NAME/KEY: MOD_RES
<222> LOCATION: (4)..(4)
<223> OTHER INFORMATION: Variable amino acid

<400> SEQUENCE: 82

Arg Arg Glu Xaa Arg Leu Gly Lys Ser Gly Ala Thr
1               5                   10

<210> SEQ ID NO 83
<211> LENGTH: 34
<212> TYPE: PRT
<213> ORGANISM: Triticum tauschii

<400> SEQUENCE: 83

Arg Ile Thr Gly Thr His Thr Arg Ala Gly Lys Ser Ser Tyr Asn Arg

```
                1               5                  10                 15
Tyr Ser Leu Thr Lys Cys Arg Met Lys Pro Thr Thr Asp Ala Ser Gly
                    20                  25                  30

Phe Glu

<210> SEQ ID NO 84
<211> LENGTH: 4
<212> TYPE: PRT
<213> ORGANISM: Triticum tauschii

<400> SEQUENCE: 84

Ile Ser Met Glu
1

<210> SEQ ID NO 85
<211> LENGTH: 20
<212> TYPE: PRT
<213> ORGANISM: Triticum tauschii
<220> FEATURE:
<221> NAME/KEY: MOD_RES
<222> LOCATION: (3)..(3)
<223> OTHER INFORMATION: Variable amino acid
<220> FEATURE:
<221> NAME/KEY: MOD_RES
<222> LOCATION: (8)..(8)
<223> OTHER INFORMATION: Variable amino acid
<220> FEATURE:
<221> NAME/KEY: MOD_RES
<222> LOCATION: (15)..(15)
<223> OTHER INFORMATION: Variable amino acid

<400> SEQUENCE: 85

Leu Asp Xaa Gly Ser Arg Phe Xaa Glu Leu Tyr Phe Phe Pro Xaa Arg
1               5                   10                  15

Gly Lys Trp Arg
            20

<210> SEQ ID NO 86
<211> LENGTH: 42
<212> TYPE: PRT
<213> ORGANISM: Triticum tauschii
<220> FEATURE:
<221> NAME/KEY: MOD_RES
<222> LOCATION: (2)..(2)
<223> OTHER INFORMATION: Variable amino acid

<400> SEQUENCE: 86

Cys Xaa Pro Arg Pro Trp Cys Tyr His Gly Phe Asp His Ser Ser Phe
1               5                   10                  15

His Ser Asp Ile Tyr Phe Leu Ile Leu Phe Leu Pro Val Leu Ala Val
            20                  25                  30

Thr Ala Ser Cys Gly Val Phe Ser Leu Leu
        35                  40

<210> SEQ ID NO 87
<211> LENGTH: 59
<212> TYPE: PRT
<213> ORGANISM: Triticum tauschii
<220> FEATURE:
<221> NAME/KEY: MOD_RES
<222> LOCATION: (26)..(26)
<223> OTHER INFORMATION: Variable amino acid

<400> SEQUENCE: 87

Ser Ser Leu His Phe Ala Gly Ala Val Leu Ser Arg Ala Ala Ser Pro
1               5                   10                  15
```

-continued

Gly Lys Val Leu Val Pro Asp Gly Glu Xaa Asp Asp Leu Ala Ser Pro
            20                  25                  30

Ala Gln Pro Glu Glu Leu Gln Val His Thr Leu Val Pro Val Asn Leu
        35                  40                  45

His Thr Ile Val Ile His Leu Pro Asn Ala Gly
    50                  55

<210> SEQ ID NO 88
<211> LENGTH: 16
<212> TYPE: PRT
<213> ORGANISM: Triticum tauschii

<400> SEQUENCE: 88

Gly Arg Tyr Val Ala Glu Leu Ser Arg Glu Gly Pro Ala Ala Arg Pro
1               5                   10                  15

<210> SEQ ID NO 89
<211> LENGTH: 11
<212> TYPE: PRT
<213> ORGANISM: Triticum tauschii

<400> SEQUENCE: 89

Arg Lys Cys Met Leu Met Val Phe Val Leu Thr
1               5                   10

<210> SEQ ID NO 90
<211> LENGTH: 10
<212> TYPE: PRT
<213> ORGANISM: Triticum tauschii

<400> SEQUENCE: 90

Leu Phe Trp Leu Trp Glu Tyr Leu Gln Leu
1               5                   10

<210> SEQ ID NO 91
<211> LENGTH: 21
<212> TYPE: PRT
<213> ORGANISM: Triticum tauschii

<400> SEQUENCE: 91

Ser Ser Cys Gly Ser Ser Ile His Cys Arg Leu Phe Lys Ile Leu Gly
1               5                   10                  15

Asp Gly Asn Ala Cys
            20

<210> SEQ ID NO 92
<211> LENGTH: 4
<212> TYPE: PRT
<213> ORGANISM: Triticum tauschii

<400> SEQUENCE: 92

Trp Phe Ser Phe
1

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93

```
cgtcgctgct cctcaggaag                                              20
```

<210> SEQ ID NO 94
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94

```
ctggctgact caatcactac g                                            21
```

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95

```
cgcaacctga agaattacag                                              20
```

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96

```
attttcggag ccatcttgac                                              20
```

<210> SEQ ID NO 97
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97

```
atcacttacc gagaatggg                                               19
```

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98

```
agctattcct catggctcac                                              20
```

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99

```
tgcaggctcc aggtgaaata                                              20
```

```
<210> SEQ ID NO 100
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
ggcttggata caatgcagtg c                                              21

<210> SEQ ID NO 101
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
tttaggtggt gaaggctatc t                                              21

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
agcagaactg cggtcgtgta                                                20

<210> SEQ ID NO 103
<211> LENGTH: 6
<212> TYPE: PRT
<213> ORGANISM: Triticum tauschii

<400> SEQUENCE: 103

Arg Trp Cys Trp Arg Pro
1               5

<210> SEQ ID NO 104
<211> LENGTH: 9
<212> TYPE: PRT
<213> ORGANISM: Triticum tauschii

<400> SEQUENCE: 104

Asn Gln Pro Arg Met Arg Gln Val Ser
1               5
```